(12) United States Patent
Amberg et al.

(10) Patent No.: US 10,280,159 B2
(45) Date of Patent: May 7, 2019

(54) FUSED (HETERO)CYCLIC COMPOUNDS AS S1P MODULATORS

(71) Applicant: AbbVie Deutschland GmbH & Co. KG, Weisbaden (DE)

(72) Inventors: Wilhelm Amberg, Ludwigshafen (DE); Udo Lange, Ludwigshafen (DE); Herve Geneste, Ludwigshafen (DE); Michael Ochse, Ludwigshafen (DE); Ralf Biesinger, Ludwigshafen (DE); Frank Oellien, Ludwigshafen (DE)

(73) Assignee: ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

(21) Appl. No.: 15/388,516

(22) Filed: Dec. 22, 2016

(65) Prior Publication Data

US 2017/0174672 A1    Jun. 22, 2017

Related U.S. Application Data

(60) Provisional application No. 62/270,624, filed on Dec. 22, 2015.

(51) Int. Cl.

| | | |
|---|---|---|
| C07D 413/12 | (2006.01) | |
| C07D 205/04 | (2006.01) | |
| C07C 229/48 | (2006.01) | |
| C07C 229/46 | (2006.01) | |
| C07D 211/62 | (2006.01) | |
| C07D 261/12 | (2006.01) | |
| C07D 209/52 | (2006.01) | |
| C07D 207/16 | (2006.01) | |
| C07D 207/08 | (2006.01) | |
| C07D 265/36 | (2006.01) | |
| C07C 59/72 | (2006.01) | |
| C07D 405/04 | (2006.01) | |
| C07D 311/04 | (2006.01) | |
| C07D 405/14 | (2006.01) | |
| C07D 311/58 | (2006.01) | |
| C07C 229/30 | (2006.01) | |
| C07C 229/36 | (2006.01) | |
| C07C 229/50 | (2006.01) | |
| C07D 207/06 | (2006.01) | |
| C07D 265/38 | (2006.01) | |
| C07D 209/94 | (2006.01) | |
| C07D 211/32 | (2006.01) | |

(52) U.S. Cl.
CPC ............ *C07D 413/12* (2013.01); *C07C 59/72* (2013.01); *C07C 229/30* (2013.01); *C07C 229/36* (2013.01); *C07C 229/46* (2013.01); *C07C 229/48* (2013.01); *C07C 229/50* (2013.01); *C07D 205/04* (2013.01); *C07D 207/06* (2013.01); *C07D 207/08* (2013.01); *C07D 207/16* (2013.01); *C07D 209/52* (2013.01); *C07D 209/94* (2013.01); *C07D 211/32* (2013.01); *C07D 211/62* (2013.01); *C07D 261/12* (2013.01); *C07D 265/36* (2013.01); *C07D 265/38* (2013.01); *C07D 311/04* (2013.01); *C07D 311/58* (2013.01); *C07D 405/04* (2013.01); *C07D 405/14* (2013.01); *C07C 2601/04* (2017.05); *C07C 2601/14* (2017.05); *C07C 2602/10* (2017.05); *C07C 2602/38* (2017.05)

(58) Field of Classification Search
CPC .......................... C07D 413/12; C07D 405/04
USPC .................................................... 514/210.18
See application file for complete search history.

(56) References Cited

U.S. PATENT DOCUMENTS

| | | | |
|---|---|---|---|
| 8,357,706 B2 * | 1/2013 | Martinborough | .... C07D 263/32 |
| | | | 514/210.18 |
| 2005/0090520 A1 | 4/2005 | Lindquist | |

FOREIGN PATENT DOCUMENTS

| | | |
|---|---|---|
| EP | 0080115 | 6/1983 |
| WO | 2011060389 A1 | 5/2011 |
| WO | 2016088834 A1 | 6/2016 |

OTHER PUBLICATIONS

Horig et al. Journal of Translational Medicine 2004, 2(44), p. 1-8.*
Schafer et al. Drug Discovery Today, 2008, 13 (21/22), 913-916.*
Bin, M. et al., "Stereochemistry-activity relationship of orally active tetralin S1P agonist prodrugs," Bioorganic Medicinal Chemistry Letters, 2010, vol. 20, pp. 2264-2269.
Butler, T. W. et al., "(3R,4S)-3-[4-(4-Fluorophenyl)-4-hydroxypiperidin-1-yl]chroman-4,7-diol: A Conformationally Restricted Analogue of the NR2B Subtype-Selective NMDA Antagonist (1S,2S)-1-(4-Hydroxyphenyl)-2-(4-hydroxy-4-phenylpiperidino)-1-propanol," J. Med. Chem., 1998, vol. 41, pp. 1172-1184.
Xiao et al., "Identification of Tricyclic Agonists of Sphingosine-1-phosphate Receptor 1 (S1P1) Employing Ligand-Based Drug Design," Journal of Medicinal Chemistry, 2016, vol. 59, pp. 9837-9854.
Del Aguila, A., et al., Lipidomic and Immunohistochemical Analysis of Sphingosine-1-phosphate and Other Sphingolipids Following Spinal Cord Injury, Sphingolipid Club Meeting—Abstracts, 2013, 1 page.
Asle-Rousta M., et al, "FTY720 (Fingolirriod) Attenuates Beta-amyloid Peptide (ab42)-induced Impairment of Spatial Learning and Memory in Rats," Journal of Molecular Neuroscience, Jul. 2013, vol. 50 (3), pp. 524-532.
Bras J., et al., "Emerging Pathways in Genetic Parkinson's Disease: Potential Role of Ceramide Metabolism in Lewy Body Disease," The Febs Journal, Dec. 2008, vol. 275 (23), pp. 5767-5773.

(Continued)

*Primary Examiner* — Yong L Chu
(74) *Attorney, Agent, or Firm* — Neal, Gerber & Eisenberg LLP

(57) ABSTRACT

The invention relates to (hetero)cyclic compounds as S1P modulators, pharmaceutical compositions comprising such compounds, and uses thereof in the treatment, alleviation or prevention of diseases or disorders mediated by an S1P receptor.

19 Claims, No Drawings

(56) References Cited

OTHER PUBLICATIONS

Brinkmann V., et al., "FTY720: Targeting G-protein-coupled Receptors for Sphingosine 1-phosphate in Transplantation and Autoimmunity," Current Opinion in Immunology, Oct. 2002, vol. 14 (5), pp. 569-575.

Camp S.M., et al., "Synthetic Analogs of FTY720 [2-amino-2-(2-[4-octylphenyl]ethyl)-1,3-propanediol] Differentially Regulate Pulmonary Vascular Permeability in Vivo and in Vitro," The Journal of Pharmacology and Experimental Therapeutics, Oct. 2009, vol. 331 (1), pp. 54-64.

Campeau P.M., et al., "Characterization of Gaucher Disease Bone Marrow Mesenchymal Stromal Cells Reveals an Altered Inflammatory Secretome," Blood, Oct. 2009, vol. 114 (15), pp. 3181-3190.

Ceccom J., et al., "Reduced Sphingosine Kinase-1 and Enhanced Sphingosine 1-phosphate Lyase Expression Demonstrate Deregulated Sphingosine 1-phosphate Signaling in Alzheimer's Disease," Acta Neuropathologica Communications, Jan. 2014, vol. 2 (12), pp. 1-10.

Cieslik M., et al., "The Molecular Mechanism of Amyloid beta42 Peptide Toxicity: The Role of Sphingosine Kinase-1 and Mitochondrial Sirtuins," PLOS One, Sep. 2015, vol. 10 (9), pp. 1-19.

Coste O., et al., "Antinociceptive Activity of the S1P-Receptor Agonist FTY720," Journal of Cellular and Molecular Medicine, 2008, vol. 12 (3), pp. 995-1004.

Couttas T.A., et al., "Loss of the Neuroprotective Factor Sphingosine 1-phosphate Early in Alzheimer's Disease Pathogenesis," Acta Neuropathologica Communications, Jan. 2014, vol. 2 (9), pp. 1-13.

Cutler R.G., et al., "Involvement of Oxidative Stress-Induced Abnormalities in Ceramide and Cholesterol Metabolism in Brain Aging and Alzheimer'S Disease," Proceedings of the National Academy of Sciences of the United States of America, 2004, vol. 101 (7), pp. 2070-2075.

Czech B., et al., "The Immunomodulatory Sphingosine 1-phosphate Analog FTY720 Reduces Lesion Size and Improves Neurological Outcome in a Mouse Model of Cerebral Ischemia," Biochemical and Biophysical Research Communications, Nov. 2009, vol. 389 (2), pp. 251-256.

Daniel C., et al., "FTY720 Ameliorates TH1-mediated Colitis in Mice by Directly Affecting the Functional Activity of CD4+CD25+ Regulatory T Cells," Journal of Immunology, Feb. 2007, vol. 178 (4), pp. 2458-2468.

Deogracias R. et al., "Fingolimod, a Sphingosine-1 Phosphate Receptor Modulator, Increases BDNF Levels and Improves Symptoms of a Mouse Model of Rett Syndrome," Proceedings of the National Academy of Sciences of the USA, Aug. 2012, vol. 109 (35), pp. 14230-14235.

Di Pardo A., et al., "FTY720 (Fingolimod) is a Neuroprotective and Disease-modifying Agent in Cellular and Mouse Models of Huntington Disease," Human Molecular Genetics, May 2014, vol. 23 (9), pp. 2251-2265.

Di Pardo A., et al., "Ganglioside GM1 Induces Phosphorylation of Mutant Huntingtin and Restores Normal Motor Behavior in Huntington Disease Mice," Proceedings of the National Academy of Sciences of the United States of America, Feb. 2012, vol. 109 (9), pp. 3528-3533.

Doi Y., et al., "Fingolimod Phosphate Attenuates Oligomeric Amyloid B-induced Neurotoxicity via Increased Brain-derived Neurotrophic Factor Expression in Neurons," PLOS One, Apr. 2013, vol. 8 (4), pp. e61988.

Ewers M., et al., "Blood-based Biomarkers of Microvascular Pathology in Alzheimer's Disease," Experimental Gerontology, Jan. 2010, vol. 45 (1), pp. 75-79.

Fukumoto K., et al., "Fingolimod Increases Brain-derived Neurotrophic Factor Levels and Ameliorates Amyloid B-induced Memory Impairment," Behavioural Brain Research, Jul. 2014, vol. 268, pp. 88-93.

Fuller M., et al., "Sphingolipids: the Nexus Between Gaucher Disease and Insulin Resistance," Lipids in Health and Disease, Oct. 2010, vol. 113, pp. 1-12.

Garcia J.G., et al., "Sphingosine 1-phosphate Promotes Endothelial Cell Barrier Integrity by Edg-dependent Cytoskeletal Rearrangement," The Journal of Clinical Investigation, Sep. 2001, vol. 108 (5), pp. 689-701.

Gomes L.,et al., "Sphingosine 1-phosphate in Acute Dengue Infection," PLOS One, Nov. 2014, vol. 9 (11), p. e113394.

Gomez-Brouchet A., et al., "Critical Role for Sphingosine Kinase-1 in Regulating Survival of Neuroblastoma Cells Exposed to Amyloid-beta Peptide," Molecular Pharmacology, Aug. 2007, vol. 72 (2), pp. 341-349.

Graler M.H., et al., "The Role of Sphingosine 1-phosphate in Immunity and Sepsis," American Journal of Clinical and Experimental Immunology, Sep. 2012, vol. 1 (2), pp. 90-100.

Han X., et al., "Substantial Sulfatide Deficiency and Ceramide Elevation in Very Early Alzheimer'S Disease: Potential Role in Disease Pathogenesis," Journal of Neurochemistry, 2002, vol. 82 (4), pp. 809-818.

Ichijo M., et al., "Sphingosine-1-Phosphate Receptor-1 Selective Aganist Enhances Collateral Growth and Protects against Subsequent Stroke," PLOS One, Sep. 2015, vol. 10 (9), pp. 1-19.

International Search Report and Written Opinion for Application No. mailed on PCT/EP2016/082422, dated Feb. 8, 2017, 10 pages.

Janes K., et al., "The Development and Maintenance of Paclitaxel-induced Neuropathic Pain Require Activation of the Sphingosine 1-Phosphate Receptor Subtype 1," The Journal of Biological Chemistry, Jul. 2014, vol. 289 (30), pp. 21082-21097.

Kaneider N.C., et al., "The Immune Modulator FTY720 Targets Sphingosine-Kinase-Dependent Migration of Human Monocytes in Response to Amyloid Beta-Protein and its Precursor," The FASEB Journal, 2004, vol. 18 (11), pp. 1309-1311.

Keul P., et al., "The Sphingosine-1-phosphate Analogue FTY720 Reduces Atherosclerosis in Apolipoprotein E-deficient Mice," Arteriosclerosis, Thrombosis, and Vascular Biology, Mar. 2007, vol. 27 (3), pp. 607-613.

Kim W.S., et al., "Role of ATP-Binding Cassette Transporters in Brain Lipid Transport and Neurological Disease," Journal of Neurochemistry, 2008, vol. 104 (5), pp. 1145-1166.

Kimura A., et al., "Essential Roles of Sphingosine 1-phosphate/S1P1 Receptor Axis in the Migration of Neural Stem Cells Toward a Site of Spinal Cord Injury," Stem Cells, Jan. 2007, vol. 25 (1), pp. 115-124.

Kolesnick R., "The Therapeutic Potential of Modulating the Ceramide/sphingomyelin Pathway," The Journal of Clinical Investigation, Jul. 2002, vol. 110 (1), pp. 3-8.

Lee H., et al., "Bone Marrow-Derived Mesenchymal Stem Cells Prevent the Loss of Niemann-Pick Type C Mouse Purkinje Neurons by Correcting Sphingolipid Metabolism and Increasing Sphingosine-1-Phosphate," Stem Cells (Dayton, Ohio), 2010, vol. 28 (4), pp. 821-831.

Lee K.D., et al., "FTY720 Reduces Inflammation and Promotes Functional Recovery After Spinal Cord Injury," Journal of Neurotrauma, Dec. 2009, vol. 26 (12), pp. 2335-2344.

Lee M.J., et al., "Vascular Endothelial Cell Adherens Junction Assembly and Morphogenesis Induced by Sphingosine-1-phosphate," Cell, Oct. 1999, vol. 99 (3), pp. 301-312.

Liang J., et al., "Sphingosine-1-phosphate Links Persistent STAT3 Activation, Chronic Intestinal Inflammation, and Development of Colitis-associated Cancer," Cancer Cell, Jan. 2013, vol. 23 (1), pp. 107-120.

Liu J., et al., "Systematic Review and Meta-analysis of the Efficacy of Sphingosine-1-phosphate (S1 p) Receptor Agonist FTY720 (Fingolimod) in Animal Models of Stroke," The International Journal of Neuroscience, Mar. 2013, vol. 123 (3), pp. 163-169.

Lloyd-Evans E., et al., "Niemann-pick Disease Type C1 Is a Sphingosine Storage Disease That Causes Deregulation of Lysosomal Calcium," Nature Medicine, Nov. 2008, vol. 14 (11), pp. 1247-1255.

Maglione V., et al., "B26 Targeting Sphingosine-1-phosphate Metabolism/axis May Be Beneficial in Huntington Disease Models," Journal of Neurology, Neurosurgery and Psychiatry, 2014, vol. 85 (1), p. A18.

(56) References Cited

OTHER PUBLICATIONS

Maglione V., et al., Further evidence of defective sphingolipid metabolism across multiple HD animal models, IRCCS Neuromed, Pozzilli Italy, 2015, 2 pages.
Maglione V., et al., Sphingosine-1-phosphate Metabolism/axis as Potential Therapeutic Target in Huntington Disease, Neuroscience, 2014, 1 page.
Malaplate-Armand C., et al., "Soluble Oligomers of Amyloid-beta Peptide Induce Neuronal Apoptosis by Activating a cPLA2-dependent Sphingomyelinase-ceramide Pathway," Neurobiology of Disease, Jul. 2006, vol. 23 (1), pp. 178-189.
Mattes H., et al., "Design and Synthesis of Selective and Potent Orally Active S1P5 Agonists," ChemMedChem, 2010, vol. 5 (10), pp. 1693-1696.
McVerry B.J., et al., "In Vitro and in Vivo Modulation of Vascular Barrier Integrity by Sphingosine 1-phosphate: Mechanistic Insights," Cellular Signalling, Feb. 2005, vol. 17 (2), pp. 131-139.
Michels M., et al., "Decreased Plasma Levels of the Endothelial Protective Sphingosine-1-phosphate are Associated with Dengue-induced Plasma Leakage," Journal of Infection, Oct. 2015, vol. 71 (4), pp. 480-487.
Miguez A., et al., "Fingolimod (FTY720) Enhances Hippocampal Synaptic Plasticity and Memory in Huntington's Disease by Preventing p75NTR Up-regulation and Astrocyte-mediated Inflammation," Human Molecular Genetics, Sep. 2015, vol. 24 (17), pp. 4958-4970.
Mistry P.K., et al., "Glucocerebrosidase 2 Gene Deletion Rescues Type 1 Gaucher Disease," Proceedings of the National Academy of Sciences of the United States of America, Apr. 2014, vol. 111 (13), pp. 4934-4939.
Mok S.W., et al., "B Cell-specific S1PR1 Deficiency Blocks Prion Dissemination Between Secondary Lymphoid Organs," Journal of Immunology, May 2012, vol. 188 (10), pp. 5032-5040.
Montrose D.C., et al., "S1P 1 Localizes to the Colonic Vasculature in Ulcerative Colitis and Maintains Blood Vessel Integrity," Journal of Lipid Research, Mar. 2013, vol. 54 (3), pp. 843-851.
Moon E., et al.. "Exogenous S1P Exposure Potentiates Ischemic Stroke Damage That is Reduced Possibly by Inhibiting S1P Receptor Signaling," Mediators of Inflammation, 2015, vol. 2015, pp. 1-13.
Moon M.H., et al., "FTY720 Protects Neuronal Cells From Damage Induced by Human Prion Protein by Inactivating the JNK Pathway," International Journal of Molecular Medicine, Dec. 2013, vol. 32 (6), pp. 1387-1393.
Neviani P., et al., "FTY720, a New Alternative for Treating Blast Crisis Chronic Myelogenous Leukemia and Philadelphia Chromosome-positive Acute Lymphocytic Leukemia," The Journal of Clinical Investigation, Sep. 2007, vol. 117 (9), pp. 2408-2421.
Norimatsu Y., et al., "FTY720 Improves Functional Recovery After Spinal Cord Injury by Primarily Nonimmunomodulatory Mechanisms," The American Journal of Pathology, Apr. 2012, vol. 180 (4), pp. 1625-1635.
Novgorodov S.A., et al., "Essential Roles of Neutral Ceramidase and Sphingosine in Mitochondrial Dysfunction Due to Traumatic Brain Injury," The Journal of Biological Chemistry, May 2014, vol. 289 (19), pp. 13142-13154.
Opal S.M., et al., "Endothelial Barrier Dysfunction in Septic Shock," Journal of Internal Medicine, Mar. 2015, vol. 277 (3), pp. 277-293.
Paik J.H., et al., "Sphingosine 1-phosphate-induced Endothelial Cell Migration Requires the Expression of EDG-1 and EDG-3 Receptors and Rho-dependent Activation of alpha Vbeta3-and beta1-containing Integrins," The Journal of Biological Chemistry, Apr. 2001, vol. 276 (15), pp. 11830-11837.
Parrini M., et al., "Aerobic Exercise and a BDNF-mimetic Therapy Rescue Learning and Memory in a Mouse Model of Down Syndrome," Scientific Reports, Dec. 2017, vol. 7 (1), pp. 16825.
Paugh S.W., et al., "A Selective Sphingosine Kinase 1 Inhibitor Integrates Multiple Molecular Therapeutic Targets in Human Leukemia," Blood, Aug. 2008, vol. 112 (4), pp. 1382-1391.

Salvemini D., et al., "Therapeutic Targeting of the Ceramideto-Sphingosine 1-phosphate Pathway in Pain," Trends in Pharmacological Sciences, Feb. 2013, vol. 34 (2), pp. 110-118.
Sanchez T., et al., "Phosphorylation and Action of the Immunomodulator FTY720 Inhibits Vascular Endothelial Cell Growth Factor-Induced Vascular Permeability," The Journal of Biological Chemistry, 2003, vol. 278 (47), pp. 47281-47290.
Savica R., et al., "Plasma Sphingolipid Changes With Autopsy-confirmed Lewy Body or Alzheimer's Pathology," Alzheimer's and Dementia, 2016, vol. 3, pp. 43-50.
Schmalzbauer R., et al., "Evidence for an Association of Prion Protein and Sphingolipid-mediated Signaling," Journal of Neurochemistry, Aug. 2008, vol. 106 (3), pp. 1459-1470.
Simonaro C.M., et al., "Mechanism of Glycosaminoglycan-mediated Bone and Joint Disease," The American Journal of Pathology, Jan. 2008, vol. 172 (1), pp. 112-122.
Snider A.J., et al., "A Role for Sphingosine Kinase 1 in Dextran Sulfate Sodium-induced Colitis," FASEB Journal, Jan. 2009, vol. 23 (1), pp. 143-152.
Stockstill K., et al., "Bortezomib-induced Neuropathic Pain Is Blocked and Reversed by Blocking the S1P/S1PR1 Axis," The Journal of Pain, Apr. 2014, vol. 15 (4), pp. S60.
Takabe K., et al., "Inside-Out Signaling of Sphingosine-1-Phosphate: Therapeutic Targets," Pharmacological reviews, 2008, vol. 60 (2), pp. 181-195.
Takasugi N., et al., "Fty720/Fingolimod, a Sphingosine Analogue, Reduces Amyloid-beta Production in Neurons," Plos One, 2013, vol. 8 (5), pp. e64050.
Van Doorn R., et al., "Sphingosine 1-Phosphate Receptor 5 Mediates the Immune Quiescence of the Human Brain Endothelial Barrier," Journal of Neuroinflammation, 2012, vol. 20 (9), p. 133.
Vyas V., et al., "Sphingosine Kinase: a Novel Putative Target for the Prevention of Infection-triggered Preterm Birth," Obstetrics and Gynecology International, 2013, vol. 2013, pp. 302952.
Wang J., et al., "Local Delivery of FTY720 in PCL Membrane Improves SCI Functional Recovery by Reducing Reactive Astrogliosis," Biomaterials, Sep. 2015, vol. 62, pp. 76-87.
Winkler M.S., et al., "Decreased Serum Concentrations of Sphingosine-1-phosphate in Sepsis," Critical Care, Oct. 2015, vol. 19 (372), pp. 1-12.
Wood H., "Neurodegenerative Disease: Could Fingolimod Provide Cognitive Benefits in Patients With Huntington Disease?," Nature Reviews Neurology, Aug. 2015, vol. 11 (8), pp. 426.
Wu Y.P., et al., "Sphingosine Kinase 1/S1P Receptor Signaling Axis Controls Glial Proliferation in Mice With Sandhoff Disease," Human Molecular Genetics, Aug. 2008, vol. 17 (15), pp. 2257-2264.
Yamagata K., et al., "Sphingosine 1-phosphate Induces the Production of Glial Cell Line-derived Neurotrophic Factor and Cellular Proliferation in Astrocytes," Glia, Jan. 2003, vol. 41 (2), pp. 199-206.
Zhang Y. H., et al., "Intracellular Sphingosine 1-phosphate Mediates the Increased Excitability Produced by Nerve Growth Factor in Rat Sensory Neurons," The Journal of Physiology, Aug. 2006, vol. 575 (1), pp. 101-113.
Zhang Z., et al., "FTY720 Attenuates Accumulation of EMAP-II+ and MHC-II+ Monocytes in Early Lesions of Rat Traumatic Brain Injury," Journal of Cellular and Molecular Medicine, Mar.-Apr. 2007, vol. 11 (2), pp. 307-314.
Amminger, G.P., et al., "Omega-3 fatty acids supplementation in children with autism: a double-blind randomized, placebo-controlled pilot study." Biol Psychiatry, 2007, vol. 61, pp. 551-553.
Asle-Rousta, M., et al., "Activation of Sphingosine 1-Phosphate Receptor-1 by SEW2871 Improves Cognitive Function in Alzheimer's Disease Model Rats," EXCLI Journal, 2013, vol. 12, pp. 449-461.
Bellettato, C.M., et al., "Pathophysiology of Neuropathic Lysosomal Storage Disorders," J. Inher. Metab. Dis., 2010, vol. 33, pp. 347-362.
Brailoiu, E., et al., "Sphingosine Sphingosine 1-phosphate enhances spontaneous transmitter release at the frog neuromuscular junction," Br J Pharmacol., 2002, vol. 136(8), pp. 1093-1097.
Di Nuzzo, L., et al., "Antidepressant Activity of Fingolimod in Mice," Pharmacol Res Perspect, 2015, vol. 3(3), pp. 1-17.

(56) References Cited

OTHER PUBLICATIONS

Farr, S.A., et al., Spingosine-1-phosphate Receptor 5 Agonist A-971432 Improves Leaning and Memory in the SAMP8 Mouse Model of Alzheimer's Disease, Alzheimer's & Dementia, 2017, vol. 13(7): Suppl. P949.

Foster, C.A., et al., "FTY720 Rescue Therapy in the Dark Agouti Rat model of Experimental Autoimmune Encephalomyelitis: Expression of Central Nervous System Genes and Reversal of Blood-Brain-Barrier Damage," Brain Pathology, 2009, vol. 19, pp. 254-266.

Fukuzako, H., et al., "Changes in Levels of Phosphorus Metabolites in Temporal Lobes of Drug-Naïve Schizophrenic Patients," Am J Psychiatry, 1999, vol. 156, pp. 1205-1208.

Gregg, J.P., et al, "Gene expression changes in children with autism," Genomics. 2008, vol. 91, pp. 22-29.

Harada, J. et al., "Sphingoshine-1-phosphate induces proliferation and morphological changes of neural progenitor cells," J. Neurochem., 2004, vol. 88, pp. 1026-1039.

Hicks, A.A., et al., "Genetic Determinants of circulating Sphingolipid Concentrations in European Populations," PLoS Genetics, 2009, vol. 5(10), pp. 1-11.

Jaillard, C., et al., "Edg8/S1P5: An Oligodendroglial Receptor with Dual Function on Process Retraction and Cell Survival," The Journal of Neuroscience, 2005, vol. 25(6), pp. 1459-1469.

Kajimoto, T., et al., "Involvement of Sphingosine-1-Phosphate in Glutamate Secretion in Hippocampal Neurons," Mol Cell Biol, 2007, vol. 27(9), pp. 3429-3440.

Kornhuber, J., et al., "The Role of Ceramide in Major Depressive Disorder," Eur Arch Psychiatry Clin Neurosci, 2009, vol. 259 (Suppl 2), pp. S199-S204.

Kurlak, L.O., et al., "Plausible explanations for effects of long chain polyunsaturated fatty acids (LCPUFA) on neonates," Arch Dis Child Fetal Neonatal Ed, 1999, vol. 80, pp. F148-F154.

Lahiri, S., et al., "Ceramide Synthesis if Modulated by the Sphingosine Analog FTY720 via a Mixture of Uncompetitive and Noncompetitive Inhibitino in an Acyl-CoA Chain Length-dependent Manner," J. Biol. Chem., 2009, vol. 284(24), pp. 16090-16098.

Miron, V.E., et al. "Central nervous system-directed effects of FTY720 (fingolimod)," J. Neuro. Sci., 2008, vol. 274(1-2), pp. 13-17.

Miron, V.E. et al., "Fingolimod (FTY720) Enhances Remyelination Following Demyelination of Organotypic Cerebellar Slices," Am. J. Pathology., 2010, vol. 176(6), pp. 2682-2694.

Narayan, S., et al., "Evidence for Disruption of Sphingolipid Metabolism in Schizophrenia," J Neurosci Res., 2009, vol. 87(1), pp. 278-288.

Novgorodov, A.S., et al., "Activation of sphingosine-1-phosphate receptor S1P5 inhibits oligodendrocyte progenitor migration," The FASEB Journal., 2007, vol. 21: 1503-1514.

Pahnke, J., et al, "Alzheimer's disease and blood-brain barrier function—Why have anti-amyloid therapies failed to prevent dementia progression?," Neuroscience and Biobehavioral Reviews, 2008, vol. 33(7), pp. 1099-1108. doi:10.1016/j.neubiorev.2009.05.006.

Sim-Selley, L.J., "Sphingosine-1-Phosphate Receptors Mediate Neuromodulatory Functions in the CNS," J Neurochem, 2009, vol. 110(4), pp. 1191-1202.

Tlili, A., et al., "BDNF and DYRK1A Are Variable and Inversely Correlated in Lymphoblastoid Cell Lines from Down Syndrome Patients," Mol. Neurobiol., 2012, vol. 46(2), pp. 297-303.

Vidal, C.N., et al., "Mapping Corpus Callosum Deficits in Autism: An Index of Aberrant Cortical Connectivity," Biol Psychiatry., 2006, vol. 60(3), pp. 218-225.

Walzer, T., et al., "Natural killer cell trafficking in vivo requires a dedicated sphingosine 1-phosphate receptor," Nature Immunol., 2007, vol. 8(12), pp. 1337-1344.

Wang, H., et al., "Potential serum biomarkers from a rnetabolomics study of autism," J Psychiatry Neurosci., 2016, vol. 41(1), pp. 27-37.

Yu, N., et al., "Characterization of Lysophosphatidic Acid and Sphingosine-1-Phosphate-Mediated Signal Transduction in Rat Cortical Oligodendrocytes," GLIA., 2004, vol. 14, pp. 17-27.

Yui, K., et al., "Effects of large doses of arachidonic acid added to DHA on social impairment in individuals with autism spectrum disorders: a double-blind, placebo-controlled, randomized trial," J Clin Psychopharmacol, 2012, vol. 32, pp. 200-206.

Clinical Study to Evaluate the Efficacy, Safety, and Tolerability of ACT-128800 in Patients With Relapsing-remitting Multiple Sclerosis. (2009) Retrieved from https://clinicaltrials.gov/ct2/show/NCT01006265? term=NCT01006265&rank=1 (Identification No. NCT01006265).

Safety, Tolerability, Efficacy and Optimal Dose Finding Study of BAF312 in Patients With Relapsing-remitting Multiple Sclerosis. (2009) Retrieved from https://clinicaltrials.gov/ct2/show/NCT00879658? term=NCT00879658&rank=1 (Identification No. NCT00879658).

* cited by examiner

FUSED (HETERO)CYCLIC COMPOUNDS AS S1P MODULATORS

CROSS REFERENCE TO RELATED APPLICATONS

This application claims the benefit of U.S. Provisional Patent Application No. 62/270,624, filed Dec. 22, 2015. This prior application is incorporated herein by reference in its entirety.

The invention relates to fused heterocyclic compounds with affinity to S1P receptors, pharmaceutical compositions comprising such compounds, the use of such compounds in the treatment, alleviation or prevention of diseases and conditions in which an S1P receptor is involved or in which modulation of the endogenous S1P signaling system via an S1P receptor is involved and the preparation of a medicament for treating, alleviating or preventing such diseases and conditions.

BACKGROUND OF THE INVENTION

Sphingosine-1-phosphate (S1P) is part of the sphingolipid class of molecules. S1P is a bioactive sphingolipid that mediates a wide variety of cellular responses, such as proliferation, autophagy, blockade of apoptosis, cell differentiation, blockade of cell senescence, cytoskeletal organization and migration, adherence- and tight junction assembly, and morphogenesis. Moreover, S1P is a modulator of APP processing via BACE1 regulation as well as lipid raft formation and can interact with ABC transporters thereby modulating cellular in- and efflux. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems. The above mentioned actions of S1P are mediated by interaction with its receptors. Therefore, S1P receptors are therapeutic targets for the treatment of, for example, neoplastic diseases, diseases of the central and peripheral nervous system, autoimmune disorders and tissue rejection in transplantation.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system (CNS; brain and spinal cord). Other tissues with S1P5 expression are skin and spleen. Moreover, S1P5 is expressed on NK cells. Early study showed that the CNS expression in mice appeared restricted to oligodendrocytes, while in men and rats expression was more diverse. Recent evidence has shown a broader distribution in all species: S1P5 expression is shown at the level of astrocytes, endothelial cells, glial cells, oligodendrocytes and to a lesser extent neurons.

The present invention relates to modulators of the S1P5 receptor, in particular agonists, and preferably to agonists with selectivity over S1P1, S1P3 and/or S1P4 receptors, in view of unwanted cardiovascular and/or peripheral immune-modulatory effects. It has now been found that S1P5 agonists can be used in the treatment of cognitive disorders, in particular age-related cognitive decline. Moreover, evidence has shown an impact on amyloid β (protein) processing, ABC transporter expression, blood-brain-barrier integrity, neuro-inflammatory processes, and (sphingo)lipid content in the CNS.

The latter is of high relevance as an altered sphingolipid metabolism is strongly implicated in several neurodegenerative and cognitive diseases. A comparison of CNS gene expression profiles of normal and Alzheimer's Disease (AD) patients indicated that genes responsible for SLP degradation were strongly upregulated, including the phosphatidic acid phosphatase PPAP2A and S1P lyase genes, while genes for ceramide production (apoptotic sphingolipid) were upregulated (Katsel et al, 2007, Neurochem Res, 32, 845-856). These gene expression data are predictive of actual changes in enzyme and lipid levels in the brain and cerebrospinal fluid (CSF): compared to normal subjects, AD brain are characterized by higher levels of ceramide and cholesterol as well as decreased levels of S1P. These changes also correlate with disease severity of the patients and are related to levels of Amyloid β and Tau, two hallmarks of Alzheimer's Disease (Cutler et al, 2004, PNAS, 101, 2070-2075; He et al, 2010, Neurobiol. Aging, 31, 398-408; Koal et al 2015. J. Alz Disease, 44, 1193-1201). The same changes have been reported in brain tissues (and CSF) from patients suffering HIV dementia, Amyotrophic Lateral Sclerosis (ALS), Parkinson's Disease, Parkison's Disease with Lewy Bodies, Multiple Sclerosis, Huntington's Disease, and several sphingolipdidosis disorders (Lysosomal Storage Disorders) such as Niemann Pick Disease and Gauchers (Cutler et al, 2002, Ann Neurol, 52, 448-457; Haughey et al, 2004, Ann Neurol, 55, 257-267; Cutler et al, 2010, Neurol, 63, 636-630; Mielke et al, 2013, PLOS ONE, 8; Bras et al, 2008, FEBS Journal, 275, 5767-5773; Vidaurre et al, 2014, Brain, 137, 2271-2286; Fan et al, 2013, J Lipid Research, 54, 2800-2814). Modulating the activity of the S1P5 receptor in the central nervous system may be a therapeutic method for such neurodegenerative or cognitive disorders by shifting the ceramide/S1P balance towards S1P effects and away from ceramide-mediated cell death.

Soluble β-amyloid (Aβ) oligomers are considered the proximate effectors of synaptic injury and neuronal death occurring in AD. Aβ induces increased ceramide levels and oxidative stress in neuronal cultures, leading to apoptosis and cell death. S1P is a potent neuroprotective factor against this Aβ-induced damage, consistent with its role as ceramide's counterpart (Cutler et al. 2004, PNAS, 101, 2070-2075, Malaplate-Armand, 2006, Neurobiol. Dis, 23, 178-189). Aβ is also pro-inflammatory, inducing the migration of monocytes to sites of injury, and the S1P1, S1P3, S1P4, S1P5 agonist FTY720/Fingolimod inhibits such migration. Aβ is known to induce expression of S1P2 and S1P5, but not of S1P1, S1P3 and S1P4 (Kaneider et al, 2004, FASEB). The actions of FTY720/FIngolimod and those expressed by monocytes suggests these effects are mediated by the S1P5 receptor. The same applies to more recent findings that FTY720/Fingolimod is able to modulate Aβ-induced memory deficits (Fukumoto et al, 2014, Beh Brain Res, 268, 88-93).

Additional studies suggest a role for S1P in modulating pain signals. In example, S1P modulates action potentials in capsaicin-sensitive sensory neurons (Zhang et al, 2006, J Physiol, 575, 101-113) and S1P levels are known to be decreased in CSF in acute and inflammatory pain models (Coste et al, 2008, J Biol Chem, 283, 32442-32451). The S1P1, S1P3, S1P4, S1P5 receptor agonist FTY720/Fingolimod is indeed able to reduce nociceptive behavior in neuropathic pain models (Coste et al, 2008, 12, 995-1004), while the selective S1P1 agonist SEW2817 fails to have an effect. Given the high CNS expression of S1P5 and lack of effects of S1P1 agonism, the effects can be contributed to effects on the S1P5 receptor.

In summary, potent and selective agents that are agonists of the S1P5 receptor will be beneficial for the treatment of cognitive disorders, neurodegenerative disorders and pain. In particular, S1P5-selective ligands would be beneficial for these diseases by not engaging the S1P1, S1P3 and/or S1P4 receptor ensuring a lack of peripheral immune suppression and cardiovascular side-effects.

WO 2011/017561 describes S1P agonists containing a fused cyclic core wherein optionally one the rings is a heterocycle. The compounds therefore structurally differ from the compounds of the present invention.

WO 2012/004373 describes S1P receptor modulators containing a fused heterocyclic core. These fused heterocyclic core structurally differs from the compounds of the present invention in the size of the rings constituting the core and the type and number of heteroatoms present in the rings.

Currently, there is still a need for new, potent S1P receptor modulators, in particular selective S1P5 receptor modulators.

SUMMARY OF THE INVENTION

It is an object of the present invention to provide S1P5 receptor modulators, in particular agonists, preferably to agonists with selectivity over in particular S1P1, S1P3 and/or S1P4 receptors to avoid unwanted cardiovascular and/or immunomodulatory effects. It is a further objection of the invention to provide a method for treatment or alleviation of a variety of CNS disorders, such as cognitive disorders, in particular age-related cognitive decline. The invention therefor provides a compound of formula (I):

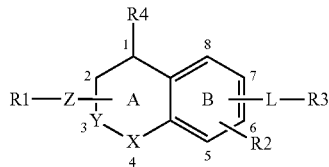

or a pharmaceutically acceptable salt, solvate, tautomer, stereoisomer or N-oxide thereof, wherein X and Y are independently selected from the group consisting of O, $CH_2$ and CH—Z—R1, with the proviso that at most one of X and Y is O and at most one of X and Y is CH—Z—R1;

Z—R1 and R4 are selected from:
  (1) Z is attached to ring A at atom 1, 2, 3 or 4 and selected from the group consisting of —O—, —NR5- and —NR5-$CH_2$— whereby NR5 is attached to R1 and $CH_2$ is attached to ring A; wherein R5 is selected from the group consisting of H, (C1-4)alkyl, (C1-4)alkyl substituted with one or more fluor atoms and benzyl optionally substituted with one or more substituents selected from the group consisting of a halogen atom, (C1-4) alkyl optionally substituted with one or more halogen atoms, and (C1-4)alkoxy optionally substituted with one or more halogen atoms;

R1 is selected from the group consisting of:
    —(C1-6)alkylene-R6 wherein one or more carbon atoms in the alkylene group, each independently, are optionally substituted with one or more halogen atoms, with $(CH_2)_2$ to form a cyclopropyl moiety, with $(CH_2)_3$ to form a cyclobutyl moiety or with $(CH_2)_4$ to form a cyclopentyl moiety;
    —(C3-6)cycloalkylene-R6, optionally substituted with (C1-4)alkyl or with (C1-4)alkyl substituted with one or more fluor atoms, and wherein one carbon atom in the (C3-6)cycloalkylene can optionally be replaced by oxygen;
    —(C1-3)alkylene-(C3-6)cycloalkylene-R6, whereby said (C3-6)cycloalkylene is optionally substituted with (C1-4)alkyl or with (C1-4) alkyl substituted with one or more fluor atoms;
    —(C3-6)cycloalkylene-(C1-3)alkylene-R6, whereby said (C3-6)cycloalkylene is optionally substituted with (C1-4)alkyl or with (C1-4) alkyl substituted with one or more fluor atoms; and
    —C(O)—(C1-4)alkylene-R6; and R4 is hydrogen; or
  (2) Z is NR5 and attached to ring A at atom 1, 2, 3 or 4, and NR5 and R1 together form a group selected from —(C3-8)-heterocycloalkylene-R6, optionally substituted with (C1-4)alkyl or with (C1-4)alkyl substituted with one or more fluor atoms and —(C3-8)heterocycloalkylene-(C1-3)-alkylene-R6, optionally substituted with (C1-4)alkyl or with (C1-4)alkyl substituted with one or more fluor atoms; and
  R4 is hydrogen; or
  (3) Z is NR5 and is attached to ring A at atom 2, and NR5 and R4 together form a group selected from pyrrolidine, pyrazolidine, imidazolidine, oxazolidine, isoxazolidine, thiazolidine, isothiazolidine, piperidine, piperazine, 1,2-diazinane, 1,3-diazinane, morpholine, 1,3-oxazinane, 1,2-oxazinane, thiomorpholine, 1,3-thiazinane and 1,2-thiazinane, and
  R1 is as defined above;

R2 is hydrogen or one or more substituents independently selected from the group consisting of a halogen atom, (C1-4)alkyl optionally substituted with one or more halogen atoms, and (C1-4)alkoxy optionally substituted with one or more halogen atoms;

R6 is selected from the group consisting of —OH, —COOH, —OPO$_3$H$_2$, —CO—O—(C1-4)alkyl, —CO—NH—OH, —CO—NH—O—(C1-4)alkyl, —CO—N(CH$_3$)—O—(C1-4)alkyl, -isoxazol-3-one, 3-isoxazolol-dihydro-2-furanone and -tetrazol-5-yl;

L is a group —W—(CH$_2$)p-T- wherein:
  W is attached to ring B at atom 5, 6, 7 or 8 and
  W is selected from the group consisting of —O—, —CO—, —S—, —SO—, —SO$_2$—, —NH—, —CH═CH—, —C(CF$_3$)═CH—, CH═C (CF$_3$)—, —C≡C—, —CH$_2$—O—, —O—CO—, —CO—O—, —CO—NH—, —NH—CO— and —O—CH$_2$-phenyl-, or W is —(CH$_2$)n- wherein n is 1 or 2 and one or both C atoms of (CH$_2$)n are optionally substituted with one or two fluoro atoms, or W is selected from the group consisting of phenyl, pyridyl, thienyl, thiazolyl and (C3-7)cycloalkylene, each optionally substituted with one or more substituents independently selected from the group consisting of:

a halogen atom, hydroxy, cyano, (C1-4)alkyl optionally substituted with one or more halogen atoms, (C1-4)alkoxy optionally substituted with one or more halogen atoms.

(C3-6)cycloalkyl optionally substituted with one or more halogen atoms and phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms;

p is an integer from 0 to 5 and one or more C atoms of (CH$_2$)p are optionally substituted with one or two methyl groups, ethyl groups or fluoro atoms;

T is absent or attached to R3 and selected from the group consisting of —O—, —S—, —SO—, —SO$_2$—, —NH—, —CO—, —C═C—, —C≡C—, cyclopropylene, —(CH$_2$)m- and —O—(CH$_2$)m- wherein m is an integer from 1 to 5 and one or more C atoms of (CH$_2$)m are optionally substituted with one or two fluoro atoms;

R3 is selected from the group consisting of:

(C3-8)alkyl, (C3-8)alkenyl or (C3-8)alkynyl wherein one or more carbon atoms in the alkyl, alkenyl or alkynyl group are optionally substituted with one or more halogen atoms;

(C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms, phenyl, biphenyl, naphthyl, pyridyl, thienyl or thiazolyl optionally substituted with one or more substituents independently selected from the group consisting of:

a halogen atom, cyano, (C1-4)alkyl optionally substituted with one or more fluoro atoms, (C1-4)alkoxy optionally substituted with one or more fluoro atoms, —S—(C1-4)-alkyl, —SF$_5$, and (C3-6)cycloalkyl optionally substituted with phenyl whereby said phenyl is optionally substituted with a substituent selected from the group consisting of (C1-4)alkyl and a halogen atom.

Also provided is a compound of formula (I):

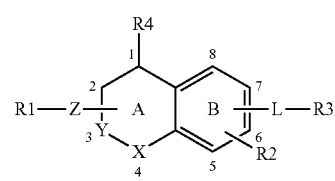

or a pharmaceutically acceptable salt, solvate, tautomer, stereoisomer or N-oxide thereof, wherein X and Y are independently selected from the group consisting of O, CH$_2$ and CH—Z—R1, with the proviso that at most one of X and Y is O and at most one of X and Y is CH—Z—R1;

Z is attached to ring A at atom 1, 2, 3 or 4 and selected from the group consisting of —NR5- and —NR5-CH$_2$— whereby NR5 is attached to R1 and CH$_2$ is attached to ring A;

R5 is selected from the group consisting of H, (C1-4)alkyl, (C1-4)alkyl substituted with one or more fluor atoms and benzyl optionally substituted with one or more substituents selected from the group consisting of a halogen atom, (C1-4)alkyl optionally substituted with one or more halogen atoms, and (C1-4)alkoxy optionally substituted with one or more halogen atoms, R1 is selected from the group consisting of —(C1-6)alkylene-R6 wherein one or more carbon atoms in the alkylene group, each independently, are optionally substituted with one or more halogen atoms, with (CH$_2$)$_2$ to form a cyclopropyl moiety or with (CH$_2$)$_3$ to form a cyclobutyl moiety;

—(C3-6)cycloalkylene-R6, optionally substituted with (C1-4)alkyl or with (C1-4)alkyl substituted with one or more fluor atoms, and wherein one carbon atom in the (C3-6)cycloalkylene can optionally be replaced by oxygen;

—(C1-3)alkylene-(C3-6)cycloalkylene-R6, whereby said (C3-6)cycloalkylene is optionally substituted with (C1-4)alkyl or with (C1-4)alkyl substituted with one or more fluor atoms;

—(C3-6)cycloalkylene-(C1-3)alkylene-R6, whereby said (C3-6)cycloalkylene is optionally substituted with (C1-4)alkyl or with (C1-4)alkyl substituted with one or more fluor atoms; and —C(O)—(C1-4)alkylene-R6, or Z is NR5, and NR5 and R1 together form a group selected from —(C3-8)heterocycloalkylene-R6, optionally substituted with (C1-4)alkyl or with (C1-4)alkyl substituted with one or more fluor atoms and —(C3-8)heterocycloalkylene-(C1-3)alkylene-R6, optionally substituted with (C1-4)alkyl or with (C1-4)alkyl substituted with one or more fluor atoms;

R6 is selected from the group consisting of —OH, —COOH, —OPO$_3$H$_2$, —CO—O—(C1-4)alkyl, —CO—NH—O—(C1-4)alkyl, —CO—N(CH$_3$)—O—(C1-4)alkyl, -isoxazol-3-one, -dihydro-2-furanone and -tetrazol-5-ylR4 is hydrogen, or Z is NR5 and is attached to ring A at atom 2, and NR5 and R4 together form a group selected from pyrrolidine, pyrazolidine, imidazolidine, oxazolidine, isoxazolidine, thiazolidine, isothiazolidine, piperidine, piperazine, 1,2-diazinane, 1,3-diazinane, morpholine, 1,3-oxazinane, 1,2-oxazinane, thiomorpholine, 1,3-thiazinane and 1,2-thiazinane;

R2 is hydrogen or a substituent selected from the group consisting of a halogen atom, (C1-4)alkyl optionally substituted with one or more halogen atoms, and (C1-4) alkoxy optionally substituted with one or more halogen atoms;

L is a group —W—(CH$_2$)p-T- wherein:
  W is attached to ring B at atom 5, 6, 7 or 8 and
    W is selected from the group consisting of —O—, —CO—, —S—, —SO—, —SO$_2$—, —NH—, —CH=CH—, —C(CF$_3$)=CH—, CH=C(CF$_3$)—, —C≡C—, —CH$_2$—O—, —O—CO—, —CO—O—, —CO—NH—, —NH—CO— and, or
    W is —(CH$_2$)n- wherein n is 1 or 2 and one or both C atoms of (CH$_2$)n are optionally substituted with one or two fluoro atoms, or
    W is selected from the group consisting of phenyl, pyridyl, thienyl, thiazolyl and (C3-7)cycloalkylene, each optionally substituted with one or more substituents independently selected from the group consisting of:
      a halogen atom,
      hydroxy.
      cyano,
      (C1-4)alkyl optionally substituted with one or more halogen atoms,
      (C1-4)alkoxy optionally substituted with one or more halogen atoms,
      (C3-6)cycloalkyl optionally substituted with one or more halogen atoms and
      phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms;
  p is an integer from 0 to 5 and one or more C atoms of (CH$_2$)p are optionally substituted with one or two fluoro atoms;
  T is absent or attached to R3 and selected from the group consisting of —O—, —S—, —SO—, —SO$_2$—, —NH—, —CO—, —C=C—, —C≡C—, cyclopropylene, —(CH$_2$)m- and —O—(CH$_2$)m- wherein m is an integer from 1 to 5 and one or more C atoms of (CH$_2$)m are optionally substituted with one or two fluoro atoms;

R3 is selected from the group consisting of:
  (C3-8)alkyl, (C3-8)alkenyl or (C3-8)alkynyl wherein one or more carbon atoms in the alkyl, alkenyl or alkynyl group are optionally substituted with one or more halogen atoms;
  (C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms,
  phenyl, biphenyl, naphthyl, pyridyl, thienyl or thiazolyl optionally substituted with one or more substituents independently selected from the group consisting of:
    a halogen atom,
    cyano,
    (C1-4)alkyl optionally substituted with one or more fluoro atoms,
    (C1-4)alkoxy optionally substituted with one or more fluoro atoms,
    —S—(C1-4)-alkyl,
    —SF$_5$, and
    (C3-6)cycloalkyl optionally substituted with phenyl whereby said phenyl is optionally substituted with a substituent selected from the group consisting of (C1-4)alkyl and a halogen atom, and
    phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)alkoxy, or (C1-4)alkoxy substituted with one or more fluoro atoms.

In a further aspect the invention provides a pharmaceutical composition comprising a compound according to the invention or a pharmaceutically acceptable salt, solvate, tautomer, stereoisomer or N-oxide thereof and at least one pharmaceutically acceptable auxiliary.

In a still further aspect the invention provides a method of treatment, alleviation or prevention of a disease or condition in which an S1P receptor is involved or in which modulation of the endogenous S1P signaling system via an S1P receptor is involved, preferably S1P5, comprising administering to a patient in need thereof a compound according to the invention or a pharmaceutically acceptable salt, solvate, tautomer, stereoisomer or N-oxide thereof.

In a still further aspect the invention provides a use of a compound according to the invention or a pharmaceutically acceptable salt, solvate, tautomer, stereoisomer or N-oxide thereof for the manufacture of a medicament for the treatment, alleviation or prevention of a disease or condition in which an S1P receptor is involved or in which modulation of the endogenous S1P signaling system via an S1P receptor is involved, preferably S1P5 receptor.

In a still further aspect the invention provides a compound according to the invention or a pharmaceutically acceptable salt, solvate, tautomer, stereoisomer or N-oxide thereof for use in therapy.

In a still further aspect the invention provides a compound according to the invention or a pharmaceutically acceptable salt, solvate, tautomer, stereoisomer or N-oxide thereof for use in the treatment, alleviation or prevention of a disease or condition in which an S1P receptor is involved or in which modulation of the endogenous S1P signaling system via an S1P receptor is involved, preferably S1P5.

DETAILED DESCRIPTION OF THE INVENTION

The compounds of the invention are modulators of the S1P receptor, in particular of the S1P5 receptor. More specifically, the compounds of the invention are S1P5 receptor agonists. The compounds of the invention and their pharmaceutically acceptable salts, solvates, tautomers, stereoisomers and N-oxides are in particular suitable for agonizing S1P5 in a subject suffering from a disorder in which modulation of S1P5 activity and the subsequent ceramide/S1P axis is beneficial. Administration of such compound to a subject is preferably such that S1P5 activity in the subject is altered and treatment is achieved. The compounds of the present invention are particularly suitable to treat, alleviate or prevent diseases and conditions in which an S1P receptor is involved or in which modulation of the endogenous S1P signaling system via an S1P receptor is involved. In particular the compounds of the present invention are suitable to treat, alleviate or prevent a disorder or condition selected from the group consisting of Alzheimer's Disease (AD) and associated dementia's, amyloid β-associated disorders, Mild Cognitive Impairment (MCI), Parkinson's Disease (PD), Lewy Body Dementia (LBD), Progressive Supranuclear Palsy (PSP), Cerebral Palsy (CP), Amyotrophic Lateral Sclerosis (ALS), Frontal Temporal Lobe Dementia (FTLD), multiple sclerosis, Huntington's Disease, neurological symptoms of sphingolipidosis disorders, a lysosomal storage disorder including Tay Sachs Disease, Sandhoff Disease, Fabry's Disease, Krabbe Disease, Gaucher's Disease, Niemann Pick A, B or C, and Batten's Disease, stroke, HIV-associated Dementia (HAD), HIV-associate Neurocognitive Disorder (HAND), HIV-associated neuropathy, schizophrenia, cognitive deficits in Schizophrenia, an attention deficit disorder including Anxiety Attention Deficit Disorder and Attention Deficit Hyperactivity Disorder (ADHD), a bipolar disorder, Obsessive-Compulsive Behavior, pain including neuropathic, back pain and pain-associated with multiple sclerosis, spinal cord injury, Parkinson's Disease, epilepsy, diabetes and cancer, cancer-induced peripheral neuropathy (CIPN), depression, treatment-resistant depression, Creutzfeld-Jakob Disease and other Prion-related Disorders, Down's Syndrome, autism, age-related cognitive decline or memory impairment, cognitive deficits associated with diabetes, dementia, dementia associated with Down's Syndrome, cognitive deficits in psychiatric disorders, dementia associated with Lewy Body pathology, diminished CNS function associated with traumatic brain injury, Pick's Disease, spinal cord injury, a demyelinating disorder, a disorder of basal ganglia and AIDS-associated dementia. Given the neuro-inflammatory actions of S1P receptors, and S1P5 in specific, as well as the peripheral localization of S1P5 in skin tissue and a role in endothelial function and NK cells, the compounds of the invention are further suitable to treat, alleviate or prevent a disease with a neuro-inflammatory component, in particular a disease or condition selected from the group consisting of psoriasis type 1 and type 2, atopic dermatitis, dermatitis scleroderma, insulin-dependent diabetes mellitus, ulcerative colitis, atherosclerosis, sepsis syndrome, septic shock, Dengue hemorrhagic fever, Dengue, atopic allergy, HIV/AIDS, barrier-integrity associated lung diseases, leukemia, contact dermatitis, encephalomyelitis, Epstein Barr virus infection and other virus infections requiring cell-cell fusion.

In formula (I), X and Y are independently selected from the group consisting of O, CH$_2$ and CH—Z—R1, with the proviso that at most one of X and Y is O and at most one of X and Y is CH—Z—R1. In a preferred embodiment, one of X and Y is O.

Compounds of formula (I) contain one group —Z—R1.

Formula (I) is preferably selected from the group consisting of

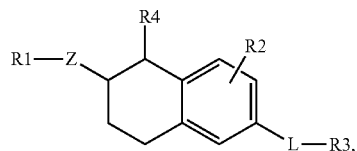
formula (Ia)

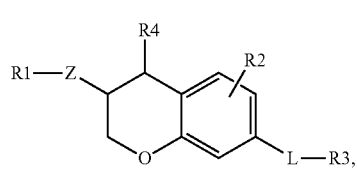
formula (Ib)

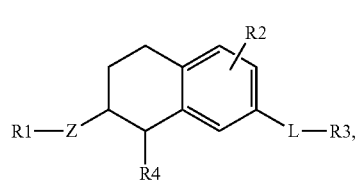
formula (Ic)

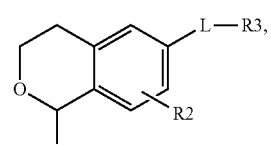
formula (Id)

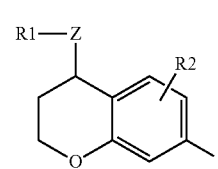
formula (Ie)

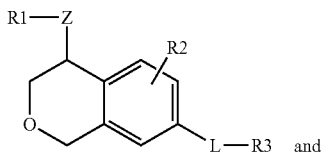
formula (If)

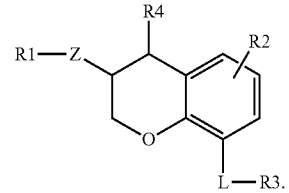
formula (Ig)

More preferably, formula (I) is selected from the group consisting of formula's (Ia), (Ib) and (Ic), most preferably from formula's (Ia) and (Ib).

In compounds of formula (Ib), (Ic), (Id), (Ie), (If) and (Ig) R4 is preferably hydrogen.

R2 is preferably attached to atom 6 or 7. In compounds of formula (Ia), (Ic), (Id), (If) and (Ig) R2 is preferably hydrogen. Formula (Ib) is preferably

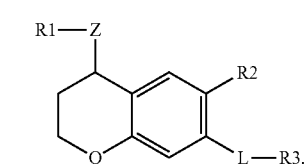
(formula (Ib'))

Formula (Ie) is preferably

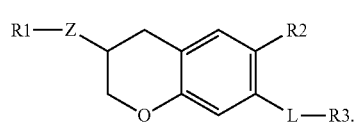
(formula (Ie'))

In formula (I) or any of (Ia)-(Ig), Z is in a first embodiment attached to ring A at atom 1, 2, 3 or 4 and selected from the group consisting of —NR5-, —NR5-CH$_2$— and —O—, whereby R4 is hydrogen. If Z is —NR5-CH$_2$—, NR5 is attached to R1 and CH$_2$ is attached to ring A.

Z is preferably attached to ring A at atom 1, 2 or 3. In a preferred embodiment, Z is attached ring A at atom 1 or 2. In another preferred embodiment Z is attached to ring A at atom 2 or 3.

Further, if X is O, Z is preferably attached to ring A at atom 1 or 2, if Y is O, Z is preferably attached to ring A at atom 1 or 4. If none of X and Y are O, Z is preferably attached to ring A at atom 2 or 3.

Z is preferably —NR5- or —O—.

R5 is selected from the group consisting of H, (C1-4)alkyl, (C1-4)alkyl substituted with one or more fluor atoms and benzyl optionally substituted with one or more substituents selected from the group consisting of a halogen atom, (C1-4)alkyl optionally substituted with one or more halogen atoms, and (C1-4)alkoxy optionally substituted with one or more halogen atoms.

Preferably, R5 is selected from the group consisting of hydrogen, C(1-4)alkyl, and benzyl optionally substituted with one or more, preferably one or two, substituents selected from the group consisting of a halogen atom, (C1-4)alkyl. More preferably R5 is selected from the group consisting of hydrogen, methyl, ethyl and benzyl substituted with two substituents selected from the group consisting of a halogen atom, preferably chloride, methyl and ethyl.

R1 is preferably selected from the group consisting of
—(C1-6)alkylene-R6 wherein one carbon atom in the alkylene group is optionally substituted with (CH$_2$)$_2$ to form a cyclopropyl moiety, with (CH$_2$)$_3$ to form a cyclobutyl moiety, or with (CH$_2$)$_4$ to form a cyclopentyl moiety;
—(C3-6)cycloalkylene-R6, optionally substituted with (C1-4)alkyl or with (C1-4)alkyl substituted with one or more fluor atoms;
—(C1-3)alkylene-(C3-6)cycloalkylene-R6, whereby said (C3-6)cycloalkylene is optionally substituted with (C1-4)alkyl or with (C1-4)alkyl substituted with one or more fluor atoms; and
—(C3-6)cycloalkylene-(C1-3)alkylene-R6, whereby said (C3-6)cycloalkylene is optionally substituted with (C1-4)alkyl or with (C1-4)alkyl substituted with one or more fluor atoms.

More preferably, R1 is selected from the group consisting of:
—(C1-6)alkylene-R6 wherein one carbon atom in the alkylene group is optionally substituted with (CH$_2$)$_2$ to form a cyclopropyl moiety, with (CH$_2$)$_3$ to form a cyclobutyl moiety or with (CH$_2$)$_4$ to form a cyclopentyl moiety,
—(C3-6)cycloalkylene-R6, and
—(C3-6)cycloalkylene-(C1-3)alkylene-R6.

More preferably, R1 is selected from the group consisting of:
—(C1-3)alkylene-R6 wherein one carbon atom in the alkylene group is optionally substituted with (CH$_2$)$_2$ to form a cyclopropyl moiety, with (CH$_2$)$_3$ to form a cyclobutyl moiety or with (CH$_2$)$_4$ to form a cyclopentyl moiety, and
—(C4-6)cycloalkylene-R6.

R6 is selected from the group consisting of —OH, —COOH, —OPO3H2, —CO—O—(C1-4)alkyl, —CO—NH—OH, —CO—NH—O—(C1-4)alkyl, —CO—NCH3-O—(C1-4)alkyl, -isoxazol-3-one, 3-isoxazolol, -dihydro-2-furanone and -tetrazol-5-yl.

Preferably, R6 is selected from the group consisting of —COOH, —CO—O—(C1-4)alkyl, —CO—NH—OH, —CO—NH—O—(C1-4)alkyl, —CO—NCH$_3$—O—(C1-4)alkyl, 3-isoxazolol and -dihydro-2-furanone. Most preferably R6 is —COOH or —CO—O—(C1-4)alkyl, in particular —COOH.

In a preferred embodiment, R1 is selected from the group consisting of —CH$_2$—COOH, —(CH$_2$)$_2$—COOH, —(CH$_2$)$_3$—COOH, —(CH$_2$)$_4$—COOH, —CH(CH$_3$)—COOH, —CH$_2$—CH(CH$_3$)—COOH, —(CH$_2$)$_2$—CH(CH$_3$)—COOH, —(CH$_2$)$_3$—CH(CH$_3$)—COOH, —CH$_2$—CH(CH$_3$)—CH$_2$—COOH, —CH(CH$_3$)—(CH$_2$)$_2$—COOH, —CH(CH$_3$)—(CH$_2$)$_3$—COOH, —C(CH$_3$)$_2$—COOH, —CH$_2$—C(CH$_3$)$_2$—COOH, —(CH$_2$)$_2$—C(CH$_3$)$_2$—COOH, —(CH$_2$)$_3$—C(CH$_3$)$_2$—COOH, —CH$_2$—C(CH$_3$)$_2$—CH$_2$—COOH, —C(CH$_3$)$_2$—(CH$_2$)$_2$—COOH, —C(CH$_3$)$_2$—(CH$_2$)$_3$ COOH, —CH(CH[CH$_3$]$_2$)—COOH, C(CH)—COOH, —CH$_2$—CH(CH[CH$_3$]$_2$)—COOH, —(CH$_2$)$_2$—CH(CH[CH$_3$]$_2$)—COOH, —CH$_2$—CO—N(CH$_3$)—O—CH$_3$, —(CH$_2$)$_2$—CO—N(CH$_3$)—O—CH$_3$, —(CH$_2$)$_3$—CO—N(CH$_3$)—O—CH$_3$, —CH$_2$—CO—NH—O—CH$_3$, —(CH$_2$)$_2$—CH$_2$—CO—NH—O—CH$_3$, —(CH$_2$)$_3$—CH$_2$—CO—NH—O—CH$_3$, —CH$_2$—CH(CH$_3$)—CO—O—CH$_3$, —(CH$_2$)$_2$—CH(CH$_3$)—CO—O—CH$_3$, —CH$_2$—CO—O—C(CH$_3$)$_3$, —(CH$_2$)$_2$—CO—O—C(CH$_3$)$_3$, —(CH$_2$)$_3$—CO—O—C(CH$_3$)$_3$,

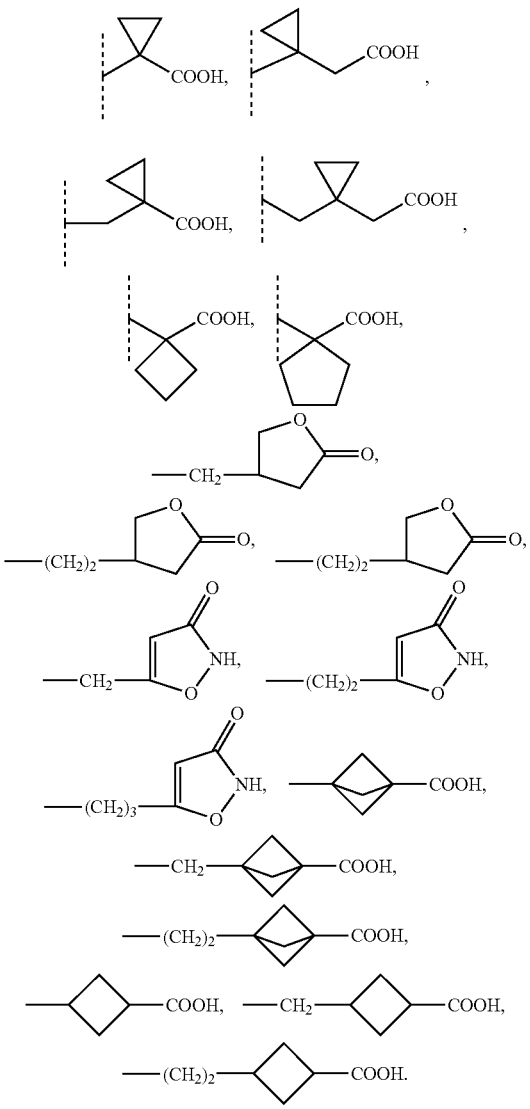

In a further preferred embodiment, R1 is selected from the group consisting of —CH₂—COOH, —(CH₂)₂—COOH, —CH(CH₃)—COOH, —CH₂—CO—N(CH₃)—O—CH₃, —CH₂—CO—NH—O—CH₃, —CH₂—CH(CH₃)—CO—O—CH₃, —CH₂—CO—O—C(CH₃)₃, —CH(CH[CH₃]₂)—COOH,

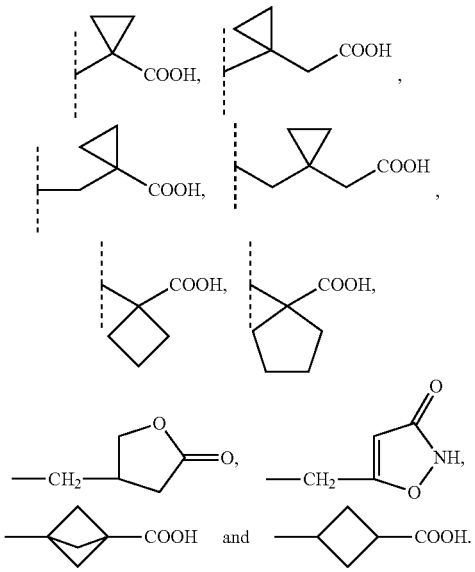

In a further embodiment, Z is NR5 and attached to ring A at atom 1, 2, 3 or 4, and NR5 and R1 together form a group selected from —(C3-8)heterocycloalkylene-R6, optionally substituted with (C1-4)alkyl or with (C1-4)alkyl substituted with one or more fluor atoms and —(C3-8)heterocycloalkylene-(C1-3)alkylene-R6, optionally substituted with (C1-4) alkyl or with (C1-4)alkyl substituted with one or more fluor atoms, wherein R6 is as defined above, and whereby R4 is hydrogen. Z is preferably attached to ring A at atom 1, 2 or 3. In a preferred embodiment, Z is attached ring A at atom 1 or 2. In another preferred embodiment Z is attached to ring A at atom 2 or 3. Preferably, NR5 and R1 together form a group selected from —(C3-6)heterocycloalkylene-R6, optionally substituted with (C1-4)alkyl, and —(C3-6)heterocycloalkylene-(C1-3)alkylene-R6, optionally substituted with (C1-4)alkyl, more preferably from —(C3-6)heterocycloalkylene-R6, optionally substituted with (C1-3)alkyl, and —(C3-6)heterocycloalkylene-CH₂—R6, optionally substituted with (C1-3)alkyl, wherein R6 is as defined above. Particularly preferred examples are for NR5 are -azetidine-3-R6, -pyrrolidine-3-R6, -piperidine-4-R6, each optionally substituted with (C1-3)alkyl. The optional substituent is preferably attached to the same atom to which R6 is attached. Preferably, herein R6 is selected from the group consisting of —COOH and —CO—N(CH3)-O—(C1-4)alkyl, more preferably from —COOH and —CO—N(CH3)-O—CH₃.

In a further embodiment, Z is NR5, attached to atom 2 and NR5 and R4 together form a group selected from pyrrolidine, pyrazolidine, imidazolidine, oxazolidine, isoxazolidine, thiazolidine, isothiazolidine, piperidine, piperazine, 1,2-diazinane, 1,3-diazinane, morpholine, 1,3-oxazinane, 1,2-oxazinane, thiomorpholine, 1,3-thiazinane and 1,2-thiazinane, and R1 is as defined above. Preferably in this embodiment, NR5 and R4 together form a group selected from pyrrolidine, imidazolidine, oxazolidine, thiazolidine, piperidine, piperazine, 1,3-diazinane, morpholine, 1,3-oxazinane, thiomorpholine and 1,3-thiazinane, more preferably selected from the group consisting of morpholine iperidine, oxazolidine and pyrrolidine, most preferably morpholine.

Most preferably R4 is hydrogen or, if Z is NR5 and is attached to ring A at atom 2, NR5 and R4 together form a morpholine, piperidine, oxazolidine or pyrrolidine, most preferably a morpholine. In a particularly preferred embodiment, R4 is hydrogen.

R2 is hydrogen or a substituent selected from the group consisting of a halogen atom, (C1-4)alkyl optionally substituted with one or more halogen atoms, and (C1-4)alkoxy optionally substituted with one or more halogen atoms. R2 is further preferably attached to ring B at atom 6 or 7, more preferably to atom 7. If R2 is attached to atom 6, -L-R3 is attached to atom 5, 7 or 8 and if R2 is attached to atom 7, -L-R3 is attached to atom 5, 6 or 8.

In a particularly preferred embodiment, R2 is hydrogen or a substituent selected from the group consisting of methyl, ethyl, methoxy and a halogen atom, more preferably selected from the group consisting of methyl, a bromo atom and a fluoro atom and attached to atom 6 or 7, preferably to atom 7.

L is a group —W—(CH₂)p-T- and preferably attached to ring B at atom 5, 6 or 7, more preferably at atom 5 or 6.

Preferably W is selected from the group consisting of —O—, —CO—, —S—, —SO—, —SO₂—, —NH—, —CH=CH—, —C(CF₃)=CH—, CH=C(CF₃)—, —C≡C—, —CH₂—O—, —O—CO—, —CO—O—, —CO—NH—, —NH—CO—, cyclopropylene, cyclobutylene, phenyl, —O—CH₂-phenyl- and —(CH₂)n-, wherein n is 1 or 2 and one or both C atoms of (CH₂)n are optionally substituted with one or two fluoro atoms; p is an integer from 0 to 4; and T is absent or selected from the group consisting of —(CH₂)m- and —O—(CH₂)m- wherein m is an integer from 1 to 5 and one or more C atoms of (CH₂)m are optionally substituted with one or two fluoro atoms.

Preferably n is 1 or 2, more preferably 2. Preferably, p is 0, 1, 2, 3 or 4. It is further preferred that p is 1, 2, 3 or 4 if W is O, if W is not O, p is preferably 0. Preferably m is an integer from 1 to 4, more preferably m is an integer from 1 to 3, more preferably m is 1 or 2, most preferably m is 1.

Preferably L is selected from the group consisting of —O—(CH₂)p-, —CH=CH—, —C≡C—, —O—SO₂—, —(CH₂)n-(CH₂)p-, —CF₂—CH₂—, —O—, —CO—, —S—, —SO—, —SO₂—, —NH—, -Ph-(CH₂)m-, -Ph-O—(CH₂)m-, —O—CO—, —CO—O—, —CO—NH—, —NH—CO—, —C(CF)=CH—, CH=C(CF)—, cyclopropylene and cyclobutylene, wherein Ph is phenyl, p is an integer from 1 to 5, n is 1 or 2 and m is an integer from 1 to 5 and one or more C atoms of (CH₂)p, (CH₂)n and/or (CH₂)m are optionally substituted with one or two fluoro atoms. Preferably none of the C atoms of (CH₂)p, (CH₂)n and/or (CH₂)m is substituted with a fluoro atom or with fluoro atoms.

More preferably L is attached to ring B at atom 5, 6 or 7, preferably 6 or 7 and selected from the group consisting of —O—(CH₂)p-, —CH=CH—, —C≡C—, —(CH₂)n-, —O—(CH₂)p-O—, —O—CH(CH₃)—, —O—, -Ph-O—(CH₂)m-, and —O—CH₂-Ph-O—CH₂—, wherein Ph is phenyl, m is 1 or 2, p is an integer from 1 to 4 and one or more C atoms of (CH₂)p are optionally substituted with one or two methyl groups, ethyl groups.

In a particularly preferred embodiment, L is selected from the group consisting of —O—CH₂—, —CH=CH—, —C≡C—, —CH₂—CH₂—, —O—CH₂—CH₂—, —O—CH$_2$—CH$_2$—CH$_2$—, —O—CH(CH$_3$)—, —O—(CH$_2$)$_2$—O—, —O—(CH$_2$)$_3$—O, —O—(CH$_2$)$_4$—O, —O—, -Ph-O—CH$_2$— and —O—CH$_2$-Ph-O—CH$_2$—, wherein Ph is phenyl.

In the definition of R3, said phenyl, biphenyl, naphthyl, pyridyl, thienyl or thiazolyl is optionally substituted with 1-3 substituents as defined herein. If R3 is phenyl, biphenyl, naphthyl, pyridyl, thienyl or thiazolyl substituted with one or more, preferably 1-3, substituents independently selected from the group consisting of:
  a halogen atom,
  cyano,
  (C1-4)alkyl optionally substituted with one or more fluoro atoms,
  (C1-4)alkoxy optionally substituted with one or more fluoro atoms,
  —S—(C1-4)-alkyl, and
  (C3-6)cycloalkyl optionally substituted with phenyl whereby said phenyl is optionally substituted with a substituent selected from the group consisting of (C1-4)alkyl and a halogen atom,
said one or more, preferably 1-3, substituents are preferably at one or more, preferably 1-3, of the ortho and meta positions with respect to L.

Further, in the definition of R3, said 8-10 membered bicyclic group preferably is a 8-10 membered fused bicyclic group comprising 0 or 1 heteroatom selected from N, O and S. Preferred examples of such 8-10 membered bicyclic group are naphthyl, quinoline, isoquinoline, benzofuran, indane, tetralin, dihydrobenzofuran, dihydroisobenzofuran, dihydroindole, dihydroisoindole, dihydrobenzopyran, dihydrobenzothiophene, and dihydrobenzo[c]thiophene, more preferably naphthyl, quinoline and isoquinoline.

R3 is preferably selected from the group consisting of:
  unsubstituted (C3-6)cycloalkyl or (C3-6)cycloalkyl substituted with one or more substituents selected from the group consisting of a halogen atom and (C1-4)alkyl,
  8-10 membered bicyclic group, comprising 0 or 1 heteroatom selected from N, O and S;
  phenyl, optionally substituted with one or more, preferably one to three, substituents independently selected from the group consisting of:
    a halogen atom, preferably Cl or Br,
    (C1-4)alkyl, preferably (C1-2)alkyl, optionally substituted with one or more fluoro atoms, preferably 2 or 3 fluoro atoms,
    (C1-4)alkoxy, preferably (C1-2)alkoxy, optionally substituted with one or more fluoro atoms, preferably 2 or 3 fluoro atoms,
    —S—(C1-4)-alkyl, preferably —S—CH$_3$—, and
    (C3-6)cycloalkyl, preferably cyclopropyl,
      preferably wherein said one or more, preferably 1-3, substituents are at one or more, preferably 1-3, of the ortho and meta positions with respect to L.

More preferably, R3 is selected from the group consisting of (C3-6)cycloalkyl, phenyl optionally substituted with one to three substituents independently selected from the group consisting of a halogen atom, (C1-4)alkyl optionally substituted with one or more fluoro atoms, (C1-4)alkoxy optionally substituted with one or more fluoro atoms, —S—(C1-4)-alkyl, and (C3-6)cycloalkyl. Said (C3-6)cycloalkyl is preferably selected from the group consisting of cyclopropyl, cyclobutyl and cyclohexyl. If R3 is phenyl, said optional one to three substituents are preferably at one to three of the ortho and meta positions with respect to L.

Particularly preferred compounds of the invention are compounds of formula (I) wherein X and Y are independently selected from the group consisting of O, CH$_2$ and CH—Z—R1, with the proviso that at most one of X and Y is O and at most one of X and Y is CH—Z—R1;

Z is attached to ring A at atom 1, 2, 3 or 4 and selected from the group consisting of —NR5-, —O— and —NR5-CH$_2$— whereby NR5 is attached to R1 and CH$_2$ is attached to ring A, preferably Z is —NR5- or —O—;

R5 is selected from the group consisting of hydrogen, (C1-4)alkyl, and (C1-4)alkyl substituted with one or more fluor atoms;

R1 is selected from the group consisting of
  —(C1-3)alkylene-R6 wherein one or more carbon atoms in the alkylene group, each independently, are optionally substituted with one or more halogen atoms, with (CH$_2$)$_2$ to form a cyclopropyl moiety, with (CH$_2$)$_3$ to form a cyclobutyl moiety or with (CH$_2$)$_4$ to form a cyclopentyl moiety;
  —(C3-6)cycloalkylene-R6, optionally substituted with (C1-4)alkyl or with (C1-4)alkyl substituted with one or more fluor atoms;
  —(C1-3)alkylene-(C3-6)cycloalkylene-R6, whereby said (C3-6)cycloalkylene is optionally substituted with (C1-4)alkyl or with (C1-4)alkyl substituted with one or more fluor atoms; and
  —(C3-6)cycloalkylene-(C1-3)alkylene-R6, whereby said (C3-6)cycloalkylene is optionally substituted with (C1-4)alkyl or with (C1-4)alkyl substituted with one or more fluor atoms;

R6 is selected from the group consisting of —COOH, —CO—O—(C1-4)alkyl, —CO—NH—OH, —CO—NH—O—(C1-4)alkyl, —CO—NCH$_3$—O—(C1-4)alkyl, 3-isoxazolol and -dihydro-2-furanone, preferably from —COOH and —CO—O—(C1-4)alkyl;

R4 is hydrogen;

R2 is hydrogen or a substituent selected from the group consisting of a halogen atom, (C1-4)alkyl optionally substituted with one or more halogen atoms, and (C1-4)alkoxy optionally substituted with one or more halogen atoms;

L is a group —W—(CH$_2$)p-T- and attached to ring B at atom 5, 6 or 7, preferably at atom 5 or 6 wherein:
  W is attached to ring B at atom 5, 6, 7 or 8 and
  W is selected from the group consisting of —O—, —CO—, —S—, —SO—, —SO$_2$—, —NH—, —CH=CH—, —C(CF$_3$)=CH—, CH=C(CF$_3$)—, —C≡C—, —CH$_2$—O—, —O—CO—, —CO—O—, —CO—NH—, —NH—CO— and —O—CH$_2$-phenyl-, or
  W is —(CH$_2$)n- wherein n is 1 or 2 and one or both C atoms of (CH$_2$)n are optionally substituted with one or two fluoro atoms, or
  W is selected from the group consisting of phenyl, pyridyl, thienyl, thiazolyl and (C3-7)cycloalkylene, each optionally substituted with one or more substituents independently selected from the group consisting of:
    a halogen atom,
    hydroxy,
    cyano,
    (C1-4)alkyl optionally substituted with one or more halogen atoms,
    (C1-4)alkoxy optionally substituted with one or more halogen atoms,
    (C3-6)cycloalkyl optionally substituted with one or more halogen atoms and phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms;
p is an integer from 0 to 5 and one or more C atoms of (CH$_2$)p are optionally substituted with one or two fluoro atoms;
T is absent or attached to R3 and selected from the group consisting of —O—, —(CH$_2$)m- and —O—(CH$_2$)m- wherein m is an integer from 1 to 5 and one or more C atoms of (CH$_2$)m are optionally substituted with one or two fluoro atoms;
R3 is selected from the group consisting of:
  (C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms,
  phenyl, biphenyl, naphthyl, pyridyl, thienyl or thiazolyl optionally substituted with one or more substituents independently selected from the group consisting of:
   a halogen atom,
   cyano,
   (C1-4)alkyl optionally substituted with one or more fluoro atoms,
   (C1-4)alkoxy optionally substituted with one or more fluoro atoms,
   —S—(C1-4)-alkyl, and
   (C3-6)cycloalkyl,
  preferably wherein said one or more substituents are at one or more of the ortho and meta positions with respect to L, and
  phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)alkoxy, or (C1-4)alkoxy substituted with one or more fluoro atoms.

Further, particularly preferred compounds of the invention are compounds of formula (I) wherein:
X and Y are independently selected from the group consisting of O, CH2 and CH—Z—R1, with the proviso that at most one of X and Y is O and at most one of X and Y is CH—Z—R1;
Z is NR5 and attached to ring A at atom 1, 2, 3 or 4, and NR5 and R1 together form a group selected from —(C3-6)heterocycloalkylene-R6, optionally substituted with (C1-4)alkyl, and —(C3-6)heterocycloalkylene-(C1-3)alkylene-R6, optionally substituted with (C1-4)alkyl;
R6 is selected from the group consisting of —COOH, —CO—O—(C1-4)alkyl, —CO—NH—OH, —CO—NH—O—(C1-4)alkyl, —CO—NCH$_3$—O—(C1-4)alkyl, 3-isoxazolol and -dihydro-2-furanone, preferably from —COOH and —CO—O—(C1-4)alkyl;
R4 is hydrogen;
R2 is hydrogen or a substituent selected from the group consisting of a halogen atom, (C1-4)alkyl optionally substituted with one or more halogen atoms, and (C1-4)alkoxy optionally substituted with one or more halogen atoms;
L is a group —W—(CH$_2$)p-T- and attached to ring B at atom 5, 6 or 7, preferably at atom 5 or 6 wherein:
 W is attached to ring B at atom 5, 6, 7 or 8 and
  W is selected from the group consisting of —O—, —CO—, —S—, —SO—, —SO$_2$—, —NH—, —CH=CH—, —C(CF$_3$)=CH—, CH=C(CF$_3$)—, —C≡C—, —CH$_2$—O—, —O—CO—, —CO—O—, —CO—NH—, —NH—CO— and —O—CH$_2$-phenyl-, or
  W is —(CH$_2$)n- wherein n is 1 or 2 and one or both C atoms of (CH$_2$)n are optionally substituted with one or two fluoro atoms, or
  W is selected from the group consisting of phenyl, pyridyl, thienyl, thiazolyl and (C3-7)cycloalkylene, each optionally substituted with one or more substituents independently selected from the group consisting of:
   a halogen atom,
   hydroxy,
   cyano,
   (C1-4)alkyl optionally substituted with one or more halogen atoms,
   (C1-4)alkoxy optionally substituted with one or more halogen atoms,
   (C3-6)cycloalkyl optionally substituted with one or more halogen atoms and
   phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms;
 p is an integer from 0 to 5 and one or more C atoms of (CH$_2$)p are optionally substituted with one or two fluoro atoms;
 T is absent or attached to R3 and selected from the group consisting of —O—, —(CH$_2$)m- and —O—(CH$_2$)m- wherein m is an integer from 1 to 5 and one or more C atoms of (CH$_2$)m are optionally substituted with one or two fluoro atoms;
R3 is selected from the group consisting of:
  (C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms,
  phenyl, biphenyl, naphthyl, pyridyl, thienyl or thiazolyl optionally substituted with one or more substituents independently selected from the group consisting of:
   a halogen atom,
   cyano,
   (C1-4)alkyl optionally substituted with one or more fluoro atoms,
   (C1-4)alkoxy optionally substituted with one or more fluoro atoms,
   —S—(C1-4)-alkyl, and
   (C3-6)cycloalkyl,
  preferably wherein said one or more substituents are at one or more of the ortho and meta positions with respect to L, and
  phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)
alkoxy, or (C1-4)alkoxy substituted with one or more
fluoro atoms.

Further particularly preferred compounds of the invention
are compounds of formula (I) wherein
- X and Y are independently selected from the group consisting of O, $CH_2$ and CH—Z—R1, with the proviso that at most one of X and Y is O and at most one of X and Y is CH—Z—R, preferably whereby at least one of X and Y is O:
- Z is attached to ring A at atom 1, 2, 3 or 4 and selected from the group consisting of —NR5-, —O— and —NR5-$CH_2$—, whereby NR5 is attached to R1 and $CH_2$ is attached to ring A, preferably Z is —NR5- or —O—;
- R5 is selected from the group consisting of hydrogen, and (C1-4)alkyl;
- R1 is selected from the group consisting of
  - —(C1-6)alkylene-R6, preferably —(C1-3)alkylene-R6 wherein one carbon atom in the alkylene group is optionally substituted with $(CH_2)_2$ to form a cyclopropyl moiety, with $(CH_2)_3$ to form a cyclobutyl moiety or with $(CH_2)_4$ to form a cyclopentyl moiety;
  - —(C3-6)cycloalkylene-R6,
  - —(C1-3)alkylene-(C3-6)cycloalkylene-R6; and
  - —(C3-6)cycloalkylene-(C1-3)alkylene-R6; R6 is selected from the group consisting of —OH, —COOH, —$OPO_3H_2$, —CO—O—(C1-4)alkyl, —CO—NH—O—(C1-4)alkyl, —CO—N($CH_3$)—O—(C1-4)alkyl, -isoxazol-3-one, 3-isoxazolol, -dihydro-2-furanone and -tetrazol-5-yl, preferably from —COOH and —CO—O—(C1-4)alkyl;
- R4 is hydrogen;
- 2 is hydrogen or a substituent selected from the group consisting of a halogen atom and (C1-4)alkyl;
- L is attached to ring B at atom 5, 6 or 7, preferably 6 or 7 and selected from the group consisting of —O—$(CH_2)p$-, —CH=CH—, —C≡C—, —$(CH_2)n$-, —O—$(CH_2)p$-O—, —O—CH($CH_3$)—, —O—, -Ph-O—$(CH_2)m$-, and —O—$CH_2$-Ph-O—$CH_2$—, wherein Ph is phenyl, m is 1 or 2, p is an integer from 1 to 4 and one or more C atoms of $(CH_2)p$ are optionally substituted with one or two methyl groups, ethyl groups;
- R3 is selected from the group consisting of:
  - (C3-6)cycloalkyl or an 8-10 membered bicyclic group, and
  - phenyl, optionally substituted with one or more substituents independently selected from the group consisting of:
    - a halogen atom,
    - cyano,
    - (C1-4)alkyl optionally substituted with one or more fluoro atoms,
    - (C1-4)alkoxy optionally substituted with one or more fluoro atoms,
    - —S—(C1-4)-alkyl, and
    - (C3-6)cycloalkyl, preferably cyclopropyl,
  - preferably wherein said one or more substituents are at one or more of the ortho and meta positions with respect to L.

Further particularly preferred compounds of the invention are compounds of formula (I) wherein
- X and Y are independently selected from the group consisting of O, $CH_2$ and CH—Z—R1, with the proviso that at most one of X and Y is O and at most one of X and Y is CH—Z—R, preferably whereby at least one of X and Y is O;
- Z is NR5 and attached to ring A at atom 1, 2, 3 or 4, and NR5 and R1 together form a group selected from —(C3-6)heterocycloalkylene-R6, optionally substituted with (C1-4)alkyl, and —(C3-6)heterocycloalkylene-(C1-3)alkylene-R6, optionally substituted with (C1-4)alkyl;
- R6 is selected from the group consisting of —OH, —COOH, —$OPO_3H_2$, —CO—O—(C1-4)alkyl, —CO—NH—O—(C1-4)alkyl, —CO—N($CH_3$)—O—(C1-4)alkyl. -isoxazol-3-one, 3-isoxazolol, -dihydro-2-furanone and -tetrazol-5-yl, preferably from —COOH and —CO—O—(C1-4)alkyl;
- R4 is hydrogen;
- R2 is hydrogen or a substituent selected from the group consisting of a halogen atom and (C1-4)alkyl;
- L is attached to ring B at atom 5, 6 or 7, preferably 6 or 7 and selected from the group consisting of —O—$(CH_2)p$-, —CH=CH—, —C≡C—, —$(CH_2)n$-, —O—$(CH_2)p$-O—, —O—CH($CH_3$)—, —O—, -Ph-O—$(CH_2)m$-, and —O—$CH_2$-Ph-O—$CH_2$—, wherein Ph is phenyl, m is 1 or 2, p is an integer from 1 to 4 and one or more C atoms of $(CH_2)p$ are optionally substituted with one or two methyl groups, ethyl groups;
- R3 is selected from the group consisting of:
  - (C3-6)cycloalkyl or an 8-10 membered bicyclic group, and
  - phenyl, optionally substituted with one or more substituents independently selected from the group consisting of:
    - a halogen atom,
    - cyano,
    - (C1-4)alkyl optionally substituted with one or more fluoro atoms,
    - (C1-4)alkoxy optionally substituted with one or more fluoro atoms,
    - —S—(C1-4)-alkyl, and
    - (C3-6)cycloalkyl, preferably cyclopropyl,
  - preferably wherein said one or more substituents are at one or more of the ortho and meta positions with respect to L.

Further particularly preferred compounds of the invention are compounds of formula (I) wherein
- X and Y are independently selected from the group consisting of O, $CH_2$ and CH—Z—R1, with the proviso that at most one of X and Y is O and at most one of X and Y is CH—Z—R1;
- Z is —NR5- or —O— and attached to ring A at atom 1, 2, 3 or 4,
- R5 is selected from the group consisting of H, (C1-4)alkyl, (C1-4)alkyl substituted with one or more fluor atoms and benzyl optionally substituted with one or more substituents selected from the group consisting of a halogen atom and (C1-4)alkyl, and
- R1 is selected from the group consisting of
  - —(C1-6)alkylene-R6 wherein one carbon atom in the alkylene group is optionally substituted with $(CH_2)_2$ to form a cyclopropyl moiety or with $(CH_2)_3$ to form a cyclobutyl moiety;
  - —(C3-6)cycloalkylene-R6, optionally substituted with (C1-4)alkyl or with (C1-4)alkyl substituted with one or more fluor atoms;
  - —(C1-3)alkylene-(C3-6)cycloalkylene-R6, whereby said (C3-6)cycloalkylene is optionally substituted with (C1-4)alkyl or with (C1-4)alkyl substituted with one or more fluor atoms; and —(C3-6)cycloalkylene-(C1-3)alkylene-R6, whereby said (C3-6)cycloalkylene is optionally substituted with (C1-4)alkyl or with (C1-4)alkyl substituted with one or more fluor atoms, or Z is NR5, and NR5 and R1 together form a group selected from —(C3-8)heterocycloalkylene-R6, optionally substituted with (C1-4)alkyl or with (C1-4)alkyl substituted with one or more fluor atoms and —(C3-8)heterocycloalkylene-(C1-3)alkylene-R6, optionally substituted with (C1-4)alkyl or with (C1-4)alkyl substituted with one or more fluor atoms;

R6 is selected from the group consisting of —OH, —COOH, —OPO$_3$H$_2$, —CO—O—(C1-4)alkyl, —CO—NH—O—(C1-4)alkyl, —CO—N(CH$_3$)—O—(C1-4)alkyl, -isoxazol-3-one, -dihydro-2-furanone and -tetrazol-5-yl;

R4 is absent;

R2 is absent or one or more substituents independently selected from the group consisting of a halogen atom and (C1-4)alkyl;

L is selected from the group consisting of —O—(CH$_2$)p-, —CH=CH—, —C≡C—, —O—SO$_2$—, —(CH$_2$)n-(CH$_2$)p-, —CF$_2$—CH$_2$—, —O—, —CO—, —S—, —SO—, —SO$_2$—, —NH—, -Ph-(CH$_2$)m-, -Ph-O—(CH$_2$)m-, —O—CO—, —CO—O—, —CO—NH—, —NH—CO—, —C(CF$_3$)=CH—, CH=C(CF$_3$)— and cyclopropylene, wherein Ph is phenyl, p is an integer from 1 to 5, n is 1 or 2 and m is an integer from 1 to 5 and one or more C atoms of (CH$_2$)p, (CH$_2$)n and/or (CH$_2$)m are optionally substituted with one or two fluoro atoms;

R3 is selected from the group consisting of:
  (C3-8)alkyl, (C3-8)alkenyl or (C3-8)alkynyl wherein one or more carbon atoms in the alkyl, alkenyl or alkynyl group are optionally substituted with one or more halogen atoms;
  (C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms, and
  phenyl, biphenyl, naphthyl, pyridyl, thienyl or thiazolyl optionally substituted with one or more substituents independently selected from the group consisting of:
    a halogen atom,
    cyano,
    (C1-4)alkyl optionally substituted with one or more fluoro atoms,
    (C1-4)alkoxy optionally substituted with one or more fluoro atoms,
    —S—(C1-4)-alkyl,
    —SF$_5$, and
    (C3-6)cycloalkyl optionally substituted with phenyl whereby said phenyl is optionally substituted with a substituent selected from the group consisting of (C1-4)alkyl and a halogen atom,
  preferably wherein said one or more substituents are at one or more of the ortho and meta positions with respect to L.

Further preferred compound are compounds of formula (I):

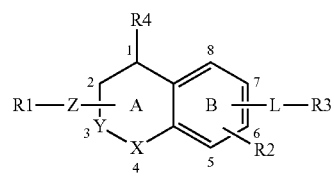

(I)

or a pharmaceutically acceptable salt, solvate, tautomer, stereoisomer or N-oxide thereof, wherein X and Y are independently selected from the group consisting of O, CH$_2$ and CH—Z—R1, with the proviso that at most one of X and Y is O and at most one of X and Y is CH—Z—R1;

Z is attached to ring A at atom 1, 2, 3 or 4 and is —NR5- or —O—;

R1 is selected from the group consisting of:
  —(C1-6)alkylene-R6 wherein one carbon atom in the alkylene group is optionally substituted with (CH$_2$)$_2$ to form a cyclopropyl moiety or with (CH$_2$)$_3$ to form a cyclobutyl moiety,
  —(C3-6)cycloalkylene-R6, and
  —(C3-6)cycloalkylene-(C1-3)alkylene-R6;

R5 is selected from the group consisting of H, (C1-4)alkyl and benzyl optionally substituted with one or more substituents selected from the group consisting of a halogen atom and (C1-4)alkyl; or NR5 and R1 together form a group -D wherein -D is selected from the group consisting of —(C3-6)heterocycloalkylene-R6 and —(C3-6)heterocycloalkylene-(C1-3)alkylene-R6.

L is attached to ring B at atom 5, 6 or 7 and selected from the group consisting of —O—(CH$_2$)p-, —CH=CH—, —C≡C—, —O—SO$_2$—, —(CH$_2$)n-(CH$_2$)p-, —CF$_2$—CH$_2$—, —O—, —CO—, —S—, —SO—, —SO$_2$—, —NH—, -Ph-(CH$_2$)m-, -Ph-O—(CH$_2$)m-, —O—CO—, —CO—O—, —CO—NH—, —NH—CO—, —C(CF$_3$)=CH—, CH=C(CF$_3$)—, cyclopropylene and cyclobutylene, wherein Ph is phenyl, p is an integer from 1 to 5, n is 1 or 2 and m is an integer from 1 to 5 and one or more C atoms of (CH$_2$)p, (CH$_2$)n and/or (CH$_2$)m are optionally substituted with one or two fluoro atoms;

R3 is phenyl, substituted with one or more substituents independently selected from the group consisting of:
  a halogen atom,
  cyano,
  (C1-4)alkyl optionally substituted with one or more fluoro atoms,
  (C1-4)alkoxy optionally substituted with one or more fluoro atoms.
  —S—(C1-4)-alkyl, and
  (C3-6)cycloalkyl optionally substituted with phenyl whereby said phenyl is optionally substituted with a substituent selected from the group consisting of (C1-4)alkyl and a halogen atom,
    wherein said one or more substituents are at one or more of the ortho and meta positions with respect to L.

Further preferred compounds of the invention are depicted in table 1 and include their pharmaceutically acceptable salts, solvates, tautomers, stereoisomers and N-oxides.

Particularly preferred compounds depicted in table 1 are compounds having a EC50 for the S1P5 receptor of 100 nM or less, as shown in table 1, i.e. compounds having an S1P5

EC50 range A or B in table 1. Such compounds having an EC50 for the S1P5 receptor of 100 nM or less further preferably have an EC50 for at least one of the S1P1 receptor, the S1P3 receptor and the S1P4 receptor of more than 1 μM. Hence, in a preferred embodiment are provided compounds depicted in table 1 having an S1P5 EC50 of 100 nM or less (indicated with range A or B in table 1) and an EC50 of more than 1 μM for at least one of the S1P1 receptor, the S1P3 receptor and the S1P4 receptor. Hence, a preferred compound according to the invention is selected from the group consisting of:

1-(7-((2,6-dichlorobenzyl)oxy)chroman-3-yl)azetidine-3-carboxylic acid,
1-(6-((2,6-dichlorobenzyl)oxy)-1,2,3,4-tetrahydronaphthalen-2-yl)azetidine-3-carboxylic acid,
1-((6-((2-chloro-6-ethylbenzyl)oxy)-1,2,3,4-tetrahydronaphthalen-2-yl)amino)cyclopropanecarboxylic acid,
3-((6-((2-chloro-6-ethylbenzyl)oxy)-1,2,3,4-tetrahydronaphthalen-2-yl)amino)propanoic acid,
3-((6-(benzyloxy)-1,2,3,4-tetrahydronaphthalen-2-yl)amino)propanoic acid,
3-((6-((2-chlorobenzyl)oxy)-1,2,3,4-tetrahydronaphthalen-2-yl)amino)propanoic acid,
3-((6-((2,6-dichlorobenzyl)oxy)-1,2,3,4-tetrahydronaphthalen-2-yl)amino)propanoic acid,
3-((6-((2,6-dichlorophenyl)ethynyl)-1,2,3,4-tetrahydronaphthalen-2-yl)amino)propanoic acid,
3-((6-((2,6-dichlorophenyl)ethynyl)-1,2,3,4-tetrahydronaphthalen-2-yl)(methyl)amino)propanoic acid,
3-((6-((3,5-difluorophenyl)ethynyl)-1,2,3,4-tetrahydronaphthalen-2-yl)amino)propanoic acid,
3-((6-((3,5-difluorophenyl)ethynyl)-1,2,3,4-tetrahydronaphthalen-2-yl)(methyl)amino)propanoic acid,
3-((6-((2-chloro-6-ethylbenzyl)oxy)-1,2,3,4-tetrahydronaphthalen-2-yl)(methyl)amino)propanoic acid,
3-((6-(2,6-dichlorostyryl)-1,2,3,4-tetrahydronaphthalen-2-yl)amino)-propanoic acid, preferably (E)-3-((6-(2,6-dichlorostyryl)-1,2,3,4-tetrahydronaphthalen-2-yl)amino)-propanoic acid,
3-((6-styryl-1,2,3,4-tetrahydronaphthalen-2-yl)amino)propanoic acid, preferably (E)-3-((6-styryl-1,2,3,4-tetrahydronaphthalen-2-yl)amino)propanoic acid,
3-((6-(3-chlorostyryl)-1,2,3,4-tetrahydronaphthalen-2-yl)amino)-propanoic acid, preferably (E)-3-((6-(3-chlorostyryl)-1,2,3,4-tetrahydronaphthalen-2-yl)amino)-propanoic acid
1-(7-((2-chloro-6-ethylbenzyl)oxy)chroman-3-yl)azetidine-3-carboxylic acid,
1-(7-((2-chloro-6-cyclopropylbenzyl)oxy)chroman-3-yl)azetidine-3-carboxylic acid,
1-(7-((2,3-difluorophenyl)ethynyl)chroman-3-yl)azetidine-3-carboxylic acid,
1-(7-((3,5-difluorophenyl)ethynyl)chroman-3-yl)azetidine-3-carboxylic acid,
2-((6-((3,5-difluorophenyl)ethynyl)-1,2,3,4-tetrahydronaphthalen-2-yl)amino)acetic acid,
2-((6-((2,6-dichlorophenyl)ethynyl)-1,2,3,4-tetrahydronaphthalon-2-yl)amino)acetic acid,
2-((6-(cyclohexylethynyl)-1,2,3,4-tetrahydronaphthalen-2-yl)amino)acetic acid,
1-(6-((2,6-dichlorobenzyl)oxy)-1,2,3,4-tetrahydronaphthalen-2-yl)piperidine-4-carboxylic acid,
3-((6-((2,6-dichlorobenzyl)oxy)-1,2,3,4-tetrahydronaphthalen-2-yl)amino)bicyclo[1.1.1]pentane-1-carboxylic acid,
2-((6-((2,6-dichlorobenzyl)oxy)-1,2,3,4-tetrahydronaphthalen-2-yl)amino)propanoic acid,
2-((7-((2-chloro-6-ethylbenzyl)oxy)chroman-3-yl)amino) acetic acid,
1-(7-((2,5-difluorophenyl)ethynyl)chroman-3-yl)azetidine-3-carboxylic acid,
1-(7-((3-chlorophenyl)ethynyl)chroman-3-yl)azetidine-3-carboxylic acid,
1-(7-((2-(trifluoromethyl)phenyl)ethynyl)chroman-3-yl)azetidine-3-carboxylic acid,
1-(7-((2-(difluoromethoxy)phenyl)ethynyl)chroman-3-yl)azetidine-3-carboxylic acid,
1-(7-((2,6-dichlorophenyl)ethynyl)chroman-3-yl)azetidine-3-carboxylic acid,
1-(7-((2,6-difluorophenyl)ethynyl)chroman-3-yl)azetidine-3-carboxylic acid,
3-((7-((2,6-dichlorobenzyl)oxy)chroman-3-yl)amino)-bicyclo[1.1.1]pentane-1-carboxylic acid,
1-(7-((2,6-dichlorobenzyl)oxy)chroman-3-yl)pyrrolidine-3-carboxylic acid,
1-(7-(4-((4-chlorobenzyl)oxy)phenyl)chroman-3-yl)azetidine-3-carboxylic acid,
1-(7-(4-(cyclohexylmethoxy)phenyl)chroman-3-yl)azetidine-3-carboxylic acid,
1-(7-(4-((2,3-difluorobenzyl)oxy)phenyl)chroman-3-yl)azetidine-3-carboxylic acid,
1-(7-((2-(trifluoromethyl)benzyl)oxy)chroman-3-yl)azetidine-3-carboxylic acid,
1-(7-((2-ethylbenzyl)oxy)chroman-3-yl)azetidine-3-carboxylic acid,
1-(7-((2-ethyl-6-fluorobenzyl)oxy)chroman-3-yl)azetidine-3-carboxylic acid,
1-(7-((2-fluoro-6-(trifluoromethyl)benzyl)oxy)chroman-3-yl)azetidine-3-carboxylic acid,
1-(7-((2-cyclopropyl-6-fluorobenzyl)oxy)chroman-3-yl)azetidine-3-carboxylic acid,
1-(7-(2,6-dichlorophenethoxy)chroman-3-yl)azetidine-3-carboxylic acid,
1-((6-((2,6-dichlorobenzyl)oxy)isochroman-1-yl)methyl)piperidine-4-carboxylic acid,
2-((7-((2-ethyl-6-fluorobenzyl)oxy)chroman-3-yl)(methyl)amino)acetic acid,
2-((6-((2-chloro-6-ethylbenzyl)oxy)-1,2,3,4-tetrahydronaphthalen-2-yl)amino)acetic acid,
1-(6-((2,6-dichlorobenzyl)oxy)-1,2,3,4-tetrahydronaphthalen-2-yl)pyrrolidine-3-carboxylic acid,
2-((6-((2,6-dichlorobenzyl)oxy)-1,2,3,4-tetrahydronaphthalen-2-yl)amino)acetic acid,
3-((6-((2,6-dichlorobenzyl)oxy)-1,2,3,4-tetrahydronaphthalen-2-yl)amino)cyclobutanecarboxylic acid, preferably (1s,3s)-3-((6-((2,6-dichlorobenzyl)oxy)-1,2,3,4-tetrahydronaphthalen-2-yl)amino)cyclobutanecarboxylic acid and/or (1r,3r)-3-((6-((2,6-dichlorobenzyl)oxy)-1,2,3,4-tetrahydronaphthalen-2-yl)amino)cyclobutanecarboxylic acid, 2-(1-(6-((2,6-dichlorobenzyl)oxy)-1,2,3,4-tetrahydronaphthalen-2-yl)azetidin-3-yl)acetic acid,
2-(1-(6-((2,6-dichlorobenzyl)oxy)-1,2,3,4-tetrahydronaphthalen-2-yl)pyrrolidin-3-yl)acetic acid,
3-(8-((2-chloro-6-ethylbenzyl)oxy)-5,6-dihydro-2H-naphtho[1,2-b][1,4]oxazin-4(3H,4aH,10bH)-yl)propanoic acid,
1-[7-[[3-fluoro-5-(trifluoromethyl)phenyl]methoxy]chroman-3-yl]azetidine-3-carboxylic acid,
1-(7-((2,6-dichlorobenzyl)oxy)chroman-3-yl)piperidine-4-carboxylic acid,
2-(1-((7-((2-chloro-6-ethylbenzyl)oxy)chroman-3-yl)amino)cyclopentyl) acetic acid,
2-(1-((7-((2-chloro-6-ethylbenzyl)oxy)chroman-3-yl)amino)cyclobutyl)acetic acid, 2-(1-((7-((2-ethyl-6-fluorobenzyl)oxy)chroman-3-yl)amino)cyclopentyl) acetic acid,
2-(1-((7-((2-ethyl-6-fluorobenzyl)oxy)chroman-3-yl)amino)cyclobutyl)acetic acid,
3-((7-((2-ethyl-6-fluorobenzyl)oxy)chroman-3-yl)amino)bicyclo[1.1.1]pentane-1-carboxylic acid,
2-((7-((2,6-dichlorobenzyl)oxy)chroman-3-yl)(methyl)amino)acetic acid,
2-((7-((2-chloro-6-ethylbenzyl)oxy)chroman-3-yl)(methyl)amino)acetic acid,
2-(1-(7-((2-chloro-6-ethylbenzyl)oxy)chroman-3-yl)pyrrolidin-3-yl)acetic acid,
2-((7-((2-fluoro-6-ethylbenzyl)oxy)chroman-3-yl)amino) acetic acid,
1-(7-((2-ethyl-6-fluorobenzyl)oxy)chroman-3-yl)pyrrolidine-3-carboxylic acid,
1-(7-((2-chloro-6-ethylbenzyl)oxy)chroman-3-yl)pyrrolidine-3-carboxylic acid,
2-(1-((7-((2-ethyl-6-fluorobenzyl)oxy)chroman-3-yl)amino)cyclopropyl) acetic acid,
2-(1-(7-((2-ethyl-6-fluorobenzyl)oxy)chroman-3-yl)pyrrolidin-3-yl)acetic acid,
(7-(4-((2,3-difluorobenzyl)oxy)phenyl)chroman-3-yl)glycine,
(7-((4-((3 chlorobenzyl)oxy)benzyl)oxy)chroman-3-yl)glycine,
2-((7-(4-((2,3-difluorobenzyl)oxy)phenyl)chroman-3-yl)(methyl)amino)acetic acid,
2-((7-(4-((3-chlorobenzyl)oxy)phenyl)chroman-3-yl)(methyl)amino)acetic acid,
2-((7-(4-((4-chlorobenzyl)oxy)phenyl)chroman-3-yl)(methyl)amino)acetic acid,
5-(((7-((2-ethyl-6-fluorobenzyl)oxy)chroman-3-yl)amino)methyl)isoxazol-3-ol, preferably (S)-5-(((7-((2-ethyl-6-fluorobenzyl)oxy)chroman-3-yl)amino)methyl)isoxazol-3-ol,
N-((3-((tert-butyldimethylsilyl)oxy)isoxazol-5-yl)methyl)-7-((2-chloro-6-ethylbenzyl)oxy)chroman-3-amine, preferably (S)—N-((3-((tert-butyldimethylsilyl)oxy)isoxazol-5-yl)methyl)-7-((2-chloro-6-ethylbenzyl)oxy)chroman-3-amine 1-(7-((2,6-dichlorobenzyl)oxy)chroman-3-yl)-3-methylazetidine-3-carboxylic acid, preferably (S)-1-(7-((2,6-dichlorobenzyl)oxy)chroman-3-yl)-3-methylazetidine-3-carboxylic acid
1-(7-((2-ethyl-6-fluorobenzyl)oxy)chroman-3-yl)-3-methylazetidine-3-carboxylic acid, preferably (S)-1-(7-((2-ethyl-6-fluorobenzyl)oxy)chroman-3-yl)-3-methylazetidine-3-carboxylic acid,
2-((6-((2-chloro-6-ethylbenzyl)oxy)-1,2,3,4-tetrahydronaphthalen-2-yl)oxy)acetic acid,
2-((6-((2-chloro-6-cyclopropylbenzyl)oxy)-1,2,3,4-tetrahydronaphthalen-2-yl)oxy)acetic acid,
2-((6-((2,6-difluoro-3-chlorobenzyl)oxy)-1,2,3,4-tetrahydronaphthalen-2-yl)oxy)acetic acid,
2-((6-((2-fluoro-5-(trifluoromethoxy)benzyl)oxy)-1,2,3,4-tetrahydronaphthalen-2-yl)oxy)acetic acid,
2-((6-((2-chloro-6-(trifluoromethyl)benzyl)oxy)-1,2,3,4-tetrahydronaphthalen-2-yl)oxy)acetic acid,
2-((6-((2-(trifluoromethyl)-5-fluorobenzyl)oxy)-1,2,3,4-tetrahydronaphthalen-2-yl)oxy)acetic acid,
2-((6-((2,6-dimethylbenzyl)oxy)-1,2,3,4-tetrahydronaphthalen-2-yl)oxy)acetic acid,
2-((6-((4-(tert-butyl)benzyl)oxy)-1,2,3,4-tetrahydronaphthalen-2-yl)oxy)acetic acid,
2-((6-((3-(trifluoromethyl)benzyl)oxy)-1,2,3,4-tetrahydronaphthalen-2-yl)oxy)acetic acid,
2-((6-((2-chloro-6-ethylbenzyl)oxy)-1,2,3,4-tetrahydronaphthalen-2-yl)amino)-1-(N-methylmethoxyamino)-1-ethanone,
(1-(6-((2-chloro-6-ethylbenzyl)oxy)-1,2,3,4-tetrahydronaphthalen-2-yl)-3-azetidinyl)(methoxyamino)formaldehyde,
5-((((6-((2-chloro-6-ethylbenzyl)oxy)-1,2,3,4-tetrahydronaphthalen-2-yl)amino)methyl)-2H-isoxazol-3-one,
1-(6-bromo-7-((2,6-dichlorobenzyl)oxy)chroman-3-yl)azetidine-3-carboxylic acid,
1-(6-methyl-7-((2,6-dichlorobenzyl)oxy)chroman-3-yl)azetidine-3-carboxylic acid;
1-(6-fluoro-7-((2,6-dichlorobenzyl)oxy)chroman-4-yl)azetidine-3-carboxylic acid,
((7-((2-chloro-6-ethylbenzyl)oxy)chroman-3-yl)oxy)acetic acid,
2-((6-((2-chloro-6-ethylbenzyl)oxy)-1,2,3,4-tetrahydronaphthalen-2-yl)amino)acetohydroxamic acid,
2-((7-(4-(benzyloxy)phenyl)chroman-3-yl)amino)acetic acid, and
2-((7-(4-(benzyloxy)phenyl)chroman-3-yl)(methyl)amino) acetic acid,
or a pharmaceutically acceptable salt, solvates, tautomer, stereoisomer or N-oxide of any of these compounds.

In a further preferred embodiment, such compound have an EC50 for the S1P5 receptor of 10 nM or less, i.e. compounds having an S1P5 EC50 range A in table 1, and an EC50 of more than 1 μM for at least one of the S1P1 receptor, the S1P3 receptor and the S1P4 receptor. Hence, a preferred compound according to the invention is selected from the group consisting of:
1-(7-((2,6-dichlorobenzyl)oxy)chroman-3-yl)azetidine-3-carboxylic acid,
1-(6-((2,6-dichlorobenzyl)oxy)-1,2,3,4-tetrahydronaphthalen-2-yl)azetidine-3-carboxylic acid,
1-((6-((2-chloro-6-ethylbenzyl)oxy)-1,2,3,4-tetrahydronaphthalen-2-yl)amino)cyclopropanecarboxylic acid,
3-((6-((2-chloro-6-ethylbenzyl)oxy)-1,2,3,4-tetrahydronaphthalen-2-yl)amino)propanoic acid,
3-((6-((2-chlorobenzyl)oxy)-1,2,3,4-tetrahydronaphthalen-2-yl)amino)propanoic acid,
3-((6-((2,6-dichlorobenzyl)oxy)-1,2,3,4-tetrahydronaphthalen-2-yl)amino)propanoic acid,
3-((6-((2,6-dichlorophenyl)ethynyl)-1,2,3,4-tetrahydronaphthalen-2-yl)amino)propanoic acid,
3-((6-((2,6-dichlorophenyl)ethynyl)-1,2,3,4-tetrahydronaphthalen-2-yl)(methyl)amino)propanoic acid,
3-((6-((3,5-difluorophenyl)ethynyl)-1,2,3,4-tetrahydronaphthalen-2-yl)amino)propanoic acid,
3-((6-((3,5-difluorophenyl)ethynyl)-1,2,3,4-tetrahydronaphthalen-2-yl)(methyl)amino)propanoic acid,
3-((6-((2-chloro-6-ethylbenzyl)oxy)-1,2,3,4-tetrahydronaphthalen-2-yl)(methyl)amino)propanoic acid,
3-((6-(2,6-dichlorostyryl)-1,2,3,4-tetrahydronaphthalen-2-yl)amino)-propanoic acid, preferably (E)-3-((6-(2,6-dichlorostyryl)-1,2,3,4-tetrahydronaphthalen-2-yl)amino)-propanoic acid,
3-((6-(3-chlorostyryl)-1,2,3,4-tetrahydronaphthalen-2-yl)amino)-propanoic acid,
preferably (E)-3-((6-(3-chlorostyryl)-1,2,3,4-tetrahydronaphthalen-2-yl)amino)-propanoic acid,
1-(7-((2-chloro-6-ethylbenzyl)oxy)chroman-3-yl)azetidine-3-carboxylic acid,
1-(7-((2-chloro-6-cyclopropylbenzyl)oxy)chroman-3-yl)azetidine-3-carboxylic acid,
1-(7-((3,5-difluorophenyl)ethynyl)chroman-3-yl)azetidine-3-carboxylic acid, 2-((6-((3,5-difluorophenyl)ethynyl)-1,2,3,4-tetrahydronaphthalen-2-yl)amino)acetic acid,
2-((6-((2,6-dichlorophenyl)ethynyl)-1,2,3,4-tetrahydronaphthalen-2-yl)amino)acetic acid,
2-(6-(cyclohexylethynyl)-1,2,3,4-tetrahydronaphthalen-2-yl)amino)acetic acid,
1-(6-((2,6-dichlorobenzyl)oxy)-1,2,3,4-tetrahydronaphthalen-2-yl)piperidine-4-carboxylic acid,
3-((6-((2,6-dichlorobenzyl)oxy)-1,2,3,4-tetrahydronaphthalen-2-yl)amino)bicyclo[1.1.1]pentane-1-carboxylic acid,
2-((6-((2,6-dichlorobenzyl)oxy)-1,2,3,4-tetrahydronaphthalen-2-yl)amino)propanoic acid,
2-((7-((2-chloro-6-ethylbenzyl)oxy)chroman-3-yl)amino)acetic acid,
1-(7-((2,5-difluorophenyl)ethynyl)chroman-3-yl)azetidine-3-carboxylic acid,
1-(7-((2,6-dichlorobenzyl)oxy)chroman-3-yl)pyrrolidine-3-carboxylic acid,
1-(7-(4-((4-chlorobenzyl)oxy)phenyl)chroman-3-yl)azetidine-3-carboxylic acid,
1-(7-(4-(cyclohexylmethoxy)phenyl)chroman-3-yl)azetidine-3-carboxylic acid,
1-(7-((2-ethyl-6-fluorobenzyl)oxy)chroman-3-yl)azetidine-3-carboxylic acid,
1-(7-((2-cyclopropyl-6-fluorobenzyl)oxy)chroman-3-yl)azetidine-3-carboxylic acid,
2-((7-((2-ethyl-6-fluorobenzyl)oxy)chroman-3-yl)(methyl)amino)acetic acid,
2-((6-((2-chloro-6-ethylbenzyl)oxy)-1,2,3,4-tetrahydronaphthalen-2-yl)amino)acetic acid,
1-(6-((2,6-dichlorobenzyl)oxy)-1,2,3,4-tetrahydronaphthalen-2-yl)pyrrolidine-3-carboxylic acid,
2-((6-((2,6-dichlorobenzyl)oxy)-1,2,3,4-tetrahydronaphthalen-2-yl)amino)acetic acid,
3-((6-((2,6-dichlorobenzyl)oxy)-1,2,3,4-tetrahydronaphthalen-2-yl)amino)cyclobutanecarboxylic acid, preferably (1s,3s)-3-((6-((2,6-dichlorobenzyl)oxy)-1,2,3,4-tetrahydronaphthalen-2-yl)amino)cyclobutanecarboxylic acid and/or (1r,3r)-3-((6-((2,6-dichlorobenzyl)oxy)-1,2,3,4-tetrahydronaphthalen-2-yl)amino)cyclobutanecarboxylic acid,
2-(1-(6-((2,6-dichlorobenzyl)oxy)-1,2,3,4-tetrahydronaphthalen-2-yl)azetidin-3-yl)acetic acid,
3-(8-((2-chloro-6-ethylbenzyl)oxy)-5,6-dihydro-2H-naphtho[1,2-b][1,4]oxazin-4(3H,4aH,10bH)-yl)propanoic acid,
2-(1-((7-((2-chloro-6-ethylbenzyl)oxy)chroman-3-yl)amino)cyclopentyl) acetic acid,
2-(1-((7-((2-chloro-6-ethylbenzyl)oxy)chroman-3-yl)amino)cyclobutyl)acetic acid,
2-(1-((7-((2-ethyl-6-fluorobenzyl)oxy)chroman-3-yl)amino)cyclopentyl) acetic acid,
2-(1-((7-((2-ethyl-6-fluorobenzyl)oxy)chroman-3-yl)amino)cyclobutyl)acetic acid,
2-((7-((2-chloro-6-ethylbenzyl)oxy)chroman-3-yl)(methyl)amino)acetic acid,
2-(1-(7-((2-chloro-6-ethylbenzyl)oxy)chroman-3-yl)pyrrolidin-3-yl)acetic acid,
2-((7-((2-fluoro-6-ethylbenzyl)oxy)chroman-3-yl)amino)acetic acid,
1-(7-((2-ethyl-6-fluorobenzyl)oxy)chroman-3-yl)pyrrolidine-3-carboxylic acid,
1-(7-((2-chloro-6-ethylbenzyl)oxy)chroman-3-yl)pyrrolidine-3-carboxylic acid,
2-(1-((7-((2-ethyl-6-fluorobenzyl)oxy)chroman-3-yl)amino)cyclopropyl) acetic acid,
2-(1-(7-((2-ethyl-6-fluorobenzyl)oxy)chroman-3-yl)pyrrolidin-3-yl)acetic acid,
(7-(4-((2,3-difluorobenzyl)oxy)phenyl)chroman-3-yl)glycine.
(7-((4-((3-chlorobenzyl)oxy)benzyl)oxy)chroman-3-yl)glycine,
2-((7-(4-((2,3-difluorobenzyl)oxy)phenyl)chroman-3-yl)(methyl)amino)acetic acid,
2-((7-(4-((3-chlorobenzyl)oxy)phenyl)chroman-3-yl)(methyl)amino)acetic acid,
5-(((7-((2-ethyl-6-fluorobenzyl)oxy)chroman-3-yl)amino)methyl)isoxazol-3-ol, preferably (S)-5-(((7-((2-ethyl-6-fluorobenzyl)oxy)chroman-3-yl)amino)methyl)isoxazol-3-ol,
N-((3-((tert-butyldimethylsilyl)oxy)isoxazol-5-yl)methyl)-7-((2-chloro-6-ethylbenzyl)oxy)chroman-3-amine, preferably (S)—N-((3-((tert-butyldimethylsilyl)oxy)isoxazol-5-yl)methyl)-7-((2-chloro-6-ethylbenzyl)oxy)chroman-3-amine,
1-(7-((2,6-dichlorobenzyl)oxy)chroman-3-yl)-3-methylazetidine-3-carboxylic acid,
preferably (S)-1-(7-((2,6-dichlorobenzyl)oxy)chroman-3-yl)-3-methylazetidine-3-carboxylic acid,
1-(7-((2-ethyl-6-fluorobenzyl)oxy)chroman-3-yl)-3-methylazetidine-3-carboxylic acid, preferably (S)-1-(7-((2-ethyl-6-fluorobenzyl)oxy)chroman-3-yl)-3-methylazetidine-3-carboxylic acid,
2-((6-((2-chloro-6-ethylbenzyl)oxy)-1,2,3,4-tetrahydronaphthalen-2-yl)oxy)acetic acid,
2-((6-((2-chloro-6-cyclopropylbenzyl)oxy)-1,2,3,4-tetrahydronaphthalen-2-yl)oxy)acetic acid,
2-((6-((2,6-difluoro-3-chlorobenzyl)oxy)-1,2,3,4-tetrahydronaphthalen-2-yl)oxy)acetic acid,
2-((6-((2-chloro-6-(trifluoromethyl)benzyl)oxy)-1,2,3,4-tetrahydronaphthalen-2-yl)oxy)acetic acid,
2-((6-((2-(trifluoromethyl)-5-fluorobenzyl)oxy)-1,2,3,4-tetrahydronaphthalen-2-yl)oxy)acetic acid,
2-((6-((2-chloro-6-ethylbenzyl)oxy)-1,2,3,4-tetrahydronaphthalen-2-yl)amino)-1-(N-methylmethoxyamino)-1-ethanone,
5-(((6-((2-chloro-6-ethylbenzyl)oxy)-1,2,3,4-tetrahydronaphthalen-2-yl)amino)methyl)-2H-isoxazol-3-one,
1-(6-fluoro-7-((2,6-dichlorobenzyl)oxy)chroman-4-yl)azetidine-3-carboxylic acid,
((7-((2-chloro-6-ethylbenzyl)oxy)chroman-3-yl)oxy)acetic acid,
2-((6-((2-chloro-6-ethylbenzyl)oxy)-1,2,3,4-tetrahydronaphthalen-2-yl)amino)acetohydroxamic acid and
2-((7-(4-(benzyloxy)phenyl)chroman-3-yl)amino)acetic acid,
or a pharmaceutically acceptable salt, solvates, tautomer, stereoisomer or N-oxide of any of these compounds.

In a further preferred embodiment, a compound of the invention has an EC50 for the S1P5 receptor of 100 nM or less, i.e. compounds having an S1P5 EC50 range A or B in table 1, and an EC50 of more than 1 µM for the S1P1 receptor. Hence, a preferred compound according to the invention is selected from the group consisting of:

1-(7-((2,6-dichlorobenzyl)oxy)chroman-3-yl)azetidine-3-carboxylic acid,
1-(6-((2,6-dichlorobenzyl)oxy)-1,2,3,4-tetrahydronaphthalen-2-yl)azetidine-3-carboxylic acid,
1-((6-((2-chloro-6-ethylbenzyl)oxy)-1,2,3,4-tetrahydronaphthalen-2-yl)amino)cyclopropanecarboxylic acid,
3-((6-(benzyloxy)-1,2,3,4-tetrahydronaphthalen-2-yl)amino)propanoic acid, 3-((6-((2-chlorobenzyl)oxy)-1,2,3,4-tetrahydronaphthalen-2-yl)amino)propanoic acid,
3-((6-((2,6-dichlorobenzyl)oxy)-1,2,3,4-tetrahydronaphthalen-2-yl)amino)propanoic acid,
3-((6-((2,6-dichlorophenyl)ethynyl)-1,2,3,4-tetrahydronaphthalen-2-yl)amino)propanoic acid,
3-((6-((2,6-dichlorophenyl)ethynyl)-1,2,3,4-tetrahydronaphthalen-2-yl)(methyl)amino)propanoic acid,
3-((6-((3,5-difluorophenyl)ethynyl)-1,2,3,4-tetrahydronaphthalen-2-yl)amino)propanoic acid,
3-((6-((3,5-difluorophenyl)ethynyl)-1,2,3,4-tetrahydronaphthalen-2-yl)(methyl)amino)propanoic acid,
3-((6-styryl-1,2,3,4-tetrahydronaphthalen-2-yl)amino)propanoic acid, preferably
(E)-3-((6-styryl-1,2,3,4-tetrahydronaphthalen-2-yl)amino)propanoic acid,
3-((6-(3-chlorostyryl)-1,2,3,4-tetrahydronaphthalen-2-yl)amino)-propanoic acid, preferably (E)-3-((6-(3-chlorostyryl)-1,2,3,4-tetrahydronaphthalen-2-yl)amino)-propanoic acid,
1-(7-((2-chloro-6-ethylbenzyl)oxy)chroman-3-yl)azetidine-3-carboxylic acid,
1-(7-((2-chloro-6-cyclopropylbenzyl)oxy)chroman-3-yl)azetidine-3-carboxylic acid,
1-(7-((2,3-difluorophenyl)ethynyl)chroman-3-yl)azetidine-3-carboxylic acid,
1-(7-((3,5-difluorophenyl)ethynyl)chroman-3-yl)azetidine-3-carboxylic acid,
2-((6-((3,5-difluorophenyl)ethynyl)-1,2,3,4-tetrahydronaphthalen-2-yl)amino)acetic acid,
2-((6-((2,6-dichlorophenyl)ethynyl)-1,2,3,4-tetrahydronaphthalen-2-yl)amino)acetic acid,
2-((6-(cyclohexylethynyl)-1,2,3,4-tetrahydronaphthalen-2-yl)amino)acetic acid,
3-((6-((2,6-dichlorobenzyl)oxy)-1,2,3,4-tetrahydronaphthalen-2-yl)amino)bicyclo[1.1.1]pentane-1-carboxylic acid,
2-((6-((2,6-dichlorobenzyl)oxy)-1,2,3,4-tetrahydronaphthalen-2-yl)amino)propanoic acid,
2-((7-((2-chloro-6-ethylbenzyl)oxy)chroman-3-yl)amino)acetic acid,
1-(7-((2,5-difluorophenyl)ethynyl)chroman-3-yl)azetidine-3-carboxylic acid,
1-(7-((3-chlorophenyl)ethynyl)chroman-3-yl)azetidine-3-carboxylic acid,
1-(7-((2-(trifluoromethyl)phenyl)ethynyl)chroman-3-yl)azetidine-3-carboxylic acid,
1-(7-((2-(difluoromethoxy)phenyl)ethynyl)chroman-3-yl)azetidine-3-carboxylic acid,
1-(7-((2,6-dichlorophenyl)ethynyl)chroman-3-yl)azetidine-3-carboxylic acid,
1-(7-((2,6-difluorophenyl)ethynyl)chroman-3-yl)azetidine-3-carboxylic acid,
3-((7-((2,6-dichlorobenzyl)oxy)chroman-3-yl)amino)-bicyclo[1.1.1]pentane-1-carboxylic acid,
1-(7-((2,6-dichlorobenzyl)oxy)chroman-3-yl)pyrrolidine-3-carboxylic acid,
1-(7-(4-((4-chlorobenzyl)oxy)phenyl)chroman-3-yl)azetidine-3-carboxylic acid,
1-(7-((2-(trifluoromethyl)benzyl)oxy)chroman-3-yl)azetidine-3-carboxylic acid,
1-(7-((2-ethylbenzyl)oxy)chroman-3-yl)azetidine-3-carboxylic acid,
1-(7-((2-ethyl-6-fluorobenzyl)oxy)chroman-3-yl)azetidine-3-carboxylic acid,
1-(7-((2-fluoro-6-(trifluoromethyl)benzyl)oxy)chroman-3-yl)azetidine-3-carboxylic acid,
1-(7-((2-cyclopropyl-6-fluorobenzyl)oxy)chroman-3-yl)azetidine-3-carboxylic acid,
1-(7-(2,6-dichlorophenethoxy)chroman-3-yl)azetidine-3-carboxylic acid,
1-((6-((2,6-dichlorobenzyl)oxy)isochroman-1-yl)methyl)piperidine-4-carboxylic acid,
2-((7-((2-ethyl-6-fluorobenzyl)oxy)chroman-3-yl)(methyl)amino)acetic acid,
1-(6-((2,6-dichlorobenzyl)oxy)-1,2,3,4-tetrahydronaphthalen-2-yl)pyrrolidine-3-carboxylic acid,
2-((6-((2,6-dichlorobenzyl)oxy)-1,2,3,4-tetrahydronaphthalen-2-yl)amino)acetic acid,
2-(1-(6-((2,6-dichlorobenzyl)oxy)-1,2,3,4-tetrahydronaphthalen-2-yl)azetidin-3-yl)acetic acid,
2-(1-(6-((2,6-dichlorobenzyl)oxy)-1,2,3,4-tetrahydronaphthalen-2-yl)pyrrolidin-3-yl)acetic acid,
1-[7-[[3-fluoro-5-(trifluoromethyl)phenyl]methoxy]chroman-3-yl]azetidine-3-carboxylic acid,
1-(7-((2,6-dichlorobenzyl)oxy)chroman-3-yl)piperidine-4-carboxylic acid,
2-(1-((7-((2-chloro-6-ethylbenzyl)oxy)chroman-3-yl)amino)cyclopentyl) acetic acid,
2-(1-((7-((2-chloro-6-ethylbenzyl)oxy)chroman-3-yl)amino)cyclobutyl)acetic acid,
2-(1-((7-((2-ethyl-6-fluorobenzyl)oxy)chroman-3-yl)amino)cyclopentyl) acetic acid,
2-(1-((7-((2-ethyl-6-fluorobenzyl)oxy)chroman-3-yl)amino)cyclobutyl)acetic acid,
3-((7-((2-ethyl-6-fluorobenzyl)oxy)chroman-3-yl)amino)bicyclo[1.1.1]pentane-1-carboxylic acid,
2-((7-((2,6-dichlorobenzyl)oxy)chroman-3-yl)(methyl)amino)acetic acid,
2-((7-((2-chloro-6-ethylbenzyl)oxy)chroman-3-yl)(methyl)amino)acetic acid,
2-(1-(7-((2-chloro-6-ethylbenzyl)oxy chroman-3-yl)pyrrolidin-3-yl)acetic acid,
2-((7-((2-fluoro-6-ethylbenzyl)oxy)chroman-3-yl)amino) acetic acid,
1-(7-((2-ethyl-6-fluorobenzyl)oxy)chroman-3-yl)pyrrolidine-3-carboxylic acid,
1-(7-((2-chloro-6-ethylbenzyl)oxy)chroman-3-yl)pyrrolidine-3-carboxylic acid,
2-(1-((7-((2-ethyl-6-fluorobenzyl)oxy)chroman-3-yl)amino)cyclopropyl) acetic acid,
2-(1-(7-((2-ethyl-6-fluorobenzyl)oxy)chroman-3-yl)pyrrolidin-3-yl)acetic acid,
(7-((4-((3-chlorobenzyl)oxy)benzyl)oxy)chroman-3-yl)glycine,
2-((7-(4-((3-chlorobenzyl)oxy)phenyl)chroman-3-yl)(methyl)amino)acetic acid,
2-((7-(4-((4-chlorobenzyl)oxy)phenyl)chroman-3-yl)(methyl)amino)acetic acid,
5-(((7-((2-ethyl-6-fluorobenzyl)oxy)chroman-3-yl)amino)methyl)isoxazol-3-ol, preferably (S)-5-(((7-((2-ethyl-6-fluorobenzyl)oxy)chroman-3-yl)amino)methyl)isoxazol-3-ol,
N-((3-((tert-butyldimethylsilyl)oxy)isoxazol-5-yl)methyl)-7-((2-cloro-6-ethylbenzyl)oxy)chroman-3-amine, preferably (S)—N-((3-((tert-butyldimethylsilyl)oxy)isoxazol-5-yl)methyl)-7-((2-chloro-6-ethylbenzyl)oxy)chroman-3-amine,
1-(7-((2,6-dichlorobenzyl)oxy)chroman-3-yl)-3-methylazetidine-3-carboxylic acid, preferably (S)-1-(7-((2,6-dichlorobenzyl)oxy)chroman-3-yl)-3-methylazetidine-3-carboxylic acid, 1-(7-((2-ethyl-6-fluorobenzyl)oxy)chroman-3-yl)-3-methyl-azetidine-3-carboxylic acid, preferably (S)-1-(7-((2-ethyl-6-fluorobenzyl)oxy)chroman-3-yl)-3-methylazetidine-3-carboxylic acid,
2-((6-((2-chloro-6-ethylbenzyl)oxy)-1,2,3,4-tetrahydronaphthalen-2-yl)oxy)acetic acid,
2-((6-((2-chloro-6-cyclopropylbenzyl)oxy)-1,2,3,4-tetrahydronaphthalen-2-yl)oxy)acetic acid,
2-((6-((2,6-difluoro-3-chlorobenzyl)oxy)-1,2,3,4-tetrahydronaphthalen-2-yl)oxy)acetic acid,
2-((6-((2-fluoro-5-(trifluoromethoxy)benzyl)oxy)-1,2,3,4-tetrahydronaphthalen-2-yl)oxy)acetic acid,
2-((6-((2-chloro-6-(trifluoromethyl)benzyl)oxy)-1,2,3,4-tetrahydronaphthalen-2-yl)oxy)acetic acid,
2-((6-((2-(trifluoromethyl)-5-fluorobenzyl)oxy)-1,2,3,4-tetrahydronaphthalen-2-yl)oxy)acetic acid,
2-((6-((2,6-dimethylbenzyl)oxy)-1,2,3,4-tetrahydronaphthalen-2-yl)oxy)acetic acid,
2-((6-((4-(tert-butyl)benzyl)oxy)-1,2,3,4-tetrahydronaphthalen-2-yl)oxy)acetic acid,
2-((6-((3-(trifluoromethyl)benzyl)oxy)-1,2,3,4-tetrahydronaphthalen-2-yl)oxy)acetic acid,
2-((6-((2-chloro-6-ethylbenzyl)oxy)-1,2,3,4-tetrahydronaphthalen-2-yl)amino)-1-(N-methylmethoxyamino)-1-ethanone,
(1-(6-((2-chloro-6-ethylbenzyl)oxy)-1,2,3,4-tetrahydronaphthalen-2-yl)-3-azetidinyl)(methoxyamino)formaldehyde,
1-(6-bromo-7-((2,6-dichlorobenzyl)oxy)chroman-3-yl)azetidine-3-carboxylic acid,
1-(6-methyl-7-((2,6-dichlorobenzyl)oxy)chroman-3-yl)azetidine-3-carboxylic acid,
1-(6-fluoro-7-((2,6-dichlorobenzyl)oxy)chroman-4-yl)azetidine-3-carboxylic acid,
((7-((2-chloro-6-ethylbenzyl)oxy)chroman-3-yl)oxy)acetic acid,
2-((6-((2-chloro-6-ethylbenzyl)oxy)-1,2,3,4-tetrahydronaphthalen-2-yl)amino)acetohydroxamic acid, and
2-((7-(4-(benzyloxy)phenyl)chroman-3-yl)amino)acetic acid, or a pharmaceutically acceptable salt, solvates, tautomer, stereoisomer or N-oxide of any of these compounds. It is preferred that these compounds have an S1P5 EC50 of 10 nM or less.

In a further preferred embodiment, a compound of the invention has an EC50 for the S1P5 receptor of 100 nM or less, i.e. compounds having an S1P5 EC50 range A or B in table 1, and an EC50 of more than 1 µM for the S1P3 receptor. Hence, a preferred compound according to the invention is selected from the group consisting of:
1-(7-((2,6-dichlorobenzyl)oxy)chroman-3-yl)azetidine-3-carboxylic acid,
1-(6-((2,6-dichlorobenzyl)oxy)-1,2,3,4-tetrahydronaphthalen-2-yl)azetidine-3-carboxylic acid,
1-((6-((2-chloro-6-ethylbenzyl)oxy)-1,2,3,4-tetrahydronaphthalen-2-yl)amino)cyclopropanecarboxylic acid,
3-((6-((2-chloro-6-ethylbenzyl)oxy)-1,2,3,4-tetrahydronaphthalen-2-yl)amino)propanoic acid,
3-((6-(benzyloxy)-1,2,3,4-tetrahydronaphthalen-2-yl)amino)propanoic acid,
3-((6-((2-chlorobenzyl)oxy)-1,2,3,4-tetrahydronaphthalen-2-yl)amino)propanoic acid,
3-((6-((2,6-dichlorobenzyl)oxy)-1,2,3,4-tetrahydronaphthalen-2-yl)amino)propanoic acid,
3-((6-((2,6-dichlorophenyl)ethynyl)-1,2,3,4-tetrahydronaphthalen-2-yl)amino)propanoic acid,
3-((6-((2,6-dichlorophenyl)ethynyl)-1,2,3,4-tetrahydronaphthalen-2-yl)(methyl)amino)propanoic acid,
3-((6-((3,5-difluorophenyl)ethynyl)-1,2,3,4-tetrahydronaphthalen-2-yl)amino)propanoic acid,
3-((6-((3,5-difluorophenyl)ethynyl)-1,2,3,4-tetrahydronaphthalen-2-yl)(methyl)amino)propanoic acid,
3-((6-((2-chloro-6-ethylbenzyl)oxy)-1,2,3,4-tetrahydronaphthalen-2-yl)(methyl)amino)propanoic acid,
3-((6-(2,6-dichlorostyryl)-1,2,3,4-tetrahydronaphthalen-2-yl)amino)-propanoic acid, preferably (E)-3-((6-(2,6-dichlorostyryl)-1,2,3,4-tetrahydronaphthalen-2-yl)amino)-propanoic acid,
3-((6-styryl-1,2,3,4-tetrahydronaphthalen-2-yl)amino)propanoic acid, preferably
(E)-3-((6-styryl-1,2,3,4-tetrahydronaphthalen-2-yl)amino)propanoic acid,
3-((6-(3-chlorostyryl)-1,2,3,4-tetrahydronaphthalen-2-yl)amino)-propanoic acid, preferably (E)-3-((6-(3-chlorostyryl)-1,2,3,4-tetrahydronaphthalen-2-yl)amino)-propanoic acid,
1-(7-((2-chloro-6-ethylbenzyl)oxy)chroman-3-yl)azetidine-3-carboxylic acid,
1-(7-((2-chloro-6-cyclopropylbenzyl)oxy)chroman-3-yl)azetidine-3-carboxylic acid,
1-(7-((2,3-difluorophenyl)ethynyl)chroman-3-yl)azetidine-3-carboxylic acid,
1-(7-((3,5-difluorophenyl)ethynyl)chroman-3-yl)azetidine-3-carboxylic acid,
2-((6-((3,5-difluorophenyl)ethynyl)-1,2,3,4-tetrahydronaphthalen-2-yl)amino)acetic acid,
2-((6-((2,6-dichlorophenyl)ethynyl)-1,2,3,4-tetrahydronaphthalen-2-yl)amino)acetic acid,
2-((6-(cyclohexylethynyl)-1,2,3,4-tetrahydronaphthalen-2-yl)amino)acetic acid,
1-(6-((2,6-dichlorobenzyl)oxy)-1,2,3,4-tetrahydronaphthalen-2-yl)piperidine-4-carboxylic acid,
3-((6-((2,6-dichlorobenzyl)oxy)-1,2,3,4-tetrahydronaphthalen-2-yl)amino)bicyclo[1.1.1]pentane-1-carboxylic acid,
2-((6-((2,6-dichlorobenzyl)oxy)-1,2,3,4-tetrahydronaphthalen-2-yl)amino)propanoic acid,
2-((7-((2-chloro-6-ethylbenzyl)oxy)chroman-3-yl)amino)acetic acid,
1-(7-((2,5-difluorophenyl)ethynyl)chroman-3-yl)azetidine-3-carboxylic acid,
1-(7-((3-chlorophenyl)ethynyl)chroman-3-yl)azetidine-3-carboxylic acid,
1-(7-((2-(trifluoromethyl)phenyl)ethynyl)chroman-3-yl)azetidine-3-carboxylic acid,
1-(7-((2-(difluoromethoxy)phenyl)ethynyl)chroman-3-yl)azetidine-3-carboxylic acid,
1-(7-((2,6-dichlorophenyl)ethynyl)chroman-3-yl)azetidine-3-carboxylic acid,
1-(7-((2,6-difluorophenyl)ethynyl)chroman-3-yl)azetidine-3-carboxylic acid,
3-((7-((2,6-dichlorobenzyl)oxy)chroman-3-yl)amino)-bicyclo[1.1.1]pentane-1-carboxylic acid,
1-(7-((2,6-dichlorobenzyl)oxy)chroman-3-yl)pyrrolidine-3-carboxylic acid,
1-(7-(4-((4-chlorobenzyl)oxy)phenyl)chroman-3-yl)azetidine-3-carboxylic acid,
1-(7-(4-(cyclohexylmethoxy)phenyl)chroman-3-yl)azetidine-3-carboxylic acid,
1-(7-(4-((2,3-difluorobenzyl)oxy)phenyl)chroman-3-yl)azetidine-3-carboxylic acid,
1-(7-((2-(trifluoromethyl)benzyl)oxy)chroman-3-yl)azetidine-3-carboxylic acid, 1-(7-((2-ethylbenzyl)oxy)chroman-3-yl)azetidine-3-carboxylic acid,
1-(7-((2-ethyl-6-fluorobenzyl)oxy)chroman-3-yl)azetidine-3-carboxylic acid,
1-(7-((2-fluoro-6-(trifluoromethyl)benzyl)oxy)chroman-3-yl)azetidine-3-carboxylic acid,
1-(7-((2-cyclopropyl-6-fluorobenzyl)oxy)chroman-3-yl)azetidin-3-carboxylic acid,
1-(7-(2,6-dichlorophenethoxy)chroman-3-yl)azetidine-3-carboxylic acid,
1-((6-((2,6-dichlorobenzyl)oxy)isochroman-1-yl)methyl)piperidine-4-carboxylic acid,
2-((6-((2-chloro-6-ethylbenzyl)oxy)-1,2,3,4-tetrahydronaphthalen-2-yl)amino)acetic acid,
1-(6-((2,6-dichlorobenzyl)oxy)-1,2,3,4-tetrahydronaphthalen-2-yl)pyrrolidine-3-carboxylic acid,
2-((6-((2,6-dichlorobenzyl)oxy)-1,2,3,4-tetrahydronaphthalen-2-yl)amino)acetic acid,
3-((6-((2,6-dichlorobenzyl)oxy)-1,2,3,4-tetrahydronaphthalen-2-yl)amino)cyclobutanecarboxylic acid, preferably (1s,3s)-3-((6-((2,6-dichlorobenzyl)oxy)-1, 2, 3, 4-tetrahydronaphthalen-2-yl)amino)cyclobutanecarboxylic acid and/or (1r,3r)-3-((6-((2,6-dichlorobenzyl)oxy)-1,2,3,4-tetrahydronaphthalen-2-yl)amino)cyclobutanecarboxylic acid,
2-(1-(6-((2,6-dichlorobenzyl)oxy)-1,2,3,4-tetrahydronaphthalen-2-yl)azetidin-3-yl)acetic acid,
2-(1-(6-((2,6-dichlorobenzyl)oxy)-1,2,3,4-tetrahydronaphthalen-2-yl)pyrrolidin-3-yl)acetic acid,
3-(8-((2-chloro-6-ethylbenzyl)oxy)-5,6-dihydro-2H-naphtho[1,2-b][1,4]oxazin-4(3H,4aH,10bH)-yl)propanoic acid,
2-((6-((2,6-difluoro-3-chlorobenzyl)oxy)-1,2,3,4-tetrahydronaphthalen-2-yl)oxy)acetic acid,
2-((6-((2-fluoro-5-(trifluoromethoxy)benzyl)oxy)-1,2,3,4-tetrahydronaphthalen-2-yl)oxy)acetic acid,
2-((6-((2-chloro-6-(trifluoromethyl)benzyl)oxy)-1,2,3,4-tetrahydronaphthalen-2-yl)oxy)acetic acid,
2-((6-((2-(trifluoromethyl)-5-fluorobenzyl)oxy)-1,2,3,4-tetrahydronaphthalen-2-yl)oxy)acetic acid,
2-((6-((2,6-dimethylbenzyl)oxy)-1,2,3,4-tetrahydronaphthalen-2-yl)oxy)acetic acid,
2-((6-((4-(tert-butyl)benzyl)oxy)-1,2,3,4-tetrahydronaphthalen-2-yl)oxy)acetic acid,
2-((6-((3-(trifluoromethyl)benzyl)oxy)-1,2,3,4-tetrahydronaphthalen-2-yl)oxy)acetic acid,
2-((6-((2-chloro-6-ethylbenzyl)oxy)-1,2,3,4-tetrahydronaphthalen-2-yl)amino)-1-(N-methylmethoxyamino)-1-ethanone,
(1-(6-((2-chloro-6-ethylbenzyl)oxy)-1,2,3,4-tetrahydronaphthalen-2-yl)-3-azetidinyl)(methoxyamino)formaldehyde,
5-(((6-((2-chloro-6-ethylbenzyl)oxy)-1,2,3,4-tetrahydronaphthalen-2-yl)amino)methyl)-2H-isoxazol-3-one,
2-((6-((2-chloro-6-ethylbenzyl)oxy)-1,2,3,4-tetrahydronaphthalen-2-yl)amino)acetohydroxamic acid and
2-((7-(4-(benzyloxy)phenyl)chroman-3-yl)(methyl)amino) acetic acid, or a pharmaceutically acceptable salt, solvates, tautomer, stereoisomer or N-oxide of any of these compounds. It is preferred that these compounds have an S1P5 EC50 of 10 nM or less.

In a further preferred embodiment, a compound of the invention has an EC50 for the S1P5 receptor of 100 nM or less, i.e. compounds having an S1P5 EC50 range A or B in table 1, and an EC50 of more than 1 μM for the S1P4 receptor. Hence, a preferred compound according to the invention is selected from the group consisting of:
1-(7-((2,6-dichlorobenzyl)oxy)chroman-3-yl)azetidine-3-carboxylic acid,
1-(7-((2,3-difluorophenyl)ethynyl)chroman-3-yl)azetidine-3-carboxylic acid,
1-(7-((2-(trifluoromethyl)phenyl)ethynyl)chroman-3-yl)azetidine-3-carboxylic acid,
1-(7-((2-(difluoromethoxy)phenyl)ethynyl)chroman-3-yl)azetidine-3-carboxylic acid,
1-(7-((2,6-dichlorophenyl)ethynyl)chroman-3-yl)azetidine-3-carboxylic acid,
3-((7-((2,6-dichlorobenzyl)oxy)chroman-3-yl)amino)-bicyclo[1.1.1]pentane-1-carboxylic acid,
1-(7-((2,6-dichlorobenzyl)oxy)chroman-3-yl)pyrrolidine-3-carboxylic acid,
1-(7-(4-((4-chlorobenzyl)oxy)phenyl)chroman-3-yl)azetidine-3-carboxylic acid,
1-(7-(4-(cyclohexylmethoxy)phenyl)chroman-3-yl)azetidine-3-carboxylic acid,
1-(7-(4-((2,3-difluorobenzyl)oxy)phenyl)chroman-3-yl)azetidine-3-carboxylic acid,
1-(7-((2-(trifluoromethyl)benzyl)oxy)chroman-3-yl)azetidine-3-carboxylic acid,
1-(7-(2,6-dichlorophenethoxy)chroman-3-yl)azetidine-3-carboxylic acid,
2-(1-((7-((2-ethyl-6-fluorobenzyl)oxy)chroman-3-yl)amino)cyclopropyl) acetic acid,
(7-(4-((2,3-difluorobenzyl)oxy)phenyl)chroman-3-yl)glycine,
(7-((4-((3-chlorobenzyl)oxy)benzyl)oxy)chroman-3-yl)glycine,
2-((7-(4-((2,3-difluorobenzyl)oxy)phenyl)chroman-3-yl)(methyl)amino)acetic acid,
2-((7-(4-((3-chlorobenzyl)oxy)phenyl)chroman-3-yl)(methyl)amino)acetic acid,
2-((7-(4-((4-chlorobenzyl)oxy)phenyl)chroman-3-yl)(methyl)amino)acetic acid,
1-(7-((2,6-dichlorobenzyl)oxy)chroman-3-yl)-3-methylazetidine-3-carboxylic acid, preferably (S)-1-(7-((2,6-dichlorobenzyl)oxy)chroman-3-yl)-3-methylazetidine-3-carboxylic acid,
2-((6-((2-chloro-6-ethylbenzyl)oxy)-1,2,3,4-tetrahydronaphthalen-2-yl)oxy)acetic acid,
2-((6-((2-chloro-6-cyclopropylbenzyl)oxy)-1,2,3,4-tetrahydronaphthalen-2-yl)oxy)acetic acid,
2-((6-((2,6-difluoro-3-chlorobenzyl)oxy)-1,2,3,4-tetrahydronaphthalen-2-yl)oxy)acetic acid,
2-((6-((2-fluoro-5-(trifluoromethoxy)benzyl)oxy)-1,2,3,4-tetrahydronaphthalen-2-yl)oxy)acetic acid,
2-((6-((2-chloro-6-(trifluoromethyl)benzyl)oxy)-1,2,3,4-tetrahydronaphthalen-2-yl)oxy)acetic acid,
2-((6-((2,6-dimethylbenzyl)oxy)-1,2,3,4-tetrahydronaphthalen-2-yl)oxy)acetic acid,
2-((6-((4-(tert-butyl)benzyl)oxy)-1,2,3,4-tetrahydronaphthalen-2-yl)oxy)acetic acid,
2-((6-((2-chloro-6-ethylbenzyl)oxy)-1,2,3,4-tetrahydronaphthalen-2-yl)amino)-1-(N-methylmethoxyamino)-1-ethanone,
(1-(6-((2-chloro-6-ethylbenzyl)oxy)-1,2,3,4-tetrahydronaphthalen-2-yl)-3-azetidinyl)(methoxyamino)formaldehyde,
1-(6-bromo-7-((2,6-dichlorobenzyl)oxy)chroman-3-yl)azetidine-3-carboxylic acid,
1-(6-methyl-7-((2,6-dichlorobenzyl)oxy)chroman-3-yl)azetidine-3-carboxylic acid, 1-(6-fluoro-7-((2,6-dichlorobenzyl)oxy)chroman-4-yl)azetidine-3-carboxylic acid,
((7-((2-chloro-6-ethylbenzyl)oxy)chroman-3-yl)oxy)acetic acid,
2-((7-(4-(benzyloxy)phenyl)chroman-3-yl)amino)acetic acid, and
2-((7-(4-(benzyloxy)phenyl)chroman-3-yl)(methyl)amino) acetic acid.
or a pharmaceutically acceptable salt, solvates, tautomer, stereoisomer or N-oxide of any of these compounds. It is preferred that these compounds have an S1P5 EC50 of 10 nM or less.

As used herein, the term "a halogen atom" refers to fluoro, chloro, bromo, or iodo. Preferred halogen atoms are fluoro and chloro.

As used herein, the term "(Cx-yl)alkyl" refers to a branched or unbranched alkyl group having x-y carbon atoms. For instance, (C1-4)alkyl means a branched or unbranched alkyl group having 1-4 carbon atoms, for example methyl, ethyl, propyl, isopropyl and butyl. Similarly, the term "(C1-2) alkyl" refers to an alkyl group having 1 or 2 carbon atoms. Preferred alkyl groups are methyl and ethyl. Branched alkyl groups for instance may have one or two $CH_3$ groups, a (double bonded) $CH_2$ group or a —CH$(CH_3)_2$ group attached to the main alkyl chain.

As used herein, the term (Cx-yl)alkoxy refers to an alkoxy group having x-y carbon atoms, wherein the alkyl moiety is as defined above. For instance, the term (C1-4)alkoxy means an alkoxy group having 1-4 carbon atoms. Preferred alkoxy groups are methoxy and ethoxy.

As used herein, the term "(Cx-yl)alkylene" refers to a branched or unbranched saturated alkylene group having x-y carbon atoms. For instance, the term "(C1-4)alkylene" means a saturated alkylene group having 1-4 carbon atoms, for example methylene, $(CH_2)_3$—CHCH$_3$—, —C(CH$_3$)$_2$—, —CHCH$_3$CH$_2$—. As another example, the term "(C3-8) alkylene" means a saturated alkylene group having 3-8 carbon atoms". In the definition of R1 as —(C1-6)alkylene-R6, one or more carbon atoms in the alkylene group may independently be substituted with $(CH_2)_2$ to form a cyclopropyl moiety, for instance to form an R1 group

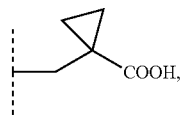

or with $(CH_2)_3$ to form a cyclobutyl moiety, for instance to form an R1 group

As used herein the term "(Cx-yl)alkenyl" means a branched or unbranched alkenyl group having x-y carbon atoms, wherein the double bond may be present at various positions in the group. For instance, the term "(C3-8) alkenyl" means a branched or unbranched alkenyl group having 3-8 carbon atoms. Examples are 1-butenyl, 2-butenyl.

As used herein, the term "(Cx-yl)alkynyl" refers to a branched or unbranched alkynyl group having x-y carbon atoms, wherein the triple bond may be present at different positions in the group. For instance, the term "(C3-8) alkynyl" refers to a branched or unbranched alkynyl group having 3-8 carbon atoms. Examples are 1-butynyl, 2-butynyl.

As used herein the term "(Cx-yl)cycloalkyl" refers to a cyclic alkyl group having x-y carbon atoms. For instance, the term "(C3-6)cycloalkyl" refers to a cyclic alkyl group having 3-6 carbon atoms, i.e. cyclopropyl, cyclobutyl, cyclopentyl or cyclohexyl.

As used herein the term "(Cx-yl)cycloalkylene" means a saturated cyclic group having x-y carbon atoms. For instance, the term "(C3-6)cycloalkylene" means a saturated cyclic group having 3-6 carbon atoms, e.g. cyclobutylene, cyclopentylene, cyclohexylene and cycloheptane.

As used herein the term "(Cx-yl)cycloalkenyl" refers to a cyclic alkenyl group having x-y carbon atoms. For instance, the term "(C3-6)cycloalkenyl" means a cyclic alkenyl group having 3-6 carbon atoms and comprising one or two double bonds, for example cyclohexenyl.

As used herein the term "(C3-8)heterocycloalkylene" means a heteroatom containing saturated cyclic group having 3-8 carbon atoms, wherein one or more of the carbon atoms is replaced by a heteroatom. Hence, the C(3-8) heterocycloalkylene has 3-8 atoms in the ring including one or more heteroatoms. In formula (I), if Z is NR5, NR5 and R1 may together form a group selected from —(C3-8) heterocycloalkylene-R6 and —(C3-8)heterocycloalkylene-(C1-3)alkylene-R6, which groups are optionally substituted with C1-4)alkyl or with (C1-4)alkyl substituted with one or more fluor atoms. Hence, a heterocycloalkylene in accordance with the present invention contains at least one nitrogen atom. Said heterocycloalkylene optionally comprises one or more further heteroatoms, preferably said heterocycloalkylene comprises one further heteroatom. Said one ore more, preferably one further heteroatom, are preferably selected from the group consisting of N, O and S. Preferably, a heterocycloalkylene in accordance with the present invention contains one heteroatom, i.e. the nitrogen atom of NR5. Hence, a preferred C(3-8)heterocycloalkylene contains one nitrogen atom and 2-7 carbon atoms. Preferred C(3-8)heterocycloalkylene groups in accordance with the invention are aziridine, azetidine, pyrrolidine, piperidine, azepane and azocane. Most preferred C(3-8)heterocycloalkylene groups are azetidine, pyrrolidine and piperidine.

As used herein the term "monocyclic heterocycle" means a heteroatom containing cyclic group. The term "monocyclic heterocycle" encompasses monocyclic heteroaryl groups and non-aromatic heteromonocyclic groups. Preferred monocyclic heterocycles are furanyl, thienyl, pyrrolyl, oxazolyl, thiazolyl, imidazolyl, pyrazolyl, isoxazolyl, isothiazolyl, triazolyl, oxadiazolyl, pyridyl, pyridazinyl, pyrimidinyl, pyrazinyl, triazinyl, tetrahydrofuranyl, tetrahydropyranyl, dioxanyl, morpholinyl.

As used herein the term "8-10 membered bicyclic group" for R3 means a fused ring system of two ring structures together having 8-10 atoms. The rings can be either aromatic or non-aromatic ring structures. Preferred 8-10 membered bicyclic groups contain up to two heteroatoms, preferably O, S and/or N. Particularly preferred 8-10 membered bicyclic groups for R3 are indane, tetralin, benzofuran, isobenzofuran, dihydrobenzofuran, dihydroisobenzofuran, tetrahydrobenzofuran, tetrahydroisobenzofuran, indoline, isoindoline, indole, isoindole, dihydroindole, dihydroisoindole, tetrahydroindole, tetrahydroisoindole, quinolone, quinoline, isoquinoline, tetrahydroquinoline, tetrahydroisoquinoline, quinoxaline, dihydroquinoxaline, tetrahydroquinoxaline, quinazoline, dihydroquinazoline, tetrahydroquinazoline, dihydrobenzopyran, benzothiophene, benzothiophene, dihydrobenzothiophene, dihydrobenzo[c]thiophene, tetrahydrobenzothiophene, tetrahydroquinoxaline, indazole, dihydroindazole, tetrahydroindazole, benzimidazole, dihydrobenzimidazole and tetrahydrobenzimidazole, benzoxazole, dihydrobenzoxazole, tetrahydrobenzoxazole, benzisoxazole, dihydrobenzisoxazole and tetrahydrobenzisoxazole. More preferred 8-10 membered bicyclic groups in the definition of R3 are indane, tetralin, dihydrobenzofuran, dihydroisobenzofuran, dihydroindole, dihydroisoindole, dihydrobenzopyran, dihydrobenzothiophene, quinolone, isoquinoline, benzofurane and dihydrobenzo[c]thiophene.

With respect to substituents, the term "optionally substituted" indicates a group may be unsubstituted or substituted with the indicated number and type of the substituent(s). The term "independently" with respect to substituents means that if a group that is substituted with more than one substituent, these substituents may be the same or different from each other. Similarly, if multiple atoms or groups are independently selected from a given group, such as X and Y in formula (I), the term "independently selected" means that each atom or group may be the same or different from the substituent of the other atom or group. Further, if a group can be more than one substituent, such as R2 in formula (I), the term "independently selected" means that each group may be the same or different form the other group(s). For instance, if two groups R2 are present, these may be the same or different.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the compound. Each such asymmetric center will independently produce two optical isomers and it is intended that all of the possible optical isomers and diastereomers in mixtures and as pure or partially purified compounds are included within the ambit of this invention. The present invention encompasses all such isomeric forms of these compounds. The independent syntheses of these diastereomers or their chromatographic separations may be achieved with any method known in the art, for instance as described in the Examples. The absolute stereochemistry of a compound may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as chiral HPLC or SFC (Supercritical Fluid Chromatography) techniques. In the Examples, two suitable SFC methods are described.

Salts of compounds according to the invention are also provided. Such salts include, but are not limited to, acid addition salts and base addition salts. The term "pharmaceutically acceptable salt" as used herein refers to those salts retain the pharmacological activity of the compounds and that are, within the scope of sound medical judgment, suitable for use in humans or animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids, for instance by reacting the free acid or free base forms of the product with one or more equivalents of the appropriate acid or base in a solvent or medium in which the salt is insoluble, or in a solvent such as water or an organic solvent which is then removed in vacuo or by freeze-drying, or by exchanging the cations of an existing salt for another cation on a suitable ion exchange resin. Examples of pharmaceutically acceptable acids and bases include organic and inorganic acids such as acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid and phosphoric acid, and bases such as ethylamine, methylamine, dimethylamine, triethylamine, isopropylamine, diisopropylamine, and other mono-, di- and trialkylamines, and arylamines.

Compounds may exist as polymorphs and as such are intended to be included in the present invention. In addition, compounds may form solvates with water (i.e., hydrates) or common organic solvents, and such solvates are also intended to be encompassed within the scope of this invention. Hydrates are a preferred type of solvate.

Isotopically-labeled compounds of formula (I) or pharmaceutically acceptable salts thereof, including compounds of formula (I) isotopically-labeled to be detectable by PET or SPECT, also fall within the scope of the invention. The same applies to compounds of formula (I) labeled with [13C]-, [14C]-, [3H]-, [18F]-, [125I]- or other isotopically enriched atoms, suitable for receptor binding or metabolism studies.

The compounds of the invention may be prepared by methods known in the art and to a skilled person. Suitable methods to prepare the compounds are described in the experimental section of this description.

Compounds according to the invention are useful in counteracting diseases or disorders mediated by an S1P receptor, preferably S1P5. They are preferably mixed with pharmaceutically suitable auxiliaries, e.g. as described in the standard reference "Remington, The Science and Practice of Pharmacy" (21st edition, Lippincott Williams & Wilkins, 2005, see especially Part 5: Pharmaceutical Manufacturing). The compounds together with pharmaceutically suitable auxiliaries may be compressed into solid dosage units, such as pills or tablets, or be processed into capsules or suppositories. By means of pharmaceutically suitable liquids the compounds can also be applied in the form of a solution, suspension or emulsion.

Provided is therefore a pharmaceutical composition comprising a compound according to the invention or a pharmaceutically acceptable salt, solvate, tautomer, stereoisomer or N-oxide thereof, and at least one pharmaceutically acceptable carrier, diluent and/or excipient. By "pharmaceutically acceptable" it is meant that the carrier, diluent or excipient must be compatible with the other ingredients of the formulation and not deleterious to the recipient thereof. In general, any pharmaceutically suitable additive which does not interfere with the function of the active compounds can be used. A pharmaceutical composition according to the invention is preferably suitable for human use.

Examples of suitable carriers comprise a solution, lactose, starch, cellulose derivatives and the like, or mixtures thereof. In a preferred embodiment said suitable carrier is a solution, for example saline. For making dosage units, e.g. tablets, the use of conventional additives such as fillers, colorants, polymeric binders and the like, is contemplated. Examples of excipients which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

The compounds of the invention may be administered enterally or parenterally. The exact dose and regimen of these compounds and compositions thereof will be dependent on the biological activity of the compound per se, the age, weight and sex of the individual, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1 mg per day of total active ingredients.

In an embodiment of the invention, a pharmaceutical kit or kit of parts is provided comprising one or more containers filled with one or more pharmaceutical compositions of the invention and optionally one or more pharmaceutically acceptable excipients as described herein. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. Preferably, a pharmaceutical kit or kit of parts comprises instructions for use.

The compounds of the invention are modulators of the S1P receptor, in particular of the S1P5 receptor. More specifically, the compounds of the invention are S1P5 receptor agonists. The compounds are useful in the treatment, alleviation and/or prevention of diseases or disorders mediated by an SLP receptor, preferably S1P5. The compounds of the present invention are particularly suitable to treat, alleviate or prevent diseases and conditions in which an S1P receptor is involved or in which modulation of the endogenous S1P signaling system via an S1P receptor is involved, preferably S1P5.

Provided is therefore a method of treatment, alleviation or prevention of a disease or condition in which an S1P receptor is involved or in which modulation of the endogenous S1P signaling system via an S1P receptor is involved, preferably S1P5, comprising administering to a patient in need thereof a compound according to the invention or a pharmaceutically acceptable salt, solvate, tautomer, stereoisomer or N-oxide thereof. Said patient is preferably a human patient.

Further provided is a use of a compound according to the invention or a pharmaceutically acceptable salt, solvate, tautomer, stereoisomer or N-oxide thereof for the manufacture of a medicament for the treatment, alleviation or prevention of a disease or condition in which an S1P receptor is involved or in which modulation of the endogenous S1P signaling system via an S1P receptor is involved, preferably S1P5 receptor.

Further provided is a compound according to the invention, or a pharmaceutically acceptable salt, solvate, tautomer, stereoisomer or N-oxide thereof for use in therapy, preferably for use as a medicament.

Further provided is a compound according to the invention or a pharmaceutically acceptable salt, solvate, tautomer, stereoisomer or N-oxide thereof, or a pharmaceutical composition comprising such compound, or a pharmaceutically acceptable salt, solvate, tautomer, stereoisomer or N-oxide thereof, for use in the treatment, alleviation or prevention of a disease or condition in which an S1P receptor is involved or in which modulation of the endogenous S1P signaling system via an S1P receptor is involved, preferably S1P5.

Said diseases or condition is preferably selected from the group consisting of Alzheimer's Disease (AD) and associated dementia's, amyloid β-associated disorders, Mild Cognitive Impairment (MCI), Parkinson's Disease (PD), Lewy Body Dementia (LBD), Progressive Supranuclear Palsy (PSP), Cerebral Palsy (CP), Amyotrophic Lateral Sclerosis (ALS), Frontal Temporal Lobe Dementia (FTLD), multiple sclerosis, Huntington's Disease, neurological symptoms of sphingolipidosis disorders, a lysosomal storage disorder including Tay Sachs Disease, Sandhoff Disease, Fabry's Disease, Krabbe Disease, Gaucher's Disease, Niemann Pick A, B or C, and Batten's Disease, stroke, HIV-associated Dementia (HAD), HIV-associate Neurocognitive Disorder (HAND), HIV-associated neuropathy, schizophrenia, cognitive deficits in Schizophrenia, an attention deficit disorder including Anxiety Attention Deficit Disorder and Attention Deficit Hyperactivity Disorder (ADHD), a bipolar disorder. Obsessive-Compulsive Behavior, pain including neuropathic, back pain and pain-associated with multiple sclerosis, spinal cord injury, Parkinson's Disease, epilepsy, diabetes and cancer, cancer-induced peripheral neuropathy (CIPN), depression, treatment-resistant depression, Creutzfeld-Jakob Disease and other Prion-related Disorders, Down's Syndrome, autism, age-related cognitive decline or memory impairment, cognitive deficits associated with diabetes, dementia, dementia associated with Down's Syndrome, cognitive deficits in psychiatric disorders, dementia associated with Lewy Body pathology, diminished CNS function associated with traumatic brain injury, Pick's Disease, spinal cord injury, a demyelinating disorder, a disorder of basal ganglia, AIDS-associated dementia, Psoriasis type 1 and type 2, atopic dermatitis, dermatitis scleroderma, insulin-dependent diabetes mellitus, ulcerative colitis, atherosclerosis, sepsis syndrome, septic shock, Dengue hemorrhagic fever, Dengue, atopic allergy, HIV/AIDS, barrier-integrity associated lung diseases, leukemia, contact dermatitis, encephalomyelitis, Epstein Barr virus infection and other virus infections requiring cell-cell fusion.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

References described herein are incorporated by reference. Neither these, nor any other documents or citations to any references, are admitted to be prior art documents or citations.

The invention will be explained in more detail in the following, non-limiting examples.

EXAMPLES

Abbreviations
AcOH acetic acid
ACN acetonitrile
DBU diazabicyclo[5.4.0]undec-7-ene
DCM dichloromethane
DEAD diethyl azodicarboxylate
DIPEA N,N-Diisopropylethylamine
DMF N,N-dimethylformamide
DMSO dimethyl sulfoxide
EA ethyl acetate
Eq molar equivalent
$Et_3N$ triethylamine
$Et_2O$ diethyl ether
EtOAc ethyl acetate
EtOH ethanol
KOH potassium hydroxyde
KOtBu potassium tert-butoxide
MeOH methanol
MTBE/MTB ether methyl tert-butyl ether
NaOH sodium hydroxide
NMP N-methyl-2-pyrrolidinone
Pd—C palladium-on-carbon
PE petroleum ether
RT room temperature
RuPHOS 2-Dicyclohexylphosphino-2',6'-di-i-propoxy-1,1'-biphenyl
TLC thin layer chromatography
TFA trifluoroacetic acid
THF tetrahydrofuran
v/v volume/volume
XPHOS 2-Dicyclohexylphosphino-2',4',6'-triisopropylbiphenyl 1. Methods Liquid Chromatography-Mass Spectrometry (LC-MS) Analytical samples were run on Agilent 1200 series instruments controlled by Agilent ChemStation Software. The system consists of an injector, a column compartment for 2 columns, a binary solvent pump, an UV-detector and a quadrupole mass spectrometer (Agilent 6100 series, ESI-ionization). If not stated otherwise, the mobile phase consisted of water and acetonitrile, both acidified with 0.1% formic acid. Separation was performed on YMC Meteoric Core C18 columns with 50 mm in length, 2.1 mm in diameter and packed with 2.7 μm material. Elution was done at 50° C. with a linear gradient ramping from 5 to 100% organic solvent over 1.8 min at a constant flow rate of 1 mL/min.

Nuclear Magnetic Resonance (NMR)

The compounds were either characterized via proton-NMR in d6-dimethylsulfoxide, d-chloroform, d-methanol or d-pyridine on a 400 MHz (Bruker) or 500 MHz NMR instrument (Bruker Avance 500 MHz with 5 mm BBFo-z-Grd) or a 600 MHz (Bruker Avance 600 MHz with 5 mm Cryoprobe CPTCI (1H-13C/15N z-Grd), and/or by mass spectrometry.

The magnetic nuclear resonance spectral properties (NMR) refer to the chemical shifts (δ) expressed in parts per million (ppm). The relative area of the shifts in the 1H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m). Signals covered by deuterated solvents are not reported.

Separation of the Pure Enantiomers of Chiral Compounds.

Two Supercritical Fluid Chromatography (SFC) methods were used to separate enantiomers from racemates of chiral compounds, referred to as "analytical SFC" and "preparative SFC". The former is in particular suitable for small scale and the latter for larger scale.

Analytical SFC

Samples were run on an Agilent 1260 Infinity Hybrid SFC System, controlled by Agilent OpenLab CDS ChemStation Edition. The system consists of an injector, a heated column compartment including a switch for 15 columns, a $CO_2$-booster pump and a binary pump module for $CO_2$ and modifier flow. Detection was done with an UV-detector and Agilent 1100 series quadrupole mass spectrometer (ESI ionization). The backpressure regulator was set to 160 bar and heated to 60° C. If not stated otherwise, the columns were 100 mm in length, 4.6 mm in diameter and packed with 5 μm material. They were kept at RT during analysis. As mobile phase, a mixture of liquefied $CO_2$ and organic modifier with additive was used as indicated for each sample. The flow rate was kept at 3.5 mL/min.

Preparative SFC

Preparative separations were carried out on a Waters Prep 100q SFC System, controlled by Waters MassLynx Software. The system consists of an open bed injector/collector, a heated column compartment including a switch for 6 columns, a $CO_2$-booster pump, a pump module for modifier flow. Detection was done by UV and a quadrupole mass spectrometer (Waters Aquity QDa, ESI-ionization). To enable quantitative collection, the gas liquid separator was driven with a make-up flow of 30 mL/min methanol. The backpressure regulator was set to 120 bar and heated to 60° C. If not stated otherwise, the columns were 250 mm in length, 20 mm in diameter and packed with 5 μm material. They were kept at 30° C. during the separation. As mobile phase, a mixture of liquefied $CO_2$ and organic modifier with additive was used as indicated for each sample. The flow rate was kept at 100 g/min.

APS Purification Method Protocol

Analytical UPLC-MS on Waters Instrument:

Analytical UPLC-MS was performed on a Waters SQD mass spectrometer and Acquity UPLC system running MassLynx 4.1 and Openlynx 4.1 software. The SQD mass spectrometer was operated under positive APCI ionization conditions. The column used was a Waters BEH C8, 1.7 μm (2.1 mm×30 mm) at a temperature of 55° C.

"Ammonium Acetate Method": A gradient of 10-100% acetonitrile (A) and 10 mM ammonium acetate in water (B) was used, at a flow rate of 1.0 mL/min (0-0.1 min 10% A, 0.1-1.1 min 10-100% A, 1.1-1.3 min 100% A, 1.3-1.4 min 100-10% A).

APS Agilent Prep-HPLC-MS Purification

Samples were purified by preparative HPLC on 2-coupled C8 5 um 100 Å columns (30 mm×75 mm each).

"Ammonium Acetate Method": A gradient of acetonitrile (A) and 10 mM ammonium acetate in water (B) was used, at a flow rate of 50 mL/min (0-0.5 min 5% A, 0.5-8.5 min linear gradient 05-100% A, 8.7-10.7 min 100% A, 10.7-11 min linear gradient 100-05% A).

Samples were injected in 1.5 mL DMSO:MeOH (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B. 10.03), Agilent A2Prep, and Leap FractPal software, with custom Chemstation macros for data export.

2. General Synthesis Methods

The compounds of the formula (I) can be prepared by analogy to methods which are well known in the art. A suitable method for the preparation of compounds of formula (I) is outlined in the following schemes.

The process depicted in scheme 1a is useful for obtaining the central tetraline core wherein X=C. The carbon atom to which —OP is attached in the phenyl in compound A can be varied.

Scheme 1a:

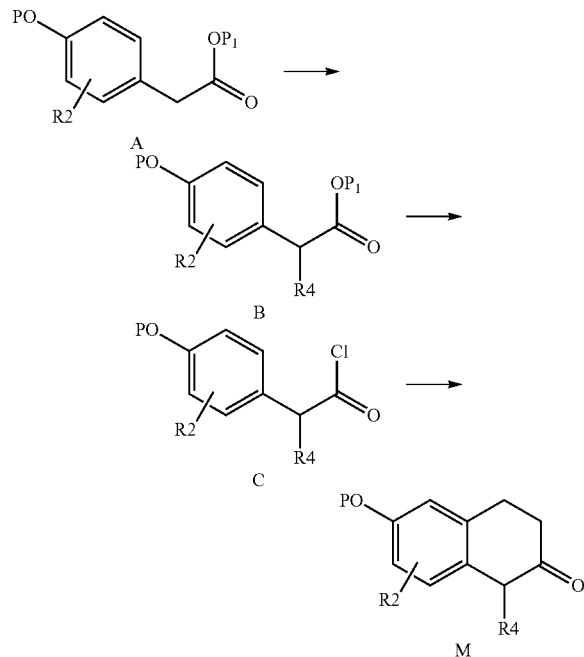

If desired and as shown in the above scheme 1a, the compound of general formula A readily undergoes alkylation to give the compound of general formula B. Conversion to the acid chloride and subsequent ring closure with ethylene in the presence of a Lewis acid (e.g. AlCl3) affords compound M (e.g. J. Het. Chem., 23 (2), 343, 1986 and Bioorg. Med. Chem. Let, 17 (22), 6160, 2007)

The variables R4, R2 are as defined herein and P, P1 are suitable protecting groups (e.g. P, P1=Me). Deprotection can be achieved e.g. in case P=Me by the use of BBr3.

The process depicted in scheme 1b is useful for obtaining the central chromane core wherein X=O. The carbon atom to which —OP is attached in the phenyl in compound E can be varied.

Scheme 1b:

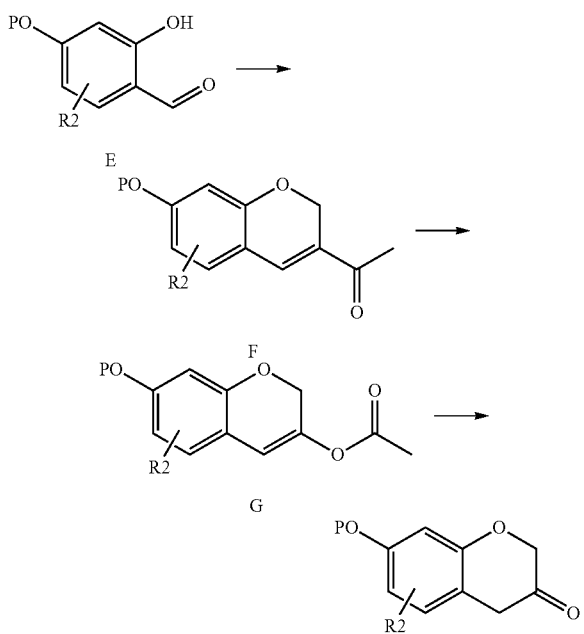

Compound E can be cyclized to F with methylvinylketone in the presence of base (e.g. DABCO). Bayer-Villiger rearrangement (e.g. with oxone) and subsequent hydrolysis of the enolester will afford compound Q The process depicted in scheme 1c is useful for obtaining the central isochromane core wherein Y=O and X=CH2-Br. The carbon atom to which —OP is attached in the phenyl in compound A4 can be varied.

Scheme 1c:

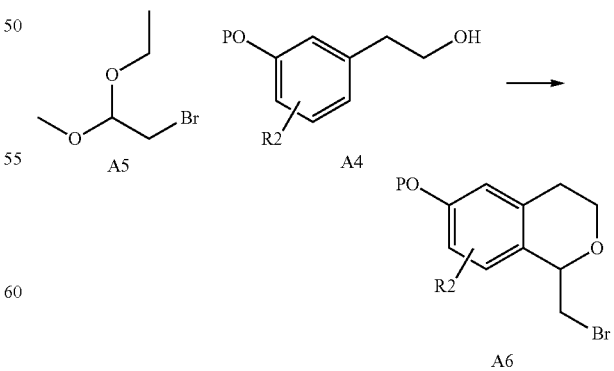

Compound A4 can be cyclized to A6 with 2-bromo-1,1-diethoxyethane in the presence of an acid (e.g. HCl) in analogy to Indian J. Chem, Vol. 16B, p. 793-796, 1978

The process depicted in scheme 1d is useful for obtaining the central chromane core wherein X=O and R4 is a carbonyl group. The carbon atom to which —OP is attached in the phenyl in compound A10 can be varied.

Scheme 1d:

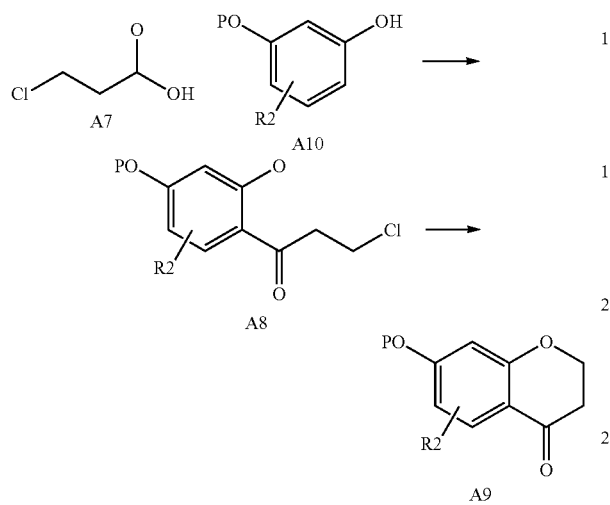

Compound A10 can be acylyzed to A8 with A7 in the presence of an acid (e.g. triflic acid). Subsequent acylation in the presence of an base (e.g. NaOH) affords compounds of type A9 in analogy to WO2009158426 or Journal of Enzyme Inhibition and Medicinal Chemistry, 31(3), 389-397; 2016

The process depicted in scheme 1e is useful for obtaining the central isochromane core wherein Y=O and R4 is a carbonyl group. The carbon atom to which —OP is attached in the phenyl in compound A14 can be varied.

Scheme 1e:

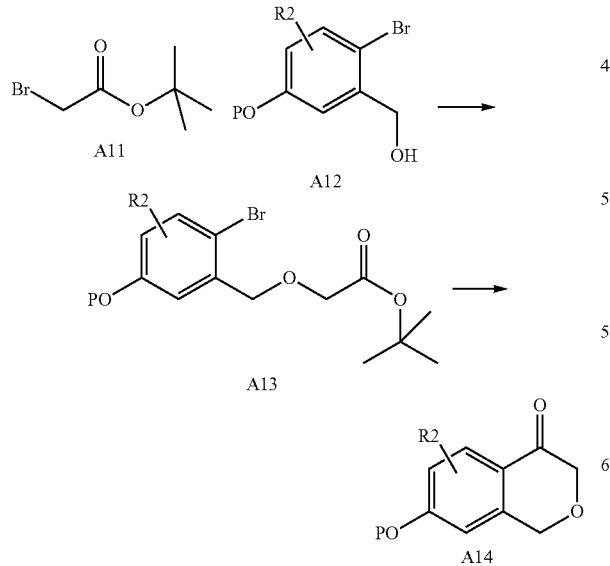

Compound A12 can be alkylated to A13 with A11 in the presence of an base (e.g. potassium carbonate). Subsequent ring closure in the presence BuLi affords compounds of type A14 in analogy to Bioorganic & Medicinal Chemistry Letters, 25(22), 5212-5216; 2015

Numerous compounds of formula M, Q, A6, A9 and A14 are also commercially available.

Compounds M, Q, A9 and A14 can be transformed to compounds A2, A15, A16 with an appropriate amine containing the R1 moiety in the presence of a reducing agent (reductive amination) as depicted in scheme 2a.

When the R1-moiety contains an ester the corresponding acid can be obtained by saponification under basic (e.g. NaOH) or acidic (e.g. TFA) conditions (see also Scheme 4)

Scheme 2a:

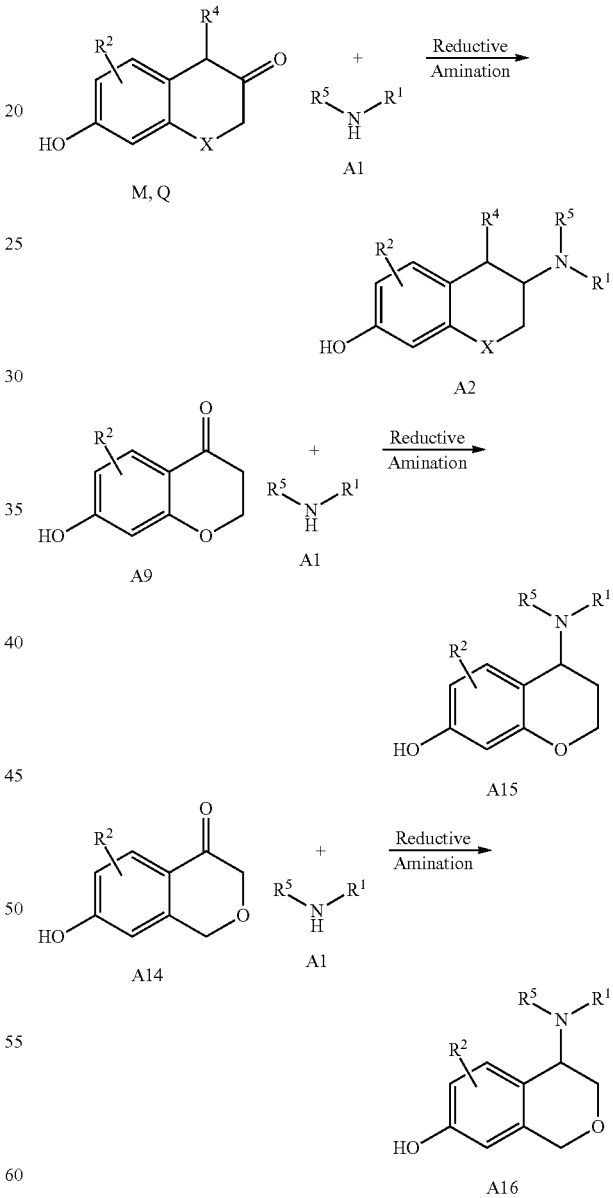

Compounds A6 can be transformed to compounds A19 and A21 by alkylation with an appropriate amine or alcohol, containing the R1 moiety, in the presence of a base (e.g. cesium carbonate) as depicted in scheme 2b. When the R1-moiety contains an ester the corresponding acid can be obtained by saponification under basic (e.g. NaOH) or acidic (e.g. TFA) conditions (see also Scheme 4)

Scheme 2b:

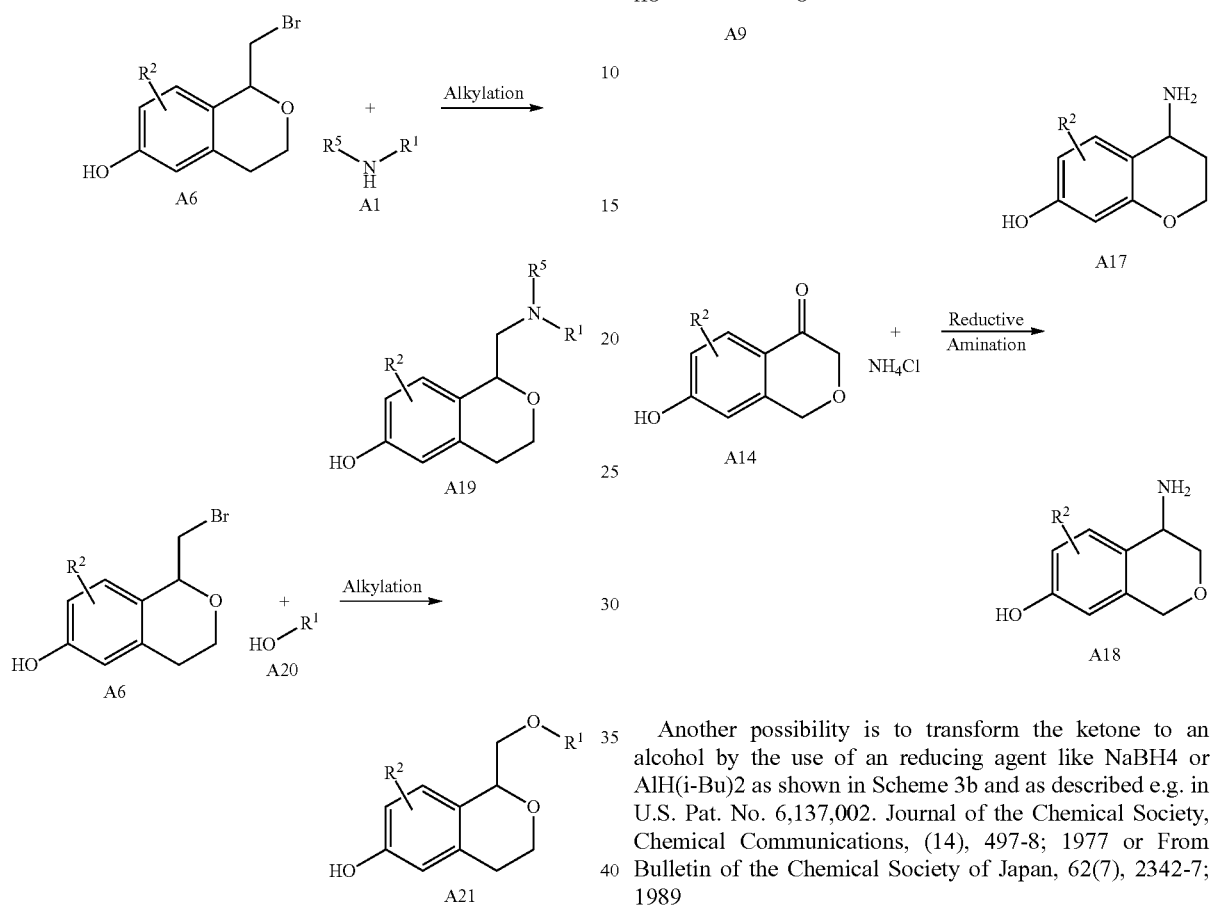

Compounds M, Q, A9 and A14 can be transformed to compounds A3, A17 and A18 with ammonium chloride in the presence of a reducing agent (reductive amination) as depicted in scheme 3a.

Scheme 3a:

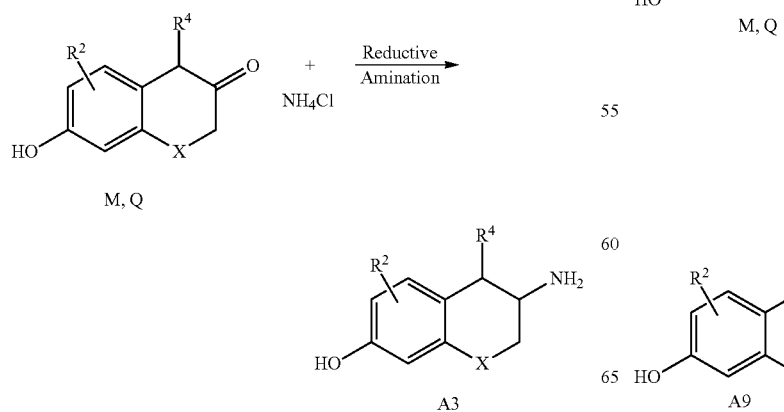

Another possibility is to transform the ketone to an alcohol by the use of an reducing agent like NaBH4 or AlH(i-Bu)2 as shown in Scheme 3b and as described e.g. in U.S. Pat. No. 6,137,002. Journal of the Chemical Society, Chemical Communications, (14), 497-8; 1977 or From Bulletin of the Chemical Society of Japan, 62(7), 2342-7; 1989

Scheme 3b:

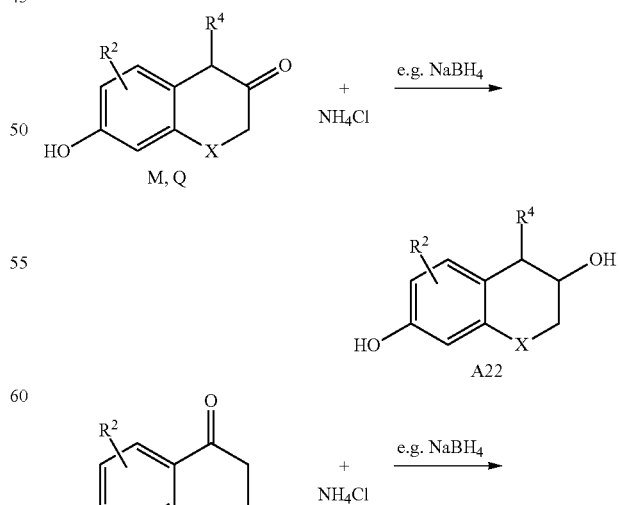

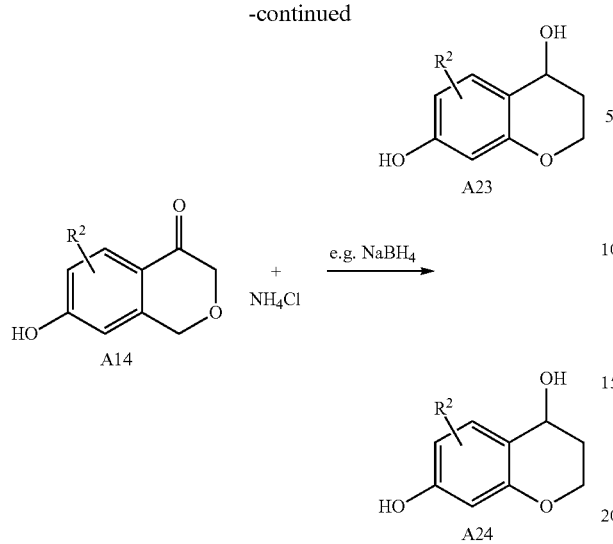
R1-moieties can then be introduced starting from compounds A3, wherein X is O or CH2. Scheme 4 shows a number of routes. It is clear to a person skilled in the art that these are suitable to introduce alternative substituents in these compounds using the appropriate reagent(s), and that these transformations can also be done using A17 or A18 as starting material
Scheme 4
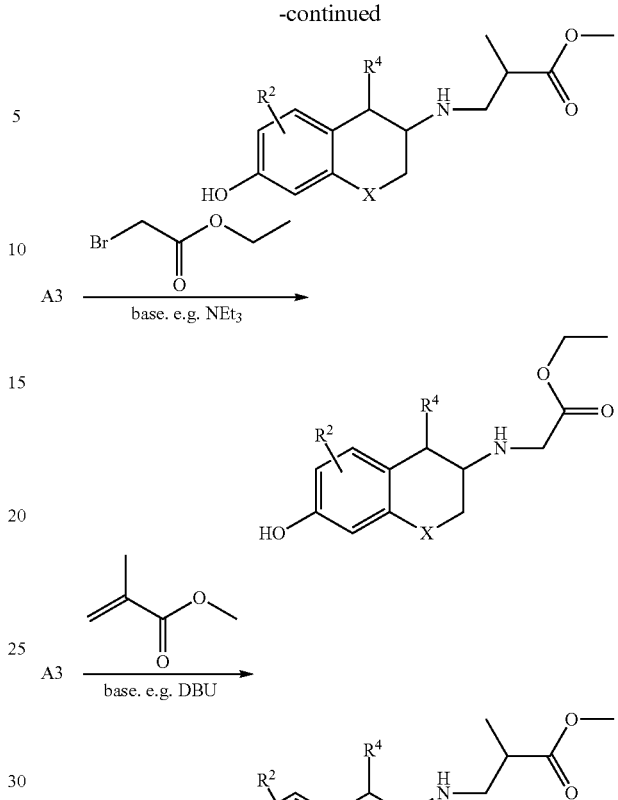
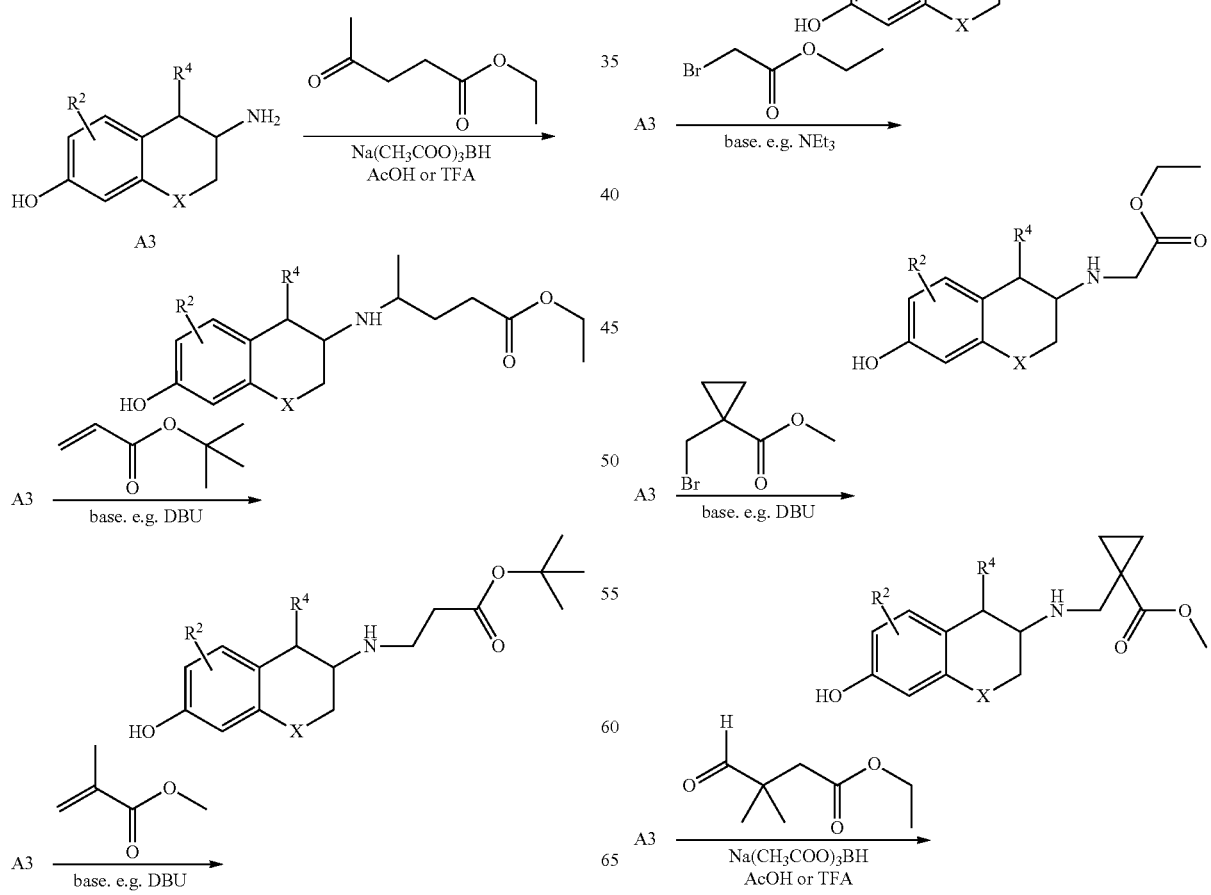

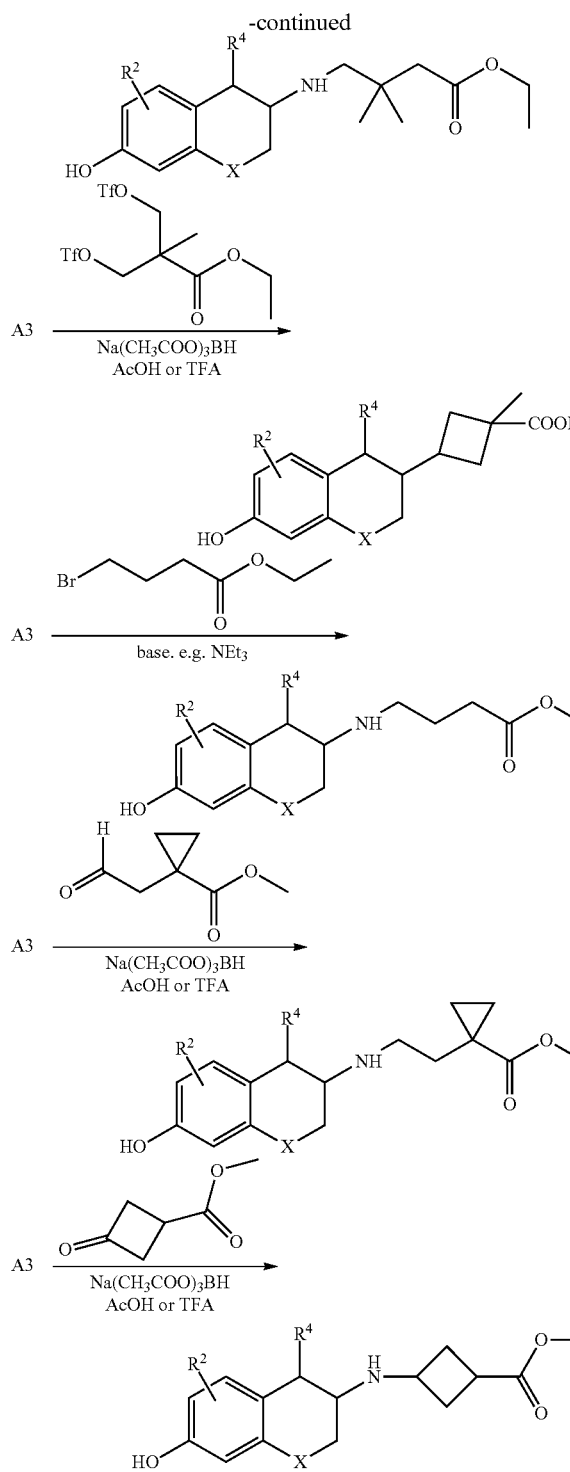

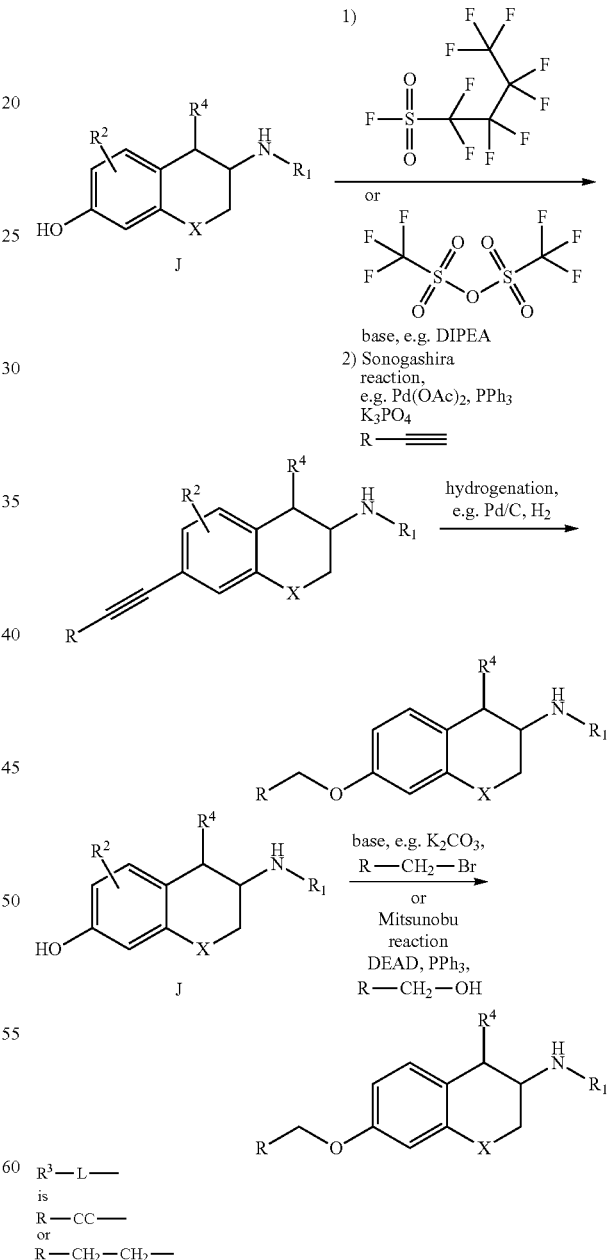

starting from the corresponding phenols via the corresponding nonaflates or triflates followed by a Suzuki reaction with an appropriate boronic acid.

If the R1-moiety contains an ester the corresponding acid can be obtained by saponification under basic (e.g. NaOH) or acidic (e.g. TFA) conditions.

Scheme 5 shows a number of routes starting from R2 substituted aminotetralines or chromanes. It is clear to a person skilled in the art that these routes are suitable to introduce R3-L-moieties the further cores of the invention as well.

Scheme 5:

R3—L—
is
R—CC—
or
R—CH$_2$—CH$_2$—
or
R—CH$_2$—O—
or
R—CH$_2$—O—Ph—

R3-L-moieties can be introduced starting from the corresponding phenols via the corresponding nonaflates or triflates followed by Sonogashira reaction with an substituted alkyne, or by the same protocol followed by hydrogenation which can yield the corresponding ethenyl derivative as shown in scheme 5. R3-L-moieties that contain a phenyl ether can be obtained under alkylating conditions using the corresponding alkylhalide precursors or under Mitsunobu conditions using the corresponding alkyl alcohols. R3-L-moieties that contain a phenyl linker can be introduced -continued

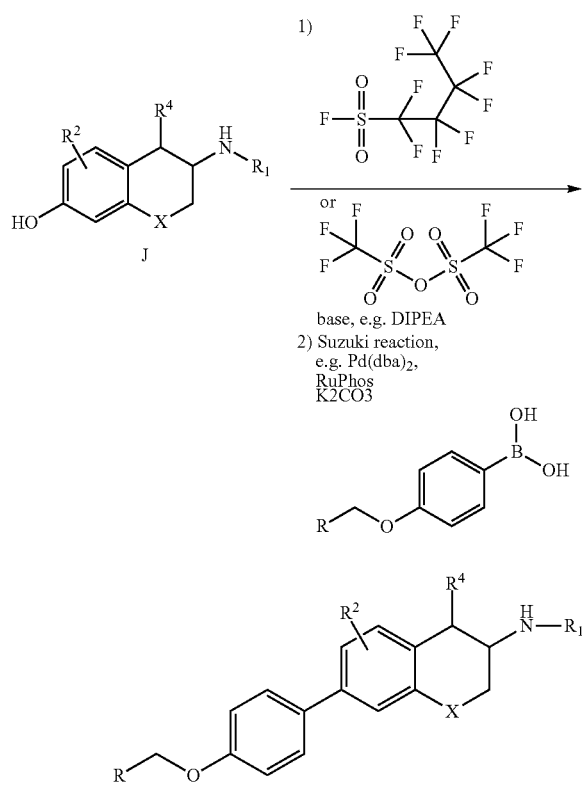

The processes depicted in schemes 6 and 7 are useful for obtaining compounds (I) wherein Z=OR1. The carbon atom to which —OH is attached in the phenyl in compounds A22 can be varied. It is clear to a person skilled in the art that these transformations can also be done using A21, A23 or A24 as starting material R3-L-moieties that contain a phenyl ether can be obtained under alkylating conditions using the corresponding alkyl halide precursors or under Mitsunobu conditions using the corresponding alkyl alcohols.

Scheme 6:

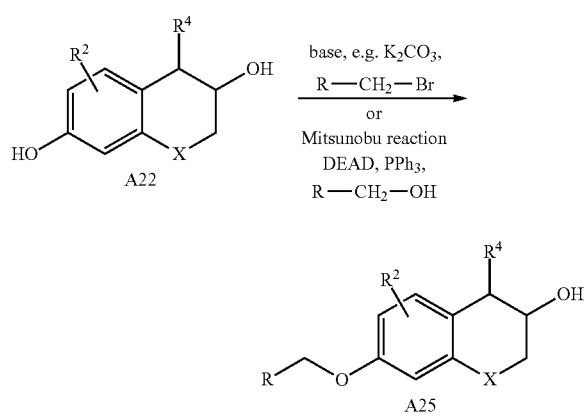

R1-moieties can then be introduced starting from compounds A25, wherein X is O or CH2. Scheme 7 shows a number of routes. It is clear to a person skilled in the art that these routes are suitable to introduce alternative substituents in these compounds using the appropriate reagent(s)

Scheme 7:

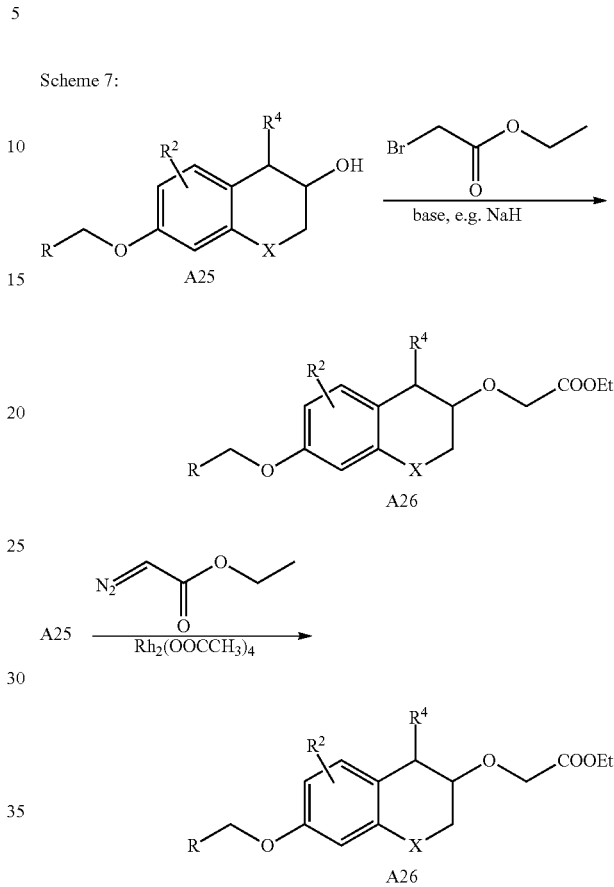

If the R1-moiety contains an ester the corresponding acid can be obtained by saponification under basic (e.g. NaOH) or acidic (e.g. TFA) conditions.

The moiety CH2-R in A26 can also be regarded as a protecting group for the phenolic OH group. Deprotection can then occur by several routes e.g. by hydrogenation in case R=Phenyl, resulting again the free phenol.

Further R3-L-moieties can then be introduced starting from such phenols via the corresponding nonaflates or triflates followed by Sonogashira reaction with an substituted alkyne, or by the same protocol followed by hydrogenation which can yield the corresponding ethenyl derivative as shown in scheme 5 for X=CH2. Also R3-L-moieties that contain a phenyl linker can be introduced via the corresponding nonaflates or triflates followed by a Suzuki reaction with an appropriate boronic acid.

In the following section the introduction of alternative linkers L and R3-L-moieties is described. It is clear to a skilled person that the routes described for specific compounds can be used to introduce the same linker L and R3-L-moieties in other compounds according to the invention.

3. Synthesis of Compounds According to the Invention

The compounds for which the synthesis is described below are shown in table 1.

1. 1-(7-((2,6-dichlorobenzyl)oxy)chroman-3-yl)azetidine-3-carboxylic acid

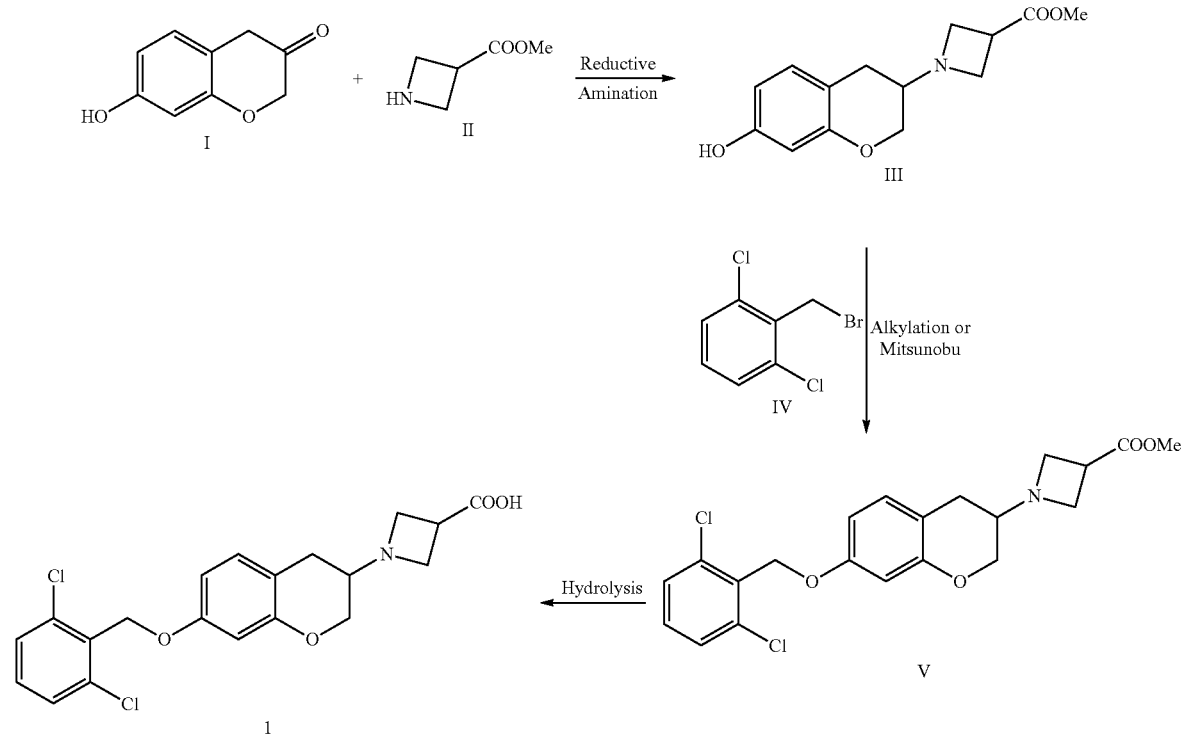

1.1. Methyl 1-(7-hydroxychroman-3-yl)azetidine-3-carboxylate 7-hydroxychroman-3-one (compound I; 48 mg, 0.3 mmol) and sodium acetate (27 mg, 0.33 mmol) were dissolved at room temperature in methanol (2 ml). Methyl-azetine-3-carboxylate hydrochloride (compound II; 48 mg, 0.32 mmol) was added and stirred at RT for 1 h. Sodium cyanoborohydride (91 mg, 1.4 mmol) was added (adjusted pH to 4-5 using HOAc) stirred at RT for 1 h, neutralized with $NaHCO_3$ (pH=7-8) and diluted with EtOAc. After phase separation, the organic layer was washed with brine, dried over $Na_2SO_4$, filtered and evaporated to obtain the crude product, which was purified by chromatography (33 mg white foam).

1.2. Methyl 1-(7-((2,6-dichlorobenzyl)oxy)chroman-3-yl)azetidine-3-carboxylate Compound III (33 mg, 0.13 mmol) was dissolved in DMF. 2-(bromomethyl)-1,3-dichlorobenzene (compound IV; 33 mg, 0.14 mmol) and potassium carbonate (26 mg, 0.19 mmol) were added and stirred at RT overnight. The mixture was diluted with water and extracted with ethylacetate. The organic layer was washed with brine dried with $Na_2SO_4$ and evaporated. The residue purified by flash chromatography (silica gel) giving product V with a yield of 34 mg.

1.3 1-(7-((2,6-dichlorobenzyl)oxy)chroman-3-yl)azetidine-3-carboxylic acid

Compound V (34 mg, 0.08 mmol) was dissolved in methanol (0.5 ml) and 0.6 ml 2N KOH (1.2 mmol) was added. The mixture was placed in a micro wave and heated to 100° C. for 30 min. Then the solvent was evaporated, the residue dissolved in water adjusted to pH4 and extracted with DCM/ethyl acetate. The organic layer was dried over $Na_2SO_4$, evaporated and diisopropyl ether was added to the residue. The resulting white solid was filtered and dried affording 22.6 mg of desired product.

$^1$H NMR (600 MHz, DMSO-$d_6$) δ 7.56 (d, J=8.1 Hz, 2H), 7.46 (dd, J=8.7, 7.5 Hz, 1H), 6.95 (d, J=8.3 Hz, 1H), 6.52 (dd, J=8.4, 2.6 Hz, 1H), 6.44 (d, J=2.5 Hz, 1H), 5.14 (s, 2H), 4.00-3.95 (m, 1H), 3.74 (dd, J=11.1, 6.2 Hz, 1H), 3.46 (t, J=7.4 Hz, 1H), 3.41 (t, J=7.4 Hz, 1H), 3.29-3.21 (m, 2H), 3.17 (p, J=7.5 Hz, 1H), 2.75 (dd, J=15.9, 4.8 Hz, 1H), 2.66-2.59 (m, 1H), 2.42-2.31 (m, 1H).

2. 1-(6-((2-chloro-6-ethylbenzyl)oxy)-1,2,3,4-tetrahydronaphthalen-2-yl)azetidine-3-carboxylic acid

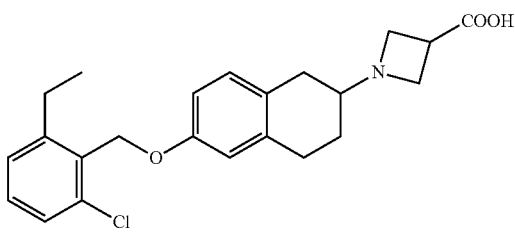 [SMILES: CCc1cccc(Cl)c1COc1ccc2c(c1)CCC(N1CC(C(=O)O)C1)C2]

Compound 2 was prepared as described for Compound 1 using 6-hydroxy-3,4-dihydronaphthalen-2(1H)-one instead of 7-hydroxychroman-3-one and 2-(bromomethyl)-1-chloro-3-ethylbenzene instead of 2-(bromomethyl)-1,3-dichlorobenzene.

$^1$H NMR (600 MHz, Methanol-d$_4$) δ 7.31-7.28 (m, 2H), 7.24-7.21 (m, 1H), 7.08 (d, J=8.3 Hz, 1H), 6.87-6.81 (m, 2H), 5.17 (d, J=0.8 Hz, 2H), 4.50-4.31 (m, 4H), 3.70-3.52 (m, 2H), 3.21-3.09 (m, 1H), 2.97-2.88 (m, 2H), 2.76 (q, J=7.6 Hz, 2H), 2.65 (dd, J=15.7, 9.5 Hz, 1H), 2.30-2.12 (m, 1H), 1.76-1.63 (m, 1H), 1.22 (t, J=7.6 Hz, 3H).

3. 1-(7-((2-fluorobenzyl)oxy)chroman-3-yl)azetidine-3-carboxylic acid

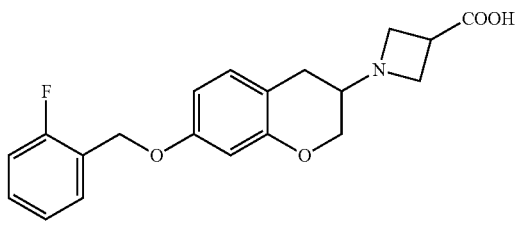 [SMILES: O=C(O)C1CN(C2COc3cc(OCc4ccccc4F)ccc3C2)C1]

Compound 3 was prepared as described for compound 1 using 1-(bromomethyl)-2-fluorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-d$_6$) δ 7.55-7.49 (m, 1H), 7.45-7.38 (m, 1H), 7.27-7.21 (m, 3H), 6.93 (d, J=8.4 Hz, 1H), 6.49 (dd, J=8.3, 2.6 Hz, 1H), 6.38 (d, J=2.5 Hz, 1H), 5.06 (s, 2H), 4.00-3.94 (m, 1H), 3.71 (dd, J=11.0, 6.4 Hz, 1H), 3.45 (t, J=7.5 Hz, 1H), 3.28-3.21 (m, 2H), 3.19-3.13 (m, 1H), 2.74 (dd, J=15.8, 4.9 Hz, 1H), 2.61-2.57 (m, 1H), 2.35 (dd, J=15.8, 6.5 Hz, 1H).

4. 1-(6-((2,6-dichlorobenzyl)oxy)-1,2,3,4-tetrahydronaphthalen-2-yl)azetidine-3-carboxylic acid

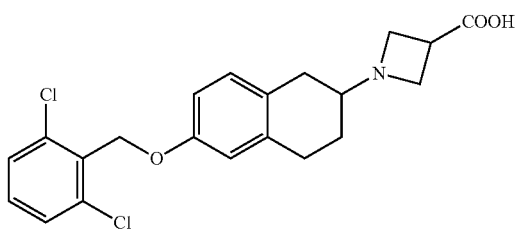 [SMILES: O=C(O)C1CN(C2CCc3cc(OCc4c(Cl)cccc4Cl)ccc3C2)C1]

4.1. tert-Butyl 1-(6-hydroxy-1,2,3,4-tetrahydronaphthalen-2-yl)azetidine-3-carboxylate Compound 4.1 was prepared as described for Compound III using 6-hydroxy-3,4-dihydronaphthalen-2(1H)-one instead of 7-hydroxychroman-3-one and tert-butyl azetidine-3-carboxylate instead of ethyl azetidine-3-carboxylate.

4.2. tert-Butyl 1-(6-hydroxy-1,2,3,4-tetrahydronaphthalen-2-yl)azetidine-3-carboxylate tert-Butyl 1-(6-hydroxy-1,2,3,4-tetrahydronaphthalen-2-yl)azetidine-3-carboxylate (79 mg, 0.26 mmol) was dissolved in DMF (2 ml) and cooled down to 0° C., followed by addition of potassium tert-butoxide 1.6M in THF (0.195 ml, 0.312 mmol). The mixture was stirred for 1 h, 2-(bromomethyl)-1,3-dichlorobenzene, (74.8 mg, 0.312 mmol) was added and the reaction mixture was stirred for 2 h, allowing the temperature to warm up to room temperature. The mixture was evaporated, water was added and extracted three-times with EtOAc, The organic layers were combined and washed with brine, dried over Na$_2$SO$_4$, filtered and evaporated (pale brown oil; 110 mg).

4.3 1-(6-((2,6-dichlorobenzyl)oxy)-1,2,3,4-tetrahydronaphthalen-2-yl)azetidine-3-carboxylic acid Crude tert-butyl 1-(6-((2,6-dichlorobenzyl)oxy)-1,2,3,4-tetrahydronaphthalen-2-yl)azetidine-3-carboxylate (110 mg, 0.238 mmol) was dissolved in formic acid (1 ml, 26 mmol, stirred at room temperature overnight and heated to 40° C. for further 2 h. The solvent was evaporated and the residue purified by chromatography yielding 13 mg of product.

$^1$H NMR (600 MHz, Methanol-d$_4$) δ 7.45 (dd, J=7.9, 1.3 Hz, 2H), 7.41-7.32 (m, 1H), 7.08 (d, J=8.8 Hz, 1H), 6.89-6.78 (m, 2H), 5.25 (s, 2H), 4.54-4.35 (m, 3H), 3.80-3.52 (m, 2H), 3.24-3.11 (m, 1H), 3.01-2.86 (m, 2H), 2.73-2.60 (m, 1H), 2.26-2.17 (m, 1H), 1.77-1.62 (m, 1H).

5. 1-((6-((2-chloro-6-ethylbenzyl)oxy)-1,2,3,4-tetrahydronaphthalen-2-yl)amino)cyclopropanecarboxylic acid

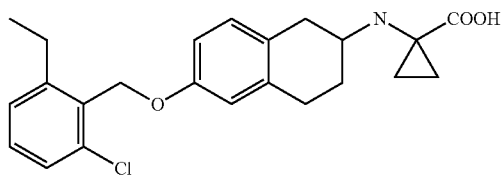 [SMILES: CCc1cccc(Cl)c1COc1ccc2c(c1)CCC(NC1(C(=O)O)CC1)C2]

5.1. Ethyl 1-((6-hydroxy-1,2,3,4-tetrahydronaphthalen-2-yl)amino)cyclopropanecarboxylate Compound 5.1 was prepared as described for Compound III using 6-hydroxy-3,4-dihydronaphthalen-2(1H)-one instead of 7-hydroxychroman-3-one and ethyl 1-aminocyclopropanecarboxylate of methyl azetidine-3-carboxylate.

5.2. Ethyl 1-((tert-butoxycarbonyl)(6-hydroxy-1,2,3,4-tetrahydronaphthalen-2-yl)amino)cyclopropanecarboxylate Ethyl 1-((6-hydroxy-1,2,3,4-tetrahydronaphthalen-2-yl)amino)cyclopropanecarboxylate (200 mg, 0.726 mmol), BOC-Anhydride (0.422 ml, 1.816 mmol) and N,N-dimethylpyridin-4-amine (222 mg, 1.816 mmol) in dioxane (3 ml), were heated to 100° C. for 2 h and stirred at room temperature overnight. The mixture was diluted with ethylacetate, washed with 0.5N HCl, dried over MgSO$_4$, filtrated and evaporated. The crude product was purified by chromatography (silica gel) affording 98 mg of desired product as clear oil.

5.3. Ethyl 1-((tert-butoxycarbonyl)(6-((2-chloro-6-ethylbenzyl)oxy)-1,2,3,4-tetrahydronaphthalen-2-yl)amino)cyclopropanecarboxylate Compound 5.3 was prepared as described for Compound 4.2 using 2-(bromomethyl)-1-chloro-3-ethylbenzene instead of 2-(bromomethyl)-1,3-dichlorobenzene.

5.4. Ethyl 1-((6-((2-chloro-6-ethylbenzyl)oxy)-1,2,3,4-tetrahydronaphthalen-2-yl)amino)cyclopropanecarboxylate Ethyl 1-((tert-butoxycarbonyl)(6-((2-chloro-6-ethylbenzyl)oxy)-1,2,3,4-tetrahydronaphthalen-2-yl)amino)cyclopropanecarboxylate (89.3 mg, 0.169 mmol) in formic acid (2 ml, 52.1 mmol) was stirred at RT overnight. The solvent was evaporated to obtain crude ethyl 1-((6-((2-chloro-6-ethylbenzyl)oxy)-1,2,3,4-tetrahydronaphthalen-2-yl)amino)cyclopropanecarboxylate as a yellow oil which was used without further purification.

5.5. 1-((6-((2-chloro-6-ethylbenzyl)oxy)-1,2,3,4-tetrahydronaphthalen-2-yl)amino)cyclopropanecarboxylic acid Ethyl 1-((6-((2-chloro-6-ethylbenzyl)oxy)-1,2,3,4-tetrahydronaphthalen-2-yl)amino)cyclopropanecarboxylate (36 mg, 0.084 mmol) was added to KOH 2N in 1 ml Methanol and stirred at room temperature overnight. Solvent was evaporated and the residue purified by chromatography (silica gel) affording 4.6 mg of product.

$^1$H NMR (600 MHz, Methanol-$d_4$) δ 7.30-7.27 (m, 2H), 7.22 (dd, J=6.3, 2.7 Hz, 1H), 7.07 (d, J=8.4 Hz, 1H), 6.84 (dd, J=8.4, 2.7 Hz, 1H), 6.81 (d, J=2.6 Hz, 1H), 5.16 (d, J=1.2 Hz, 2H), 4.07-4.00 (m, 1H), 3.27-3.20 (m, 1H), 3.03-2.90 (m, 2H), 2.87 (dd, J=15.3, 10.8 Hz, 1H), 2.76 (q, J=7.6 Hz, 2H), 2.40-2.34 (m, 1H), 1.90-1.80 (m, 1H), 1.73-1.62 (m, 2H), 1.53-1.43 (m, 2H), 1.22 (t, J=7.6 Hz, 3H).

6. 3-((6-((2-chloro-6-ethylbenzyl)oxy)-1,2,3,4-tetrahydronaphthalen-2-yl)amino)propanoic acid

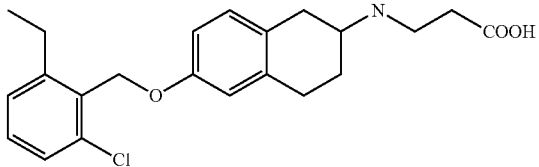 [SMILES: CCc1cccc(Cl)c1COc1ccc2c(c1)CCC(NCCC(=O)O)C2]

6.1. Ethyl 3-((6-hydroxy-1,2,3,4-tetrahydronaphthalen-2-yl)amino)propanoate A mixture of 6-hydroxy-3,4-dihydronaphthalen-2(1H)-one (1.5 g, 9.25 mmol), Titanium tetraisopropylate (5.50 ml, 18.50 mmol) and ethyl 3-aminopropanoate hydrochloride (1.705 g, 11.10 mmol) in dry THF (10 ml) was stirred for 8 h at RT under Argon. Sodium borohydride (1.050 g, 27.7 mmol) and ethanol (10 ml) were added and the resulting mixture was stirred for 12 h at RT. The mixture was diluted with 15 ml NaHCO$_3$ and 150 ml DCM filtered over celite and extracted with 50 ml DCM. The combined organic layers were washed with water and brine to obtain crude ethyl 3-((6-hydroxy-1,2,3,4-tetrahydronaphthalen-2-yl)amino)propanoate (1.26 g).

6.2 3-((6-((2-chloro-6-ethylbenzyl)oxy)-1,2,3,4-tetrahydronaphthalen-2-yl)amino)propanoic acid Compound 6 was subsequently prepared in analogy to compound 5 steps 5.2-5-5.

$^1$H NMR (600 MHz, Methanol-$d_4$) δ 7.30-7.26 (m, 2H), 7.22 (dd, J=6.3, 2.6 Hz, 1H), 7.08 (d, J=8.4 Hz, 1H), 6.84 (dd, J=8.4, 2.7 Hz, 1H), 6.82 (d, J=2.6 Hz, 1H), 5.16 (d, J=1.0 Hz, 2H), 3.59-3.51 (m, 1H), 3.44-3.36 (m, 2H), 3.23 (ddd, J=15.6, 5.3, 1.7 Hz, 1H), 3.02-2.89 (m, 2H), 2.86 (dd, J=15.5, 10.1 Hz, 1H), 2.81-2.72 (m, 4H), 2.36-2.28 (m, 1H), 1.92-1.82 (m, 1H), 1.22 (t, J=7.6 Hz, 3H).

7. 3-((6-(benzyloxy)-1,2,3,4-tetrahydronaphthalen-2-yl)amino)propanoic acid

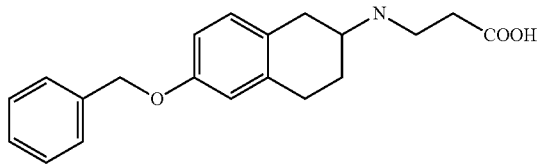 [SMILES: O=C(O)CCNC1CCc2cc(OCc3ccccc3)ccc2C1]

Compound 7 was prepared as described for Compound 6 using benzylbromide instead of 2-(bromomethyl)-1-chloro-3-ethylbenzene.

$^1$H NMR (600 MHz, Methanol-$d_4$) δ 7.43-7.39 (m, 2H), 7.38-7.33 (m, 2H), 7.32-7.27 (m, 1H), 7.05 (d, J=8.5 Hz, 1H), 6.81 (dd, J=8.4, 2.7 Hz, 1H), 6.77 (d, J=2.6 Hz, 1H), 5.04 (s, 2H), 3.57-3.50 (m, 1H), 3.40-3.36 (m, 2H), 3.23-3.17 (m, 1H), 2.98-2.87 (m, 2H), 2.82 (dd, J=15.6, 10.1 Hz, 1H), 2.74 (t, J=6.6 Hz, 2H), 2.33-2.26 (m, 1H), 1.89-1.80 (m, 1H).

8. 3-((6-((2-chlorobenzyl)oxy)-1,2,3,4-tetrahydronaphthalen-2-yl)amino)propanoic acid

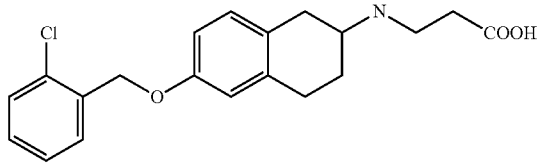 [SMILES: O=C(O)CCNC1CCc2cc(OCc3ccccc3Cl)ccc2C1]

Compound 8 was prepared as described for Compound 6 using 1-(bromomethyl)-2-chlorobenzene instead of 2-(bromomethyl)-1-chloro-3-ethylbenzene.

$^1$H NMR (600 MHz, Methanol-$d_4$) δ 7.56-7.50 (m, 1H), 7.44-7.40 (m, 1H), 7.34-7.28 (m, 2H), 7.07 (d, J=8.4 Hz, 1H), 6.82 (dd, J=8.4, 2.7 Hz, 1H), 6.78 (d, J=2.6 Hz, 1H), 5.13 (s, 2H), 3.58-3.50 (m, 0H), 3.43-3.36 (m, 2H), 3.25-3.17 (m, 1H), 2.99-2.88 (m, 2H), 2.83 (dd, J=15.6, 10.1 Hz, 1H), 2.78 (t, J=6.6 Hz, 2H), 2.35-2.27 (m, 0H), 1.90-1.81 (m, 1H).

9. 3-((6-((2,6-dichlorobenzyl)oxy)-1,2,3,4-tetrahydronaphthalen-2-yl)amino)propanoic acid

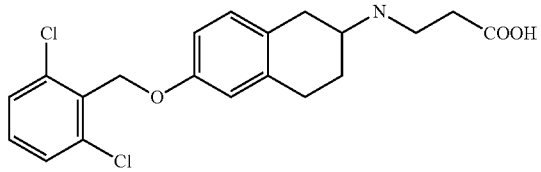 [SMILES: O=C(O)CCNC1CCc2cc(OCc3c(Cl)cccc3Cl)ccc2C1]

Compound 9 was prepared as described for Compound 6 using 2-(bromomethyl)-1,3-dichlorobenzene instead of 2-(bromomethyl)-1-chloro-3-ethylbenzene and methyl 3-aminopropanoate hydrochloride instead of ethyl 3-aminopropanoate hydrochloride.

$^1$H NMR: (600 MHz, DMSO-d$_6$) δ 7.64-7.50 (m, 2H), 7.50-7.43 (m, 1H), 7.14-7.03 (m, 1H), 6.93-6.79 (m, 2H), 5.18 (s, 2H), 3.52-3.43 (m, 1H), 3.25 (t, J=7.0 Hz, 2H), 3.15-3.07 (m, 1H), 2.92-2.70 (m, 3H), 2.70-2.64 (m, 2H), 2.25-2.13 (m, 1H), 1.82-1.68 (m, 1H).

10. 3-((7-((2,6-dichlorobenzyl)oxy)-1,2,3,4-tetrahydronaphthalen-2-yl)amino)propanoic acid

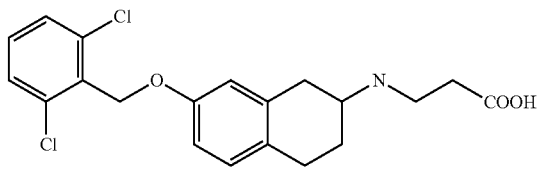 [SMILES: O=C(O)CCNC1CCc2ccc(OCc3c(Cl)cccc3Cl)cc2C1]

10.1 7-((2,6-dichlorobenzyl)oxy)-3,4-dihydronaphthalen-2(1H)-one

7-Hydroxy-tetralone (200 mg, 1.233 mmol) in DMF (1 ml) at 0° C. under Argon was mixed with potassium tert-butoxide (1.6M in THF, 0.925 ml, 1.480 mmol) and stirred for 1 h. 2-(bromomethyl)-1,3-dichlorobenzene (325 mg, 1.356 mmol) was added and the reaction mixture was stirred for 2 h, allowing the temperature to warm up to RT. The mixture was poured into cold 0.5M HCL and extracted with EtOAc. The combined organic layers were washed with water, dried over Na$_2$SO$_4$ filtered. After evaporation of the solvent a brown oil (559 mg) was obtained which was used without further purification.

10.2 7-((2,6-dichlorobenzyl)oxy)-1,2,3,4-tetrahydronaphthalen-2-amine

Ammonium chloride (72.5 mg, 1.356 mmol) was added to a solution of 7-((2,6-dichlorobenzyl)oxy)-3,4-dihydronaphthalen-2(1H)-one (from 10.1, 396 mg, 1.233 mmol) in methanol (3 ml) followed by NaCNBH$_4$ (116 mg, 1.849 mmol). The mixture was stirred at room temperature for 2 days. After evaporation of the solvent the residue was dissolved in DCM/sat. NaHCO$_3$ and subsequently extracted with DCM. The combined organic layers were dried over MgSO$_4$, filtered and the solvent evaporated affording crude 7-((2,6-dichlorobenzyl)oxy)-1,2,3,4-tetrahydronaphthalen-2-amine (279 mg, 0.433 mmol) as a brown solid

10.3. tert-Butyl 3-((7-((2,6-dichlorobenzyl)oxy)-1,2,3,4-tetrahydronaphthalen-2-yl)amino)propanoate To a solution of crude 7-((2,6-dichlorobenzyl)oxy)-1,2,3,4-tetrahydronaphthalen-2-amine (279 mg, 0.866 mmol) in MeOH (3 ml) was added 2,3,4,6,7,8,9,10-octahydropyrimido[1,2-a]azepine (0.710 ml, 4.71 mmol) followed by tert-butyl acrylate (0.190 ml, 1.299 mmol). After stirring at RT overnight the reaction mixture reduced to dryness. Then the residue was dissolved in DCM, which was washed subsequently with saturated NH4Cl and brine. The organic layer was dried, filtered and evaporated affording crude tert-butyl 3-((7-((2,6-dichlorobenzyl)oxy)-1,2,3,4-tetrahydronaphthalen-2-yl)amino)propanoate (309 mg) as a brown that was used without further purification.

10.4. 3-((7-((2,6-dichlorobenzyl)oxy)-1,2,3,4-tetrahydronaphthalen-2-yl)amino)propanoic acid Sodium hydroxide 1N (3.43 ml, 3.43 mmol) was added to crude tert-butyl 3-((7-((2,6-dichlorobenzyl)oxy)-1,2,3,4-tetrahydronaphthalen-2-yl)amino)propanoate (309 mg, 0.686 mmol) in THF (1 ml)/MeOH (1 ml) and stirred at room temperature for 48 h. The solvent was evaporated and the residue purified by chromatography (silica gel) affording 2 mg of product.

11. 3-((6-((4-chlorobenzyl)oxy)-1,2,3,4-tetrahydronaphthalen-2-yl)amino) propanoic acid

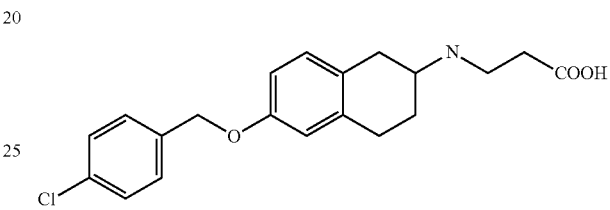

11.1 1-(6-hydroxy-1,2,3,4-tetrahydronaphthalen-2-yl)azetidin-2-one

A solution of ethyl 3-((6-hydroxy-1,2,3,4-tetrahydronaphthalen-2-yl)amino)propanoate (step 6.1, 73 mg, 0.277 mmol) in dry diethyl ether (2 ml) was mixed with tert-butylmagnesium chloride 1M in THF (0.554 ml, 0.554 mmol) stirred under Argon at RT overnight followed by slow addition of aqueous (20%) NH4Cl solution containing some drops of HCl conc. The mixture was extracted with DCM, dried over MgSO$_4$, filtered and the solvent evaporated to obtain the crude product which was purified by chromatography (silica gel) affording 23 mg of the product as a white solid.

11.2. 1-(6-((4-chlorobenzyl)oxy)-1,2,3,4-tetrahydronaphthalen-2-yl)azetidin-2-one Compound 9 was prepared as described for Compound 4.2 using 2-(bromomethyl)-4-chlorobenzene instead of 2-(bromomethyl)-1,3-dichlorobenzene.

11.3. 3-((6-((4-chlorobenzyl)oxy)-1,2,3,4-tetrahydronaphthalen-2-yl)amino)propanoic acid 1-(6-((4-chlorobenzyl)oxy)-1,2,3,4-tetrahydronaphthalen-2-yl)azetidin-2-one (12.8 mg, 0.037 mmol) was dissolved in 4N HCl in dioxane (1 ml, 4.00 mmol) and stirred at room temperature overnight. The reaction mixture was filtered, the solvent evaporated and the residue purified by chromatography (silica gel) affording 6.6 mg of desired product.

$^1$H NMR (600 MHz, Methanol-d$_4$) δ 7.43-7.38 (m, 2H), 7.38-7.33 (m, 2H), 7.05 (d, J=8.4 Hz, 1H), 6.81 (dd, J=8.4, 2.7 Hz, 1H), 6.76 (d, J=2.6 Hz, 1H), 5.04 (s, 2H), 3.59-3.48 (m, 1H), 3.43-3.37 (m, 2H), 3.24-3.16 (m, 1H), 2.99-2.86 (m, 2H), 2.82 (dd, J=15.6, 10.2 Hz, 1H), 2.77 (t, J=6.6 Hz, 2H), 2.34-2.26 (m, 1H), 1.90-1.77 (m, 1H).

12. 3-((6-((2,6-dichlorophenyl)ethynyl)-1,2,3,4-tetrahydronaphthalen-2-yl)amino)propanoic acid

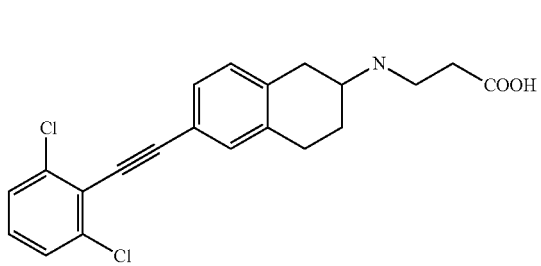 [SMILES: O=C(O)CCNC1CCc2cc(C#Cc3c(Cl)cccc3Cl)ccc2C1]

12.1. 6-(2-oxoazetidin-1-yl)-5,6,7,8-tetrahydronaphthalen-2-yl 1,1,2,2,3,3,4,4-nonafluorobutane-1-sulfonate Crude 1-(6-hydroxy-1,2,3,4-tetrahydronaphthalen-2-yl)azetidin-2-one (30.6 mg, 0.141 mmol) was added to a solution of nonafluorobutanesulfonyl fluoride (0.049 ml, 0.282 mmol) and N-ethyl-N-isopropylpropan-2-amine (0.049 ml, 0.282 mmol) in dry DCM (1 ml) and stirred at RT overnight. The reaction was diluted with water, extracted with EtOAc, the organic layers dried with $Na_2SO_4$, filtered and evaporated affording 70.3 mg of crude product, which was used without further purification.

12.2. 1-(6-((2,6-dichlorophenyl)ethynyl)-1,2,3,4-tetrahydronaphthalen-2-yl)azetidin-2-one 6-(2-oxoazetidin-1-yl)-5,6,7,8-tetrahydronaphthalen-2-yl 1,1,2,2,3,3,4,4-nonafluorobutane-1-sulfonate (70.3 mg, 0.141 mmol) and (2,6-dichlorophenyl)acetylene (26.5 mg, 0.155 mmol) were dissolved in DMSO (2 ml) and degassed. Diacetoxypalladium (1.896 mg, 8.45 µmol), potassium phosphate hydrate (38.9 mg, 0.169 mmol) and triphenylphosphine (7.39 mg, 0.028 mmol) were subsequently added. The mixture was placed in the micro wave and heated to 80° C. for 1 h, followed by addition of sat. $NaHCO_3$ and extracted with DCM. The combined organic layers were washed with NH4Cl, dried over $Na_2SO_4$ and filtered. The solvent was evaporated to obtain the crude product, which was purified by chromatography (silica gel) affording 21.7 mg 1-(6-((2,6-dichlorophenyl)ethynyl)-1,2,3,4-tetrahydronaphthalen-2-yl)azetidin-2-one as a brown oil.

12.3. 3-((6-((2,6-dichlorophenyl)ethynyl)-1,2,3,4-tetrahydronaphthalen-2-yl)amino)propanoic acid Compound 12.3 was prepared from 1-(6-((2,6-dichlorophenyl)ethynyl)-1,2,3,4-tetrahydronaphthalen-2-yl)azetidin-2-one as described in step 11.3.

$^1$H NMR (600 MHz, Methanol-$d_4$) δ 7.46 (d, J=8.1 Hz, 2H), 7.38 (d, J=7.5 Hz, 2H), 7.31 (dd, J=8.5, 7.7 Hz, 1H), 7.24-7.20 (m, 1H), 3.61 (m, 1H), 3.43 (t, J=6.4 Hz, 2H), 3.07-2.91 (m, 3H), 2.80 (t, J=6.6 Hz, 2H), 2.40-2.33 (m, 1H), 1.94-1.85 (m, 1H).

13. 3-((6-((2,6-dichlorophenyl)ethynyl)-1,2,3,4-tetrahydronaphthalen-2-yl)(methyl)amino)propanoic acid

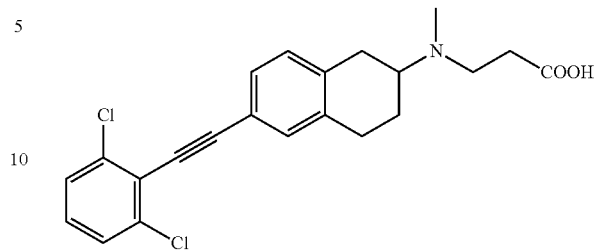

3-((6-((2,6-dichlorophenyl)ethynyl)-1,2,3,4-tetrahydronaphthalen-2-yl)amino)propanoic acid (7 mg, 0.018 mmol) and formaldehyde 37% (2.128 µl, 0.027 mmol) were stirred in EtOH (1 ml) for 1 h. Sodium cyanoborohydride (2.6 mg, 0.036 mmol) was added and the reaction mixture was stirred at room temperature overnight. The solvent was evaporated and the residue purified by chromatography (silica gel) affording 2.2 mg of desired product.

$^1$H NMR (600 MHz, Methanol-$d_4$) δ 7.46 (d, J=8.1 Hz, 2H), 7.40-7.35 (m, 2H), 7.31 (dd, J=8.6, 7.8 Hz, 1H), 7.24 (d, J=8.3 Hz, 1H), 3.83-3.74 (m, 1H), 3.56-3.43 (m, 2H), 3.27-3.22 (m, 1H), 3.21-3.16 (m, 1H), 3.12-3.06 (m, 1H), 3.03-2.95 (m, 1H), 2.94 (s, 3H), 2.82 (t, J=6.5 Hz, 2H), 2.38-2.31 (m, 1H), 2.03-1.94 (m, 1H).

14. 3-((6-((3,5-difluorophenyl)ethynyl)-1,2,3,4-tetrahydronaphthalen-2-yl)amino)propanoic acid

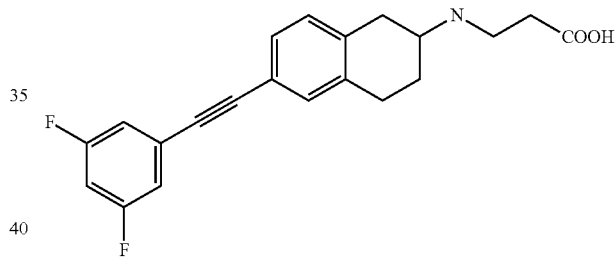

Compound 14 was prepared as described for Compound 12 using (3,5-difluorophenyl)acetylene instead of (2,6-dichlorophenyl)acetylene.

$^1$H NMR (600 MHz, DMSO-$d_6$) δ 7.40-7.29 (m, 5H), 7.23 (d, J=7.9 Hz, 1H), 3.51-3.43 (m, 1H), 3.21 (t, J=7.4 Hz, 2H), 2.96-2.88 (m, 1H), 2.87-2.78 (m, 2H), 2.63 (t, J=6.9 Hz, 2H), 2.24-2.16 (m, 1H), 1.79-1.69 (m, 1H).

15. 3-((6-((3,5-difluorophenyl)ethynyl)-1,2,3,4-tetrahydronaphthalen-2-yl)(methyl)amino)propanoic acid

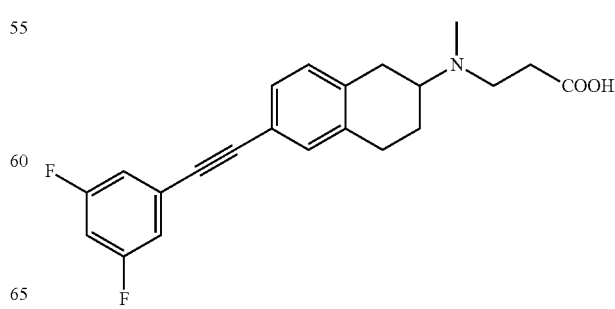

Compound 15 was prepared in analogy to Compound 13.
¹H NMR (600 MHz, Methanol-d₄) δ 7.38-7.31 (m, 2H), 7.21 (d, J=7.8 Hz, 1H), 7.15-7.08 (m, 2H), 7.00 (tt, J=9.2, 2.4 Hz, 1H), 3.80-3.72 (m, 1H), 3.51-3.42 (m, 2H), 3.25-3.20 (m, 1H), 3.19-3.12 (m, 1H), 3.09-3.02 (m, 1H), 3.01-2.93 (m, 1H), 2.92 (s, 3H), 2.76-2.72 (m, 2H), 2.37-2.30 (m, 1H), 1.97 (qd, J=12.1, 5.5 Hz, 1H).

16. 3-((6-((2-chlorobenzyl)oxy)-1,2,3,4-tetrahydronaphthalen-2-yl)(methyl)amino)propanoic acid

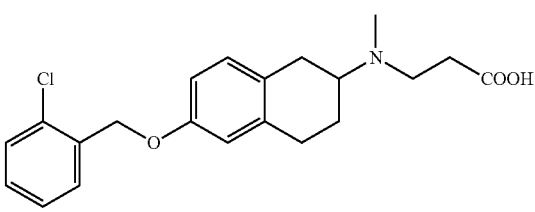 [SMILES: CN(CCC(=O)O)C1CCc2cc(OCc3ccccc3Cl)ccc2C1]

16.1 Ethyl 3-((6-hydroxy-1,2,3,4-tetrahydronaphthalen-2-yl)(methyl)amino)-propanoate Compound 16.1 was prepared as described for Compound 6.1 using 3-(methyl-amino)propanoic acid instead of 3-aminopropanoic acid.

16.2. Ethyl 3-((6-((2-chlorobenzyl)oxy)-1,2,3,4-tetrahydronaphthalen-2-yl)(methyl)amino)propanoate Compound 16.2 was prepared as described for Compound 1.2 using 1-(bromomethyl)-2-chlorobenzene instead of 2-(bromomethyl)-1,3-dichlorobenzene.

16.3. 3-((6-((2-chlorobenzyl)oxy)-1,2,3,4-tetrahydronaphthalen-2-yl)(methyl)amino)propanoic acid Compound 16.3 was prepared by hydrolysis of ethyl 3-((6-((2-chlorobenzyl)oxy)-1,2,3,4-tetrahydronaphthalen-2-yl)(methyl)amino)propanoate as described for Compound 1.3.
¹H NMR (600 MHz, Methanol-d₄) δ 7.58-7.50 (m, 1H), 7.48-7.40 (m, 1H), 7.34-7.28 (m, 2H), 7.09 (d, J=8.5 Hz, 1H), 6.83 (dd, J=8.4, 2.7 Hz, 1H), 6.78 (d, J=2.6 Hz, 1H), 5.13 (s, 2H), 3.76-3.68 (m, 1H), 3.64-3.37 (m, 2H), 3.16-3.10 (m, 1H), 3.09-2.93 (m, 3H), 2.92 (s, 3H), 2.86 (t, J=6.5 Hz, 2H), 2.36-2.27 (m, 1H), 1.94 (qd, J=12.0, 5.7 Hz, 1H).

17. 3-((6-((2-chloro-6-ethylbenzyl)oxy)-1,2,3,4-tetrahydronaphthalen-2-yl)(methyl)amino)propanoic acid

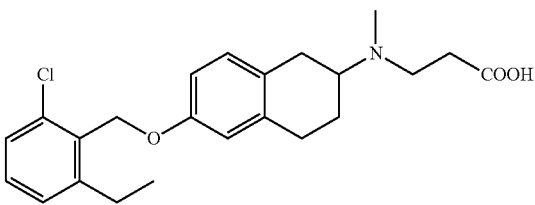 [SMILES: CCc1cccc(Cl)c1COc1ccc2c(c1)CCC(N(C)CCC(=O)O)C2]

Compound 17 was prepared as described for Compound 16 using 2-(bromomethyl)-1-chloro-3-ethylbenzene instead 1-(bromomethyl)-2-chlorobenzene.
¹H NMR (600 MHz, Methanol-d₄) δ 7.31-7.26 (m, 2H), 7.23 (dd, J=6.3, 2.7 Hz, 1H), 7.11 (d, J=8.4 Hz, 1H), 6.85 (dd, J=8.3, 2.7 Hz, 1H), 6.84-6.81 (m, 1H), 5.17 (s, 2H), 3.77-3.70 (m, 1H), 3.18-3.13 (m, 1H), 3.10-2.95 (m, 2H), 2.93 (s, 3H), 2.89 (t, J=6.6 Hz, 2H), 2.76 (q, J=7.5 Hz, 2H), 2.33 (ddt, J=12.1, 5.4, 2.6 Hz, 1H), 1.96 (dq, J=13.1, 7.2 Hz, 1H), 1.22 (t, J=7.6 Hz, 3H).

18. (E)-3-((6-(2,6-dichlorostyryl)-1,2,3,4-tetrahydronaphthalen-2-yl)amino)-propanoic acid

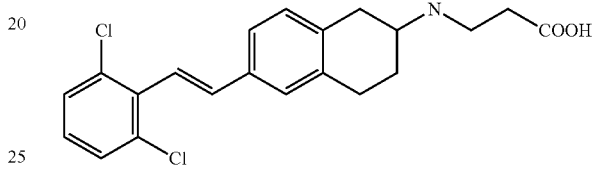

18.1 1-(6-bromo-1,2,3,4-tetrahydronaphthalen-2-yl)azetidin-2-one

Compound 18.1 was prepared as described for Compound 11.2 using 6-bromo-3,4-dihydronaphthalen-2(1H)-one instead 6-hydroxy-3,4-dihydronaphthalen-2(1H)-one.

18.2 (E)-1-(6-(2,6-dichlorostyryl)-1,2,3,4-tetrahydronaphthalen-2-yl)azetidin-2-one A microwave tube was charged with 1-(6-bromo-1,2,3,4-tetrahydronaphthalen-2-yl)azetidin-2-one (50 mg, 0.178 mmol), acetoxy(2-(di-o-tolylphosphino)benzyl)palladium (Herrmann's Catalyst) (3.35 mg, 3.57 µmol), 2,6-dichlorostyrene (31 mg 0.178 mmol) and potassium carbonate (49.3 mg, 0.357 mmol) in DMF (1 ml), placed in a microwave and heated to 130° C. for 1.5 h. The resulting mixture was diluted with water and extracted with DCM, which was dried over MgSO₄, filtrated and evaporated The residue was purified by chromatography (silica gel) affording 26 mg (E)-1-(6-(2,6-dichlorostyryl)-1,2,3,4-tetrahydronaphthalen-2-yl)azetidin-2-one as a pale white solid.

18.3. (E)-3-((6-(2,6-dichlorostyryl)-1,2,3,4-tetrahydronaphthalen-2-yl)amino)-propanoic acid Compound 18.3 was prepared from (E)-1-(6-(2,6-dichlorostyryl)-1,2,3,4-tetrahydronaphthalen-2-yl)azetidin-2-one in analogy to compound 11.3.
¹H NMR (600 MHz, Methanol-d₄) δ 7.42 (d, J=8.1 Hz, 2H), 7.39 (dd, J=8.0, 1.8 Hz, 1H), 7.35-7.32 (m, 1H), 7.21 (t, J=8.1 Hz, 1H), 7.19 (d, J=8.0 Hz, 1H), 7.13 (d, J=16.7 Hz, 1H), 7.07 (d, J=16.6 Hz, 1H), 3.64-3.57 (m, 1H), 3.45-3.40 (m, 2H), 3.08-2.89 (m, 3H), 2.79 (t, J=6.6 Hz, 2H).

19. (E)-3-((6-styryl-1,2,3,4-tetrahydronaphthalen-2-yl)amino)propanoic acid

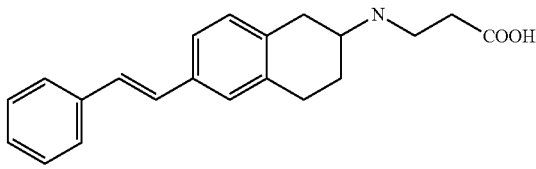 [SMILES: O=C(O)CCNC1CCc2cc(/C=C/c3ccccc3)ccc2C1]

Compound 19 was prepared as described for Compound 18 using styrene instead of 2,6-dichlorostyrene.

$^1$H NMR (600 MHz, DMSO-$d_6$) δ 7.61-7.56 (m, 2H), 7.43-7.33 (m, 4H), 7.29-7.24 (m, 1H), 7.21 (d, J=1.0 Hz, 2H), 7.15 (d, J=8.0 Hz, 1H), 3.48-3.42 (m, 1H), 3.22 (t, J=6.9 Hz, 2H), 3.17 (s, 1H), 2.95-2.74 (m, 3H), 2.62 (t, J=6.9 Hz, 2H), 2.24-2.16 (m, 1H), 1.80-1.70 (m, 1H).

20. (E)-3-((6-(3-chlorostyryl)-1,2,3,4-tetrahydronaphthalen-2-yl)amino)-propanoic acid

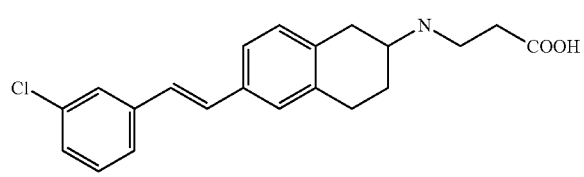 [SMILES: O=C(O)CCNC1CCc2cc(/C=C/c3cccc(Cl)c3)ccc2C1]

Compound 20 was prepared as described for Compound 18 using 3-chlorostyrene instead of 2,6-dichlorostyrene.

$^1$H NMR (600 MHz, Methanol-$d_4$) δ 7.57-7.54 (m, 1H), 7.48-7.45 (m, 1H), 7.40 (dd, J=8.0, 1.8 Hz, 1H), 7.35 (s, 1H), 7.32 (t, J=7.8 Hz, 1H), 7.26-7.22 (m, 1H), 7.19-7.15 (m, 2H), 7.11 (d, J=16.4 Hz, 1H), 3.63-3.56 (m, 1H), 3.44-3.40 (m, 2H), 3.07-2.87 (m, 3H), 2.79 (t, J=6.6 Hz, 2H), 2.38-2.33 (m, 1H), 1.93-1.85 (m, 1H).

21. 3-((6-((2-chloro-6-cyclopropylbenzyl)oxy)-1,2,3,4-tetrahydronaphthalen-2-yl)amino)propanoic acid

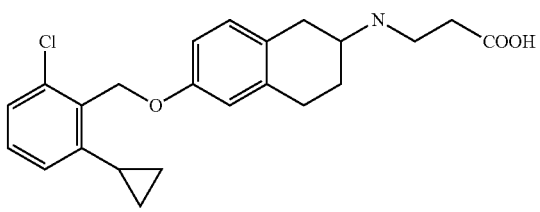 [SMILES: O=C(O)CCNC1CCc2cc(OCc3c(Cl)cccc3C3CC3)ccc2C1]

Compound 21 was prepared as described for Compound 6 using 2-(bromomethyl)-1-chloro-3-cyclopropylbenzene instead of 2-(bromomethyl)-1-chloro-3-ethylbenzene.

$^1$H NMR (600 MHz, Methanol-$d_4$) δ 7.45-7.41 (m, 2H), 7.17-7.12 (m, 1H), 7.00 (d, J=8.3 Hz, 1H), 6.62 (dd, J=8.3, 2.6 Hz, 1H), 6.57 (d, J=2.5 Hz, 1H), 5.49 (s, 1H), 3.96-3.88 (m, 1H), 3.80-3.49 (m, 2H), 3.21-3.15 (m, 1H), 3.04-2.90 (m, 2H), 2.89-2.81 (m, 2H), 2.50-2.40 (m, 2H), 2.17-2.10 (m, 1H), 1.20-1.12 (m, 2H), 0.91-0.78 (m, 1H).

22. Methyl 2-(((2-chloro-6-ethylbenzyl)(6-((2-chloro-6-ethylbenzyl)oxy)-1,2,3,4-tetrahydronaphthalen-2-yl)amino)methyl)acrylate

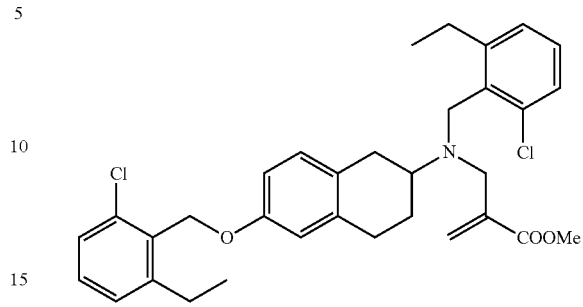

Compound 22 was isolated as side product during synthesis of compound 2.

$^1$H NMR (600 MHz, Chloroform-d) δ 7.29-7.25 (m, 2H), 7.23 (t, J=7.8 Hz, 1H), 7.18-7.13 (m, 2H), 7.10 (t, J=7.7 Hz, 1H), 7.06 (dd, J=7.6, 1.5 Hz, 1H), 7.02 (d, J=8.4 Hz, 1H), 6.79 (dd, J=8.3, 2.7 Hz, 1H), 6.74 (d, J=2.6 Hz, 1H), 6.16 (d, J=1.8 Hz, 1H), 5.71 (d, J=1.7 Hz, 1H), 5.12 (s, 2H), 3.95 (d, J=12.6 Hz, 1H), 3.87 (d, J=12.8 Hz, 1H), 3.57 (d, J=14.2 Hz, 1H), 3.24 (d, J=14.3 Hz, 1H), 3.00-2.79 (m, 4H), 2.79-2.70 (m, 5H), 2.26-2.18 (m, 1H), 1.70 (qd, J=12.1, 5.4 Hz, 1H), 1.23 (t, J=7.5 Hz, 3H), 1.17 (t, J=7.5 Hz, 3H).

23. 1-(7-((2-chloro-6-ethylbenzyl)oxy)chroman-3-yl)azetidine-3-carboxylic acid

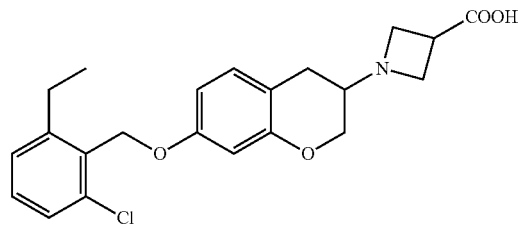 [SMILES: CCc1cccc(Cl)c1COc1ccc2c(c1)OCC(N1CC(C(=O)O)C1)C2]

Compound 23 was prepared as described for Compound 1 using 2-(bromomethyl)-1-chloro-3-ethylbenzene instead of 2-(bromomethyl)-1,3-dichlorobenzene.

$^1$H NMR (600 MHz, DMSO-$d_6$) δ 7.44-7.21 (m, 3H), 7.09-6.94 (m, 1H), 6.67-6.44 (m, 2H), 5.09 (d, J=8.3 Hz, 2H), 2.70 (q, J=7.5 Hz, 2H), 1.16 (t, J=7.6 Hz, 3H). All further protons gave very broad signals

24. 1-(7-((3-chlorobenzyl)oxy)chroman-3-yl)azetidine-3-carboxylic acid

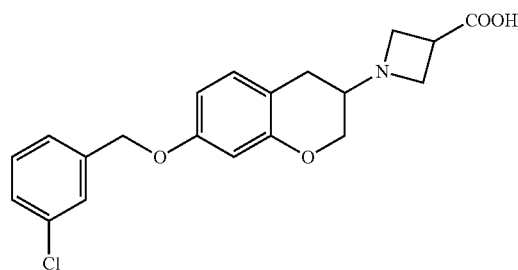 [SMILES: O=C(O)C1CN(C2COc3cc(OCc4cccc(Cl)c4)ccc3C2)C1]

Compound 24 was prepared as described for Compound 1 using 1-(bromomethyl)-3-chlorobenzene instead of 2-(bromomethyl)-1,3-dichlorobenzene.

¹H NMR (600 MHz, DMSO-d₆) δ 7.49-7.44 (m, 1H), 7.44-7.34 (m, 4H), 6.93 (d, J=8.4 Hz, 1H), 6.49 (dd, J=8.4, 2.6 Hz, 1H), 6.36 (d, J=2.6 Hz, 1H), 5.06 (s, 2H), 4.01-3.93 (m, 1H), 3.72 (s, 1H), 3.20-3.14 (m, 1H), 2.78-2.69 (m, 1H), 2.37-2.29 (m, 1H). All further protons gave very broad signals at δ 3.54-3.20

25. 1-(7-((2-chloro-6-cyclopropylbenzyl)oxy)chroman-3-yl)azetidine-3-carboxylic acid

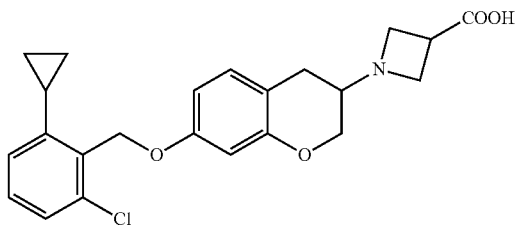 [SMILES: O=C(O)C1CN(C2COc3cc(OCc4c(Cl)cccc4C4CC4)ccc3C2)C1]

Compound 25 was prepared as described for Compound 1 using 2-(bromomethyl)-1-chloro-3-cyclopropylbenzene instead of 2-(bromomethyl)-1,3-dichlorobenzene.

¹H NMR (600 MHz, Chloroform-d) δ 7.20 (t, J=7.8 Hz, 1H), 7.00-6.94 (m, 2H), 6.60 (dd, J=8.4, 2.6 Hz, 1H), 6.55 (d, J=2.5 Hz, 1H), 5.30 (s, 2H), 4.18-4.13 (m, 1H), 4.02-3.98 (m, 1H), 3.96-3.84 (m, 4H), 3.40-3.32 (m, 1H), 3.16-3.09 (m, 1H), 2.95-2.88 (m, 1H), 2.78 (dd, J=15.8, 8.0 Hz, 1H), 1.27-1.23 (m, 1H), 0.96-0.89 (m, 2H), 0.73-0.65 (m, 2H).

26. 1-(7-((2,3-difluorophenyl)ethynyl)chroman-3-yl)azetidine-3-carboxylic acid

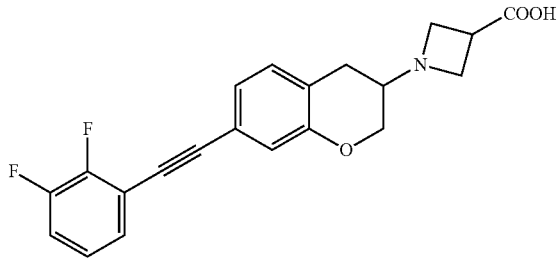 [SMILES: O=C(O)C1CN(C2COc3cc(C#Cc4cccc(F)c4F)ccc3C2)C1]

26.1. Methyl 1-(7-((((perfluorobutyl)sulfonyl)oxy)chroman-3-yl)azetidine-3-carboxylate Compound 26.1 was prepared as described for Compound 12.1 using methyl 1-(7-hydroxychroman-3-yl)azetidine-3-carboxylate instead of 1-(6-hydroxy-1,2,3,4-tetrahydronaphthalen-2-yl)azetidin-2-one.

26.2. Methyl 1-(7-((2,3-difluorophenyl)ethynyl)chroman-3-yl)azetidine-3-carboxylate Compound 26.2 was prepared as described for Compound 12.2 using 1-ethynyl-2,3-difluorobenzene instead of (2,6-dichlorophenyl)acetylene.

26.3. 3-((6-((2,6-dichlorophenyl)ethynyl)-1,2,3,4-tetrahydronaphthalen-2-yl)amino)propanoic acid Sodium hydroxide (2N, 0.1 ml, 0.2 mmol) was added to a solution of methyl 1-(7-((2,3-difluorophenyl)ethynyl)chroman-3-yl)azetidine-3-carboxylate (12.6 mg, 0.033 mmol) in methanol/THF and stirred at RT over the weekend. Then the solvent was evaporated, the residue dissolved in water, adjusted to pH4 with 1N HCl and extracted with ethylacetate. The organic layer was dried over Na₂SO₄, evaporated, and the residue repeatedly crystallized from DCM affording 4.9 mg of desired product.

¹H NMR (600 MHz, DMSO-d₆) δ 7.57-7.48 (m, 1H), 7.47-7.42 (m, 1H), 7.32-7.23 (m, 1H), 7.13 (d, J=7.8 Hz, 1H), 7.04 (d, J=7.7 Hz, 1H), 6.90 (s, 1H), 4.09-3.99 (m, 1H), 3.88-3.78 (m, 1H), 2.91-2.83 (m, 1H), 2.71-2.62 (m, 1H).

27. 1-(7-((3,5-difluorophenyl)ethynyl)chroman-3-yl)azetidine-3-carboxylic acid

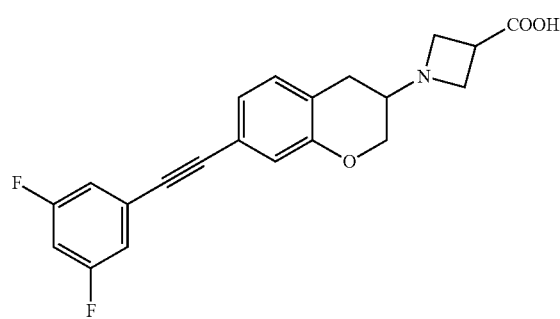 [SMILES: O=C(O)C1CN(C2COc3cc(C#Cc4cc(F)cc(F)c4)ccc3C2)C1]

Compound 27 was prepared as described for Compound 26 using 1-ethynyl-3,5-difluorobenzene instead of 1-ethynyl-2,3-difluorobenzene.

¹H NMR (600 MHz, DMSO-d₆) δ 7.38-7.29 (m, 3H), 7.12 (d, J=7.8 Hz, 1H), 7.03 (dd, J=7.7, 1.7 Hz, 1H), 6.90 (d, J=1.6 Hz, 1H), 4.05-3.99 (m, 1H), 3.82 (ddd, J=11.2, 5.9, 1.4 Hz, 1H), 3.47 (t, J=7.4 Hz, 1H), 3.42 (t, J=7.5 Hz, 1H), 3.28-3.23 (m, 2H), 3.17 (q, J=7.5 Hz, 1H), 2.89-2.83 (m, 1H), 2.69-2.63 (m, 1H), 2.49-2.45 (m, 1H).

28. 2-((6-((3,5-difluorophenyl)ethynyl)-1,2,3,4-tetrahydronaphthalen-2-yl)amino)acetic acid

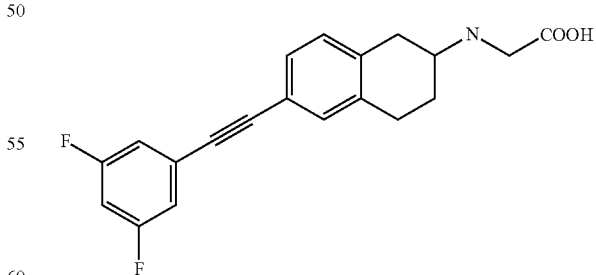

28.1 tert-Butyl 2-((6-hydroxy-1,2,3,4-tetrahydronaphthalen-2-yl)amino)acetate Compound 28.1 was prepared as described for Compound 1 using 6-hydroxy-3,4-dihydronaphthalen-2(1H)-one instead of 7-hydroxychroman-3-one and glycine tert-butyl ester hydrochloride instead of Methylazetine-3-carboxylate hydrochloride.

28.2 tert-Butyl 2-((6-((3,5-difluorophenyl)ethynyl)-1,2,3,4-tetrahydro-naphthalen-2-yl)amino)acetate Compound 28.2 was prepared as described for Compound 12.2 starting with tert-Butyl 2-((6-hydroxy-1,2,3,4-tetrahydronaphthalen-2-yl)amino)acetate instead of 1-(6-hydroxy-1,2,3,4-tetrahydronaphthalen-2-yl)azetidin-2-one and using 1-ethynyl-3,5-difluorobenzene instead of 1-ethynyl-2,6-dichlorobenzene.

28.3 2-((6-((3,5-difluorophenyl)ethynyl)-1,2,3,4-tetrahydronaphthalen-2-yl)amino)acetic acid Compound 28.3 was prepared following the procedure described for compound 4.3.
$^1$H NMR (500 MHz, Methanol-$d_4$) δ 7.36-7.31 (m, 2H), 7.19 (d, J=7.9 Hz, 1H), 7.14-7.07 (m, 2H), 7.03-6.96 (m, 1H), 4.00 (s, 2H), 3.63-3.54 (m, 1H), 3.06-2.88 (m, 3H), 2.40-2.32 (m, 1H), 1.91-1.81 (m, 1H).

29. 2-((6-((2,6-dichlorophenyl)ethynyl)-1,2,3,4-tetrahydronaphthalen-2-yl)amino)acetic acid

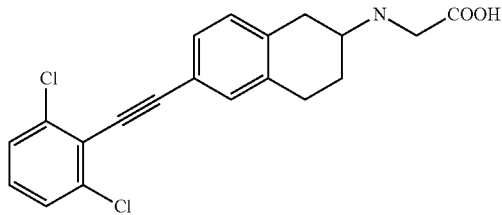 [SMILES: O=C(O)CNC1CCc2cc(C#Cc3c(Cl)cccc3Cl)ccc2C1]

Compound 29 was prepared as described for Compound 28 using 1-ethynyl-2,6-dichlorobenzene instead of 1-ethynyl-3,5-difluorobenzene.
$^1$H NMR (500 MHz, Methanol-$d_4$) δ 7.45 (d, J=8.2 Hz, 2H), 7.39-7.34 (m, 2H), 7.33-7.28 (m, 1H), 7.21 (d, J=8.1 Hz, 1H), 4.00-3.95 (m, 2H), 3.64-3.56 (m, 1H), 3.08-3.00 (m, 1H), 3.00-2.89 (m, 2H), 2.41-2.32 (m, 1H), 1.92-1.82 (m, 1H).

30. 2-((6-(cyclohexylethynyl)-1,2,3,4-tetrahydronaphthalen-2-yl)amino)acetic acid

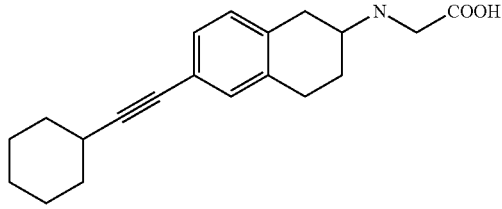 [SMILES: O=C(O)CNC1CCc2cc(C#CC3CCCCC3)ccc2C1]

Compound 30 was prepared as described for Compound 28 using ethynylcyclohexane instead of 1-ethynyl-3,5-difluorobenzene.
$^1$H NMR (600 MHz, Methanol-$d_4$) δ 7.14-7.11 (m, 2H), 7.07 (d, J=8.4 Hz, 1H), 3.79 (s, 2H), 3.57-3.49 (m, 1H), 3.26-3.21 (m, 1H), 2.98-2.82 (m, 3H), 2.60-2.53 (m, 1H), 2.35-2.24 (m, 1H), 1.91-1.70 (m, 5H), 1.61-1.46 (m, 3H), 1.45-1.32 (m, 3H).

31. 1-(6-((2,6-dichlorobenzyl)oxy)-1,2,3,4-tetrahydronaphthalen-2-yl)piperidine-4-carboxylic acid

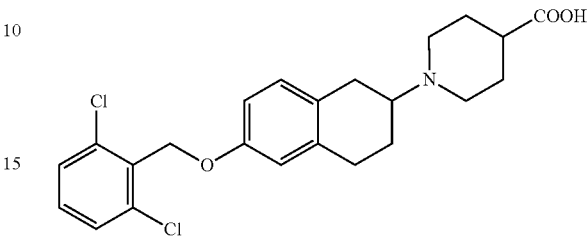

Compound 31 was prepared as described for compound 1 using 6-hydroxy-3,4-dihydronaphthalen-2(1H)-one instead of 7-hydroxychroman-3-one and ethyl piperidine-4-carboxylate instead of methylazetine-3-carboxylate hydrochloride.
$^1$H NMR (500 MHz, Methanol-$d_4$) δ 7.48-7.39 (m, 2H), 7.38-7.30 (m, 1H), 7.05 (d, J=8.5 Hz, 1H), 6.82-6.74 (m, 2H), 5.23 (s, 2H), 3.14-2.80 (m, 3H), 2.79-2.61 (m, 2H), 2.33-2.18 (m, 2H), 2.09-1.95 (m, 2H), 1.94-1.80 (m, 2H), 1.79-1.65 (m, 1H).

32. 3-((6-((2,6-dichlorobenzyl)oxy)-1,2,3,4-tetrahydronaphthalen-2-yl)amino)bicyclo[1.1.1]pentane-1-carboxylic acid

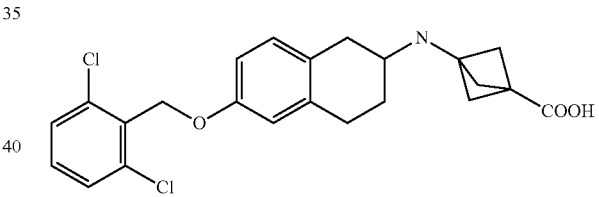

Compound 32 was prepared as described for Compound 1 using 6-hydroxy-3,4-dihydronaphthalen-2(1H)-one instead of 7-hydroxychroman-3-one and methyl 3-aminobicyclo[1.1.1]pentane-1-carboxylate hydrochloride instead of methylazetine-3-carboxylate hydrochloride.
$^1$H NMR (500 MHz, DMSO-$d_6$) δ 7.56 (d, J=8.1 Hz, 2H), 7.47 (dd, J=8.8, 7.4 Hz, 1H), 7.09 (d, J=8.5 Hz, 1H), 6.90-6.80 (m, 2H), 5.18 (s, 2H), 3.56-3.46 (m, 1H), 3.19-3.10 (m, 1H), 2.87-2.81 (m, 2H), 2.81-2.71 (m, 1H), 2.36 (s, 6H), 2.25-2.14 (m, 1H), 1.83-1.72 (m, 1H).

33. 2-((6-((2,6-dichlorobenzyl)oxy)-1,2,3,4-tetrahydronaphthalen-2-yl)amino)propanoic acid

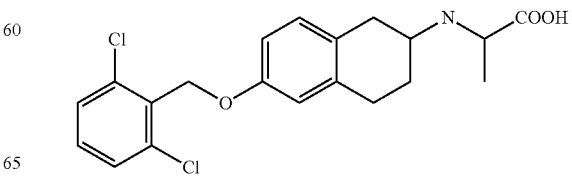

Compound 33 was prepared as described for Compound 1 using 6-hydroxy-3,4-dihydronaphthalen-2(1H)-one instead of 7-hydroxychroman-3-one and methyl 2-aminopropanoate hydrochloride instead of methylazetine-3-carboxylate hydrochloride.

$^1$H NMR (600 MHz, Methanol-$d_4$) δ 7.45 (d, J=8.0 Hz, 2H), 7.36 (t, J=8.1 Hz, 1H), 7.08 (d, J=8.4 Hz, 1H), 6.90-6.78 (m, 2H), 5.25 (s, 2H), 4.22-4.08 (m, 1H), 3.67-3.52 (m, 1H), 3.22-3.15 (m, 2H), 3.04-2.90 (m, 2H), 2.88-2.77 (m, 1H), 2.38-2.28 (m, 1H), 1.91-1.76 (m, 1H), 1.60 (d, J=7.2 Hz, 3H).

34. 2-((7-((2-chloro-6-ethylbenzyl)oxy)chroman-3-yl)amino)acetic acid

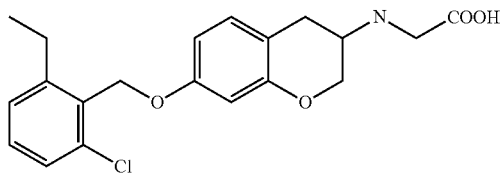 [SMILES: CCc1cccc(Cl)c1COc1ccc2c(c1)OCC(NCC(=O)O)C2]

Compound 34 was prepared as described for Compound 1 using tert-butyl 2-aminoacetate hydrochloride instead of methylazetine-3-carboxylate hydrochloride and 2-(bromomethyl)-1-chloro-3-ethylbenzene instead of 2-(bromomethyl)-1,3-dichlorobenzene. Hydrolysis of the tert-butylester was performed in formic acid as described for step 4.3.

$^1$H NMR (600 MHz, Chloroform-d) δ 7.27-7.24 (m, 1H), 7.24-7.19 (m, 1H), 7.15 (dd, J=7.5, 1.5 Hz, 1H), 6.97 (d, J=8.4 Hz, 1H), 6.58 (dd, J=8.4, 2.5 Hz, 1H), 6.53 (d, J=2.5 Hz, 1H), 5.09 (s, 2H), 4.27 (s, 2H), 3.66-3.45 (m, 3H), 3.16-3.05 (m, 1H), 3.05-2.93 (m, 1H), 2.72 (q, J=7.6 Hz, 2H), 1.21 (t, J=7.6 Hz, 3H).

35. 2-((7-((2,6-dichlorobenzyl)oxy)chroman-3-yl)amino)acetic acid

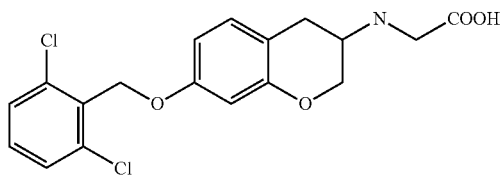 [SMILES: O=C(O)CNC1COc2cc(OCc3c(Cl)cccc3Cl)ccc2C1]

Compound 35 was prepared as described for Compound 1 using tert-butyl 2-aminoacetate hydrochloride instead of methylazetine-3-carboxylate hydrochloride. Hydrolysis of the tert-butylester was performed in formic acid as described for step 4.3.

$^1$H NMR (600 MHz, Chloroform-d) δ 7.33 (d, J=8.1 Hz, 2H), 7.22 (dd, J=8.6, 7.5 Hz, 1H), 6.97 (d, J=8.4 Hz, 1H), 6.57 (dd, J=8.3, 2.5 Hz, 1H), 6.52 (d, J=2.5 Hz, 1H), 5.17 (s, 2H), 4.27 (s, 2H), 3.68-3.40 (m, 3H), 3.15-3.05 (m, 1H), 3.05-2.93 (m, 1H).

36. 2-(6-((2,6-dichlorobenzyl)oxy)-1,2,3,4-tetrahydronaphthalen-2-yl)-2-azabicyclo[3.1.0]hexane-1-carboxylic acid

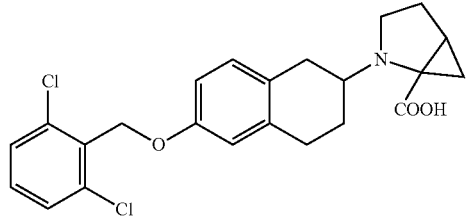 [SMILES: O=C(O)C12CC1CCN2C1CCc2cc(OCc3c(Cl)cccc3Cl)ccc2C1]

Compound 36 was prepared as described for Compound 1 using 6-hydroxy-3,4-dihydronaphthalen-2(1H)-one instead of 7-hydroxychroman-3-one and ethyl 2-azabicyclo[3.1.0]hexane-1-carboxylate instead of methylazetine-3-carboxylate hydrochloride.

$^1$H NMR (600 MHz, DMSO-$d_6$) δ 7.57 (d, J=8.1 Hz, 2H), 7.47 (dd, J=8.7, 7.5 Hz, 1H), 7.10 (d, J=8.3 Hz, 1H), 6.91-6.81 (m, 2H), 5.18 (s, 2H), 4.02-3.94 (m, 1H), 3.70-3.63 (m, 1H), 3.29-3.15 (m, 1H), 3.11-2.90 (m, 3H), 2.89-2.80 (m, 1H), 2.37-2.30 (m, 1H), 2.30-2.15 (m, 1H), 2.15-2.03 (m, 1H), 2.03-1.96 (m, 1H), 1.86-1.71 (m, 2H).

37. 2-((6-((2,6-dichlorobenzyl)oxy)-1,2,3,4-tetrahydronaphthalen-2-yl)amino)-3-methylbutanoic acid

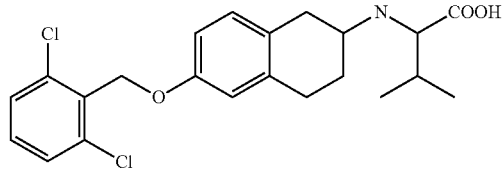 [SMILES: CC(C)C(NC1CCc2cc(OCc3c(Cl)cccc3Cl)ccc2C1)C(=O)O]

Compound 37 was prepared as described for Compound 1 using 6-hydroxy-3,4-dihydronaphthalen-2(1H)-one instead of 7-hydroxychroman-3-one and methyl 2-amino-3-methylbutanoate instead of methylazetine-3-carboxylate hydrochloride $^1$H NMR (600 MHz, Methanol-$d_4$) δ 7.44 (d, J=8.1 Hz, 2H), 7.35 (dd, J=8.7, 7.5 Hz, 1H), 7.09-7.03 (m, 1H), 6.83 (dd, J=8.3, 2.7 Hz, 1H), 6.80 (dd, J=2.7, 1.3 Hz, 1H), 5.24 (s, 2H), 3.62 (d, J=4.1 Hz, 1H), 3.52-3.46 (m, 0.5H), 3.46-3.38 (m, 0.5H), 3.27-3.22 (m, 0.5H), 3.22-3.16 (m, 0.5H), 3.00-2.79 (m, 3H), 2.39-2.30 (m, 0.5H), 2.30-2.23 (m, 0.5H), 1.90 (qd, J=11.9, 5.9 Hz, 0.5H), 1.80 (qd, J=12.1, 5.7 Hz, 0.5H), 1.16-1.08 (m, 7H).

38. 1-(7-((2,5-difluorophenyl)ethynyl)chroman-3-yl)azetidine-3-carboxylic acid

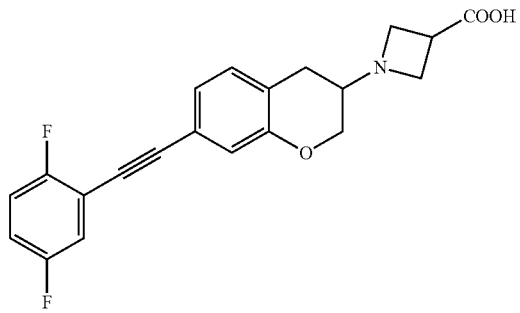 [SMILES: O=C(O)C1CN(C2COc3cc(C#Cc4cc(F)ccc4F)ccc3C2)C1]

Compound 38 was prepared as described for Compound 26 using 1-ethynyl-2,5-difluorobenzene instead of 1-ethynyl-2,3-difluorobenzene.

¹H NMR (600 MHz, DMSO-d₆) δ 7.56-7.50 (m, 1H), 7.40 (td, J=9.0, 4.6 Hz, 1H), 7.37-7.31 (m, 1H), 7.12 (d, J=7.8 Hz, 1H), 7.02 (dd, J=7.8, 1.7 Hz, 1H), 6.89 (d, J=1.6 Hz, 1H), 4.05-4.00 (m, 1H), 3.85-3.79 (m, 1H), 3.49-3.39 (m, 3H), 3.29-3.23 (m, 2H), 3.16 (p, J=7.5 Hz, 1H), 2.87 (dd, J=16.7, 4.8 Hz, 1H), 2.71-2.63 (m, 1H).

39. 1-(7-(cyclohexylethynyl)chroman-3-yl)azetidine-3-carboxylic acid

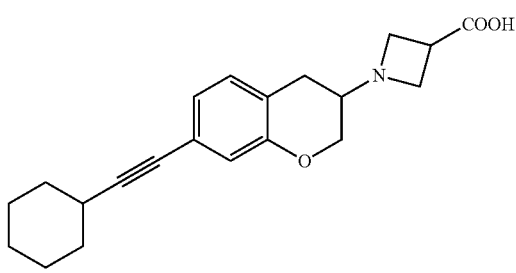 [SMILES: O=C(O)C1CN(C2COc3cc(C#CC4CCCCC4)ccc3C2)C1]

Compound 39 was prepared as described for Compound 26 using ethynylcyclohexane instead of 1-ethynyl-2,3-difluorobenzene.

¹H NMR (600 MHz, DMSO-d₆) δ 7.07-6.99 (m, 1H), 6.92-6.80 (m, 1H), 6.71 (s, 1H), 4.10-3.98 (m, 1H), 2.64-2.55 (m, 1H), 1.89-1.74 (m, 2H), 1.74-1.60 (m, 2H), 1.57-1.38 (m, 3H), 1.38-1.25 (m, 4H). Several further protons gave very broad signals

40. 1-(7-((3-chlorophenyl)ethynyl)chroman-3-yl)azetidine-3-carboxylic acid

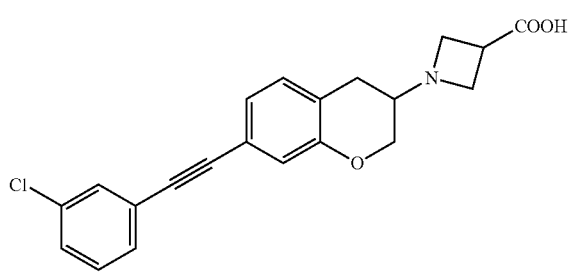 [SMILES: O=C(O)C1CN(C2COc3cc(C#Cc4cccc(Cl)c4)ccc3C2)C1]

Compound 40 was prepared as described for Compound 26 using 1-ethynyl-3-chlorobenzene instead of 1-ethynyl-2,3-difluorobenzene.

¹H NMR (600 MHz, DMSO-d₆) δ 7.65-7.61 (m, 1H), 7.53-7.48 (m, 2H), 7.48-7.43 (m, 1H), 7.21-6.89 (m, 3H), aliphatic protons gave very broad signals

MS: =368.20 [M+H⁺], 735.30 [2M+H⁺]

41. 1-(7-((2-(trifluoromethyl)phenyl)ethynyl)chroman-3-yl)azetidine-3-carboxylic acid

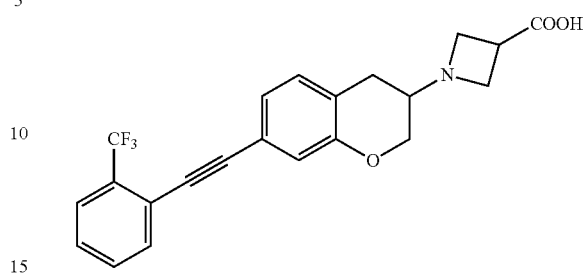

Compound 41 was prepared as described for Compound 26 using 1-ethynyl-2-(trifluoromethyl)benzene instead of 1-ethynyl-2,3-difluorobenzene.

¹H NMR (600 MHz, DMSO-d₆) δ 7.83 (d, J=7.8 Hz, 1H), 7.79 (d, J=7.6 Hz, 1H), 7.72 (t, J=7.6 Hz, 1H), 7.62 (t, J=7.7 Hz, 1H), 7.22-7.12 (m, 1H), 7.11-6.99 (m, 1H), 6.98-6.82 (m, 1H), ), aliphatic protons gave very broad signals

MS: 402.20 [M+H⁺], 803.30 [2M+H⁺]

42. 1-(7-((2-(difluoromethoxy)phenyl)ethynyl)chroman-3-yl)azetidine-3-carboxylic acid

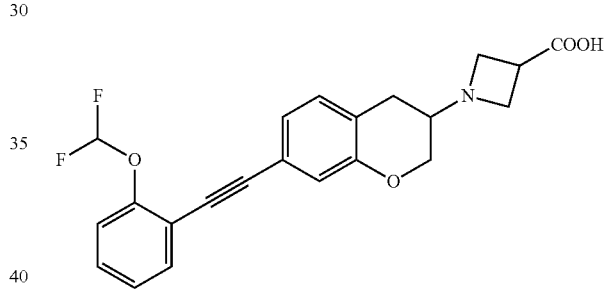

Compound 42 was prepared as described for Compound 26 using 1-(difluoromethoxy)-2-ethynylbenzene instead of 1-ethynyl-2,3-difluorobenzene.

¹H NMR (600 MHz, DMSO-d₆) δ 7.63 (d, J=7.5 Hz, 1H), 7.51-7.46 (m, 1H), 7.34-7.28 (m, 3H), 7.16-7.14 (m, 1H), 7.07-7.01 (m, 1H), 6.91 (s, 1H), aliphatic protons gave very broad signals

MS: 400.25 [M+H⁺], 799.35 [2M+H⁺]

43. 1-(7-((3-(methyl)phenyl)ethynyl)chroman-3-yl)azetidine-3-carboxylic acid

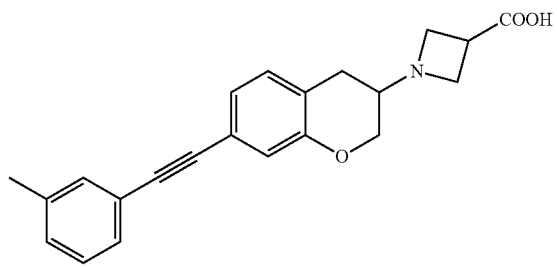 [SMILES: Cc1cccc(C#Cc2ccc3c(c2)OCC(N2CC(C(=O)O)C2)C3)c1]

Compound 43 was prepared as described for Compound 26 using 1-ethynyl-3-methylbenzene instead of 1-ethynyl-2,3-difluorobenzene.

$^1$H NMR (600 MHz, DMSO-$d_6$) δ 7.39-7.35 (m, 1H), 7.34-7.27 (m, 2H), 7.27-7.21 (m, 1H), 7.16-7.08 (m, 1H), 7.08-6.98 (m, 1H), 6.94-6.85 (m, 1H), 2.32 (s, 3H) ), aliphatic protons gave very broad signals

MS: 348.25 [M+H$^+$], 695.35 [2M+H$^+$]

44. 1-(7-((2,6-dichlorophenyl)ethynyl)chroman-3-yl)azetidine-3-carboxylic acid

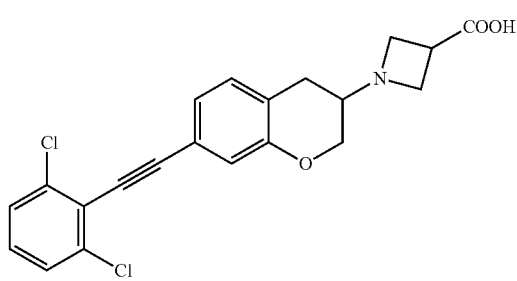 [SMILES: O=C(O)C1CN(C2COc3cc(C#Cc4c(Cl)cccc4Cl)ccc3C2)C1]

Compound 44 was prepared as described for Compound 26 using 1,3-dichloro-2-ethynylbenzene instead of 1-ethynyl-2,3-difluorobenzene.

$^1$H NMR (600 MHz, DMSO-$d_6$) δ 7.61 (d, J=8.2 Hz, 2H), 7.49-7.42 (m, 1H), 7.27-7.10 (m, 2H), 7.10-6.94 (m, 1H), aliphatic protons gave very broad signals

MS: 403.15 [M+H$^+$], 805.20 [2M+H$^+$]

45. 1-(7-((4-ethoxyphenyl)ethynyl)chroman-3-yl)azetidine-3-carboxylic acid

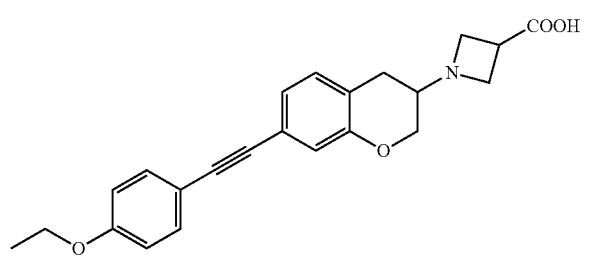 [SMILES: CCOc1ccc(C#Cc2ccc3c(c2)OCC(N2CC(C(=O)O)C2)C3)cc1]

Compound 45 was prepared as described for Compound 26 using 1-ethoxy-4-ethynylbenzene instead of 1-ethynyl-2,3-difluorobenzene.

$^1$H NMR (600 MHz, DMSO-$d_6$) δ 7.47-7.42 (m, 2H), 7.07 (d, J=7.8 Hz, 1H), 6.99-6.92 (m, 3H), 6.83 (d, J=1.6 Hz, 1H), 4.06 (q, J=7.0 Hz, 2H), 4.01 (ddd, J=11.1, 2.6, 1.3 Hz, 1H), 3.79 (ddd, J=11.1, 6.1, 1.4 Hz, 1H), 3.46 (t, J=7.4 Hz, 1H), 3.44-3.39 (m, 1H), 3.29-3.23 (m, 2H), 3.21-3.12 (m, 1H), 2.84 (dd, J=16.5, 4.8 Hz, 1H), 2.68-2.63 (m, 1H), 2.46 (dd, J=16.6, 6.2 Hz, 1H), 1.33 (t, J=7.0 Hz, 3H).

46. 1-(7-((4-chlorobenzyl)oxy)chroman-3-yl)azetidine-3-carboxylic acid

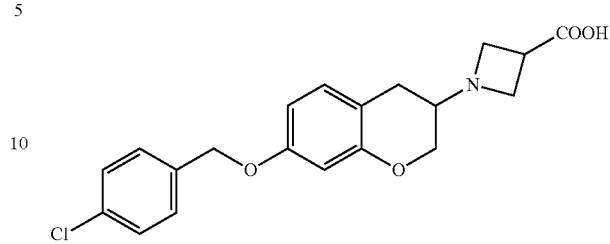

Compound 46 was prepared as described for compound 1 using 1-(bromomethyl)-4-chlorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-$d_6$) δ 7.44 (s, 4H), 6.92 (d, J=8.4 Hz, 1H), 6.48 (dd, J=8.4, 2.6 Hz, 1H), 6.35 (d, J=2.5 Hz, 1H), 5.04 (s, 2H), 3.99-3.93 (m, 1H), 3.75-3.67 (m, 1H), 3.21-3.14 (m, 1H), 2.76-2.70 (m, 1H), 2.34 (dd, J=15.9, 6.5 Hz, 1H).

47. 1-(7-((2,6-difluorophenyl)ethynyl)chroman-3-yl)azetidine-3-carboxylic acid

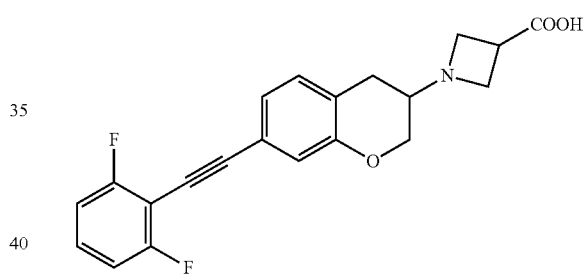

Compound 47 was prepared as described for Compound 26 using 1-ethynyl-2,6-difluorobenzene instead of 1-ethynyl-2,3-difluorobenzene.

$^1$H NMR (600 MHz, DMSO-$d_6$) δ 7.57-7.49 (m, 1H), 7.28-7.21 (m, 2H), 7.14 (d, J=7.8 Hz, 1H), 7.09-7.02 (m, 1H), 6.95-6.88 (m, 1H), aliphatic protons gave very broad signals

MS: 370.20 [M+H$^+$], 739.30 [2M+H$^+$]

48. 3-((7-((2,6-dichlorobenzyl)oxy)chroman-3-yl)amino)-bicyclo[1.1.1]pentane-1-carboxylic acid

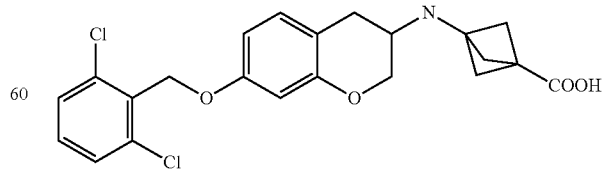

Compound 48 was prepared as described for compound 1 using methyl 3-aminobicyclo[1.1.1]pentane-1-carboxylate hydrochloride instead of methylazetine-3-carboxylate hydrochloride. Hydrolysis of the methylester was performed in analogy to step 10.3 at RT in methanol with 2N NaOH.

$^1$H NMR (600 MHz, Methanol-d$_4$) δ 7.50-7.42 (m, 2H), 7.36 (dd, J=8.7, 7.4 Hz, 1H), 7.09-7.03 (m, 1H), 6.65 (dd, J=8.4, 2.5 Hz, 1H), 6.57 (d, J=2.6 Hz, 1H), 5.24 (s, 2H), 4.28-4.22 (m, 1H), 4.19 (dd, J=11.9, 2.0 Hz, 1H), 3.77-3.74 (m, 1H), 3.22 (dd, J=17.1, 5.5 Hz, 1H), 2.83-2.77 (m, 1H), 2.36 (s, 6H).

49. 1-(((7-((2,6-dichlorobenzyl)oxy)chroman-3-yl)amino)methyl)cyclopropanecarboxylic acid

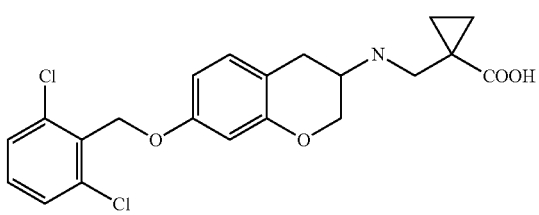 [SMILES: O=C(O)C1(CNC2COc3cc(OCc4c(Cl)cccc4Cl)ccc3C2)CC1]

Compound 49 was prepared as described for compound 1 using ethyl 1-(aminomethyl)cyclopropanecarboxylate instead of methylazetine-3-carboxylate hydrochloride. Hydrolysis of the ethylester was performed in analogy to step 10.3 at RT in methanol with 2N NaOH.

$^1$H NMR (600 MHz, Methanol-d$_4$) δ 7.45 (d, J=8.1 Hz, 2H), 7.36 (dd, J=8.7, 7.5 Hz, 1H), 7.08 (d, J=8.4 Hz, 1H), 6.66 (dd, J=8.4, 2.6 Hz, 1H), 6.59 (d, J=2.6 Hz, 1H), 5.24 (s, 2H), 4.65-4.59 (m, 1H), 4.42-4.37 (m, 1H), 4.29-4.24 (m, 1H), 3.84-3.79 (m, 1H), 3.25-3.23 (m, 2H), 3.04-2.97 (m, 1H), 1.28-1.23 (m, 2H), 0.86-0.81 (m, 2H).

50. 1-(7-((2,6-dichlorobenzyl)oxy)chroman-3-yl)pyrrolidine-3-carboxylic acid

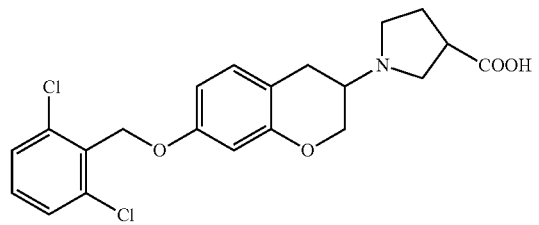 [SMILES: O=C(O)C1CCN(C2COc3cc(OCc4c(Cl)cccc4Cl)ccc3C2)C1]

Compound 50 was prepared as described for compound 1 using 3-(ethoxycarbonyl)pyrrolidin hydrochloride instead of methylazetine-3-carboxylate hydrochloride. Hydrolysis of the ethylester was performed in analogy to step 10.3 at RT in methanol with 2N NaOH. Mixture of diastereoisomers 4:1.

Signals of Main Isomere:

$^1$H NMR (600 MHz, Methanol-d$_4$) δ 7.47-7.43 (m, 2H), 7.35 (dt, J=8.6, 7.2 Hz, 1H), 7.11-7.06 (m, 1H), 6.68-6.64 (m, 1H), 6.58 (d, J=2.6 Hz, 1H), 5.24 (s, 2H), 4.46-4.38 (m, 1H), 4.31 (dd, J=12.8, 1.5 Hz, 1H), 3.70-3.67 (m, 1H), 3.67-3.61 (m, 1H), 3.61-3.53 (m, 1H), 3.49-3.38 (m, 2H), 3.21-3.13 (m, 1H), 3.10-3.03 (m, 1H), 2.36-2.28 (m, 1H), 2.25 (ddq, J=13.8, 10.7, 7.0 Hz, 1H).

51. 1-(7-((2,3-difluorobenzyl)oxy)chroman-3-yl)azetidine-3-carboxylic acid

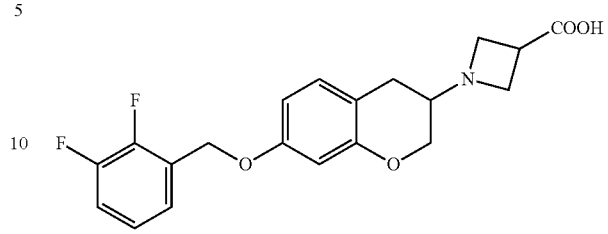

Compound 51 was prepared as described for compound 1 using 1-(bromomethyl)-2,3-difluorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-d$_6$) δ 7.47-7.40 (m, 1H), 7.37-7.32 (m, 1H), 7.26-7.21 (m, 1H), 6.94 (d, J=8.4 Hz, 1H), 6.50 (dd, J=8.3, 2.6 Hz, 1H), 6.39 (d, J=2.5 Hz, 1H), 5.12 (s, 2H), 4.00-3.94 (m, 1H), 3.72 (dd, J=11.1, 6.3 Hz, 1H), 3.17 (p, J=7.5 Hz, 1H), 2.74 (dd, J=15.9, 4.8 Hz, 1H), 2.35 (dd, J=15.9, 6.5 Hz, 1H).

52. 1-(7-((2,5-dichlorobenzyl)oxy)chroman-3-yl)azetidine-3-carboxylic acid

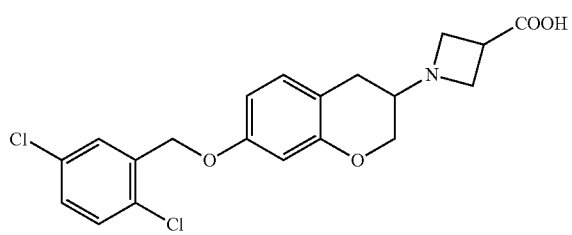 [SMILES: O=C(O)C1CN(C2COc3cc(OCc4cc(Cl)ccc4Cl)ccc3C2)C1]

Compound 52 was prepared as described for compound 1 using 2-(bromomethyl)-1,4-dichlorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-d$_6$) δ 7.62 (d, J=2.6 Hz, 1H), 7.55 (d, J=8.5 Hz, 1H), 7.47 (dd, J=8.6, 2.6 Hz, 1H), 6.95 (d, J=8.5 Hz, 1H), 6.51 (dd, J=8.4, 2.6 Hz, 1H), 6.38 (d, J=2.5 Hz, 1H), 5.07 (s, 2H), 4.00-3.94 (m, 1H), 3.73 (dd, J=11.0, 6.3 Hz, 1H), 3.17 (p, J=7.5 Hz, 1H), 2.75 (dd, J=15.9, 4.8 Hz, 1H), 2.66-2.59 (m, 2H), 2.36 (dd, J=15.9, 6.4 Hz, 1H).

53. 1-(7-((2-fluoro-6-methylbenzyl)oxy)chroman-3-yl)azetidine-3-carboxylic acid

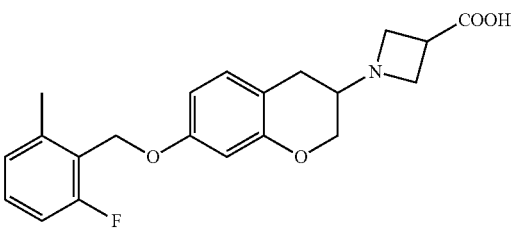

Compound 53 was prepared as described for compound 1 using 2-(bromomethyl)-1-fluoro-3-methylbenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-d$_6$) δ 7.36-7.28 (m, 1H), 7.14-7.05 (m, 2H), 6.94 (d, J=8.4 Hz, 1H), 6.50 (dd, J=8.3, 2.6 Hz, 1H), 6.42 (d, J=2.5 Hz, 1H), 5.01 (s, 2H), 4.00-3.95 (m, 1H), 3.78-3.69 (m, 1H), 3.22-3.15 (m, 1H), 2.75 (dd, J=16.3, 4.7 Hz, 1H), 2.67-2.57 (m, 1H), 2.41-2.36 (m, 1H), 2.35 (s, 3H), several aliphatic protons gave very broad signals.

54. 1-(7-(4-((4-chlorobenzyl)oxy)phenyl)chroman-3-yl)azetidine-3-carboxylic acid

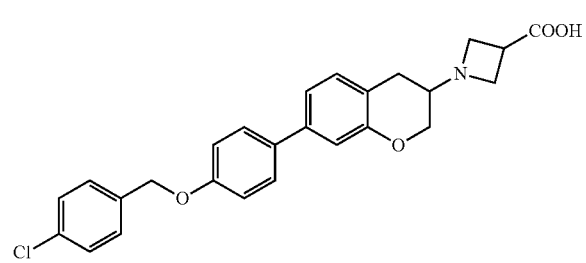 [SMILES: O=C(O)C1CN(C2COc3cc(-c4ccc(OCc5ccc(Cl)cc5)cc4)ccc3C2)C1]

54.1 Methyl 1-(7-(4-(benzyloxy)phenyl)chroman-3-yl)azetidine-3-carboxylate

A solution of methyl 1-(7-(((perfluorobutyl)sulfonyl)oxy)chroman-3-yl)azetidine-3-carboxylate (568 mg, 1.04 mmol, step 26.1) in 10 ml Toluol and 1 ml H$_2$O was flushed with argon for 30 minutes and then added to a microwave vial charged with 4-(benzyloxy)phenyl)boronic acid (237 mg, 1.04 mmol). Potassium carbonate (431 mg, 3.1 mmol), bis(dibenzylideneacetone)palladium(0) (30.5 mg, 0.053 mmol) and 2-Dicyclohexylphosphino-2',6'-di-i-propoxy-1,1'-biphenyl (RuPhos, 25 mg, 0.053 mmol). The vial was placed in a micro wave and heated for 1 hour to 110° C. after which the solvent was evaporated. The remaining residue was dissolved in DCM, washed with water and brine, dried over Na$_2$SO$_4$ and evaporated. The resulting brown oil was purified by chromatography (silica gel) affording 145 mg of desired product.

54.2 Methyl 1-(7-(4-hydroxyphenyl)chroman-3-yl)azetidine-3-carboxylate

Palladium-on-carbon (Pd/C 10%, 30 mg)) was added to a solution of methyl 1-(7-(4-(benzyloxy)phenyl)chroman-3-yl)azetidine-3-carboxylate (145 mg, 0.34 mmol) dissolved in 50 ml methanol. The mixture was hydrogenated by stirring at RT under hydrogen atmosphere over the weekend. Then reaction mixture was filtered and the organic layer was evaporated 113 mg of desired product.

54.3 Methyl 1-(7-(4-((4-chlorobenzyl)oxy)phenyl)chroman-3-yl)azetidine-3-carboxylate Potassium carbonate (14.4 mg, 0.1 mmol) and 1-(bromomethyl)-4-chlorobenzene (15.7 mg, 0.076 mmol) was added to a solution of methyl 1-(7-(4-hydroxyphenyl)chroman-3-yl)azetidine-3-carboxylate (24.6 mg, 0.07 mmol) in DMF which was subsequently stirred over night at RT. The reaction mixture was diluted with water and extracted with ethyl acetate. The combined organic layers were washed with brine, dried over Na$_2$SO$_4$, filtered and the solvent evaporated. The residue was purified by chromatography (silica gel) affording 29 mg of the desired product.

54.4 1-(7-(4-((4-chlorobenzyl)oxy)phenyl)chroman-3-yl)azetidine-3-carboxylic acid Sodium hydroxide (2N, 0.15 ml, 0.3 mmol) was added to a solution of methyl 1-(7-(4-((4-chlorobenzyl)oxy)phenyl)chroman-3-yl)azetidine-3-carboxylate (14.3 mg, 0.03 mmol) in 0.5 ml MeOH. The Mixture was stirred at RT for two hours after which the solvent was evaporated. The residue was dissolved in water, pH adjusted to 5 with 2N HCl and the solution stirred overnight. The yet formed precipitate was filtered and dried at 60° C. affording 9.2 mg of desired product.

$^1$H NMR (600 MHz, DMSO-d$_6$) δ 7.57-7.51 (m, 2H), 7.51-7.44 (m, 4H), 7.09-7.01 (m, 4H), 6.94-6.91 (m, 1H), 5.15 (s, 3H), 4.04-3.99 (m, 1H), 3.79 (dd, J=11.1, 6.2 Hz, 1H), 3.51-3.46 (m, 1H), 3.46-3.41 (m, 0H), 3.20-3.14 (m, 1H), 2.84 (dd, J=16.4, 4.7 Hz, 1H), 2.69-2.63 (m, 1H).

55. 1-(7-(4-(cyclohexylmethoxy)phenyl)chroman-3-yl)azetidine-3-carboxylic acid

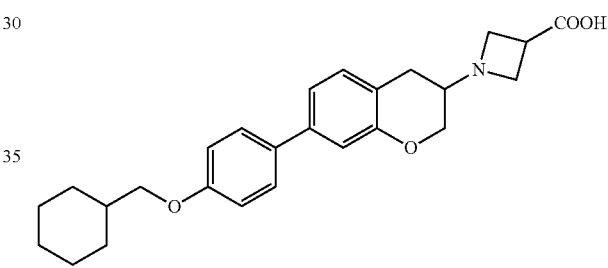

Compound 55 was prepared as described for compound 54 using (bromomethyl)cyclohexane instead of 1-(bromomethyl)-4-chlorobenzene.

$^1$H NMR (500 MHz, DMSO-d$_6$) δ 7.53-7.47 (m, 2H), 7.07 (d, J=7.9 Hz, 1H), 7.03 (dd, J=7.9, 1.9 Hz, 1H), 6.99-6.94 (m, 2H), 6.90 (d, J=2.1 Hz, 1H), 4.02-3.97 (m, 1H), 3.80 (d, J=6.4 Hz, 2H), 3.73 (dd, J=10.8, 6.5 Hz, 1H), 3.30-3.23 (m, 1H), 3.13 (q, J=6.5 Hz, 2H), 2.84-2.76 (m, 1H), 2.70 (p, J=7.8 Hz, 1H), 2.45-2.38 (m, 1H), 1.86-1.59 (m, 6H), 1.31-1.11 (m, 3H), 1.06 (td, J=12.1, 3.3 Hz, 2H).

56. 1-(7-(4-((2,3-difluorobenzyl)oxy)phenyl)chroman-3-yl)azetidine-3-carboxylic acid

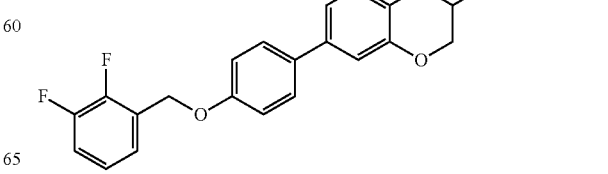

Compound 56 was prepared as described for compound 54 using 1-(bromomethyl)-2,3-difluorobenzene instead of 1-(bromomethyl)-4-chlorobenzene.

¹H NMR (600 MHz, DMSO-d₆) δ 7.58-7.53 (m, 2H), 7.49-7.43 (m, 1H), 7.42-7.37 (m, 1H), 7.29-7.24 (m, 1H), 7.11-7.05 (m, 4H), 6.93 (d, J=1.7 Hz, 1H), 5.23 (s, 2H), 4.05-3.99 (m, 1H), 3.84-3.77 (m, 1H), 3.22-3.15 (m, 1H), 2.90-2.81 (m, 1H), 2.74-2.60 (m, 1H).

57. 1-(7-((4-(trifluoromethyl)benzyl)oxy)chroman-3-yl)azetidine-3-carboxylic acid

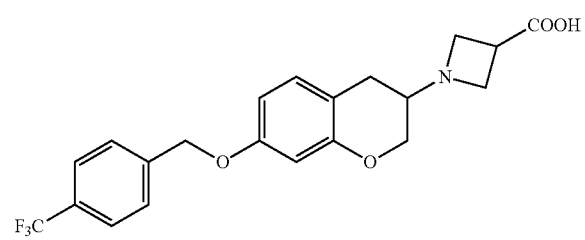 [SMILES: O=C(O)C1CN(C2COc3cc(OCc4ccc(C(F)(F)F)cc4)ccc3C2)C1]

Compound 57 was prepared as described for compound 1 using 1-(bromomethyl)-4-(trifluoromethyl)benzene instead of 2-(bromomethyl)-1,3-dichlorobenzene. Hydrolysis of the methylester was performed in analogy to step 10.3 at RT in methanol with 2N NaOH.

¹H NMR (500 MHz, DMSO-d₆) δ 7.75 (d, J=8.0 Hz, 2H), 7.63 (d, J=8.0 Hz, 2H), 6.93 (d, J=8.4 Hz, 1H), 6.50 (dd, J=8.4, 2.6 Hz, 1H), 6.37 (d, J=2.6 Hz, 1H), 5.16 (s, 2H), 4.00-3.91 (m, 1H), 3.75-3.67 (m, 1H), 3.20-3.12 (m, 1H), 2.78-2.70 (m, 1H), 2.62-2.56 (m, 1H), 2.35-2.31 (m, 1H).

58. 1-(7-((3-methylbenzyl)oxy)chroman-3-yl)azetidine-3-carboxylic acid

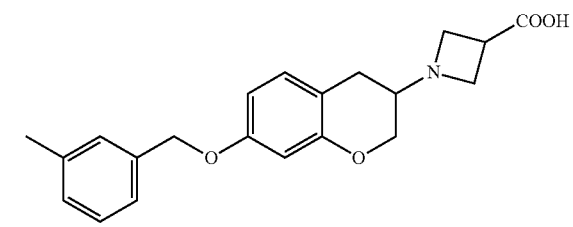 [SMILES: Cc1cccc(COc2ccc3c(c2)OCC(N2CC(C(=O)O)C2)C3)c1]

Compound 58 was prepared as described for compound 1 using 1-(bromomethyl)-3-methylbenzene instead of 2-(bromomethyl)-1,3-dichlorobenzene. Hydrolysis of the methylester was performed in analogy to step 10.3 at RT in methanol with 2N NaOH.

¹H NMR (500 MHz, DMSO-d₆) δ 7.26 (t, J=7.5 Hz, 1H), 7.23-7.16 (m, 2H), 7.12 (d, J=7.3 Hz, 1H), 6.91 (d, J=8.4 Hz, 1H), 6.47 (dd, J=8.4, 2.6 Hz, 1H), 6.34 (d, J=2.6 Hz, 1H), 4.98 (s, 2H), 3.95 (dd, J=11.1, 2.5 Hz, 1H), 3.70 (dd, J=11.0, 6.3 Hz, 1H), 3.45 (t, J=7.3 Hz, 1H), 3.40 (t, J=7.3 Hz, 1H), 3.27-3.21 (m, 2H), 3.19-3.12 (m, 1H), 2.72 (dd, J=15.9, 4.9 Hz, 1H), 2.62-2.56 (m, 1H), 2.38-2.32 (m, 1H), 2.31 (s, 3H).

59. 1-(7-((3-(trifluoromethyl)benzyl)oxy)chroman-3-yl)azetidine-3-carboxylic acid

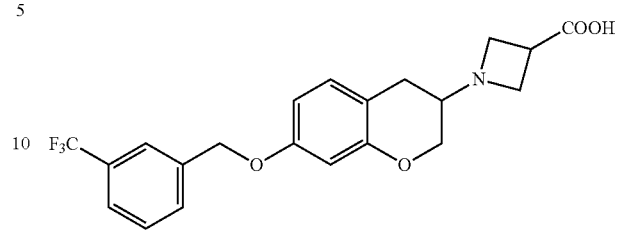

Compound 59 was prepared as described for compound 1 using 1-(bromomethyl)-3-(trifluoromethyl)benzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.79-7.76 (m, 1H), 7.73 (d, J=7.7 Hz, 1H), 7.69 (d, J=7.8 Hz, 1H), 7.63 (t, J=7.7 Hz, 1H), 6.94 (d, J=8.4 Hz, 1H), 6.51 (dd, J=8.3, 2.6 Hz, 1H), 6.39 (d, J=2.6 Hz, 1H), 5.14 (s, 2H), 4.01-3.93 (m, 1H), 3.75-3.68 (m, 1H), 3.22-3.14 (m, 1H), 2.79-2.70 (m, 1H), 2.35 (dd, J=15.8, 6.4 Hz, 1H).

60. 1-(7-((2,6-difluorobenzyl)oxy)chroman-3-yl)azetidine-3-carboxylic acid

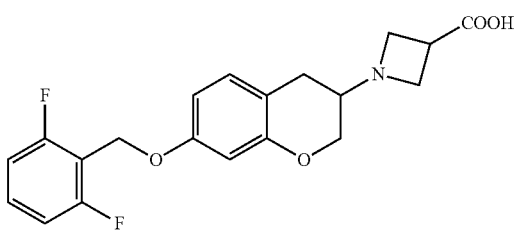

Compound 60 was prepared as described for compound 1 using 2-(bromomethyl)-1,3-difluorobenzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.52 (tt, J=8.3, 6.5 Hz, 1H), 7.21-7.13 (m, 2H), 6.94 (d, J=8.4 Hz, 1H), 6.49 (dd, J=8.4, 2.6 Hz, 1H), 6.41 (d, J=2.5 Hz, 1H), 5.03 (s, 2H), 4.02-3.93 (m, 1H), 3.75-3.69 (m, 1H), 3.46 (t, J=7.4 Hz, 1H), 3.27-3.22 (m, 2H), 3.20-3.13 (m, 1H), 2.74 (dd, J=15.8, 4.9 Hz, 1H), 2.61-2.58 (m, 1H), 2.35 (dd, J=15.8, 6.6 Hz, 1H).

61. 1-(7-((2-chloro-6-fluorobenzyl)oxy)chroman-3-yl)azetidine-3-carboxylic acid

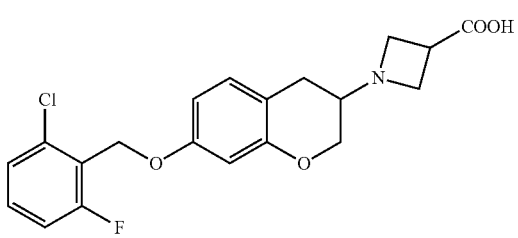 [SMILES: O=C(O)C1CN(C2COc3cc(OCc4c(F)cccc4Cl)ccc3C2)C1]

Compound 61 was prepared as described for compound 1 using 2-(bromomethyl)-1-chloro-3-fluorobenzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.54-7.46 (m, 1H), 7.45-7.39 (m, 1H), 7.36-7.27 (m, 1H), 6.95 (d, J=8.4 Hz, 1H), 6.51 (dd, J=8.3, 2.6 Hz, 1H), 6.42 (d, J=2.5 Hz, 1H), 5.06 (s, 2H), 3.98 (ddd, J=11.0, 2.7, 1.3 Hz, 1H), 3.76-3.69 (m, 1H), 3.48-3.43 (m, 1H), 3.27-3.23 (m, 2H), 3.20-3.12 (m, 1H), 2.75 (dd, J=15.8, 4.9 Hz, 1H), 2.62-2.59 (m, 1H), 2.36 (dd, J=15.8, 6.4 Hz, 1H).

62. 1-(7-((2-(trifluoromethyl)benzyl)oxy)chroman-3-yl)azetidine-3-carboxylic acid

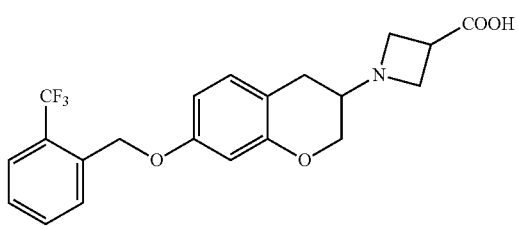 [SMILES: O=C(O)C1CN(C2COc3cc(OCc4ccccc4Cl)ccc3C2)C1]

Compound 62 was prepared as described for compound 1 using 1-(bromomethyl)-2-(trifluoromethyl)benzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.79 (d, J=7.7 Hz, 1H), 7.74-7.68 (m, 2H), 7.60-7.54 (m, 1H), 6.94 (d, J=8.5 Hz, 1H), 6.48 (dd, J=8.3, 2.6 Hz, 1H), 6.33 (d, J=2.5 Hz, 1H), 5.17 (s, 2H), 3.99-3.93 (m, 1H), 3.75-3.69 (m, 1H), 3.47-3.37 (m, 2H), 3.29-3.20 (m, 2H), 3.20-3.12 (m, 1H), 2.73 (dd, J=15.8, 4.9 Hz, 1H), 2.62-2.56 (m, 1H), 2.35 (dd, J=15.8, 6.4 Hz, 1H).

63. 1-(7-((2-chlorobenzyl)oxy)chroman-3-yl)azetidine-3-carboxylic acid

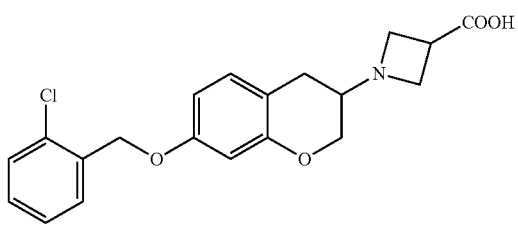

Compound 63 was prepared as described for compound 1 using 1-(bromomethyl)-2-chlorobenzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.59-7.48 (m, 2H), 7.44-7.33 (m, 2H), 6.94 (d, J=8.4 Hz, 1H), 6.50 (dd, J=8.4, 2.6 Hz, 1H), 6.36 (d, J=2.5 Hz, 1H), 5.08 (s, 2H), 4.00-3.93 (m, 1H), 3.72 (dd, J=11.1, 6.3 Hz, 1H), 3.21-3.13 (m, 1H), 2.74 (dd, J=15.9, 4.8 Hz, 1H), 2.64-2.57 (m, 1H), 2.36 (dd, J=15.9, 6.4 Hz, 1H).

64. 1-(7-((2-ethylbenzyl)oxy)chroman-3-yl)azetidine-3-carboxylic acid

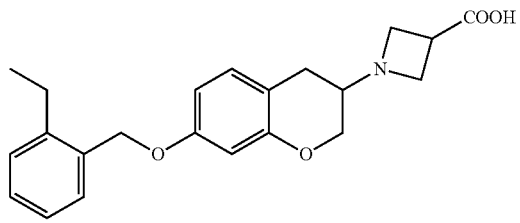 [SMILES: CCc1ccccc1COc1ccc2c(c1)OCC(N1CC(C(=O)O)C1)C2]

Compound 64 was prepared as described for compound 1 using 1-(bromomethyl)-2-ethylbenzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.38 (dd, J=7.5, 1.3 Hz, 1H), 7.32-7.27 (m, 1H), 7.27-7.24 (m, 1H), 7.22-7.16 (m, 1H), 6.93 (d, J=8.4 Hz, 1H), 6.49 (dd, J=8.3, 2.5 Hz, 1H), 6.38 (d, J=2.5 Hz, 1H), 5.01 (s, 2H), 3.98-3.95 (m, 1H), 3.75-3.69 (m, 1H), 3.45 (t, J=7.4 Hz, 1H), 3.27-3.22 (m, 2H), 3.19-3.12 (m, 1H), 2.74 (dd, J=15.7, 4.9 Hz, 1H), 2.65 (q, J=7.6 Hz, 2H), 2.62-2.58 (m, 1H), 2.35 (dd, J=15.8, 6.5 Hz, 1H), 1.17 (t, J=7.5 Hz, 3H).

65. 1-(7-((2-ethyl-6-fluorobenzyl)oxy)chroman-3-yl)azetidine-3-carboxylic acid

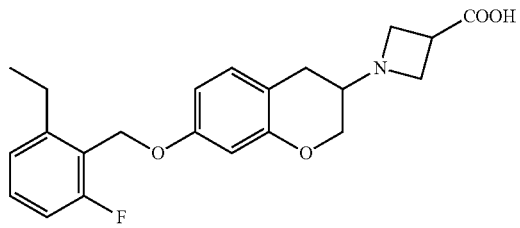 [SMILES: CCc1cccc(F)c1COc1ccc2c(c1)OCC(N1CC(C(=O)O)C1)C2]

Compound 65 was prepared as described for compound 1 using 2-(bromomethyl)-1-ethyl-3-fluorobenzene instead of 2-(bromomethyl)-1,3-dichlorobenzene. Hydrolysis of the methylester was performed in analogy to step 10.3 at RT in methanol with 2N NaOH.

¹H NMR (600 MHz, DMSO-d₆) δ 7.40-7.34 (m, 1H), 7.15-7.12 (m, 1H), 7.11-7.06 (m, 1H), 6.94 (d, J=8.4 Hz, 1H), 6.50 (dd, J=8.3, 2.6 Hz, 1H), 6.42 (d, J=2.5 Hz, 1H), 5.00 (s, 2H), 3.99-3.95 (m, 1H), 3.76-3.69 (m, 1H), 3.46 (t, J=7.4 Hz, 1H), 3.27-3.22 (m, 2H), 3.20-3.13 (m, 1H), 2.74 (dd, J=15.8, 4.9 Hz, 1H), 2.69 (q, J=7.6 Hz, 2H), 2.64-2.58 (m, 1H), 2.36 (dd, J=15.8, 6.5 Hz, 1H).

66. 1-(7-((2-fluoro-6-(trifluoromethyl)benzyl)oxy)chroman-3-yl)azetidine-3-carboxylic acid

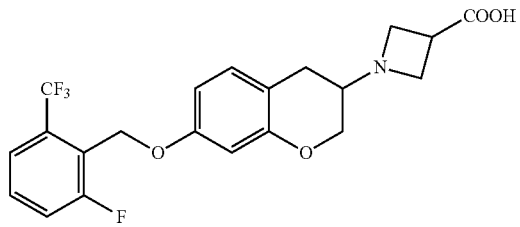

Compound 66 was prepared as described for compound 1 using 2-(bromomethyl)-1-fluoro-3-(trifluoromethyl)benzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-$d_6$) δ 7.75-7.64 (m, 3H), 6.95 (d, J=8.4 Hz, 1H), 6.49 (dd, J=8.4, 2.6 Hz, 1H), 6.41 (d, J=2.6 Hz, 1H), 5.07 (s, 2H), 4.01-3.96 (m, 1H), 3.76-3.71 (m, 1H), 3.46 (t, J=7.4 Hz, 1H), 3.27-3.23 (m, 2H), 3.20-3.13 (m, 1H), 2.75 (dd, J=15.8, 4.9 Hz, 1H), 2.61 (qq, J=6.1, 2.6 Hz, 1H), 2.39-2.33 (m, 1H).

67. 1-(7-((2-cyclopropyl-6-fluorobenzyl)oxy)chroman-3-yl)azetidine-3-carboxylic acid

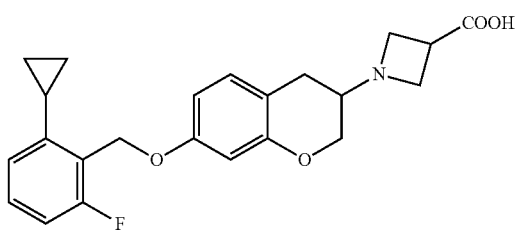 [SMILES: O=C(O)C1CN(C2COc3cc(OCc4c(F)cccc4C4CC4)ccc3C2)C1]

Compound 67 was prepared as described for compound 1 using 2-(bromomethyl)-1-cyclopropyl-3-fluorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-$d_6$) δ 7.36-7.28 (m, 1H), 7.05 (dd, J=9.6, 8.3 Hz, 1H), 6.94 (d, J=8.4 Hz, 1H), 6.85 (d, J=7.8 Hz, 1H), 6.52 (dd, J=8.4, 2.6 Hz, 1H), 6.44 (d, J=2.5 Hz, 1H), 5.14 (s, 2H), 4.01-3.92 (m, 1H), 3.73 (dd, J=11.0, 6.2 Hz, 1H), 3.45 (t, J=7.4 Hz, 1H), 3.41 (t, J=7.4 Hz, 1H), 3.27-3.21 (m, 2H), 3.21-3.13 (m, 1H), 2.74 (dd, J=15.8, 4.9 Hz, 1H), 2.64-2.58 (m, 1H), 2.36 (dd, J=15.8, 6.5 Hz, 1H), 2.09-2.00 (m, 1H), 0.97-0.89 (m, 2H), 0.72-0.64 (m, 2H).

68. 1-(7-((2,4-dichlorobenzyl)oxy)chroman-3-yl)azetidine-3-carboxylic acid

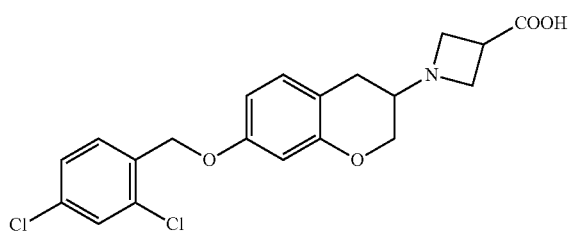 [SMILES: O=C(O)C1CN(C2COc3cc(OCc4ccc(Cl)cc4Cl)ccc3C2)C1]

Compound 68 was prepared as described for compound 1 using 1-(bromomethyl)-2,4-dichlorobenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-$d_6$) δ 7.69 (d, J=2.2 Hz, 1H), 7.57 (d, J=8.3 Hz, 1H), 7.47 (dd, J=8.3, 2.2 Hz, 1H), 6.94 (d, J=8.4 Hz, 1H), 6.49 (dd, J=8.4, 2.6 Hz, 1H), 6.36 (d, J=2.6 Hz, 1H), 5.07 (s, 2H), 3.98-3.93 (m, 1H), 3.76-3.69 (m, 1H), 3.48-3.42 (m, 1H), 3.42-3.38 (m, 1H), 3.28-3.21 (m, 2H), 3.21-3.13 (m, 1H), 2.74 (dd, J=15.8, 4.9 Hz, 1H), 2.63-2.56 (m, 2H), 2.35 (dd, J=15.8, 6.4 Hz, 1H).

69. 1-(7-(2,6-dichlorophenethoxy)chroman-3-yl)azetidine-3-carboxylic acid

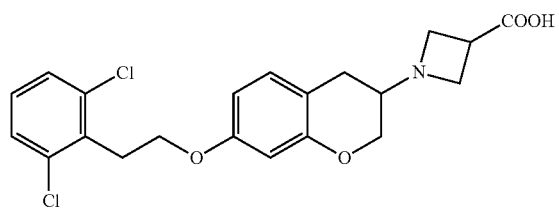 [SMILES: O=C(O)C1CN(C2COc3cc(OCCc4c(Cl)cccc4Cl)ccc3C2)C1]

69.1 Methyl 1-(7-(2,6-dichlorophenethoxy)chroman-3-yl)azetidine-3-carboxylate Triphenylphosphine (125 mg, 0.475 mmol) was added to a solution of methyl 1-(7-hydroxychroman-3-yl)azetidine-3-carboxylate (50 mg, 0.19 mmol) with 2-(2,6-dichlorophenyl)ethanol (54.4 mg, 0.285 mmol) in DCM and stirred for 30 minutes. (E)-Diisopropyl diazene-1,2-dicarboxylate (DIAD, 96 mg, 0,475 mmol) was added drop wise and the mixture was stirred overnight. Then the mixture was concentrated and the residue dissolved in ethyl acetate and sat. NaHCO$_3$, The organic phase was dried (Na$_2$SO$_4$), filtered, evaporated and the crude purified by chromatography (silica gel) affording 80 mg of the desired product as clear oil.

69.2 1-(7-(2,6-dichlorophenethoxy)chroman-3-yl)azetidine-3-carboxylic acid

Sodium hydroxide (2N, 0.275 ml, 0.55 mmol) was added to a solution of methyl 1-(7-(2,6-dichlorophenethoxy)chroman-3-yl)azetidine-3-carboxylate (80 mg, 0.183 mmol) in methanol/THF and stirred for 3 hours at RT. Then the solvent was evaporated, the residue taken up in water and neutralized with aqueous H$_2$SO$_4$. The precipitate was filtered off, washed with water, dried in vacuo and purified by chromatography affording 14 mg of the desired product.

$^1$H NMR (600 MHz, Chloroform-d) δ 7.31 (d, J=8.0 Hz, 2H), 7.12 (t, J=8.1 Hz, 1H), 6.95 (d, J=8.6 Hz, 1H), 6.56 (dd, J=8.5, 2.5 Hz, 1H), 6.42 (d, J=2.5 Hz, 1H), 4.50-4.36 (m, 2H), 4.34-4.23 (m, 3H), 4.22-4.16 (m, 2H), 4.10 (t, J=7.6 Hz, 2H), 3.88-3.75 (m, 1H), 3.63-3.56 (m, 1H), 3.43 (t, J=7.6 Hz, 2H), 3.09 (dd, J=16.3, 5.7 Hz, 1H), 2.97 (dd, J=16.3, 7.1 Hz, 1H).

70. 1-((6-((2,6-dichlorobenzyl)oxy)isochroman-1-yl)methyl)piperidine-4-carboxylic acid

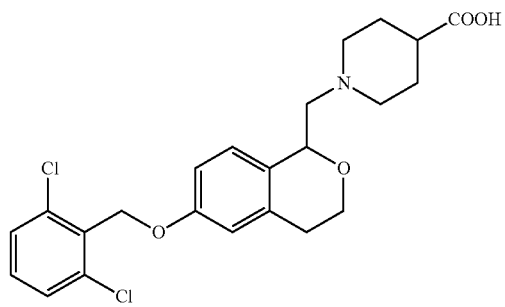 [SMILES: O=C(O)C1CCN(CC2OCCc3cc(OCc4c(Cl)cccc4Cl)ccc32)CC1]

70.1 1-(bromomethyl)-6-methoxyisochroman 2-bromo-1,1-diethoxyethane (6.47 g, 33 mmol) was added at 0° C. to 2-(3-methoxyphenyl)ethanol (5 g, 33 mmol) dissolved in dioxane, followed by addition of hydrochloric acid (4N in dioxane, 82 ml, 330 mmol). The mixture was then stirred for three days allowing to warm up to RT followed by evaporation of the solvent. The residue was extracted with hexane, which was then evaporated. The crude material was purified by chromatography (silica gel) affording 3.41 g of desired bromo compound.

70.2 Methyl 1-((6-methoxyisochroman-1-yl)methyl)piperidine-4-carboxylate 1-(bromomethyl)-6-methoxyisochroman (400 mg, 1.4 mmol), methyl piperidine-4-carboxylate (200 mg, 1.4 mmol) and triethylamine (213 mg, 0.29 ml, 2.1 mmol) in ethylene glycol was stirred overnight at RT and further 8 hours at 50° C. purified by chromatography (silica gel) affording 3.41 g of desired bromo compound. The mixture was partitioned between dichloromethane and 10% aq. potassium carbonate. The organic phase was dried ($Na_2SO_4$), filtered and evaporated and the residue purified by chromatography affording 26 mg of product

70.3 Methyl 1-((6-hydroxyisochroman-1-yl)methyl)piperidine-4-carboxylate

Borontribromide (1N in DCM, 0.4 ml, 04 mmol) was added at −78° C. to methyl 1-((6-methoxyisochroman-1-yl)methyl)piperidine-4-carboxylate (26 mg, 0.08 mmol) dissolved in DCM. The mixture was stirred for 2 hours at −78° C. then for further 5 hours at −50° C. after which the reaction was quenched at −78° C. with methanol/dichloromethane 2:3 and then warmed up to RT. The solvent was evaporated and the residue (25 mg) used without further purification.

70.4 Methyl 1-((6-((2,6-dichlorobenzyl)oxy)isochroman-1-yl)methyl)piperidine-4-carboxylate Potassium carbonate (20.3 mg, 0.15 mmol) was added to a solution of crude methyl 1-((6-hydroxyisochroman-1-yl)methyl)piperidine-4-carboxylate (25 mg, 0.07 mmol) and 2-(bromomethyl)-1,3-dichlorobenzene (19.4 mg, 0.08 mmol). The mixture was stirred at RT over the weekend, then diluted with ethyl acetate, washed with water, dried over $Na_2SO_4$, filtered and the solvent evaporated. The residue was purified by chromatography (silica gel) affording 8 mg of the benzylated product

70.4 1-((6-((2,6-dichlorobenzyl)oxy)isochroman-1-yl)methyl)piperidine-4-carboxylic acid Sodium hydroxide (2N, 0.1 ml, 0.2 mmol) was added to a solution of methyl 1-((6-((2,6-dichlorobenzyl)oxy)isochroman-1-yl)methyl)piperidine-4-carboxylate (8 mg, 0.02 mmol) in methanol/THF and the mixture stirred for two days at RT. Then the solvent was evaporated, the residue taken up in water, neutralized 2N HCl, extracted with ethyl acetate, the organic phase dried ($Na_2SO_4$), filtered and evaporated affording 2.7 mg of the desired product.

$^1$H NMR (600 MHz, Chloroform-d) δ 7.31 (d, J=8.0 Hz, 2H), 7.12 (t, J=8.1 Hz, 1H), 6.95 (d, J=8.6 Hz, 1H), 6.56 (dd, J=8.5, 2.5 Hz, 1H), 6.42 (d, J=2.5 Hz, 1H), 4.50-4.36 (m, 2H), 4.34-4.23 (m, 3H), 4.22-4.16 (m, 2H), 4.10 (t, J=7.6 Hz, 2H), 3.88-3.75 (m, 1H), 3.63-3.56 (m, 1H), 3.43 (t, J=7.6 Hz, 2H), 3.09 (dd, J=16.3, 5.7 Hz, 1H), 2.97 (dd, J=16.3, 7.1 Hz, 1H).

71. 1-(7-((2-chloro-6-methylbenzyl)oxy)chroman-3-yl)azetidine-3-carboxylic acid

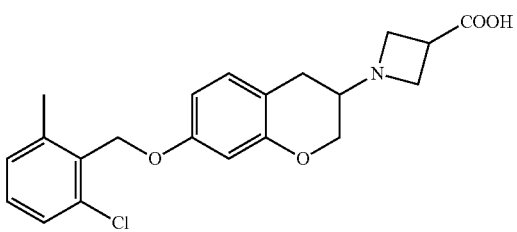 [SMILES: Cc1cccc(Cl)c1COc1ccc2c(c1)OCC(N1CC(C(=O)O)C1)C2]

Compound 71 was prepared as described for compound 1 using 2-(bromomethyl)-1-chloro-3-methylbenzene instead of 2-(bromomethyl)-1,3-dichlorobenzene. Hydrolysis of the methylester was performed in analogy to step 10.3 at RT in methanol with 2N NaOH.

$^1$H NMR (600 MHz, DMSO-$d_6$) δ 7.35 (dd, J=8.1, 1.3 Hz, 1H), 7.30 (t, J=7.7 Hz, 1H), 7.26-7.21 (m, 1H), 6.95 (d, J=8.5 Hz, 1H), 6.51 (dd, J=8.4, 2.6 Hz, 1H), 6.43 (d, J=2.5 Hz, 1H), 5.09 (s, 2H), 4.01-3.95 (m, 1H), 3.74 (dd, J=11.1, 6.2 Hz, 1H), 3.46 (t, J=7.4 Hz, 1H), 3.41 (t, J=7.4 Hz, 1H), 3.29-3.22 (m, 2H), 3.21-3.13 (m, 1H), 2.75 (dd, J=15.8, 4.9 Hz, 1H), 2.63 (m, 1H), 2.65-2.59 (m, 1H), 2.62-2.59 (m, 1H), 2.37 (s, 3H), 2.39-2.32 (m, 1H).

72. 2-((7-((2-ethyl-6-fluorobenzyl)oxy)chroman-3-yl)(methyl)amino)acetic acid

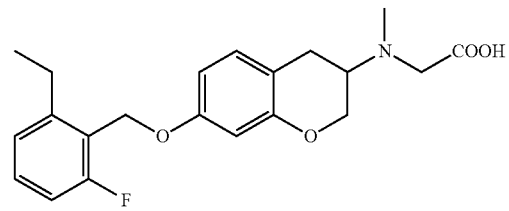 [SMILES: CCc1cccc(F)c1COc1ccc2c(c1)OCC(N(C)CC(=O)O)C2]

Compound 72 was prepared as described for compound 1 using methyl 2-(methylamino)acetate hydrochloride instead of methylazetine-3-carboxylate hydrochloride and 2-(bromomethyl)-1-ethyl-3-fluorobenzene instead of 2-(bromomethyl)-1,3-dichlorobenzene. Hydrolysis of the methyl ester was performed in analogy to step 10.3 at RT in methanol with 2N NaOH.

$^1$H NMR (600 MHz, DMSO-$d_6$) δ 7.41-7.34 (m, 1H), 7.13 (d, J=7.7 Hz, 1H), 7.11-7.05 (m, 1H), 6.99 (d, J=8.3 Hz, 1H), 6.52 (dd, J=8.3, 2.6 Hz, 1H), 6.45 (d, J=2.5 Hz, 1H), 5.01 (s, 2H), 4.29-4.23 (m, 1H), 3.85 (dd, J=10.7, 8.2 Hz, 1H), 3.16-3.09 (m, 1H), 2.86-2.79 (m, 1H), 2.74-2.65 (m, 3H), 2.42 (s, 2H), 1.16 (t, J=7.6 Hz, 3H).

73. 2-((6-((2-chloro-6-ethylbenzyl)oxy)-1,2,3,4-tetrahydronaphthalen-2-yl)amino)acetic acid

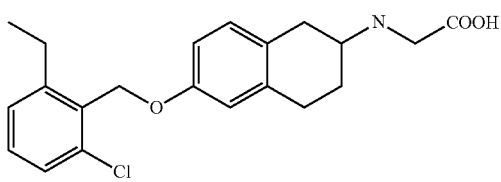 [SMILES: CCc1cccc(Cl)c1COc1ccc2c(c1)CCC(NCC(=O)O)C2]

73.1 6-((2-chloro-6-ethylbenzyl)oxy)-3,4-dihydronaphthalen-2(1H)-one (E)-Diisopropyl diazene-1,2-dicarboxylate (DIAD, 1.499 ml, 7.71 mmol)) was added to a solution of 6-hydroxytetralone (1 g, 6.17 mmol), (2-chloro-6-ethylphenyl)methanol (1.206 g, 6.78 mmol) and triphenylphosphine (2.021 g, 7.71 mmol) in THF (20 ml) at 0° C. and stirred at RT overnight. The volatile components were removed and the crude product purified by chromatography (silica gel) affording 6-((2-chloro-6-ethylbenzyl)oxy)-3,4-dihydronaphthalen-2(1H)-one (240 mg) as a pale yellow oil.

73.2 2-((6-((2-chloro-6-ethylbenzyl)oxy)-1,2,3,4-tetrahydronaphthalen-2-yl)amino)acetic acid Compound 73.2 was prepared by reductive amination in analogy to step 1.1 using 2-aminoacetic acid instead of methylazetine-3-carboxylate hydrochloride and 2-(bromomethyl)-1-chloro-3-ethylbenzene instead of 2-(bromomethyl)-1,3-dichlorobenzene.

$^1$H NMR (600 MHz, DMSO-d$_6$) δ 7.39-7.33 (m, 2H), 7.31-7.25 (m, 1H), 7.07-7.02 (m, 1H), 6.85-6.80 (m, 2H), 5.10 (s, 2H), 3.80 (s, 2H), 3.42-3.36 (m, 1H), 3.14-3.07 (m, 1H), 2.91-2.84 (m, 1H), 2.83-2.76 (m, 1H), 2.71 (q, J=7.6 Hz, 2H), 2.25-2.19 (m, 1H), 1.72 (qd, J=12.9, 12.0, 6.5 Hz, 1H), 1.16 (t, J=7.6 Hz, 3H).

74. 1-(6-((2,6-dichlorobenzyl)oxy)-1,2,3,4-tetrahydronaphthalen-2-yl)pyrrolidine-3-carboxylic acid

74.1 6'-methoxy-3',4'-dihydro-1'H-spiro[[1,3]dioxolane-2,2'-naphthalene]

A mixture of 6-methoxy-2-tetralone (compound VI; 3.0 g, 17.02 mmol), 1,1,1-trimethoxyethane (3.47 ml, 27.2 mmol), ethylene glycol (5.70 ml, 102 mmol) and 4-methylbenzenesulfonic acid hydrate (0.097 g, 0.511 mmol) were stirred at room temperature for 24 h. The reaction mixture was poured into a NaHCO$_3$ solution and extracted with EtOAc. The organic layer was washed with brine and dried over MgSO$_4$, filtrated, evaporated and the residue purified by flash chromatography (silica gel) affording 2.99 g product (VII).

74.2 3',4'-dihydro-1'H-spiro[[1,3]dioxolane-2,2'-naphthalen]-6'-ol

A mixture of 6'-methoxy-3',4'-dihydro-1'H-spiro[[1,3]dioxolane-2,2'-naphthalene](compound VII; 2.99 g, 13.57 mmol) and sodiummethanethiolate (3.14 g, 44.8 mmol) in DMF (25 ml) was stirred at 135° C. for 6 h, cooled to RT, diluted with ethyl acetate and washed with brine. The organic layer was dried over MgSO$_4$, filtered, evaporated and the residue purified by flash chromatography (silica gel) giving 1.86 g of product VIII.

74.3 6'-((2,6-dichlorobenzyl)oxy)-3',4'-dihydro-1'H-spiro[[1,3]dioxolane-2,2'-naphthalene]

3',4'-dihydro-1'H-spiro[[1,3]dioxolane-2,2'-naphthalen]-6'-ol (compound VIII; 280 mg, 1.358 mmol), potassium carbonate (469 mg, 3.39 mmol) and 2,6-dichlorobenzylbromide (358 mg, 1.493 mmol) were dissolved in dry DMF (4 ml) and stirred at room temperature overnight. Then the solvent was evaporated, the residue dissolved in ethylacetate, the organic layer washed with water and brine, then dried over Na$_2$SO$_4$, and evaporated giving 557 mg of product (compound IX).

74.4 6-((2-chloro-6-ethylbenzyl)oxy)-3,4-dihydronaphthalen-2(1H)-one

A microwave vial was charged with a solution of 6'-((2,6-dichlorobenzyl)oxy)-3',4'-dihydro-1'H-spiro[[1,3]dioxolane-2,2'-naphthalene] (compound IX; 20 mg, 0.055 mmol) and pyridium p-toluenesulfonate (4.13 mg, 0.016 mmol) in

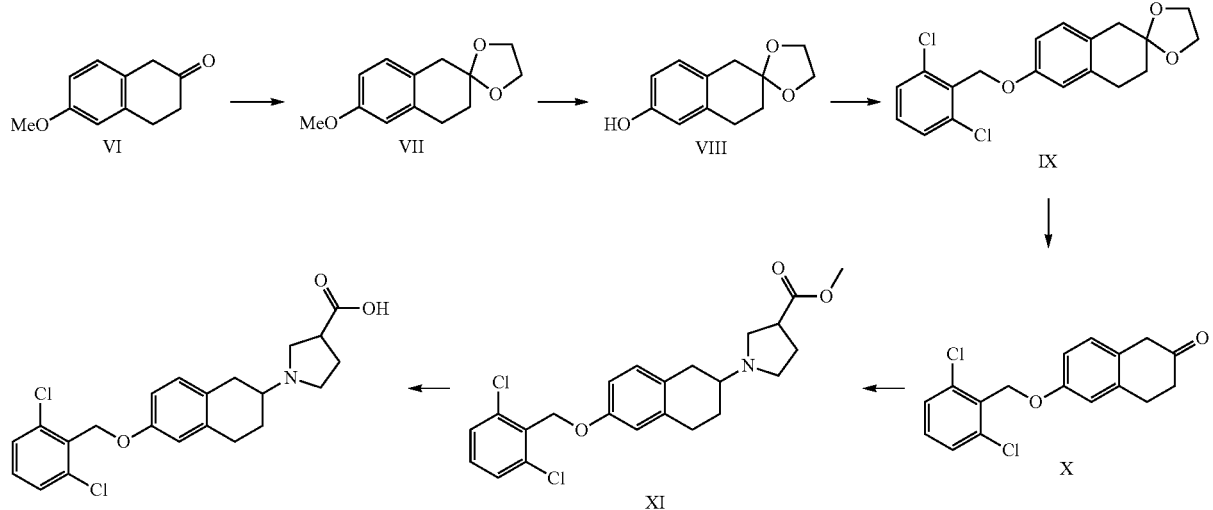

wet Acetone (0.5 ml), placed in a microwave and heated to 100° C. for 2 h. Then the solvent was evaporated the residue dissolved with EtOAc, the organic layer washed with NaHCO₃ and dried over MgSO₄. The solvent was evaporated and the residue purified by flash chromatography (silica gel) giving 220 mg of product (compound X).

74.5 Methyl 1-(6-((2,6-dichlorobenzyl)oxy)-1,2,3,4-tetrahydronaphthalen-2-yl)pyrrolidine-3-carboxylate Methyl pyrrolidine-3-carboxylate (21.50 mg, 0.166 mmol) was added at RT to a solution of 6-((2,6-dichlorobenzyl)oxy)-3,4-dihydronaphthalen-2(1H)-one (compound X; 48.6 mg, 0.151 mmol) and sodium acetate (13.65 mg, 0.166 mmol) in MeOH (1 ml)/THF (1 ml) and stirred at RT for 1 h. Then sodium cyanoborohydride (14.26 mg, 0.227 mmol) was added, the mixture adjusted pH to 4-5 using HOAc and stirred at RT for 0.5 hours. Then the mixture was neutralized with NaHCO₃ (pH=7-8), diluted with ethylacetate. After separation, the organic layer was washed with brine, dried over MgSO₄, filtered and evaporated giving 59.6 mg of product (compound XI).

74.6 1-(6-((2,6-dichlorobenzyl)oxy)-1,2,3,4-tetrahydronaphthalen-2-yl)pyrrolidine-3-carboxylic acid A microwave vial was charged with methyl 1-(6-((2,6-dichlorobenzyl)oxy)-1,2,3,4-tetrahydronaphthalen-2-yl)-3-((methylperoxy)methyl)pyrrolidine-3-carboxylate (compound XI; 59.6 mg, 0.137 mmol) and 2N KOH in methanol (500 μl, 1.000 mmol), placed in a micro wave and heated to 100° C. for 30 min. Then the solvent was evaporated and the residue purified by preparative SFC giving 2.7 mg of final product (compound 74).

¹H NMR (500 MHz, Methanol-d₄) δ 7.48-7.41 (m, 2H), 7.35 (dd, J=8.8, 7.3 Hz, 1H), 7.10 (dd, J=8.4, 2.0 Hz, 1H), 6.91-6.80 (m, 2H), 5.26 (s, 2H), 3.04-2.89 (m, 3H), 2.40 (s, 2H), 1.97-1.84 (m, 1H). Several further protons gave very broad signals 75. 2-((6-((2,6-dichlorobenzyl)oxy)-1,2,3,4-tetrahydronaphthalen-2-yl)amino)acetic acid

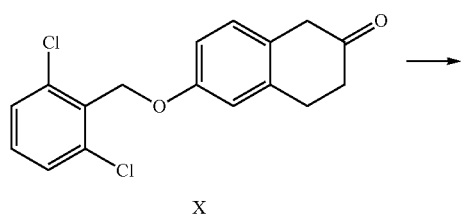

X

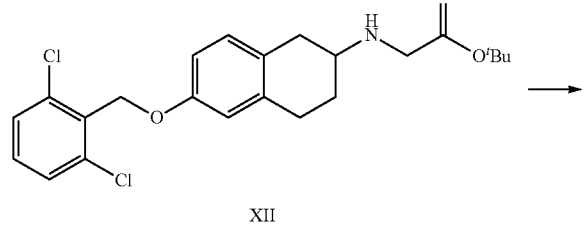

XII

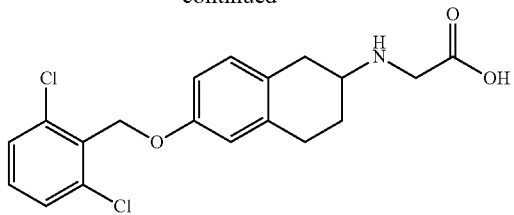

75

75.1 tert-butyl 2-((6-((2,6-dichlorobenzyl)oxy)-1,2,3,4-tetrahydronaphthalen-2-yl)amino)acetate 6-((2,6-dichlorobenzyl)oxy)-3,4-dihydronaphthalen-2(1H)-one (compound X; 111 mg, 0.346 mmol) and sodium acetate (31.2 mg, 0.380 mmol) were stirred at room temperature in THF (1 ml)/MeOH (1.000 ml). Glycinetertbutylester (63.7 mg, 0.380 mmol) was added and stirred at RT for 1 hour followed by addition of sodiumcyano-borohydride (43.4 mg, 0.691 mmol) keeping pH at 4-5 using HOAc. The mixture was stirred at RT for 30 minutes, then neutralized with NaHCO₃ (pH=7-8), diluted with ethyl acetate. After separation, the organic layer was washed with brine, dried over MgSO₄, filtered and evaporated giving 139 mg of product (compound XII).

75.2. 2-((6-((2,6-dichlorobenzyl)oxy)-1,2,3,4-tetrahydronaphthalen-2-yl)amino)acetic acid tert-Butyl 2-((6-((2,6-dichlorobenzyl)oxy)-1,2,3,4-tetrahydronaphthalen-2-yl)amino)acetate (compound XII; 138.8 mg, 0.318 mmol) was dissolved in formic acid (2 ml, 52.1 mmol) and stirred at 40° C. for 36 h. then the solvent was evaporated affording 33 mg of desired product.

¹H NMR (600 MHz, Methanol-d₄) δ 7.50-7.41 (m, 2H), 7.39-7.31 (m, 1H), 7.08 (d, J=8.4 Hz, 1H), 6.86-6.80 (m, 2H), 5.26-5.24 (m, 2H), 3.73 (s, 2H), 3.56-3.47 (m, 1H), 3.00-2.90 (m, 2H), 2.83 (dd, J=15.6, 10.2 Hz, 1H), 2.36-2.26 (m, 1H), 1.87-1.78 (m, 1H).

76. 1-(((6-((2-chloro-6-ethylbenzyl)oxy)-1,2,3,4-tetrahydronaphthalen-2-yl)amino)methyl)cyclopropanecarboxylic acid

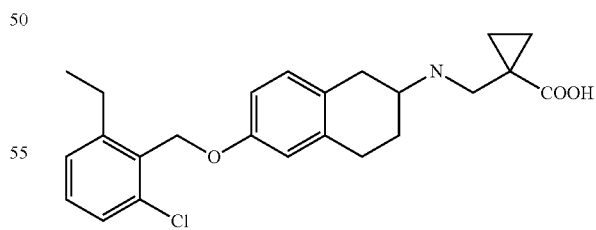

Compound 76 was prepared as described for compound 74 using 1-(aminomethyl)cyclopropanecarboxylic acid instead of methyl pyrrolidine-3-carboxylate and 2-(bromomethyl)-1-chloro-3-ethylbenzene instead of 2-(bromomethyl)-1,3-dichlorobenzene.

¹H NMR (600 MHz, DMSO-d₆) δ 7.39-7.34 (m, 2H), 7.31-7.24 (m, 1H), 7.09-7.03 (m, 1H), 6.86-6.81 (m, 2H), 5.10 (s, 2H), 3.24 (d, J=13.1 Hz, 1H), 3.17 (d, J=13.1 Hz,

1H), 3.16-3.11 (m, 1H), 2.94-2.77 (m, 3H), 2.71 (q, J=7.5 Hz, 2H), 2.31-2.20 (m, 1H), 1.86-1.73 (m, 1H), 1.27-1.06 (m, 7H).

77. (1s,3s)-3-((6-((2,6-dichlorobenzyl)oxy)-1,2,3,4-tetrahydronaphthalen-2-yl)amino)cyclobutanecarboxylic acid

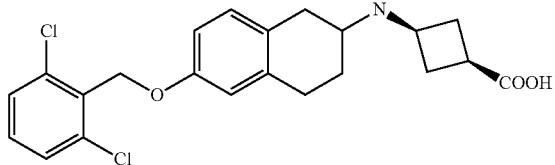 [SMILES: O=C(O)[C@H]1C[C@@H](NC2CCc3cc(OCc4c(Cl)cccc4Cl)ccc3C2)C1]

Compound 77 was prepared as described for compound 74 using (1s,3s)-methyl 3-aminocyclobutanecarboxylate instead of methyl pyrrolidine-3-carboxylate.

$^1$H NMR (600 MHz, DMSO-d$_6$) δ 7.56 (d, J=8.1 Hz, 2H), 7.47 (dd, J=8.7, 7.5 Hz, 1H), 7.06 (d, J=8.1 Hz, 1H), 6.87-6.82 (m, 2H), 5.17 (s, 2H), 3.84-3.74 (m, 1H), 3.07-2.99 (m, 1H), 2.93-2.76 (m, 3H), 2.72-2.64 (m, 1H), 2.36-2.26 (m, 2H), 2.14-2.07 (m, 1H), 1.73-1.65 (m, 1H).

78. 2-(1-(6-((2,6-dichlorobenzyl)oxy)-1,2,3,4-tetrahydronaphthalen-2-yl)azetidin-3-yl)acetic acid

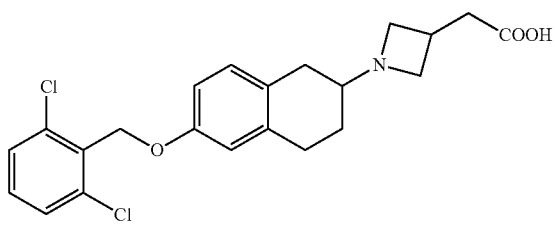 [SMILES: O=C(O)CC1CN(C2CCc3cc(OCc4c(Cl)cccc4Cl)ccc3C2)C1]

Compound 78 was prepared as described for compound 74 using methyl 2-(azetidin-3-yl)acetate instead of methyl pyrrolidine-3-carboxylate.

$^1$H NMR (600 MHz, DMSO-d$_6$) δ 7.57 (d, J=8.1 Hz, 2H), 7.47 (dd, J=8.7, 7.5 Hz, 1H), 7.09-7.02 (m, 1H), 6.89-6.82 (m, 2H), 5.18 (s, 2H), 4.24-4.10 (m, 2H), 4.00-3.70 (m, 2H), 3.07-2.99 (m, 1H), 2.90-2.83 (m, 1H), 2.80-2.56 (m, 2H), 2.10-2.02 (m, 1H), 1.66-1.53 (m, 1H).

79. (1r,3r)-3-((6-((2,6-dichlorobenzyl)oxy)-1,2,3,4-tetrahydronaphthalen-2-yl)amino)cyclobutanecarboxylic acid

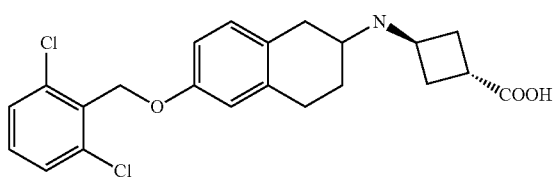 [SMILES: O=C(O)[C@H]1C[C@H](NC2CCc3cc(OCc4c(Cl)cccc4Cl)ccc3C2)C1]

Compound 79 was prepared as described for compound 74 using (1r,3r)-methyl 3-aminocyclobutanecarboxylate instead of methyl pyrrolidine-3-carboxylate.

$^1$H NMR (600 MHz, Methanol-d$_4$) δ 7.46-7.42 (m, 2H), 7.35 (dd, J=8.7, 7.5 Hz, 1H), 7.08 (d, J=8.3 Hz, 1H), 6.84 (dd, J=8.4, 2.7 Hz, 1H), 6.82 (d, J=2.6 Hz, 1H), 5.25 (d, J=0.8 Hz, 2H), 3.55-3.48 (m, 1H), 3.20-3.11 (m, 2H), 2.98-2.92 (m, 2H), 2.82-2.74 (m, 1H), 2.72-2.63 (m, 2H), 2.55-2.47 (m, 2H), 2.28-2.21 (m, 1H), 1.87-1.78 (m, 1H).

80. 2-(1-(6-((2,6-dichlorobenzyl)oxy)-1,2,3,4-tetrahydronaphthalen-2-yl)pyrrolidin-3-yl)acetic acid

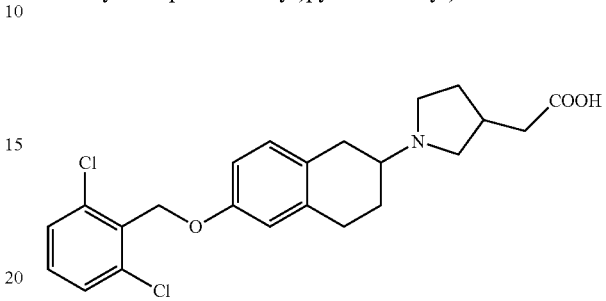

Compound 80 was prepared as described for compound 74 using methyl 2-(pyrolidine-3-yl)acetate hydrochloride instead of methyl pyrrolidine-3-carboxylate.

$^1$H NMR (600 MHz, Methanol-d$_4$) δ 7.47-7.43 (m, 2H), 7.36 (dd, J=8.7, 7.5 Hz, 1H), 7.12-7.07 (m, 1H), 6.85 (dd, J=8.4, 2.7 Hz, 1H), 6.83 (d, J=2.6 Hz, 1H), 5.25 (s, 2H), 3.84-3.69 (m, 1H), 3.61-3.52 (m, 1H), 3.29-3.22 (m, 1H), 3.05-2.82 (m, 3H), 2.64-2.56 (m, 1H), 1.93-1.83 (m, 2H). Several further protons gave very broad signals

81. 1-(7-(3,5-difluorophenethyl)chroman-3-yl)azetidine-3-carboxylic acid

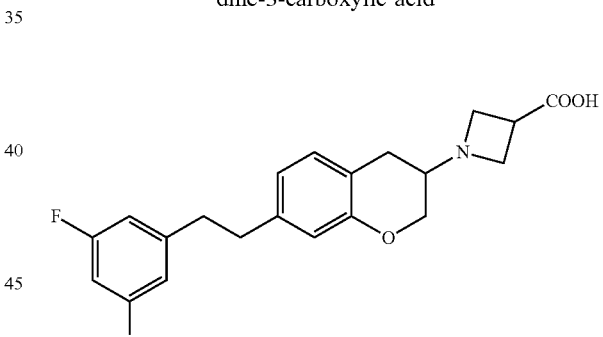

81.1 Methyl 1-(7-((3,5-difluorophenyl)ethynyl)chroman-3-yl)azetidine-3-carboxylate Compound 81.1 was prepared as described for Compound 12.2 using 1-ethynyl-3,5-difluorobenzene instead (2,6-dichlorophenyl)acetylene.

81.2 Methyl 1-(7-((3,5-difluorophenyl)ethynyl)chroman-3-yl)azetidine-3-carboxylate Palladium-on-carbon (Pd/C 10%, 5.6 mg)) was added to a solution of crude methyl 1-(7-((3,5-difluorophenyl)ethynyl)chroman-3-yl)azetidine-3-carboxylate (38.3 mg, 0.1 mmol) dissolved in methanol/tetrahydrofuran. The mixture was hydrogenated by stirring at RT under hydrogen atmosphere overnight. Then reaction mixture was filtered, the organic layer evaporated and the residue stirred over diisopropyleter. The formed precipitate was filtered and the solvent evaporated affording 12.7 mg of crude product as yellow oil.

81.3 1-(7-(3,5-difluorophenethyl)chroman-3-yl)azetidine-3-carboxylic acid

Hydrolysis of ester was performed in analogy to procedure described for compound 10.4.

$^1$H NMR (600 MHz, Chloroform-d) 6.94 (d, J=7.8 Hz, 1H), 6.73-6.58 (m, 5H), 4.20-4.07 (m, 1H), 3.99-3.78 (m, 5H), 3.41-3.27 (m, 1H), 3.20-3.05 (m, 1H), 2.96-2.71 (m, 5H).

82. 3-(8-((2-chloro-6-ethylbenzyl)oxy)-5,6-dihydro-2H-naphtho[1,2-b][1,4]oxazin-4(3H,4aH,10bH)-yl) propanoic acid hydrochloride ml) and stirred at 120° C. for 4 h. The reaction mixture was extracted using water/ethyl acetate. The combined organic layers were washed with NaHCO$_3$ and NaCl subsequently, and dried over MgSO$_4$. After removal of the solvent in vacuum the residue was purified by MPLC chromatography (Biotage Cisco) on silica gel using CH$_2$Cl$_2$/MeOH 98:2->95:5 as the eluent to give the desired product (compound XV) as a yellow oil (160 mg, 0.50 mmol, 43%).

82.2 Ethyl 3-(8-hydroxy-5,6-dihydro-2H-naphtho[1,2-b][1,4]oxazin-4(3H,4aH,10bH)-yl)propanoate Ethyl 3-(8-methoxy-5,6-dihydro-2H-naphtho[1,2-b][1,4]oxazin-4(3H,4aH,10bH)-yl)propanoate (compound XV; 180 mg, 0.56 mmol) and tribromoborane (424 mg, 1.17 mmol, 1.69 ml of a 1 molar solution in CH$_2$Cl$_2$) were dissolved in

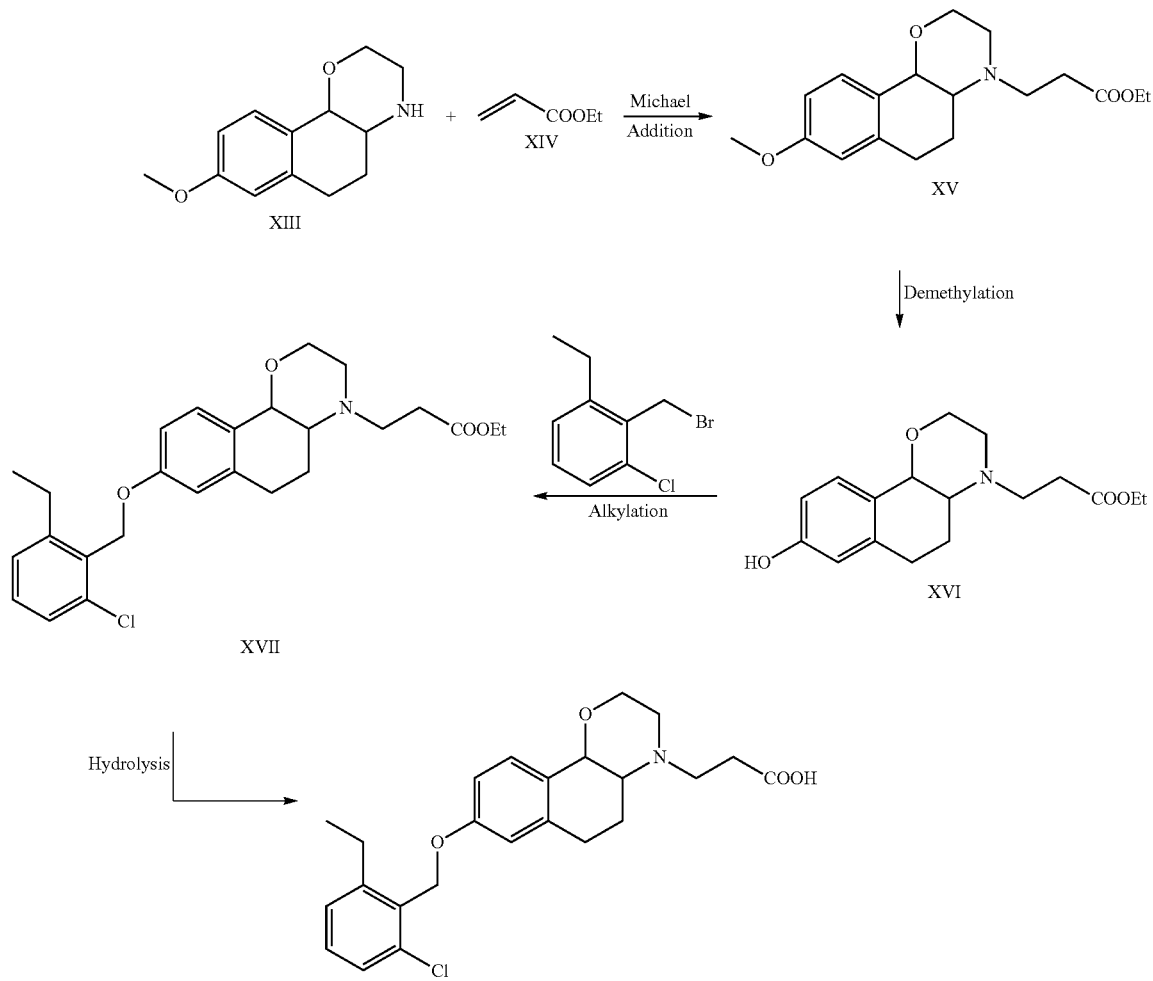

82.1 Ethyl 3-(8-methoxy-5,6-dihydro-2H-naphtho[1,2-b][1,4]oxazin-(3H,4aH,10bH)-yl)propanoate Commercially available (Aurora Fine Chemicals) 8-methoxy-3,4,4a,5,6,10b-hexahydro-2H-naphtho[1,2-b][1,4]oxazine hydrochloride (compound XIII; 300 mg, 1.17 mmol), ethyl acrylate (0.26 ml, 235 mg, 2.35 mmol), and 2,3,4,6,7,8,9,10-octahydropyrimido[1,2-a]azepine (DBU, 0.53 ml, 536 mg, 3.52 mmol) were dissolved in DMF (10

CH$_2$Cl$_2$ (10 ml) and stirred at −20° C. for 14 h. After quenching the reaction mixture with cold ethanol and extraction with NaHCO$_3$, water, and ethyl acetate the solvent was removed under vacuum. The crude mixture was purified by MPLC chromatography (Biotage Cisco) on silica gel using CH$_2$Cl$_2$/MeOH 97:3->90:10 as the eluent to give the desired product (compound XVI) as a yellow solid (30 mg, 0.098 mmol, 17%).

82.3 Ethyl 3-(8-((2-chloro-6-ethylbenzyl)oxy)-5,6-dihydro-2H-naphtho[1,2-b][1,4]oxazin-4(3H,4aH,10bH)-yl)propanoate Ethyl 3-(8-hydroxy-5,6-dihydro-2H-naphtho[1,2-b][1,4]oxazin-4(3H,4aH,10bH)-yl)propanoate (compound XVI; 30 mg, 0.098 mmol) was dissolved in DMF (10 ml). Potassium carbonate (27.2 mg, 0.196 mmol) was added and the mixture was stirred for 30 min. Commercially available 2-(bromomethyl)-1-chloro-3-ethylbenzene (22.9 mg, 0.098 mmol) was added and the mixture was stirred at RT for 14 h under argon. Half-concentrated aqueous HCl solution was added followed by extraction with ethyl acetate. The combined organic layer were washed with saturated NaCl in water and dried with MgSO$_4$. After removal of the solvent the desired product (compound XVII) was obtained as orange oil (31 mg, 0.068 mmol, 69%) which was used in the next step without further purification.

82.4 3-(8-((2-chloro-6-ethylbenzyl)oxy)-5,6-dihydro-2H-naphtho[1,2-b][1,4]oxazin-4(3H,4aH,10bH)-yl)propanoic acid Hydrochloride Ethyl 3-(8-((2-chloro-6-ethylbenzyl)oxy)-5,6-dihydro-2H-naphtho[1,2-b][1,4]oxazin-4(3H,4aH,10bH)-yl)propanoate (compound XVII; 31 mg, 0.068 mmol) was dissolved in ethanol (5 ml) and aqueous NaOH solution in water (2 molar, 0.5 ml) was added. The mixture was stirred for 12 hr at RT. After addition of water (5 ml) the solution was neutralized with aqueous HCl (1N) and extracted with ethyl acetate. The combined organic layers were washed with saturated NaCl in water and dried with MgSO$_4$. After removal of the solvent in vacuum the residue was purified by MPLC chromatography (Biotage Cisco) on silica gel using CH$_2$Cl$_2$/MeOH 97:3->90:10 as the eluent to give the desired product which was transferred into the HCl salt by dissolving it in isopropanol and adding HCl dissolved in isopropanol. Removing of the solvent by decantation and drying the resulting residue under vacuum at 40° C. gave the purified product as a white solid (14 mg, 0.03 mmol, 44%). LCMS (ESI+) m/z 430.3 (M+H)+.

$^1$H NMR (600 MHz, DMSO-d$_6$) δ 12.78 (s, 1H), 7.40-7.33 (m, 2H), 7.32-7.24 (m, 2H), 6.93-6.86 (m, 2H), 5.14 (s, 2H), 4.66 (s, 1H), 3.95 (s, 2H), 3.57 (s, 1H), 2.96 (d, J=16.9 Hz, 1H), 2.80 (s, 2H), 2.71 (q, J=7.5 Hz, 2H), 2.13 (s, 1H), 2.01 (s, 1H), 1.16 (t, J=7.5 Hz, 3H), 1.04 (d, J=6.1 Hz, 3H).

84. 1-[7-[(4-fluoro-3-methyl-phenyl)methoxy]chroman-3-yl]azetidine-3-carboxylic acid

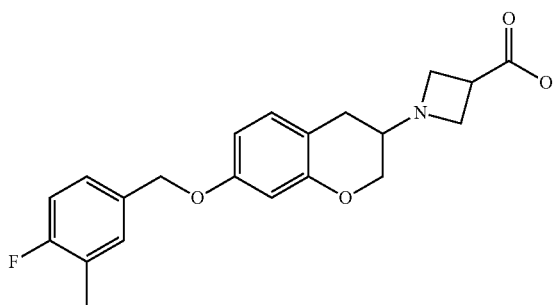 [SMILES: Cc1cc(COc2ccc3c(c2)OCC(N2CC(C(=O)O)C2)C3)ccc1F]

A vial was charged with a stir bar, a 500 μL solution of methyl 1-(7-hydroxychroman-3-yl)azetidine-3-carboxylate in DMF (22.2 mg, 0.08 mmol), 170 μL of a 0.6 mmol pre-weighed solution of 4-(bromomethyl)-1-fluoro-2-methylbenzene in 1000 μL of DMF (1.2 eq, 20.5 mg, 0.10 mmol), and ground K$_2$CO$_3$ (2 eq, 23.3 mg, 0.16 mmol). The vial was capped and placed to stir overnight at room temperature. Upon completion the vial was concentrated to dryness and the crude material was re-dissolved with 1000 μL of a 1M aqueous solution of LiOH in 75% MeOH. This was place capped once more and placed to stir with heating at 60° C. for 1 hour. Upon completion the compound was concentrated to dryness and re-dissolved in 1.4 mL of DMSO/Acetonitrile (1:1 v/v). The crude material was filtered using a 3 mL disposable syringe with filter. The crude material was submitted to APS for reverse phase HPLC purification where 1-[7-[(4-fluoro-3-methyl-phenyl)methoxy]chroman-3-yl]azetidine-3-carboxylic acid was afforded (14.3 mg, 38.7%).

$^1$H NMR (400 MHz, DMSO-d6) δ 7.31 (dd, J=7.6, 2.2 Hz, 1H), 7.25 (ddd, J=7.7, 5.0, 2.3 Hz, 1H), 7.11 (dd, J=9.9, 8.4 Hz, 1H), 6.93 (d, J=8.4 Hz, 1H), 6.47 (dd, J=8.4, 2.6 Hz, 1H), 6.33 (d, J=2.6 Hz, 1H), 4.95 (s, 2H), 3.95 (ddd, J=11.1, 2.9, 1.4 Hz, 1H), 3.66 (dd, J=10.9, 6.6 Hz, 1H), 3.38 (dt, J=15.1, 7.3 Hz, 2H), 3.19 (td, J=7.1, 4.3 Hz, 2H), 2.95 (p, J=7.8 Hz, 1H), 2.72 (dd, J=15.5, 4.6 Hz, 1H), 2.59 (qd, J=7.0, 3.0 Hz, 1H), 2.33 (dd, J=15.9, 6.7 Hz, 1H), 2.22 (d, J=1.9 Hz, 3H).

The following compounds were prepared according to the procedure of compound 84:

85. 1-[7-[[4-fluoro-3-(trifluoromethyl)phenyl]methoxy]chroman-3-yl]azetidine-3-carboxylic acid

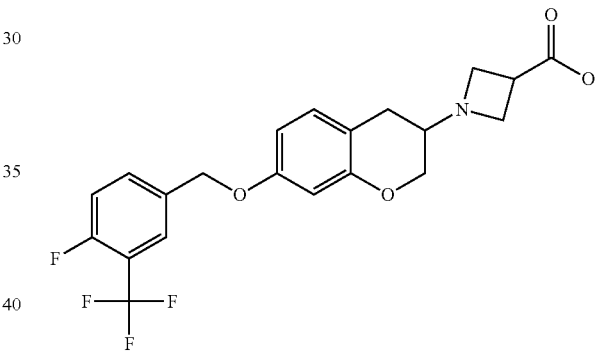

$^1$H NMR (400 MHz, DMSO-d6) δ 7.79 (ddd, J=13.7, 7.3, 2.2 Hz, 2H), 7.50 (dd, J=10.8, 8.5 Hz, 1H), 6.95 (d, J=8.5 Hz, 1H), 6.50 (dd, J=8.4, 2.6 Hz, 1H), 6.37 (d, J=2.6 Hz, 1H), 5.09 (s, 2H), 3.96 (ddd, J=11.1, 2.8, 1.3 Hz, 1H), 3.72-3.66 (m, 1H), 3.43 (dt, J=15.4, 7.4 Hz, 2H), 3.25 (td, J=7.1, 4.2 Hz, 2H), 3.06 (p, J=7.6 Hz, 1H), 2.74 (dd, J=15.8, 4.9 Hz, 1H), 2.67-2.60 (m, 1H), 2.35 (dd, J=15.8, 6.6 Hz, 1H).

86. 1-[7-[(2-fluoro-3-methoxy-phenyl)methoxy]chroman-3-yl]azetidine-3-carboxylic acid

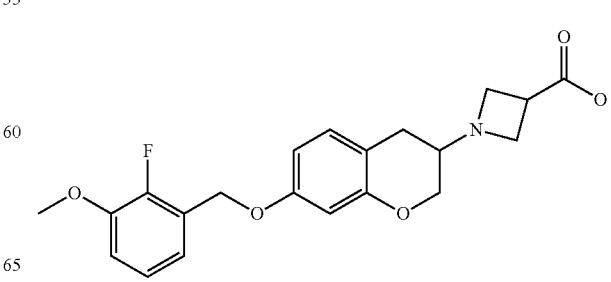

¹H NMR (400 MHz, DMSO-d₆) δ 7.17-7.11 (m, 2H), 7.02 (td, J=6.2, 3.1 Hz, 1H), 6.95 (d, J=8.4 Hz, 1H), 6.50 (dd, J=8.4, 2.6 Hz, 1H), 6.36 (d, J=2.6 Hz, 1H), 5.04 (d, J=1.2 Hz, 2H), 3.98 (dt, J=11.2, 1.8 Hz, 1H), 3.83 (s, 3H), 3.79 (dd, J=11.2, 5.6 Hz, 1H), 3.57 (dt, J=15.8, 7.8 Hz, 2H), 3.41 (s, 2H), 3.25-3.17 (m, 1H), 2.85-2.75 (m, 2H), 2.40 (dd, J=15.8, 5.5 Hz, 1H).

87. 1-[7-[(3-fluoro-5-methyl-phenyl)methoxy]chroman-3-yl]azetidine-3-carboxylic acid

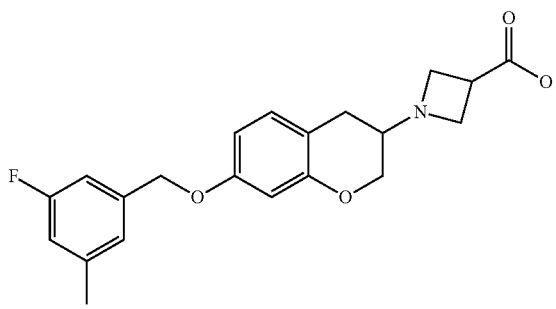 [SMILES: Cc1cc(F)cc(COc2ccc3c(c2)OCC(N2CC(C(=O)O)C2)C3)c1]

¹H NMR (400 MHz, DMSO-d₆) δ 7.06 (s, 1H), 7.02-6.95 (m, 2H), 6.93 (d, J=8.4 Hz, 2H), 6.48 (dd, J=8.4, 2.6 Hz, 1H), 6.33 (d, J=2.6 Hz, 1H), 5.00 (s, 2H), 3.95 (ddd, J=11.0, 2.9, 1.4 Hz, 1H), 3.67 (dd, J=11.0, 6.5 Hz, 1H), 3.39 (dt, J=15.3, 7.4 Hz, 2H), 3.20 (td, J=7.1, 4.1 Hz, 2H), 2.96 (p, J=7.8 Hz, 1H), 2.72 (dd, J=15.9, 5.0 Hz, 1H), 2.60 (qd, J=6.6, 2.9 Hz, 1H), 2.37-2.33 (m, 1H), 2.31 (s, 3H).

88. 1-[7-[(2-fluoro-4-methyl-phenyl)methoxy]chroman-3-yl]azetidine-3-carboxylic acid

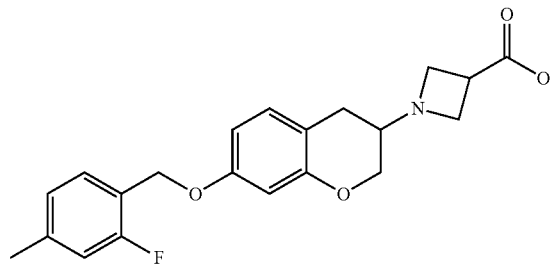 [SMILES: Cc1ccc(COc2ccc3c(c2)OCC(N2CC(C(=O)O)C2)C3)c(F)c1]

¹H NMR (400 MHz, DMSO-d₆) δ 7.06 (s, 1H), 7.02-6.95 (m, 2H), 6.93 (d, J=8.4 Hz, 2H), 6.48 (dd, J=8.4, 2.6 Hz, 1H), 6.33 (d, J=2.6 Hz, 1H), 5.00 (s, 2H), 3.95 (ddd, J=11.0, 2.9, 1.4 Hz, 1H), 3.67 (dd, J=11.0, 6.5 Hz, 1H), 3.39 (dt, J=15.3, 7.4 Hz, 2H), 3.20 (td, J=7.1, 4.1 Hz, 2H), 2.96 (p, J=7.8 Hz, 1H), 2.72 (dd, J=15.9, 5.0 Hz, 1H), 2.60 (qd, J=6.6, 2.9 Hz, 1H), 2.37-2.33 (m, 1H), 2.31 (s, 3H).

89. 1-[7-[(4-cyano-2-fluoro-phenyl)methoxy]chroman-3-yl]azetidine-3-carboxylic acid

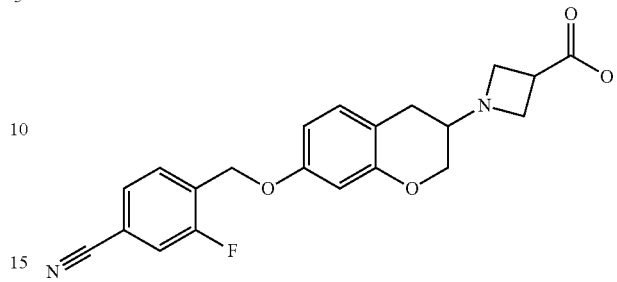

¹H NMR (400 MHz, DMSO-d₆) δ 7.85 (dt, J=9.7, 0.8 Hz, 1H), 7.74-7.69 (m, 2H), 6.97 (d, J=8.5 Hz, 1H), 6.53 (dd, J=8.4, 2.6 Hz, 1H), 6.39 (d, J=2.6 Hz, 1H), 5.16 (s, 2H), 3.98 (d, J=11.2 Hz, 1H), 3.77 (d, J=7.7 Hz, 1H), 3.56-3.45 (m, 2H), 3.33 (s, 2H), 3.19 (q, J=7.3 Hz, 1H), 2.77 (d, J=15.7 Hz, 1H), 2.43-2.35 (m, 1H).

90. 1-[7-[[3-fluoro-5-(trifluoromethyl)phenyl]methoxy]chroman-3-yl]azetidine-3-carboxylic acid

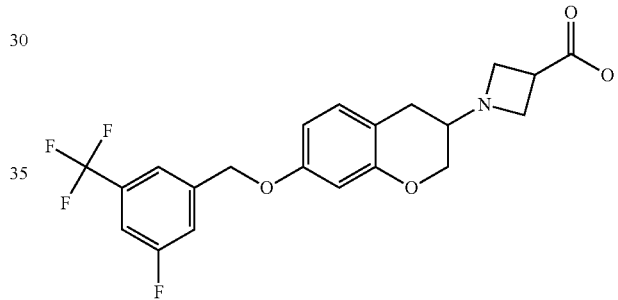

¹H NMR (400 MHz, DMSO-d₆) δ 7.61 (dd, J=18.4, 10.0 Hz, 3H), 6.97 (d, J=8.4 Hz, 1H), 6.53 (dd, J=8.4, 2.6 Hz, 1H), 6.39 (d, J=2.6 Hz, 1H), 5.16 (s, 2H), 3.97 (dt, J=10.8, 2.2 Hz, 1H), 3.70 (d, J=9.1 Hz, 1H), 3.47-3.36 (m, 2H), 3.22 (td, J=7.1, 4.2 Hz, 2H), 3.05-2.95 (m, 1H), 2.74 (dd, J=15.9, 4.9 Hz, 1H), 2.66-2.60 (m, 1H), 2.35 (dd, J=15.7, 7.0 Hz, 1H).

91. 1-[7-[[5-fluoro-2-(trifluoromethyl)phenyl]methoxy]chroman-3-yl]azetidine-3-carboxylic acid

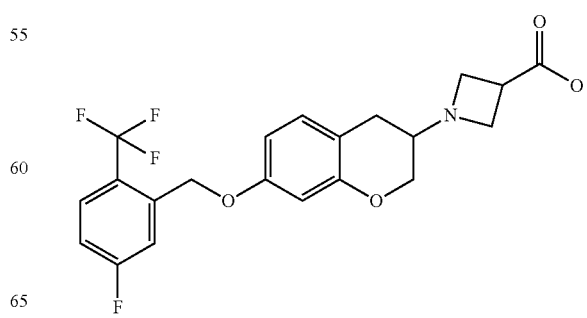

¹H NMR (400 MHz, DMSO-d₆) δ 7.88 (dd, J=8.8, 5.4 Hz, 1H), 7.54 (dd, J=9.7, 2.7 Hz, 1H), 7.40 (td, J=8.5, 2.7 Hz, 1H), 6.98 (d, J=8.4 Hz, 1H), 6.50 (dd, J=8.4, 2.6 Hz, 1H), 6.34 (d, J=2.5 Hz, 1H), 5.17 (s, 2H), 3.97 (ddd, J=11.0, 2.9, 1.3 Hz, 1H), 3.72-3.67 (m, 1H), 3.40 (dt, J=15.1, 7.3 Hz, 2H), 3.20 (td, J=7.1, 4.0 Hz, 2H), 2.96 (t, J=7.8 Hz, 1H), 2.74 (dd, J=15.9, 4.9 Hz, 1H), 2.65-2.59 (m, 1H), 2.36 (dd, J=15.8, 6.8 Hz, 1H).

92. 1-[7-[(4-fluoro-3-methoxy-phenyl)methoxy]chroman-3-yl]azetidine-3-carboxylic acid

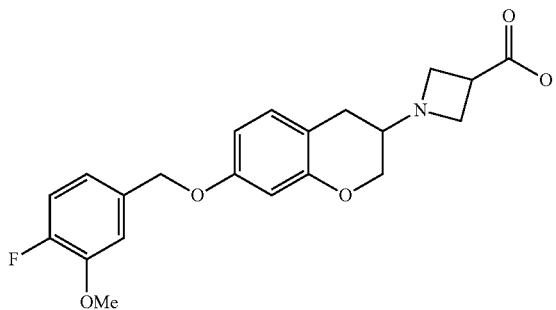 [SMILES: COc1cc(COc2ccc3c(c2)OCC(N2CC(C(=O)O)C2)C3)ccc1F]

¹H NMR (400 MHz, DMSO-d₆) δ 7.24-7.16 (m, 2H), 7.02-6.97 (m, 1H), 6.95 (d, J=8.4 Hz, 1H), 6.50 (dd, J=8.4, 2.6 Hz, 1H), 6.36 (d, J=2.5 Hz, 1H), 4.99 (s, 2H), 3.99-3.94 (m, 1H), 3.84 (s, 3H), 3.67 (dd, J=11.0, 6.7 Hz, 1H), 3.39 (dt, J=15.2, 7.4 Hz, 2H), 3.19 (td, J=7.1, 4.6 Hz, 2H), 3.00-2.88 (m, 1H), 2.78-2.69 (m, 1H), 2.65-2.57 (m, 1H), 2.34 (dd, J=15.8, 6.8 Hz, 1H).

93. 1-[7-[2-(4-fluorophenoxy)ethoxy]chroman-3-yl]azetidine-3-carboxylic acid

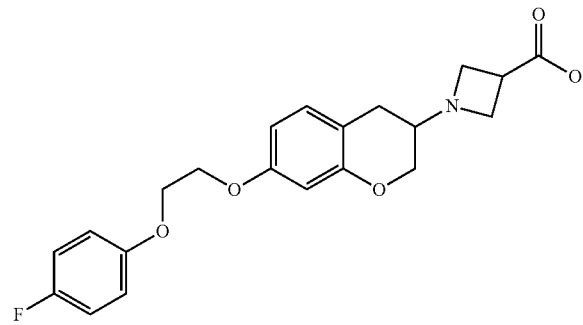 [SMILES: O=C(O)C1CN(C2COc3cc(OCCOc4ccc(F)cc4)ccc3C2)C1]

¹H NMR (400 MHz, DMSO-d₆) δ 7.16-7.09 (m, 2H), 7.02-6.94 (m, 3H), 6.47 (dd, J=8.3, 2.5 Hz, 1H), 6.34 (d, J=2.5 Hz, 1H), 4.23 (qd, J=5.5, 4.6, 3.2 Hz, 4H), 4.01-3.96 (m, 1H), 3.74 (d, J=10.6 Hz, 1H), 3.54-3.43 (m, 1H), 3.30 (td, J=7.0, 4.6 Hz, 2H), 3.16 (d, J=7.6 Hz, 1H), 2.77 (dd, J=15.8, 4.9 Hz, 1H), 2.70 (q, J=2.0 Hz, 0H), 2.41-2.33 (m, 1H).

94. 1-[7-[[2-fluoro-3-(trifluoromethyl)phenyl]methoxy]chroman-3-yl]azetidine-3-carboxylic acid

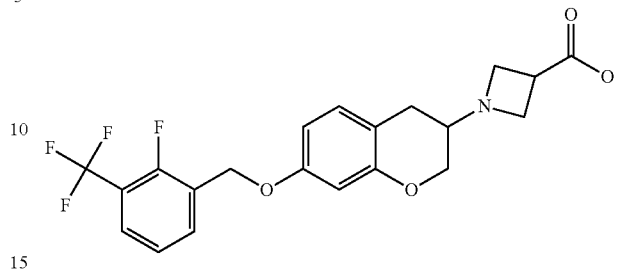

¹H NMR (400 MHz, DMSO-d₆) δ 7.89-7.76 (m, 2H), 7.45 (t, J=7.8 Hz, 1H), 6.97 (d, J=8.4 Hz, 1H), 6.53 (dd, J=8.3, 2.6 Hz, 1H), 6.40 (d, J=2.5 Hz, 1H), 5.15 (s, 2H), 3.98 (dt, J=10.9, 2.2 Hz, 1H), 3.73-3.65 (m, 1H), 3.40 (dt, J=15.4, 7.4 Hz, 2H), 3.21 (td, J=7.1, 4.2 Hz, 2H), 2.97 (p, J=7.8 Hz, 1H), 2.75 (dd, J=15.9, 4.9 Hz, 1H), 2.62 (dd, J=7.3, 4.7 Hz, 1H), 2.40-2.31 (m, 1H).

95. 1-[7-[(3-fluoro-4-methoxy-phenyl)methoxy]chroman-3-yl]azetidine-3-carboxylic acid

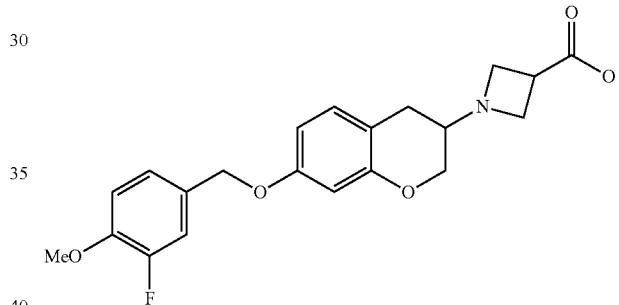

¹H NMR (400 MHz, DMSO-d₆) δ 7.27-7.18 (m, 2H), 7.16 (t, J=8.4 Hz, 1H), 6.94 (d, J=8.5 Hz, 1H), 6.48 (dd, J=8.4, 2.6 Hz, 1H), 6.34 (d, J=2.6 Hz, 1H), 4.96 (s, 2H), 3.99-3.93 (m, 1H), 3.83 (s, 3H), 3.68 (dd, J=11.1, 6.8 Hz, 1H), 3.39 (dt, J=15.4, 7.4 Hz, 2H), 3.20 (td, J=7.1, 4.3 Hz, 2H), 2.97 (q, J=7.9 Hz, 1H), 2.76-2.69 (m, 1H), 2.63-2.58 (m, 1H), 2.39-2.30 (m, 1H).

96. 1-[7-[(3-fluoro-2-methyl-phenyl)methoxy]chroman-3-yl]azetidine-3-carboxylic acid

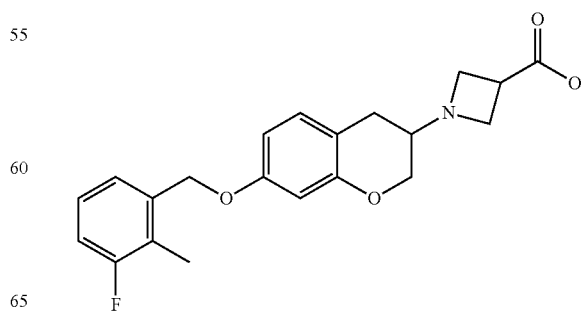

¹H NMR (400 MHz, DMSO-d₆) δ 7.24 (td, J=3.9, 2.5 Hz, 2H), 7.13 (ddd, J=9.6, 6.0, 3.6 Hz, 1H), 6.96 (d, J=8.4 Hz, 1H), 6.52 (dd, J=8.3, 2.6 Hz, 1H), 6.39 (d, J=2.5 Hz, 1H), 5.04 (s, 2H), 3.97 (dt, J=10.5, 2.1 Hz, 1H), 3.70 (dd, J=10.4, 5.6 Hz, 1H), 3.41 (dt, J=15.1, 7.4 Hz, 2H), 3.22 (td, J=7.1, 4.1 Hz, 2H), 2.99 (q, J=7.8 Hz, 1H), 2.74 (dd, J=15.9, 4.9 Hz, 1H), 2.62 (t, J=3.8 Hz, 1H), 2.35 (dd, J=16.0, 6.7 Hz, 1H), 2.21 (d, J=1.9 Hz, 3H).

97. 1-[7-[2-(3-fluorophenoxy)ethoxy]chroman-3-yl]azetidine-3-carboxylic acid

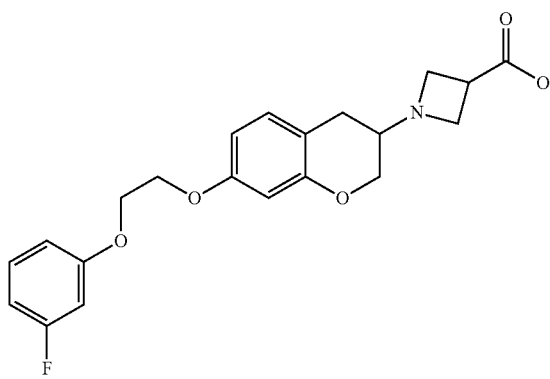 [SMILES: O=C(O)C1CN(C2COc3cc(OCCOc4cccc(F)c4)ccc3C2)C1]

¹H NMR (400 MHz, DMSO-d₆) δ 7.33 (td, J=8.7, 7.3 Hz, 1H), 6.96 (d, J=8.4 Hz, 1H), 6.87-6.81 (m, 2H), 6.81-6.75 (m, 1H), 6.48 (dd, J=8.4, 2.6 Hz, 1H), 6.34 (d, J=2.6 Hz, 1H), 4.31-4.21 (m, 4H), 3.99 (dd, J=11.1, 1.8 Hz, 1H), 3.76-3.71 (m, 1H), 3.48 (dt, J=16.1, 7.6 Hz, 2H), 3.31 (q, J=6.8 Hz, 2H), 3.16 (q, J=7.6 Hz, 1H), 2.77 (dd, J=15.9, 4.9 Hz, 1H), 2.72-2.66 (m, 1H), 2.42-2.33 (m, 1H).

98. 1-[7-[(2-fluoro-5-methoxy-phenyl)methoxy]chroman-3-yl]azetidine-3-carboxylic acid

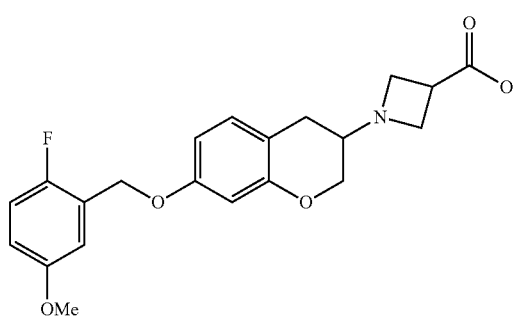 [SMILES: COc1ccc(F)c(COc2ccc3c(c2)OCC(N2CC(C(=O)O)C2)C3)c1]

¹H NMR (400 MHz, DMSO-d₆) δ 7.16 (t, J=9.3 Hz, 1H), 7.03 (dd, J=5.9, 3.2 Hz, 1H), 6.98-6.91 (m, 2H), 6.52 (dd, J=8.4, 2.6 Hz, 1H), 6.38 (d, J=2.6 Hz, 1H), 5.02 (s, 2H), 3.99 (d, J=11.1 Hz, 1H), 3.78 (s, 1H), 3.74 (s, 3H), 3.59-3.47 (m, 2H), 3.37 (s, 2H), 3.21 (q, J=7.7 Hz, 1H), 2.78 (d, J=14.0 Hz, 2H), 2.45-2.34 (m, 1H).

99. 1-[7-[3-(3-fluorophenyl)propoxy]chroman-3-yl]azetidine-3-carboxylic acid

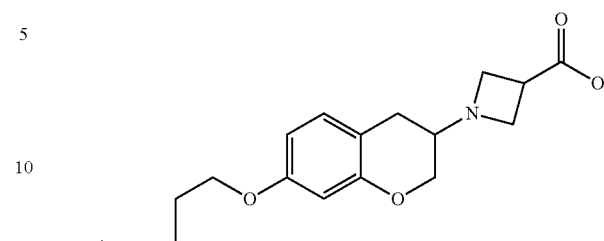

¹H NMR (400 MHz, DMSO-d₆) δ 7.33 (td, J=8.0, 6.3 Hz, 1H), 7.09-7.04 (m, 2H), 7.03-6.97 (m, 1H), 6.93 (d, J=8.4 Hz, 1H), 6.42 (dd, J=8.3, 2.5 Hz, 1H), 6.27 (d, J=2.6 Hz, 1H), 4.00-3.95 (m, 1H), 3.87 (t, J=6.3 Hz, 2H), 3.67 (dd, J=11.0, 6.8 Hz, 1H), 3.41 (dt, J=15.0, 7.4 Hz, 2H), 3.22 (td, J=7.2, 4.7 Hz, 2H), 2.98 (p, J=7.7 Hz, 1H), 2.78-2.69 (m, 3H), 2.66-2.58 (m, 1H), 2.38-2.30 (m, 1H), 2.02-1.93 (m, 2H).

100. 1-[7-[(3-fluoro-5-methoxy-phenyl)methoxy]chroman-3-yl]azetidine-3-carboxylic acid

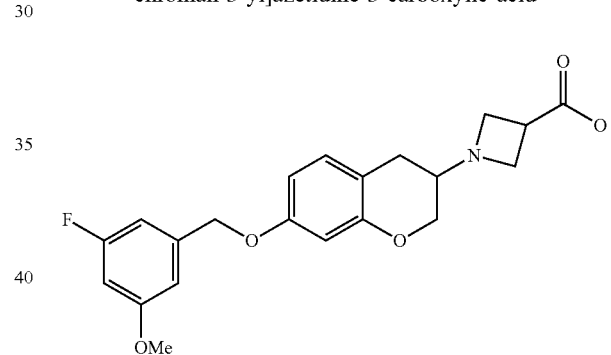

¹H NMR (400 MHz, DMSO-d₆) δ 6.94 (d, J=8.5 Hz, 1H), 6.84-6.78 (m, 2H), 6.74 (dt, J=11.0, 2.4 Hz, 1H), 6.49 (dd, J=8.4, 2.6 Hz, 1H), 6.34 (d, J=2.6 Hz, 1H), 5.02 (s, 2H), 3.96 (ddd, J=10.9, 2.8, 1.3 Hz, 1H), 3.77 (s, 3H), 3.68 (dd, J=11.1, 6.8 Hz, 1H), 3.40 (dt, J=15.1, 7.4 Hz, 2H), 3.20 (td, J=7.1, 4.1 Hz, 2H), 2.96 (p, J=7.8 Hz, 1H), 2.73 (dd, J=15.6, 4.6 Hz, 1H), 2.64-2.57 (m, 1H), 2.34 (dd, J=15.8, 6.7 Hz, 1H).

101. 1-[7-[(2-fluoro-6-methoxy-phenyl)methoxy]chroman-3-yl]azetidine-3-carboxylic acid

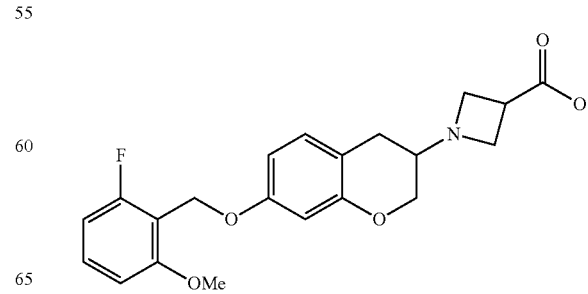

¹H NMR (400 MHz, DMSO-d₆) δ 7.42 (td, J=8.4, 7.0 Hz, 1H), 6.94 (t, J=8.6 Hz, 2H), 6.85 (ddd, J=9.3, 8.4, 0.9 Hz, 1H), 6.48 (dd, J=8.4, 2.6 Hz, 1H), 6.38 (d, J=2.5 Hz, 1H), 4.96 (d, J=1.6 Hz, 2H), 4.02-3.95 (m, 1H), 3.83 (s, 3H), 3.72-3.69 (m, 1H), 3.45 (dt, J=16.2, 7.5 Hz, 2H), 3.26 (td, J=7.1, 4.1 Hz, 2H), 3.06 (p, J=7.8 Hz, 1H), 2.76 (dd, J=15.8, 4.9 Hz, 1H), 2.66 (dd, J=6.9, 4.2 Hz, 1H), 2.37 (dd, J=16.0, 6.3 Hz, 1H).

102. 1-[7-[4-(3-fluorophenoxy)butoxy]chroman-3-yl]azetidine-3-carboxylic acid

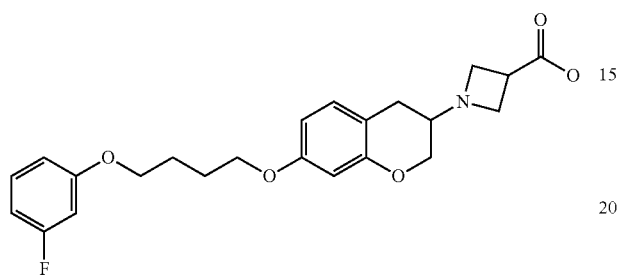

¹H NMR (400 MHz, DMSO-d₆) δ 7.36-7.27 (m, 1H), 6.94 (d, J=8.4 Hz, 1H), 6.81-6.72 (m, 3H), 6.44 (dd, J=8.4, 2.5 Hz, 1H), 6.30 (d, J=2.5 Hz, 1H), 3.99 (dt, J=30.0, 5.3 Hz, 5H), 3.78 (m, 1H), 3.59-3.47 (m, 2H), 3.36 (s, 2H), 3.19 (p, J=7.2 Hz, 1H), 2.78 (d, J=14.9 Hz, 2H), 2.44-2.34 (m, 1H), 1.83 (h, J=2.8 Hz, 4H).

103. 1-[7-[[3-fluoro-4-(trifluoromethyl)phenyl]methoxy]chroman-3-yl]azetidine-3-carboxylic acid

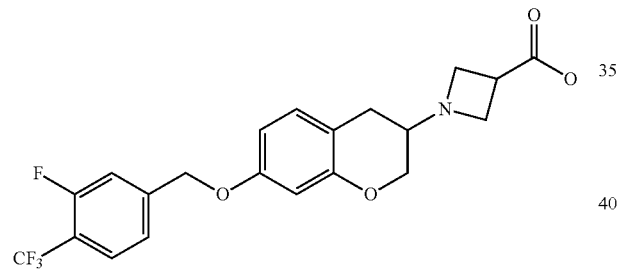

¹H NMR (400 MHz, DMSO-d₆) δ 7.80 (t, J=7.9 Hz, 1H), 7.56-7.44 (m, 2H), 6.97 (d, J=8.5 Hz, 1H), 6.53 (dd, J=8.4, 2.6 Hz, 1H), 6.38 (d, J=2.6 Hz, 1H), 5.17 (s, 2H), 4.01-3.95 (m, 1H), 3.78 (m, 1H), 3.55 (d, J=11.7 Hz, 2H), 3.37 (s, 2H), 3.25-3.14 (m, 1H), 2.78 (d, J=13.9 Hz, 2H), 2.46-2.34 (m, 1H).

104. 1-[7-[[2-fluoro-5-(trifluoromethoxy)phenyl]methoxy]chroman-3-yl]azetidine-3-carboxylic acid

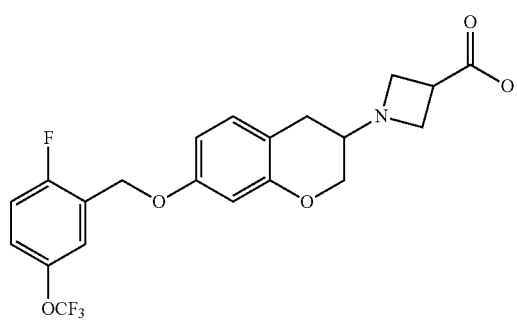 [SMILES: O=C(O)C1CN(C2COc3cc(OCc4cc(OC(F)(F)F)ccc4F)ccc3C2)C1]

¹H NMR (400 MHz, DMSO-d₆) δ 7.53 (dd, J=5.9, 2.8 Hz, 1H), 7.48-7.35 (m, 2H), 6.97 (d, J=8.4 Hz, 1H), 6.52 (dd, J=8.4, 2.6 Hz, 1H), 6.40 (d, J=2.6 Hz, 1H), 5.09 (s, 2H), 3.98 (dt, J=10.9, 2.1 Hz, 1H), 3.69 (d, J=6.5 Hz, 0H), 3.42 (dt, J=15.5, 7.4 Hz, 2H), 3.23 (td, J=7.1, 4.1 Hz, 2H), 3.01 (p, J=7.9 Hz, 1H), 2.75 (dd, J=15.9, 4.9 Hz, 1H), 2.67-2.61 (m, 1H), 2.40-2.32 (m, 1H).

105. 1-[7-[(2-fluoro-3-methyl-phenyl)methoxy]chroman-3-yl]azetidine-3-carboxylic acid

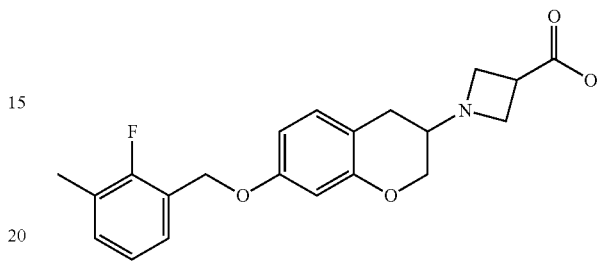

¹H NMR (400 MHz, Pyridine-d₅) δ 7.40 (td, J=7.2, 1.9 Hz, 1H), 7.13-7.08 (m, 1H), 7.03 (dd, J=8.0, 6.8 Hz, 2H), 6.82 (d, J=2.5 Hz, 1H), 6.75 (dd, J=8.3, 2.6 Hz, 1H), 5.18 (d, J=1.2 Hz, 2H), 4.07 (ddd, J=10.8, 3.0, 1.6 Hz, 1H), 3.85-3.80 (m, 1H), 3.68-3.64 (m, 3H), 3.60 (dd, J=7.8, 6.4 Hz, 1H), 3.48 (dt, J=8.4, 7.1 Hz, 1H), 2.74 (dd, J=15.2, 4.9 Hz, 1H), 2.70-2.62 (m, 1H), 2.49 (dd, J=15.3, 7.2 Hz, 1H), 2.15 (d, J=2.2 Hz, 3H).

106. 1-[7-[[2-fluoro-4-(trifluoromethyl)phenyl]methoxy]chroman-3-yl]azetidine-3-carboxylic acid

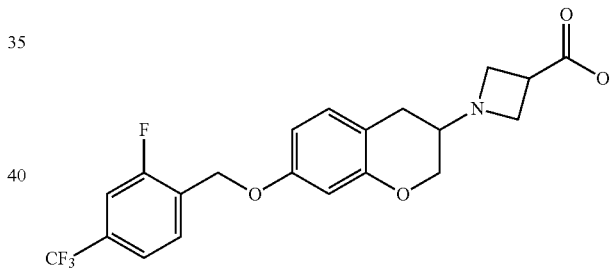

¹H NMR (400 MHz, Pyridine-d₅) δ 7.69 (t, J=7.6 Hz, 1H), 7.53-7.42 (m, 2H), 7.07-7.03 (m, 1H), 6.82 (d, J=2.6 Hz, 1H), 6.75 (dd, J=8.3, 2.6 Hz, 1H), 5.21 (s, 2H), 4.09 (ddd, J=10.9, 3.0, 1.6 Hz, 1H), 3.85 (ddd, J=10.8, 7.0, 1.0 Hz, 1H), 3.70-3.64 (m, 3H), 3.61 (dd, J=7.9, 6.4 Hz, 1H), 3.51-3.42 (m, 1H), 2.76 (dd, J=15.3, 4.9 Hz, 1H), 2.71-2.64 (m, 1H), 2.51 (dd, J=15.4, 7.1 Hz, 1H).

107. 1-[7-[1-(2-fluorophenyl)ethoxy]chroman-3-yl]azetidine-3-carboxylic acid

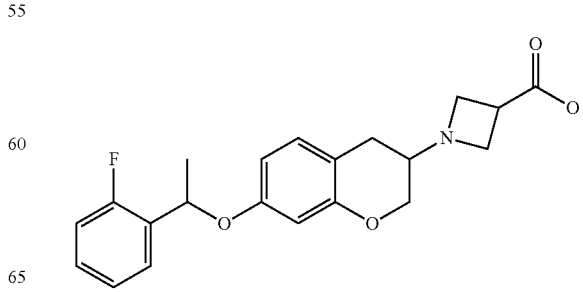

¹H NMR (400 MHz, Pyridine-d₅) δ 7.57 (td, J=7.6, 1.8 Hz, 1H), 7.25-7.20 (m, 1H), 7.19-7.08 (m, 2H), 6.97-6.92 (m, 1H), 6.70-6.64 (m, 2H), 5.76 (qd. J=6.3, 2.7 Hz, 1H), 4.00 (dddd, J=12.5, 10.9, 2.8, 1.5 Hz, 1H), 3.80-3.70 (m, 1H), 3.64-3.59 (m, 1H), 3.58-3.52 (m, 3H), 3.46-3.36 (m, 1H), 2.68 (dd, J=15.5, 4.8 Hz, 1H), 2.64-2.55 (m, 1H), 2.41 (dd, J=15.4, 7.0 Hz, 1H), 2.12 (s, 3H), 1.60 (d, J=6.3 Hz, 3H).

108. 1-[7-[(6-fluoro-2-quinolyl)methoxy]chroman-3-yl]azetidine-3-carboxylic acid

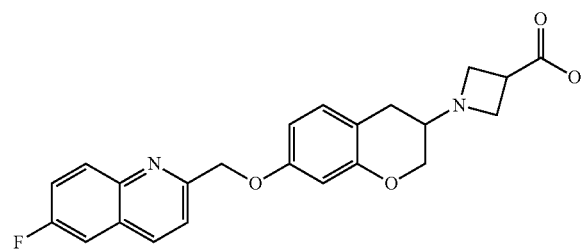 [SMILES: O=C(O)C1CN(C2COc3cc(OCc4ccc5cc(F)ccc5n4)ccc3C2)C1]

¹H NMR (400 MHz, Pyridine-d₅) δ 8.21 (dd, J=8.8, 5.4 Hz, 1H), 8.11 (d, J=8.5 Hz, 1H), 7.70 (d, J=8.5 Hz, 1H), 7.54 (d, J=8.7 Hz, 2H), 7.01 (d, J=8.3 Hz, 1H), 6.87 (d, J=2.5 Hz, 1H), 6.80 (dd, J=8.4, 2.6 Hz, 1H), 5.47 (s, 2H), 4.05 (ddd, J=10.8, 2.9, 1.5 Hz, 1H), 3.80 (dd, J=10.8, 7.0 Hz, 1H), 3.68-3.62 (m, 3H), 3.59 (dd, J=7.9, 6.5 Hz, 1H), 3.45 (p, J=7.4 Hz, 1H), 2.73 (dd, J=15.2, 4.8 Hz, 1H), 2.68-2.60 (m, 1H), 2.48 (dd, J=15.4, 7.1 Hz, 1H).

The following compound were prepared according to the procedure of compound 1:

109. 1-[7-(cyclohexylmethoxy)chroman-3-yl]azetidine-3-carboxylic acid

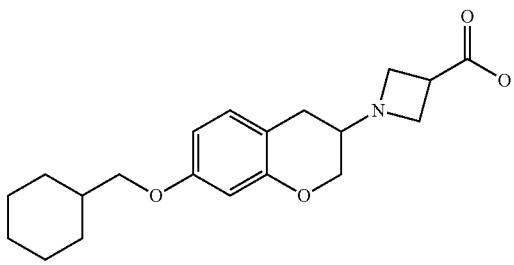 [SMILES: O=C(O)C1CN(C2COc3cc(OCC4CCCCC4)ccc3C2)C1]

¹H NMR (600 MHz, DMSO-d6) δ 6.89 (d, J=8.4 Hz, 1H), 6.39 (dd, J=8.3, 2.6 Hz, 1H), 6.25 (d, J=2.6 Hz, 1H), 3.96 (d, J=10.8 Hz, 1H), 3.69 (dd, J=9.2, 6.4 Hz, 3H), 3.70-3.10 (m, incl. H₂O), 2.72 (dd, J=15.7, 4.9 Hz, 1H), 2.33 (dd, J=15.7, 6.7 Hz, 1H), 1.77 (d, J=12.9 Hz, 2H), 1.67 (ddt, J=17.2, 14.3, 8.6 Hz, 5H), 1.30-1.17 (m, 8H), 0.99 (qd, J=12.4, 3.5 Hz, 2H); other aliphatic H gave very broad signals and were partly covered by H₂O & DMSO.

The following compounds were prepared according to the procedure of compound 1 using methyl piperidine-4-carboxylate instead of methyl azetidine-4-carboxylate:

110. 1-[7-[(2,6-dichlorophenyl)methoxy]chroman-3-yl]piperidine-4-carboxylic acid; Salt with 2,2,2-trifluoroacetic acid

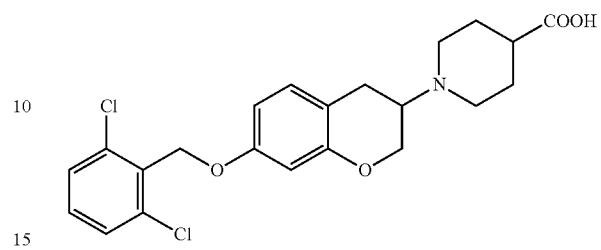

¹H NMR (600 MHz, DMSO-d6) δ 12.59 (s br., 1H, OH), 9.63 (s br., 1H, N⁺H), 7.57 (d, 2H), 7.47 (dd, 1H), 7.09 (d, 1H), 6.67 (d, 1H), 6.60 (s, 1H), 5.18 (s, 2H), 4.38 (s, 2H), 3.82 (s br., 1H), 3.6 (m br., 2H), 3.2 (m br., 4H), 2.08 (d, 2H), 1.77 (t, 2H); other aliphatic H were partly covered by H₂O & DMSO.

111. 1-[7-[(2-chloro-6-ethyl-phenyl)methoxy]chroman-3-yl]piperidine-4-carboxylic acid; Salt with 2,2,2-trifluoroacetic acid

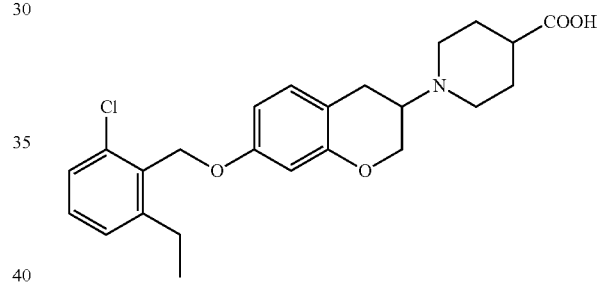

¹H NMR (600 MHz, DMSO-d6) δ 12.58 (s br., 1H, OH), 9.57 (s br., 1H, N⁺H), 7.36 (m, 2H), 7.28 (dd, 1H), 7.09 (d, 1H), 6.66 (d, 1H), 6.59 (s, 1H), 5.10 (s, 2H), 4.38 (s, 2H), 3.82 (s br., 1H), 3.56 (s br., 2H), 3.2 (m br., 4H), 2.70 (q, 2H), 2.08 (d br., 3H), 1.78 (t, 2H), 1.16 (t, 3H); other aliphatic H were partly covered by H₂O & DMSO.

112. 1-(7-benzyloxychroman-3-yl)piperidine-4-carboxylic acid

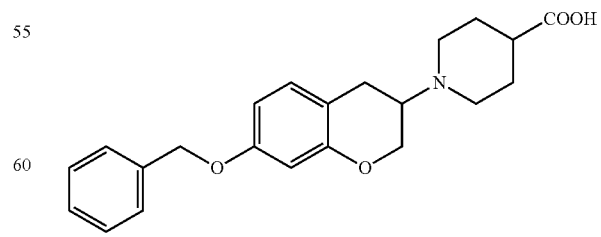

¹H NMR (600 MHz, DMSO-d6) δ 12.56 (s, 1H), 10.06 (d, J=50.1 Hz, 1H), 7.46-7.29 (m, 5H), 7.06 (dd, J=8.6, 3.1 Hz, 1H), 6.63 (dt, J=8.7, 2.7 Hz, 1H), 6.50 (d, J=2.5 Hz, 1H), 5.06 (s, 2H), 4.47-4.28 (m, 2H), 3.83 (d, J=53.7 Hz, 1H), 3.52 (d, J=11.7 Hz, 2H), 3.22-3.01 (m, 4H), 2.06 (d, J=14.6 Hz, 3H), 1.84 (p, J=14.7, 13.7 Hz, 2H)

The following compounds were prepared according to the procedure of compound 1 using methyl glycinate instead of methyl azetidine-4-carboxylate:

113. 2-[[7-(cyclohexylmethoxy)chroman-3-yl]amino]acetic acid

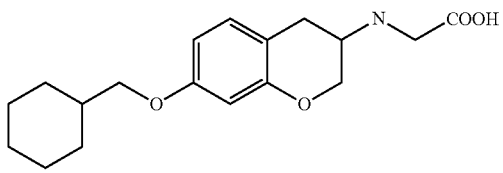 [SMILES: O=C(O)CNC1COc2cc(OCC3CCCCC3)ccc2C1]

¹H NMR (600 MHz, DMSO-d6) δ 9.19 (s, 2H), 6.99 (d, J=8.5 Hz, 1H), 6.51 (dd, J=8.5, 2.5 Hz, 1H), 6.37 (d, J=2.5 Hz, 1H), 4.32-4.26 (m, 1H), 4.15-4.07 (m, 1H), 3.93 (s, 2H), 3.71 (d, J=6.4 Hz, 2H), 3.66 (s, 1H), 3.07 (s, 1H), 2.83 (dd, J=16.5, 6.7 Hz, 1H), 1.81-1.60 (m, 6H), 1.29-1.09 (m, 3H), 1.00 (qd, J=12.3, 3.4 Hz, 2H).

114. 2-[[7-[2-(2,6-dichlorophenyl)ethoxy]chroman-3-yl]amino]acetic acid

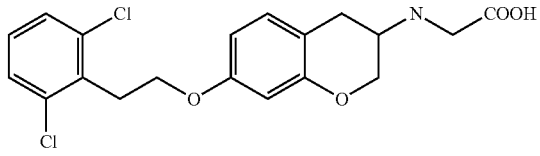 [SMILES: O=C(O)CNC1COc2cc(OCCc3c(Cl)cccc3Cl)ccc2C1]

¹H NMR (600 MHz, DMSO-d6) δ 7.50 (d, J=8.1 Hz, 2H), 7.36-7.29 (m, 1H), 6.99 (d, J=8.5 Hz, 1H), 6.57 (s, 1H), 6.51 (dd, J=8.4, 2.6 Hz, 1H), 6.39 (d, J=2.6 Hz, 1H), 4.31-4.22 (m, 1H), 4.09 (t, J=7.4 Hz, 2H), 4.00 (d, J=10.2 Hz, 1H), 3.74 (s, 2H), 3.03 (dd, J=16.1, 5.4 Hz, 1H), 2.75 (dd, J=16.2, 7.0 Hz, 1H), other aliphatic H were partly covered by H₂O.

115. 2-(1-((7-((2-chloro-6-ethylbenzyl)oxy)chroman-3-yl)amino)cyclopentyl) acetic acid

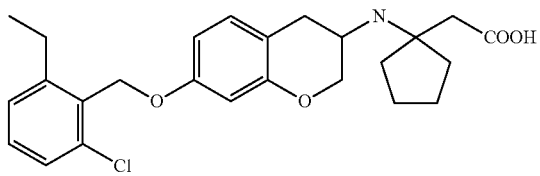 [SMILES: CCc1cccc(Cl)c1COc1ccc2c(c1)OCC(NC1(CC(=O)O)CCCC1)C2]

Compound 115 was prepared as described for Compound 1 using methyl 2-(1-aminocyclopentyl)acetate instead of methylazetine-3-carboxylate hydrochloride and 2-(bromomethyl)-1-chloro-3-ethylbenzene instead of 2-(bromomethyl)-1,3-dichlorobenzene.

¹H NMR (600 MHz, DMSO-d₆) 7.39-7.32 (m, 2H), 7.27 (dd, J=6.0, 2.8 Hz, 1H), 6.99 (d, J=8.3 Hz, 1H), 6.55 (dd, J=8.3, 2.5 Hz, 1H), 6.50 (d, J=2.6 Hz, 1H), 5.08 (d, J=1.0 Hz, 2H), 4.11 (ddd, J=10.6, 3.3, 1.7 Hz, 1H), 3.75 (dd, J=10.7, 8.2 Hz, 1H), 3.21-3.27 (m, 1H), 2.97-2.90 (m, 1H), 2.70 (q, J=7.5 Hz, 2H), 1.67-1.73 (m, 4H), 1.62-1.51 (m, 4H), 1.16 (t, J=7.5 Hz, 3H).

116. 2-(1-((7-((2-chloro-6-ethylbenzyl)oxy)chroman-3-yl)amino)cyclobutyl)acetic acid

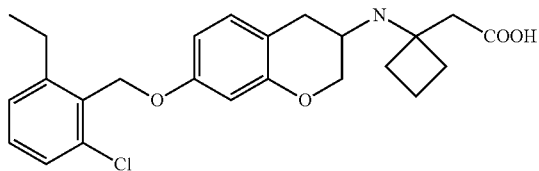 [SMILES: CCc1cccc(F)c1COc1ccc2c(c1)OCC(NC1(CC(=O)O)CCC1)C2]

Compound 115 was prepared as described for Compound 1 using methyl 2-(1-aminocyclobutyl)acetate instead of methylazetine-3-carboxylate hydrochloride and 2-(bromomethyl)-1-chloro-3-ethylbenzene instead of 2-(bromomethyl)-1,3-dichlorobenzene.

¹H NMR (600 MHz, DMSO-d₆) δ 8.8-7.8 (br, s, 2H), 7.39-7.32 (m, 2H), 7.27 (dd, J=6.0, 2.9 Hz, 1H), 6.98 (d, J=8.4 Hz, 1H), 6.55 (dd, J=8.3, 2.6 Hz, 1H), 6.49 (d, J=2.5 Hz, 1H), 5.08 (s, 2H), 4.11 (d, J=11.9 Hz, 1H), 3.73 (t, J=9.4 Hz, 1H), 3.25-3.17 (m, 1H), 2.89 (dd, J=15.8, 5.1 Hz, 1H), 2.70 (q, J=7.5 Hz, 2H), 2.61-2.52 (m, 2H), 2.13-2.03 (m, 2H), 1.97-1.87 (m, 2H), 1.77-1.67 (m, 2H), 1.16 (t, J=7.6 Hz, 3H).

117. 2-(1-((7-((2-ethyl-6-fluorobenzyl)oxy)chroman-3-yl)amino)cyclopentyl) acetic acid

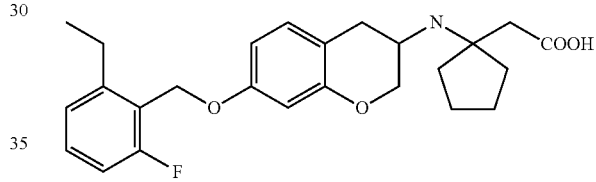

Compound 117 was prepared as described for Compound 1 using methyl 2-(1-aminocyclopentyl)acetate instead of methylazetine-3-carboxylate hydrochloride and 2-(bromomethyl)-1-ethyl-3-fluorobenzene instead of 2-(bromomethyl)-1,3-dichlorobenzene.

¹H NMR (600 MHz, DMSO-d₆) δ 9.0-8.0 (br, s, 2H), 7.13 (dd, J=7.7, 1.0 Hz, 1H), 7.08 (ddd, J=9.6, 8.3, 1.2 Hz, 1H), 6.98 (d, J=8.4 Hz, 1H), 6.53 (dd, J=8.4, 2.5 Hz, 1H), 6.48 (d, J=2.5 Hz, 1H), 5.02 (d, J=1.7 Hz, 2H), 4.10 (ddd, J=10.7, 3.4, 1.8 Hz, 1H), 3.74 (dd, J=10.6, 8.3 Hz, 1H), 3.26-3.20 (m, 1H), 2.92 (dd, J=15.4, 5.3 Hz, 1H), 2.69 (q, J=7.5 Hz, 2H), 2.58 (dd, J=15.8, 8.4 Hz, 1H), 2.49-2.39 (m, 2H), 1.75-1.65 (m, 4H), 1.62-1.49 (m, 4H), 1.16 (t, J=7.6 Hz, 3H).

118. 2-(1-((7-((2-ethyl-6-fluorobenzyl)oxy)chroman-3-yl)amino)cyclobutyl)acetic acid

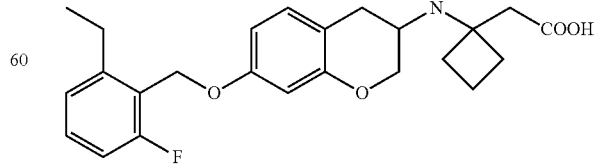

Compound 118 was prepared as described for Compound 1 using methyl 2-(1-aminocyclobutyl)acetate instead of methylazetine-3-carboxylate hydrochloride and 2-(bromomethyl)-1-ethyl-3-fluorobenzene instead of 2-(bromomethyl)-1,3-dichlorobenzene.

¹H NMR (600 MHz, DMSO-d₆) δ 7.37 (td, J=8.0, 5.9 Hz, 1H), 7.13 (d, J=7.6 Hz, 1H), 7.11-7.04 (m, 1H), 6.97 (d, J=8.4 Hz, 1H), 6.53 (dd, J=8.3, 2.6 Hz, 1H), 6.47 (d, J=2.5 Hz, 1H), 5.01 (d, J=1.6 Hz, 2H), 4.11 (ddd, J=10.6, 3.3, 1.7 Hz, 1H), 3.72 (dd, J=10.6, 8.3 Hz, 1H), 3.20 (tdd, J=8.4, 5.3, 3.3 Hz, 1H), 2.88 (ddd, J=16.2, 5.3, 1.7 Hz, 1H), 2.69 (q, J=7.6 Hz, 2H), 2.64-2.54 (m, 3H), 2.11-2.03 (m, 2H), 1.96-1.87 (m, 2H), 1.77-1.66 (m, 2H), 1.16 (t, J=7.5 Hz, 3H).

119. 1-((7-((2,6-dichlorobenzyl)oxy)chroman-3-yl)amino)cyclobutane-1-carboxylic acid

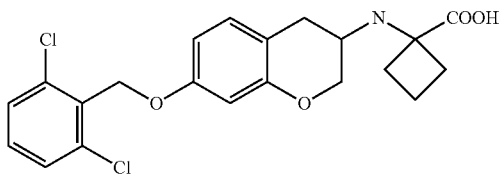 [SMILES: O=C(O)C1(NC2COc3cc(OCc4c(Cl)cccc4Cl)ccc3C2)CCC1]

Compound 119 was prepared as described for Compound 1 using methyl 1-aminocyclobutane-1-carboxylate instead of methylazetine-3-carboxylate hydrochloride ¹H NMR (600 MHz, DMSO-d₆) δ 7.56 (d, J=8.1 Hz, 2H), 7.47 (dd, J=8.7, 7.5 Hz, 1H), 6.96 (d, J=8.4 Hz, 1H), 6.54 (dd, J=8.3, 2.6 Hz, 1H), 6.47 (d, J=2.6 Hz, 1H), 5.15 (s, 2H), 4.08 (ddd, J=10.6, 3.3, 1.8 Hz, 1H), 3.69 (dd, J=10.5, 8.3 Hz, 1H), 3.04-2.97 (m, 1H), 2.82 (ddd, J=16.0, 5.2, 1.7 Hz, 1H), 2.37-2.30 (m, 1H), 2.07-1.90 (m, 2H), 1.87-1.62 (m, 2H).

120. 1-((7-((2-chloro-6-ethylbenzyl)oxy)chroman-3-yl)amino)cyclobutane-1-carboxylic acid

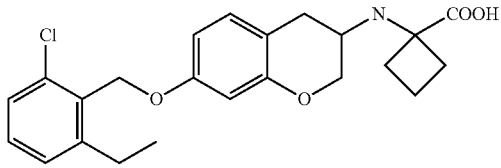 [SMILES: CCc1cccc(Cl)c1COc1ccc2c(c1)OCC(NC1(C(=O)O)CCC1)C2]

Compound 120 was prepared as described for Compound 1 using methyl 1-aminocyclobutane-1-carboxylate instead of methylazetine-3-carboxylate hydrochloride and 2-(bromomethyl)-1-chloro-3-ethylbenzene instead of 2-(bromomethyl)-1,3-dichlorobenzene.

¹H NMR (600 MHz, DMSO-d₆) δ 7.40-7.31 (m, 2H), 7.27 (dd, J=6.0, 2.9 Hz, 1H), 6.95 (d, J=8.4 Hz, 1H), 6.53 (dd, J=8.3, 2.6 Hz, 1H), 6.47 (d, J=2.5 Hz, 1H), 5.07 (s, 2H), 4.08 (ddd, J=10.6, 3.3, 1.8 Hz, 1H), 3.76-3.67 (m, 1H), 3.01 (br, 1H), 2.87-2.78 (m, 1H), 2.70 (q, J=7.6 Hz, 2H), 2.37-2.30 (m, 2H), 2.06-1.95 (m, 2H), 1.88-1.71 (m, 2H), 1.19-1.13 (t, J=7.6 Hz, 3H).

121. 3-((7-((2-chloro-6-ethylbenzyl)oxy)chroman-3-yl)amino)bicyclo[1.1.1]pentane-1-carboxylic acid

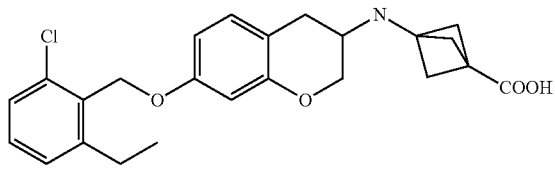 [SMILES: CCc1cccc(Cl)c1COc1ccc2c(c1)OCC(NC13CC(C(=O)O)(C1)C3)C2]

Compound 121 was prepared as described for Compound 1 using methyl 3-aminobicyclo[1.1.1]pentane-1-carboxylate hydrochloride instead of methylazetine-3-carboxylate hydrochloride and 2-(bromomethyl)-1-chloro-3-ethylbenzene instead of 2-(bromomethyl)-1,3-dichlorobenzene.

¹H NMR (600 MHz, DMSO-d₆) δ 7.39-7.32 (m, 2H), 7.27 (dd, J=6.1, 2.9 Hz, 1H), 6.96 (d, J=8.3 Hz, 1H), 6.53 (dd, J=8.3, 2.6 Hz, 1H), 6.46 (d, J=2.5 Hz, 1H), 5.07 (d, J=1.4 Hz, 2H), 4.10 (ddd, J=10.4, 3.3, 1.7 Hz, 1H), 3.63 (dd, J=10.5, 8.4 Hz, 1H), 3.07-3.01 (m, 1H), 2.86 (ddd, J=15.9, 5.2, 1.7 Hz, 1H), 2.70 (q, J=7.6 Hz, 2H), 2.45 (dd, J=15.8, 8.7 Hz, 1H), 2.04-1.93 (m, 6H), 1.16 (t, J=7.6 Hz, 3H).

122. 3-((7-((2-ethyl-6-fluorobenzyl)oxy)chroman-3-yl)amino)bicyclo[1.1.1]pentane-1-carboxylic acid

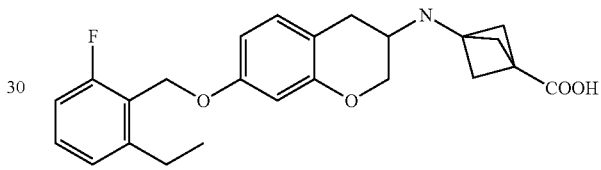

Compound 122 was prepared as described for Compound 1 using methyl 3-aminobicyclo[1.1.1]pentane-1-carboxylate hydrochloride instead of methylazetine-3-carboxylate hydrochloride and 2-(bromomethyl)-1-ethyl-3-fluorobenzene instead of 2-(bromomethyl)-1,3-dichlorobenzene.

¹H NMR (600 MHz, DMSO-d₆) δ 7.37 (td, J=8.0, 5.9 Hz, 1H), 7.13 (dd, J=7.8, 1.1 Hz, 1H), 7.08 (ddd, J=9.6, 8.3, 1.1 Hz, 1H), 6.95 (d, J=8.4 Hz, 1H), 6.51 (dd, J=8.4, 2.6 Hz, 1H), 6.44 (d, J=2.5 Hz, 1H), 5.01 (d, J=1.6 Hz, 2H), 4.09 (ddd, J=10.5, 3.3, 1.8 Hz, 1H), 3.68-3.56 (m, 1H), 3.09-2.99 (m, 1H), 2.90-2.81 (m, 1H), 2.69 (q, J=7.5 Hz, 2H), 1.97 (qd, J=9.4, 1.3 Hz, 6H), 1.16 (t, J=7.5 Hz, 3H).

123. 2-((7-((2-ethyl-6-fluorobenzyl)oxy)chroman-3-yl)(methyl)amino)acetic acid

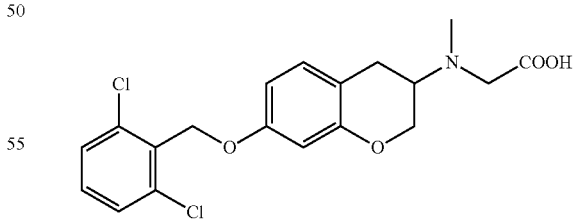

Compound 123 was prepared as described for compound 1 using methyl 2-(methylamino)acetate hydrochloride instead of methylazetine-3-carboxylate hydrochloride ¹H NMR (600 MHz, DMSO-d₆) δ 7.56 (d, J=8.1 Hz, 2H), 7.46 (dd, J=8.7, 7.5 Hz, 1H), 7.00 (d, J=8.4 Hz, 1H), 6.54 (dd, J=8.4, 2.6 Hz, 1H), 6.47 (d, J=2.6 Hz, 1H), 5.15 (s, 2H), 4.26 (dt, J=10.7, 2.3 Hz, 1H), 3.86 (dd, J=10.7, 8.2 Hz, 1H), 3.16-3.10 (m, 1H), 2.87-2.80 (m, 1H), 2.71 (dd, J=15.6, 8.8 Hz, 1H), 2.42 (s, 3H).

124. N-(7-((2-chloro-6-ethylbenzyl)oxy)chroman-3-yl)-N-methylglycine

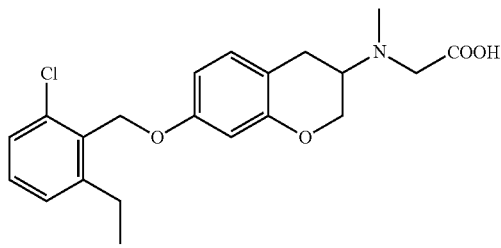 [SMILES: CCc1cccc(Cl)c1COc1ccc2c(c1)OCC(N(C)CC(=O)O)C2]

Compound 124 was prepared as described for compound 1 using methyl 2-(methylamino)acetate hydrochloride instead of methylazetine-3-carboxylate hydrochloride and 2-(bromomethyl)-1-chloro-3-ethylbenzene instead of 2-(bromomethyl)-1,3-dichlorobenzene.

$^1$H NMR (600 MHz, DMSO-d$_6$) δ 7.42-7.32 (m, 2H), 7.27 (dd, J=6.0, 3.0 Hz, 1H), 7.00 (d, J=8.4 Hz, 1H), 6.53 (dd, J=8.3, 2.6 Hz, 1H), 6.47 (d, J=2.6 Hz, 1H), 5.08 (s, 2H), 4.26 (dt, J=10.8, 2.4 Hz, 1H), 3.87 (dd, J=10.8, 8.2 Hz, 1H), 3.1-3.10 (m, 1H), 2.84 (dd, J=15.8, 4.9 Hz, 1H), 2.74-2.67 (m, 3H), 2.42 (s, 3H), 1.16 (t, J=7.6 Hz, 3H).

125. 2-(1-(7-((2-chloro-6-ethylbenzyl)oxy)chroman-3-yl)pyrrolidin-3-yl)acetic acid

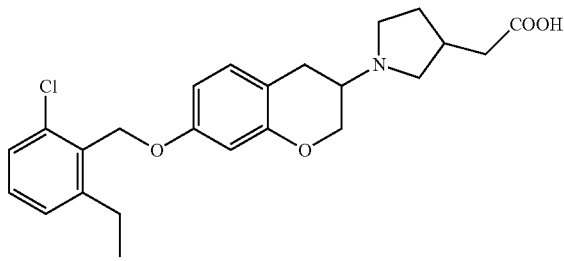 [SMILES: CCc1cccc(Cl)c1COc1ccc2c(c1)OCC(N1CCC(CC(=O)O)C1)C2]

Compound 125 was prepared as described for compound 1 using methyl 2-(pyrrolidin-3-yl)acetate hydrochloride instead of methylazetine-3-carboxylate hydrochloride and 2-(bromomethyl)-1-chloro-3-ethylbenzene instead of 2-(bromomethyl)-1,3-dichlorobenzene.

$^1$H NMR (600 MHz, DMSO-d$_6$) δ 7.40-7.31 (m, 2H), 7.27 (dd, J=6.0, 2.9 Hz, 1H), 6.99 (dd, J=8.4, 2.8 Hz, 1H), 6.53 (ddd, J=8.3, 2.6, 1.1 Hz, 1H), 6.47 (dd, J=2.6, 1.1 Hz, 1H), 5.08 (d, J=1.2 Hz, 2H), 4.29-4.21 (m, 1H), 3.89-3.74 (m, 1H), 2.95-2.84 (m, 2H), 2.70 (q, J=7.5 Hz, 2H), 2.32-2.16 (m, 2H), 2.00-1.91 (m, 1H), 1.41-1.32 (m, 1H), 1.16 (t, J=7.5 Hz, 3H).

126. (7-((2-ethyl-6-fluorobenzyl)oxy)chroman-3-yl)glycine

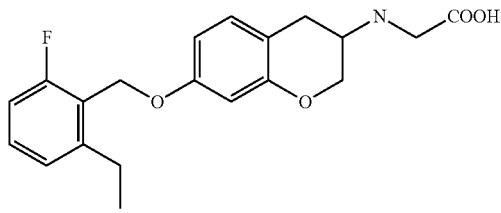 [SMILES: CCc1cccc(F)c1COc1ccc2c(c1)OCC(NCC(=O)O)C2]

Compound 126 was prepared as described for Compound 1 using methyl glycinate instead of methylazetine-3-carboxylate hydrochloride and 2-(bromomethyl)-1-ethyl-3-fluorobenzene instead of 2-(bromomethyl)-1,3-dichlorobenzene.

$^1$H NMR (600 MHz, DMSO-d$_6$) δ 7.37 (td, J=8.0, 5.9 Hz, 1H), 7.13 (d, J=7.6 Hz, 1H), 7.11-7.05 (m, 1H), 6.98 (d, J=8.4 Hz, 1H), 6.54 (dt, J=8.3, 2.0 Hz, 1H), 6.47 (d, J=2.4 Hz, 1H), 5.01 (d, J=1.7 Hz, 2H), 4.23-4.17 (m, 1H), 3.85-3.79 (m, 1H), 3.19 (m, 2H), 2.93 (dd, J=16.0, 5.0 Hz, 1H), 2.69 (q, J=7.6 Hz, 2H), 2.61-2.55 (m, 1H), 1.16 (t, J=7.5 Hz, 3H).

127. 1-(7-((2-ethyl-6-fluorobenzyl)oxy)chroman-3-yl)pyrrolidine-3-carboxylic acid

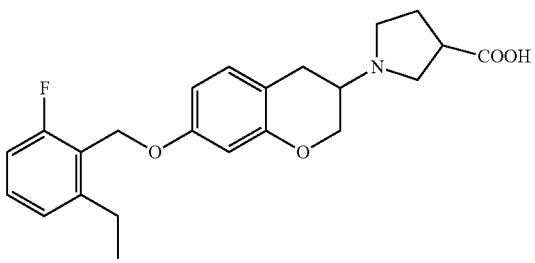 [SMILES: CCc1cccc(F)c1COc1ccc2c(c1)OCC(N1CCC(C(=O)O)C1)C2]

Compound 127 was prepared as described for compound 1 using ethyl pyrrolidine-3-carboxylate hydrochloride instead of methylazetine-3-carboxylate hydrochloride and 2-(bromomethyl)-1-ethyl-3-fluorobenzene instead of 2-(bromomethyl)-1,3-dichlorobenzene.

$^1$H NMR (600 MHz, DMSO-d$_6$) δ 7.37 (td, J=8.0, 6.0 Hz, 1H), 7.16-7.05 (m, 2H), 6.99 (dd, J=8.5, 2.7 Hz, 1H), 6.55-6.50 (m, 1H), 6.46 (s, 1H), 5.01 (d, J=1.7 Hz, 2H), 4.30-4.24 (m, 1H), 3.83 (m, 1H), 2.93 (m, 3H), 2.69 (q, J=7.5 Hz, 2H), 1.95 (m, 2H), 1.16 (t, J=7.6 Hz, 3H).

128. 1-(7-((2-chloro-6-ethylbenzyl)oxy)chroman-3-yl)pyrrolidine-3-carboxylic acid

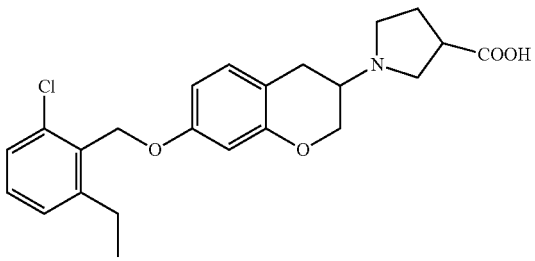 [SMILES: CCc1cccc(Cl)c1COc1ccc2c(c1)OCC(N1CCC(C(=O)O)C1)C2]

Compound 128 was prepared as described for compound 1 using ethyl pyrrolidine-3-carboxylate hydrochloride instead of methylazetine-3-carboxylate hydrochloride and 2-(bromomethyl)-1-chloro-3-ethylbenzene instead of 2-(bromomethyl)-1,3-dichlorobenzene.

$^1$H NMR (600 MHz, DMSO-d$_6$) δ 7.41-7.31 (m, 2H), 7.27 (dd, J=6.0, 3.0 Hz, 1H), 6.99 (dd, J=8.5, 2.5 Hz, 1H), 6.54 (dd, J=8.5, 2.5 Hz, 1H), 6.48 (d, J=2.5 Hz, 1H), 5.08 (s, 2H), 4.30-4.24 (m, 1H), 3.91-3.78 (br, 1H), 3.00-2.86 (m, 3H), 2.70 (q, J=7.5 Hz, 2H), 2.00-1.90 (m, 2H), 1.16 (t, J=7.5 Hz, 3H).

129. 2-(1-((7-((2-ethyl-6-fluorobenzyl)oxy)chroman-3-yl)amino)cyclopropyl) acetic acid

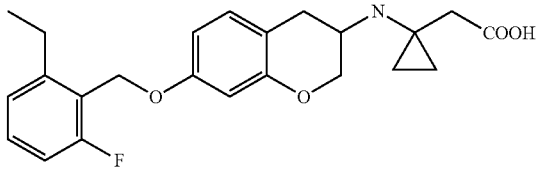 [SMILES: CCc1cccc(F)c1COc1ccc2c(c1)OCC(NC1(CC(=O)O)CC1)C2]

Compound 129 was prepared as described for Compound 1 using methyl 2-(1-aminocyclopropyl)acetate hydrochloride instead of methylazetine-3-carboxylate hydrochloride and 2-(bromomethyl)-1-ethyl-3-fluorobenzene instead of 2-(bromomethyl)-1,3-dichlorobenzene.

$^1$H NMR (600 MHz, DMSO-$d_6$) δ 7.37 (td, J=8.0, 6.0 Hz, 1H), 7.13 (dd, J=7.8, 1.1 Hz, 1H), 7.08 (ddd, J=9.6, 8.3, 1.1 Hz, 1H), 6.95 (d, J=8.4 Hz, 1H), 6.50 (dd, J=8.4, 2.6 Hz, 1H), 6.44 (d, J=2.6 Hz, 1H), 5.00 (d, J=1.7 Hz, 2H), 4.14 (ddd, J=10.6, 3.2, 1.7 Hz, 1H), 3.68 (dd, J=10.6, 7.9 Hz, 1H), 3.28-3.23 (m, 1H), 2.86 (ddd, J=16.0, 5.1, 1.6 Hz, 1H), 2.69 (q, J=7.5 Hz, 2H), 2.47-2.41 (m, 1H), 2.35 (d, J=16.0 Hz, 1H), 1.91 (s, 2H), 1.16 (t, J=7.6 Hz, 4H), 0.61-0.52 (m, 2H), 0.49 (q, J=1.7 Hz, 2H).

130. 2-(1-(7-((2-ethyl-6-fluorobenzyl)oxy)chroman-3-yl)pyrrolidin-3-yl)acetic acid

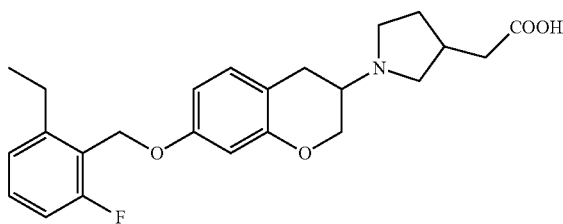 [SMILES: CCc1cccc(F)c1COc1ccc2c(c1)OCC(N1CCC(CC(=O)O)C1)C2]

Compound 130 was prepared as described for compound 1 using methyl 2-(pyrrolidin-3-yl)acetate hydrochloride instead of methylazetine-3-carboxylate hydrochloride and 2-(bromomethyl)-1-ethyl-3-fluorobenzene instead of 2-(bromomethyl)-1,3-dichlorobenzene.

$^1$H NMR (500 MHz, Chloroform-d) δ 7.30-7.24 (m, 1H), 7.05 (d, J=7.7 Hz, 1H), 7.00-6.89 (m, 2H), 6.57 (dd, J=8.4, 2.5 Hz, 1H), 6.53-6.49 (m, 1H), 5.04 (d, J=1.8 Hz, 2H), 4.43-4.32 (m, 1H), 4.07-3.95 (m, 1H), 3.22 (tt, J=8.8, 3.9 Hz, 1H), 3.07-2.94 (m, 3H), 2.95-2.81 (m, 3H), 2.74 (q, J=7.6 Hz, 2H), 2.72-2.64 (m, 1H), 2.64-2.56 (m, 2H), 2.29-2.18 (m, 1H), 1.76-1.66 (m, 1H), 1.24 (t, J=7.6 Hz, 3H).

131. (7-(4-((2,3-difluorobenzyl)oxy)phenyl)chroman-3-yl)glycine

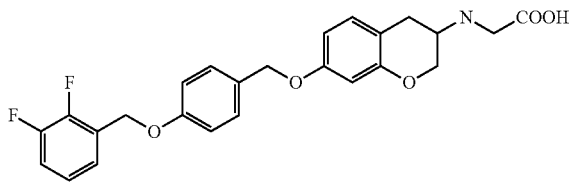 [SMILES: O=C(O)CNC1COc2cc(OCc3ccc(OCc4cccc(F)c4F)cc3)ccc2C1]

Compound 131 was prepared as described for compound 54 using methyl 2-aminoacetate hydrochloride instead of methylazetine-3-carboxylate hydrochloride and 1-(bromomethyl)-2,3-difluorobenzene instead of 1-(bromomethyl)-4-chlorobenzene.

$^1$H NMR (600 MHz, DMSO-$d_6$) δ 7.57 (d, J=8.5 Hz, 2H), 7.50-7.35 (m, 2H), 7.29-7.22 (m, 1H), 7.15-7.11 (m, 2H), 7.11 (d, J=8.5, 2H), 6.99 (s, 1H), 5.23 (s, 2H), 4.24 (d, J=10.7 Hz, 1H), 3.88 (dd, J=10.7, 7.5 Hz, 1H), 3.02 (dd, J=16.4, 5.2 Hz, 1H), 2.68 (dd, J=16.3, 7.7 Hz, 1H).

132. (7-((4-((3-chlorobenzyl)oxy)benzyl)oxy)chroman-3-yl)glycine

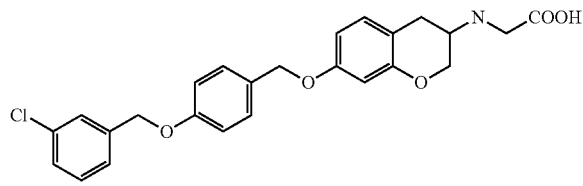 [SMILES: O=C(O)CNC1COc2cc(OCc3ccc(OCc4cccc(Cl)c4)cc3)ccc2C1]

Compound 132 was prepared as described for compound 54 using methyl 2-aminoacetate hydrochloride instead of methylazetine-3-carboxylate hydrochloride and 1-(bromomethyl)-3-chlorobenzene instead of 1-(bromomethyl)-4-chlorobenzene.

$^1$H NMR (600 MHz, DMSO-$d_6$) δ 7.58-7.54 (m, 2H), 7.53 (d, J=2.1 Hz, 1H), 7.47-7.37 (m, 3H), 7.14-7.09 (m, 2H), 7.08-7.05 (m, 2H), 6.98 (d, 1.7 Hz, 1H), 5.17 (s, 2H), 4.27-4.22 (m, 1H), 3.89 (dd, J=10.8, 7.5 Hz, 1H), 3.02 (dd, J=16.2, 5.2 Hz, 1H), 2.68 (dd, J=16.3, 7.7 Hz, 1H).

133. N-(7-((4-((2,3-difluorobenzyl)oxy)benzyl)oxy)chroman-3-yl)-N-methylglycine

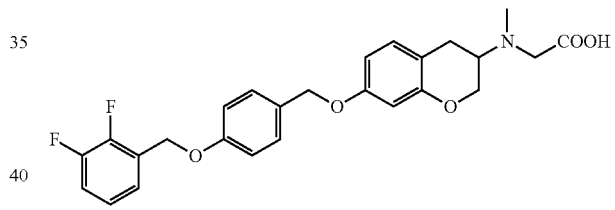

Compound 133 was prepared as described for compound 54 using methyl 2-(methylamino)acetate hydrochloride instead of methylazetine-3-carboxylate hydrochloride and 1-(bromomethyl)-2,3-difluorobenzene instead of 1-(bromomethyl)-4-chlorobenzene.

$^1$H NMR (600 MHz, DMSO-$d_6$) δ 7.61-7.54 (m, 2H), 7.48-7.42 (m, 1H), 7.42-7.37 (m, 1H), 7.29-7.23 (m, 1H), 7.14 (d, J=7.9 Hz, 1H), 7.09 (dd, J=8.4, 2.1 Hz, 3H), 6.97 (d, J=1.8 Hz, 1H), 5.23 (s, 2H), 4.30 (dt, J=10.8, 2.5 Hz, 1H), 3.91 (dd, J=10.8, 8.0 Hz, 1H), 3.20-3.14 (m, 1H), 2.92 (ddd, J=16.4, 5.0, 1.7 Hz, 1H), 2.80 (dd, J=16.1, 8.7 Hz, 1H), 2.44 (s, 3H).

134. N-(7-((4-((3-chlorobenzyl)oxy)benzyl)oxy)chroman-3-yl)-N-methylglycine

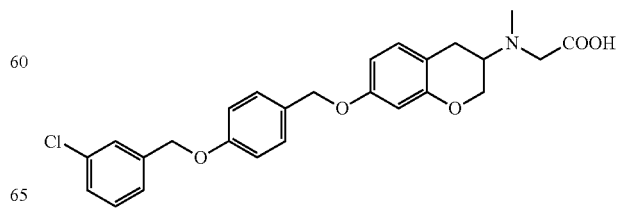

Compound 134 was prepared as described for compound 54 using methyl 2-(methylamino)acetate hydrochloride instead of methylazetine-3-carboxylate hydrochloride and 1-(bromomethyl)-3-chlorobenzene instead of 1-(bromomethyl)-4-chlorobenzene.

¹H NMR (600 MHz, DMSO-d₆) δ 7.61-7.51 (m, 3H), 7.48-7.36 (m, 3H), 7.13 (d, J=7.9 Hz, 1H), 7.09 (dd, J=7.9, 1.9 Hz, 1H), 7.06 (d, J=2.0 Hz, 1H), 6.96 (d, J=1.8 Hz, 1H), 5.17 (s, 2H), 4.30 (dt, J=10.6, 2.4 Hz, 1H), 3.91 (dd, J=10.8, 8.1 Hz, 1H), 3.20-3.14 (m, 1H), 2.92 (ddd, J=16.3, 5.0, 1.7 Hz, 1H), 2.80 (dd, J=16.1, 8.7 Hz, 1H), 2.44 (s, 3H).

135. N-(7-((4-((4-chlorobenzyl)oxy)benzyl)oxy)chroman-3-yl)-N-methylglycine

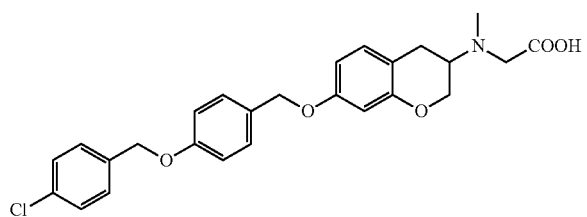 [SMILES: CN(CC(=O)O)C1COc2cc(OCc3ccc(OCc4ccc(Cl)cc4)cc3)ccc2C1]

Compound 135 was prepared as described for compound 54 using methyl 2-(methylamino)acetate hydrochloride instead of methylazetine-3-carboxylate hydrochloride and 1-(bromomethyl)-4-chlorobenzene instead of 1-(bromomethyl)-4-chlorobenzene.

¹H NMR (600 MHz, DMSO-d₆) δ 7.58-7.52 (m, 2H), 7.51-7.45 (m, 4H), 7.13 (d, J=8.0 Hz, 1H), 7.10-7.03 (m, 3H), 6.96 (d, J=1.8 Hz, 1H), 5.15 (s, 2H), 3.91 (dd, J=10.9, 8.1 Hz, 1H), 3.21-3.15 (m, 1H), 2.90 (dd, J=5.0, 1.8 Hz, 1H), 2.84-2.76 (m, 1H), 2.43 (s, 3H).

136. Synthesis of (S)-5-(((7-((2-ethyl-6-fluorobenzyl)oxy)chroman-3-yl)amino)methyl)isoxazol-3-ol at RT for 14 h. The solvent was evaporated and the residue distributed in water/ethylacetate. The organic layer was dried over MgSO₄, filtered, the solvent removed under vacuum and the residue purified by chromatography on silica gel affording compound XIX as colorless oil that became solid on standing (3.2 g).

136.2 (S)-tert-butyl (7-((2-ethyl-6-fluorobenzyl)oxy)chroman-3-yl)carbamate Compound XIX (500 mg, 1.9 mmol) was dissolved in DMF. 2-(bromomethyl)-1-ethyl-3-fluorobenzene (410 mg, 1.9 mmol) and potassium carbonate (260 mg, 1.9 mmol) were added and stirred at RT overnight. The mixture was diluted with water and extracted with ethylacetate. The organic layer was with MgSO₄ and evaporated and the residue purified by chromatography (silica gel) giving product XX with a yield of 677 mg.

136.3 (S)-7-((2-ethyl-6-fluorobenzyl)oxy)chroman-3-amine 2,2,2-trifluoroacetate Compound XX (677 mg, 1.7 mmol) was dissolved in DCM together with 2,2,2-trifluoroacetic acid (1.3 ml, 16.9 mmol). The reaction was stirred at RT for 14 h and then the volume reduced to half. Upon addition of diisopropylether the product XXI precipitated and was filtered of (425 mg)

136.4 (S)-5-(((7-((2-ethyl-6-fluorobenzyl)oxy)chroman-3-yl)amino)methyl)isoxazol-3-ol Compound XXI (173 mg, 0.41 mmol) and trimethylamine (38 mg, 0.37 mmol) were stirred for 15 min at RT in MeOH. 3-((tert-butyldimethylsilyl)oxy)isoxazole-5-carbaldehyde (99 mg, 0.44 mmol) was added and after 2 h sodium cyanotrihydroborate (52 mg, 0.83 mmol). Then the mixture was stirred for 14 h at RT, after which the solvent was evaporated. The residue was distributed between NaHCO3

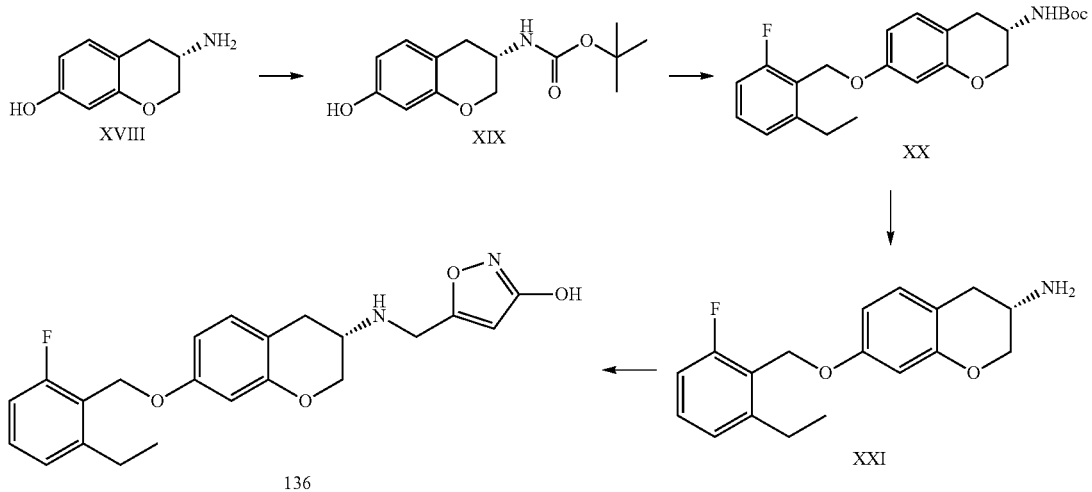

136.1 (S)-tert-butyl (7-hydroxychroman-3-yl)carbamate

Commercially available (S)-3-aminochroman-7-ol hydrochloride (2 g, 9.9 mmol) and triethylamine (2.2 g, 21.8 mmol) were dissolved in MeOH. After addition of di-tert-butyl dicarbonate (2.4 g, 10.9 mmol) the reaction was stirred (1M) and ethylacetate. The organic layer was separated, dried and evaporated. The aqueous layer was acidified with citric acid to pH5, extracted with DCM. The organic layer was dried (MgSO₄), filtered and the reduced to dryness. The combined residues (ethyl acetate and DCM) were purified by chromatography (silica gel) giving product 136 with a yield of 75 mg ¹H NMR (600 MHz, DMSO-d₆) δ 7.41-7.35 (m, 1H), 7.22-7.04 (m, 2H), 6.96 (d, J=8.5 Hz, 1H), 6.51 (dd, J=8.4, 2.6 Hz, 1H), 6.45 (d, J=2.5 Hz, 1H), 5.89 (s, 1H), 5.00 (d, J=1.9 Hz, 2H), 4.19-4.13 (m, 1H), 3.84-3.74 (m, 2H), 3.71 (ddd, J=11.7, 7.9, 3.9 Hz, 1H), 3.00-2.93 (m, 1H), 2.90-2.83 (m, 1H), 2.69 (q, J=7.5 Hz, 2H), 1.19-1.13 (t, J=7.5 Hz, 3H).

137 (S)—N-((3-((tert-butyldimethylsilyl)oxy)isoxazol-5-yl)methyl)-7-((2-chloro-6-ethylbenzyl)oxy)chroman-3-amine

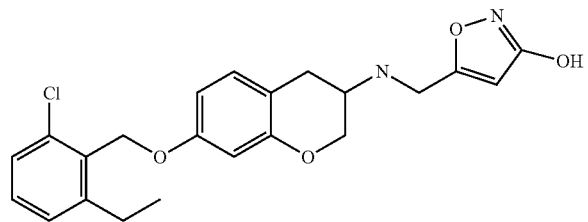 [SMILES: CCc1cccc(Cl)c1COc1ccc2c(c1)OCC(NCc1cc(O)no1)C2]

Compound 137 was prepared as described for compound 136 using 2-(bromomethyl)-1-chloro-3-ethylbenzene instead of 2-(bromomethyl)-1-ethyl-3-fluorobenzene.

¹H NMR (600 MHz, DMSO-d₆) δ 7.38-7.33 (m, 2H), 7.27 (dd, J=6.1, 2.9 Hz, 1H), 6.97 (d, J=8.4 Hz, 1H), 6.53 (dd, J=8.4, 2.6 Hz, 1H), 6.46 (d, J=2.5 Hz, 1H), 5.89 (s, 1H), 4.16 (ddd, J=10.7, 3.1, 1.7 Hz, 1H), 3.79 (d, J=4.1 Hz, 2H), 3.72 (dd, J=10.6, 7.8 Hz, 1H), 3.00-2.94 (m, 1H), 2.88 (ddd, J=16.1, 5.0, 1.6 Hz, 1H), 2.70 (q. J=7.5 Hz, 2H), 1.15 (t, J=7.5 Hz, 4H).

138. (S)-1-(7-((2,6-dichlorobenzyl)oxy)chroman-3-yl)-3-methylazetidine-3-carboxylic acid

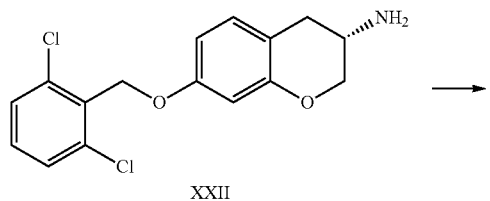

XXII

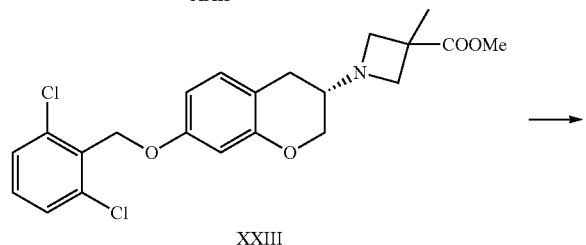

XXIII

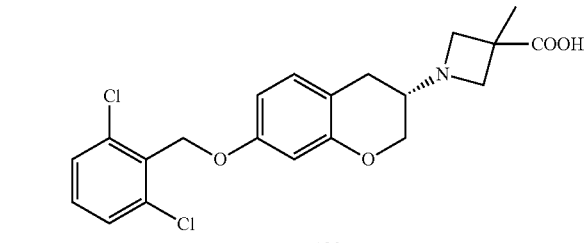

138

138.1 (S)-7-((2,6-dichlorobenzyl)oxy)chroman-3-amine Hydrochloride

Compound XXII was prepared as described for Compound 136 using 2-(bromomethyl)-1,3-dichlorobenzene instead of 2-(bromomethyl)-1-ethyl-3-fluorobenzene.

138.2 (S)-methyl 1-(7-((2,6-dichlorobenzyl)oxy)chroman-3-yl)-3-methylazetidine-3-carboxylate A mixture of (S)-7-((2,6-dichlorobenzyl)oxy)chroman-3-amine hydrochloride (150 mg, 0.42 mmol), methyl 2-methyl-3-(((trifluoromethyl)sulfonyl)oxy)-2-((((trifluoromethyl)sulfonyl)oxy)methyl)propanoate (206 mg, 0.5 mmol, WO2007053394) and triethylamine (126 mg, 1.25 mmol) in acetonitrile was stirred for 4 h under reflux. The reaction was distributed among DCM and HCl (3%), the organic layer separated, dried and the solvent evaporated. The residue was purified by chromatography (silica gel) giving product XXIII with a yield of 95 mg as colorless oil

138.3 (S)-1-(7-((2,6-dichlorobenzyl)oxy)chroman-3-yl)-3-methylazetidine-3-carboxylic acid A mixture of (S)-methyl 1-(7-((2,6-dichlorobenzyl)oxy)chroman-3-yl)-3-methylazetidine-3-carboxylate (95 mg, 0.22 mmol) and NaOH (800 μl, 2M, 1.6 mmol) in THF/MeOH 1:1 was stirred for 14 h at RT. Then the solvent was reduced to half, and 800 μl 2N HCl were added. The mixture was extracted with DCM, the organic layer dried and the solvent evaporated affording 60 mg of product as off white powder.

¹H NMR (600 MHz, DMSO-d₆) δ 12.39 (br, 1H), 7.55 (d, J=8.1 Hz, 2H), 7.46 (dd, J=8.7, 7.5 Hz, 1H), 6.96 (d, J=8.3 Hz, 1H), 6.52 (dd, J=8.4, 2.5 Hz, 1H), 6.45 (d, J=2.6 Hz, 1H), 5.14 (s, 2H), 3.99 (ddd, J=10.8, 2.9, 1.5 Hz, 1H), 3.69 (dd, J=10.9, 6.8 Hz, 1H), 3.46 (dd, J=14.9, 6.8 Hz, 2H), 3.09 (dd, J=20.1, 6.8 Hz, 2H), 2.75 (dd, J=15.6, 4.9 Hz, 1H), 2.67-2.61 (m, 1H), 2.36 (dd, J=15.8, 7.1 Hz, 1H), 1.40 (s, 3H).

139. (S)-1-(7-((2-ethyl-6-fluorobenzyl)oxy)chroman-3-yl)-3-methylazetidine-3-carboxylic acid

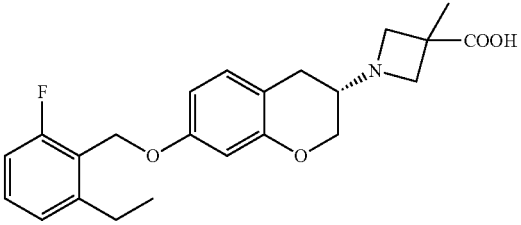 [SMILES: CCc1cccc(F)c1COc1ccc2c(c1)OC[C@@H](N1CC(C)(C(=O)O)C1)C2]

Compound 139 was prepared as described for compound 138 starting from compound XXI ¹H NMR (600 MHz, Chloroform-d) δ 7.32-7.23 (m, 1H), 7.04 (dd, J=7.7, 1.0 Hz, 1H), 6.97-6.89 (m, 2H), 6.56 (dd, J=8.4, 2.6 Hz, 1H), 6.50 (d, J=2.5 Hz, 1H), 5.02 (d, J=1.6 Hz, 2H), 4.30 (t, J=10.3 Hz, 2H), 4.23-4.18 (m, 1H), 4.04 (dd, J=11.1, 8.5 Hz, 1H), 3.66 (dd, J=22.8, 8.9 Hz, 2H), 3.36-3.28 (m, 1H), 2.99-2.88 (m, 2H), 2.72 (q, J=7.5 Hz, 2H), 1.48 (s, 3H), 1.24 (t, J=7.4 Hz, 3H).

140. (S)-1-(7-((2,6-dichlorobenzyl)oxy)chroman-3-yl)-3-ethylazetidine-3-carboxylic acid

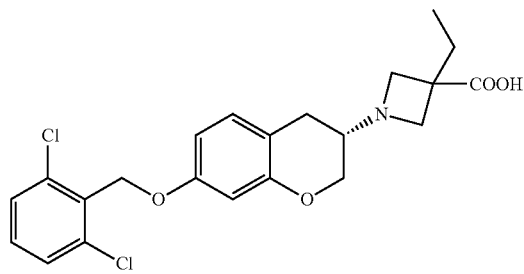 [SMILES: CCC1(C(=O)O)CN([C@@H]2COc3cc(OCc4c(Cl)cccc4Cl)ccc3C2)C1]

Compound 140 was prepared as described for compound 138 using methyl 2,2-bis((((trifluoromethyl)sulfonyl)oxy)methyl)butanoate instead of methyl 2-methyl-3-(((trifluoromethyl)sulfonyl)oxy)-2-((((trifluoromethyl)sulfonyl)oxy)methyl)propanoate $^1$H NMR (500 MHz, DMSO-d$_6$) δ 7.55 (d, J=8.2 Hz, 2H), 7.46 (dd, J=8.8, 7.3 Hz, 1H), 6.96 (d, J=8.3 Hz, 1H), 6.59-6.49 (m, 1H), 6.46 (d, J=2.7 Hz, 1H), 5.15 (s, 2H), 4.01 (d, J=11.0 Hz, 1H), 1.88-1.79 (m, 2H), 0.80 (t, J=7.4 Hz, 3H) several signal gave very broad signals.

141. (S)-1-(7-((2,6-dichlorobenzyl)oxy)chroman-3-yl)-3-propylazetidine-3-carboxylic acid

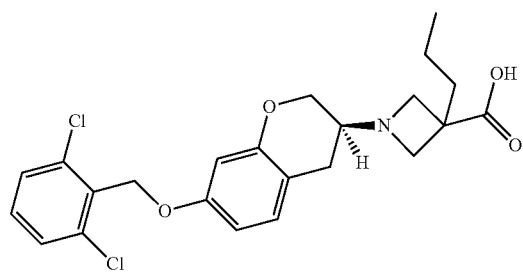 [SMILES: CCCC1(C(=O)O)CN([C@@H]2COc3cc(OCc4c(Cl)cccc4Cl)ccc3C2)C1]

Compound 141 was prepared as described for compound 138 using methyl 2,2-bis((((trifluoromethyl)sulfonyl)oxy)methyl)pentanoate instead of methyl 2-methyl-3-(((trifluoromethyl)sulfonyl)oxy)-2-((((trifluoromethyl)sulfonyl)oxy)methyl)propanoate $^1$H NMR (500 MHz, DMSO-d$_6$) δ 7.55 (d, J=8.0 Hz, 2H), 7.46 (dd, J=8.9, 7.4 Hz, 1H), 6.96 (d, J=8.4 Hz, 1H), 6.54 (d, J=6.9 Hz, 1H), 6.45 (s, 1H), 5.15 (s, 2H), 4.00 (d, J=10.7 Hz, 1H), 3.77-3.63 (m, 1H), 1.84-1.73 (m, 2H), 1.25-1.14 (m, 2H), 0.87 (t, J=7.3 Hz, 3H).

142. 2-[6-[(2-chloro-6-ethyl-phenyl)methoxy]tetralin-2-yl]oxyacetic acid

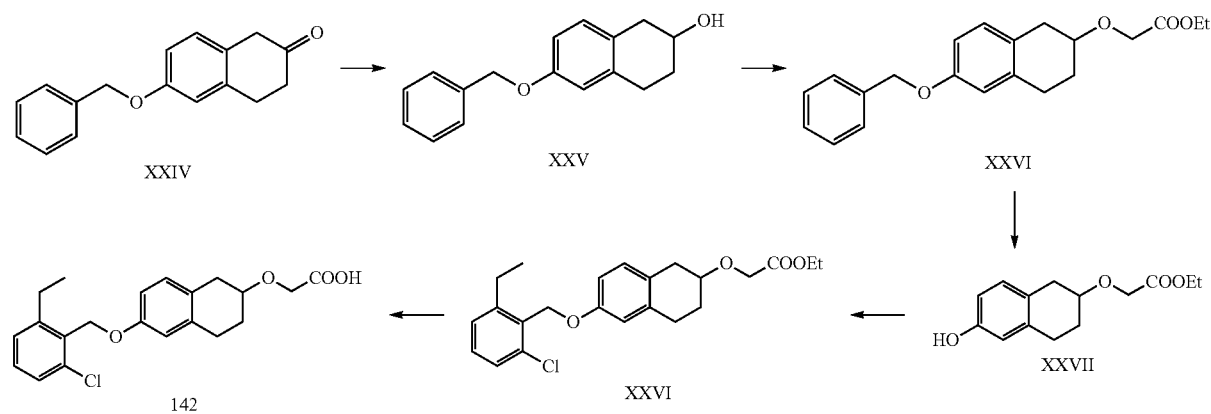

142.1 6-(benzyloxy)-1,2,3,4-tetrahydronaphthalen-2-ol

Sodium tetrahydroborate (8.32 g, 220 mmol) was added to 6-(benzyloxy)-3,4-dihydronaphthalen-2(1H)-one (37 g, 147 mmol) dissolved in 300 ml THF at 0° C. The mixture was stirred for 3 hours at 0° C., then washed successively with water. The organic layer was dried over magnesium sulfate, concentrated and purified by column chromatography (silica gel) to afford 6-(benzyloxy)-1,2,3,4-tetrahydronaphthalen-2-ol (30 g, 118 mmol, 80% yield)

142.2 Ethyl 2-((6-(benzyloxy)-1,2,3,4-tetrahydronaphthalen-2-yl)oxy)acetate 6-(benzyloxy)-1,2,3,4-tetrahydronaphthalen-2-ol (15 g, 59.0 mmol) and Rhodium (II) acetate dimer (0.130 g, 0.295 mmol), were dissolved in a 300 ml DCM. Then diazoacetic acid ethyl ester (6.79 g, 59.0 mmol) was added. The solution was stirred for 1 h at r.t. The reaction was purified with TLC(EA/PE=1/5) affording 12 g of desired product.

142.3 Ethyl 2-((6-hydroxy-1,2,3,4-tetrahydronaphthalen-2-yl)oxy)acetate

Ethyl 2-((6-(benzyloxy)-1,2,3,4-tetrahydronaphthalen-2-yl)oxy)acetate (12 g, 35.3 mmol), and Palladium on carbon (3.75 g, 35.3 mmol), were placed together with 100 ml ethanol in an 250 ml flask. Then the solution was stirred overnight at r.t under hydrogen (3 atm). The reaction mixture was filtered and the filtrate was concentrated under vacuum affording 9.2 g of desired product as white solid.

142.4 Ethyl 2-((6-((2-chloro-6-ethylbenzyl)oxy)-1,2,3,4-tetrahydronaphthalen-2-yl)oxy)acetate Compound XXVII (100 mg, 0.4 mmol) was dissolved in DMF. 2-(bromomethyl)-1-chloro-3-ethylbenzene (112 mg, 0.48 mmol) and cesium carbonate (195 mg, 0.6 mmol) were added and stirred at RT overnight. The solvent was evaporated, the residue dissolved in DCM and subsequently washed with water. The organic layer was dried, evaporated and the residue purified by chromatography (silica gel) giving product XXVIII with a yield of 160 mg as a colorless oil.

142.5 2-((6-((2-chloro-6-ethylbenzyl)oxy)-1,2,3,4-tetrahydronaphthalen-2-yl)oxy)acetic acid A mixture of ethyl 2-((6-((2-chloro-6-ethylbenzyl)oxy)-1,2,3,4-tetrahydronaphthalen-2-yl)oxy)acetate (130 mg, 0,323 mmol) and NaOH (1 ml, 2M, 2.0 mmol) in THF/MeOH 1:1 was stirred for 14 h at RT. The solvent was evaporated, the residue dissolved in water acidified with 2N HCl, and extracted with DCM. The organic layer was dried, evaporated and the residue purified by chromatography (silica gel) giving product 142 with a yield of 65 mg as a colorless oil.

$^1$H NMR (600 MHz, DMSO-d$_6$) δ 7.38-7.32 (m, 2H), 7.27 (dd, J=6.2, 2.8 Hz, 1H), 7.03-6.95 (m, 1H), 6.82-6.73 (m, 2H), 5.09 (s, 2H), 4.08 (d, J=1.7 Hz, 2H), 3.83-3.77 (m, 1H), 2.96 (dd, J=16.1, 4.8 Hz, 1H), 2.83 (dt, J=16.9, 6.1 Hz, 1H), 2.71 (q, J=7.6 Hz, 3H), 2.75-2.62 (m, 2H), 2.01-1.93 (m, 1H), 1.77-1.70 (m, 1H), 1.16 (t, J=7.6 Hz, 3H).

143. 2-((6-((2-chloro-6-cyclopropylbenzyl)oxy)-1,2,3,4-tetrahydronaphthalen-2-yl)oxy)acetic acid Compound 143 was prepared as described for compound 142 using 2-(bromomethyl)-1-chloro-3-cyclopropylbenzene instead of 2-(bromomethyl)-1-chloro-3-ethylbenzene.

$^1$H NMR (600 MHz, DMSO-d$_6$) δ 7.36-7.29 (m, 2H), 7.03 (dd, J=7.5, 1.5 Hz, 1H), 7.01-6.98 (m, 1H), 6.81-6.78 (m, 2H), 5.25 (s, 2H), 4.08 (d, J=1.8 Hz, 2H), 3.84-3.77 (m, 1H), 2.95 (dd, J=16.1, 4.8 Hz, 1H), 2.83 (dt, J=16.9, 6.1 Hz, 1H), 2.73-2.67 (m, 1H), 2.65 (dd, J=16.1, 7.1 Hz, 1H), 2.09-2.03 (m, 1H), 2.00-1.93 (m, 1H), 1.78-1.69 (m, 1H), 0.95-0.89 (m, 2H), 0.71-0.66 (m, 2H).

Pure Enantiomers of 1-(7-((2,6-dichlorobenzyl)oxy)chroman-3-yl)azetidine-3-carboxylic acid (Compounds 144 and 145)

Compounds 144 and 145 are the pure enantiomers of compound 1. The racemate was separated as methyl esters by SFC and subsequently hydrolyzed to the free acid Separation of rac-methyl 1-(7-((2,6-dichlorobenzyl)oxy)chroman-3-yl)azetidine-3-carboxylate by Preparative SFC Two peaks were separated on a YMC Amylose-C column (20×250, 5 μm), at a total flow of 100 ml/min isocratic at 30° C. (t$_R$ [min]=3.4, 4.5). The mobile phase consisted of 80% CO$_2$ and 20% modifier which was EtOH with addition of 0.2% aqueous ammonia solution.

Enantiomer 1 (Peak A, Compound 144.1) was Hydrolyzed to Enantiomerically Pure acid as Described for Compound 138

$^1$H NMR (600 MHz, DMSO-d$_6$) δ 7.56 (d, J=8.1 Hz, 2H), 7.46 (dd, J=8.7, 7.5 Hz, 1H), 6.96 (d, J=8.3 Hz, 1H), 6.52 (dd, J=8.4, 2.6 Hz, 1H), 6.44 (d, J=2.6 Hz, 1H), 5.14 (s, 2H), 3.99 (dt, J=11.1, 1.9 Hz, 1H), 3.83-3.73 (m, 1H), 3.51-3.39 (m, 2H), 3.30-3.15 (m, 3H), 2.77 (d, J=15.3 Hz, 1H), further aliphatic hydrogens gave broad signals Enantiomer 2 (Peak B, Compound 145.1) was Hydrolyzed to Enantiomerically Pure acid as Described for Compound 138

$^1$H NMR (600 MHz, DMSO-d$_6$) δ 7.56 (d, J=8.1 Hz, 2H), 7.46 (dd, J=8.7, 7.5 Hz, 1H), 6.96 (d, J=8.3 Hz, 1H), 6.53 (dd, J=8.3, 2.6 Hz, 1H), 6.45 (d, J=2.6 Hz, 1H), 5.15 (s, 2H), 4.02-3.97 (m, 1H), 3.83-3.73 (m, 1H), further aliphatic hydrogens gave broad signals

Pure Enantiomers of 1-(7-((2-ethyl-6-fluorobenzyl)oxy)chroman-3-yl)azetidine-3-carboxylic acid (Compounds 146 and 147)

Compounds 146 and 147 are the pure enantiomers of compound 65. The racemate was separated as methyl esters by SFC and subsequently hydrolyzed to the free acid Separation of rac-methyl 1-(7-((2-ethyl-6-fluorobenzyl)oxy)chroman-3-yl)azetidine-3-carboxylate by Preparative SFC Two peaks were separated on a Chromega CCO F4 column (20×250, 5 μm), at a total flow of 100 ml/min, isocratic, at 30° C. (t$_R$ [min]=3.5, 4.4). The mobile phase consisted of 95% CO$_2$ and 5% modifier which was MeOH.

Enantiomer 1 (Peak A, Compound 146.1) was Hydrolyzed to Enantiomerically Pure acid as Described for Compound 138

$^1$H NMR (600 MHz, DMSO-d$_6$) δ 7.40-7.34 (m, 1H), 7.13 (d, J=7.7 Hz, 1H), 7.10-7.06 (m, 1H), 6.94 (d, J=8.4 Hz, 1H), 6.50 (dd, J=8.3, 2.6 Hz, 1H), 6.42 (d, J=2.5 Hz, 1H), 5.00 (d, J=1.9 Hz, 2H), 3.97 (ddd, J=11.1, 2.7, 1.3 Hz, 1H), 3.77-3.70 (m, 1H), 3.46 (t, J=7.4 Hz, 1H), 3.25 (dd, J=7.1, 5.4 Hz, 2H), 3.21-3.14 (m, 1H), 2.74 (dd, J=15.8, 4.9 Hz, 1H), 2.69 (q, J=7.6 Hz, 2H), 2.63-2.59 (m, 1H), 2.38-2.32 (m, 1H), 1.16 (t, J=7.6 Hz, 3H).

Enantiomer 2 (Peak B, Compound 147.1) was Hydrolyzed to Enantiomerically Pure acid as Described for Compound 138

1H NMR (600 MHz, DMSO-d6) δ 7.37 (td, J=7.9, 6.0 Hz, 1H), 7.13 (dd, J=7.7, 1.1 Hz, 1H), 7.10-7.06 (m, 1H), 6.94 (d, J=8.4 Hz, 1H), 6.50 (dd, J=8.4, 2.6 Hz, 1H), 6.42 (d, J=2.6 Hz, 1H), 5.00 (d, J=1.9 Hz, 2H), 4.01-3.94 (m, 1H), 3.73 (ddd, J=11.1, 6.3, 1.2 Hz, 1H), 3.46 (t, J=7.4 Hz, 1H), 3.28-3.22 (m, 2H), 3.21-3.14 (m, 1H), 2.75 (dd, J=15.8, 4.8 Hz, 1H), 2.69 (q, J=7.6 Hz, 2H), 2.64-2.58 (m, 1H), 2.36 (dd, J=15.8, 6.4 Hz, 1H), 1.16 (t, J=7.5 Hz, 3H).

148. 1-(7-((2-methoxy-4-propylbenzyl)oxy)chroman-3-yl)azetidine-3-carboxylic acid

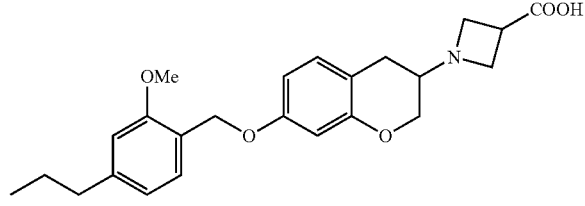 [SMILES: CCCc1ccc(COc2ccc3c(c2)OCC(N2CC(C(=O)O)C2)C3)c(OC)c1]

Compound 148 was prepared as described for Compound 1 using 1-(chloromethyl)-2-methoxy-4-propylbenzene instead of 2-(bromomethyl)-1,3-dichlorobenzene.

$^1$H NMR (600 MHz, DMSO-d$_6$) δ 7.22 (d, J=7.6 Hz, 1H), 6.91 (d, J=8.5 Hz, 1H), 6.86 (d, J=1.4 Hz, 1H), 6.77 (dd, J=7.7, 1.4 Hz, 1H), 6.44 (dd, J=8.4, 2.5 Hz, 1H), 6.31 (d, J=2.6 Hz, 1H), 4.92 (s, 2H), 3.96 (dt, J=10.8, 2.1 Hz, 1H), 3.70 (dd, J=11.1, 6.5 Hz, 1H), 3.48-3.43 (m, 1H), 3.27-3.21 (m, 2H), 3.20-3.14 (m, 1H), 2.54 (dd, J=15.0, 7.0 Hz, 3H), 2.34 (dd, J=15.9, 6.5 Hz, 1H), 1.66-1.56 (m, 2H), 0.90 (t, J=7.3 Hz, 3H).

General Procedure I for Compounds 149-176

A 4 mL vial was charged with a stir bar to which was added NaH (7 mg, 0.27 mmol). To this NaH was then added a solution of ethyl 2-((6-hydroxy-1,2,3,4-tetrahydronaphthalen-2-yl)oxy)acetate core (22 mg, 0.10 mmol) in dimethyl formamide (250 μl) at 0 degrees and stirred for 30 minutes. After 30 minutes, to this mixture was added a solution of 2-(bromomethyl)-1,3-difluoro-4-methylbenzene halide monomer (25 mg, 1.3 eq., 0.13 mmol) also in dimethylformamide (200 μl). This was allowed to stir at rt for 2 hours. Upon completion of the first step, to the crude material was added 500 μl of 1M lithium hydroxide and further allowed to be stirred for 1 hour at room temperature. The residues were dissolved in 1:1 DMSO/MeOH and purified by reverse phase HPLC (AA method). Samples were purified by preparative HPLC on a Phenomenex Luna C8(2) 5 um 100 Å AXIA column (30 mm×150 mm). A gradient of ACN (A) and 10 mM ammonium acetate in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain title compounds. Product was characterized by $^1$H NMR, and LC/MS.

149. 2-[6-[(2,6-difluoro-3-methyl-phenyl)methoxy]tetralin-2-yl]oxyacetic acid

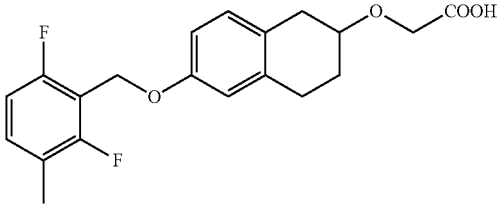 [SMILES: Cc1ccc(F)c(COc2ccc3c(c2)CCC(OCC(=O)O)C3)c1F]

$^1$H NMR (400 MHz, DMSO-d$_6$) δ 7.35 (td, J=8.6, 6.6 Hz, 1H), 7.08-6.94 (m, 2H), 6.75 (d, J=2.7 Hz, 1H), 6.72 (s, 1H), 5.01 (d, J=1.3 Hz, 2H), 3.85 (s, 2H), 2.92 (dd, J=16.3, 4.8 Hz, 1H), 2.80 (dt, J=17.1, 6.1 Hz, 1H), 2.63 (td, J=16.6, 15.1, 7.8 Hz, 2H), 2.24-2.18 (m, 3H), 1.93 (ddt, J=13.0, 6.1, 3.9 Hz, 1H), 1.69 (ddt, J=12.5, 8.3, 4.2 Hz, 1H).

MS (APCI) m/z 380.3 (M+NH4)$^+$

150. 2-[6-[(6-chloro-2-fluoro-3-methyl-phenyl)methoxy]tetralin-2-yl]oxyacetic acid

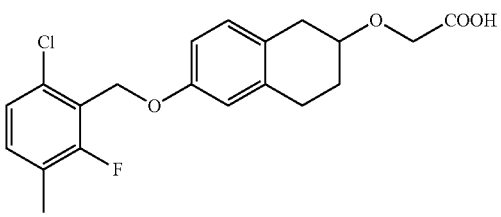 [SMILES: Cc1ccc(Cl)c(COc2ccc3c(c2)CCC(OCC(=O)O)C3)c1F]

$^1$H NMR (400 MHz, DMSO-d$_6$) δ 7.35 (t, J=8.2 Hz, 1H), 7.27 (dd, J=8.2, 1.0 Hz, 1H), 7.03-6.95 (m, 1H), 6.75 (d, J=7.2 Hz, 2H), 5.06 (d, J=2.1 Hz, 2H), 3.94 (s, 2H), 2.93 (dd, J=16.4, 4.8 Hz, 1H), 2.81 (dt, J=17.0, 6.1 Hz, 1H), 2.73-2.57 (m, 2H), 2.23 (d, J=2.0 Hz, 3H), 1.93 (t, J=10.7 Hz, 1H), 1.71 (ddt, J=12.3, 8.1, 4.3 Hz, 1H).

MS (APCI) m/z 396.2 (M+NH4)$^+$

151. 2-[6-[[2-chloro-5-(trifluoromethyl)phenyl]methoxy]tetralin-2-yl]oxyacetic acid

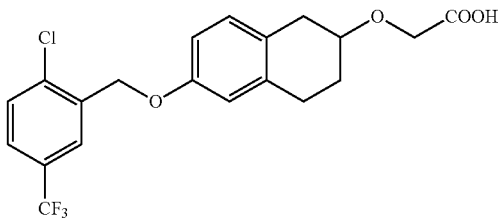

$^1$H NMR (400 MHz, DMSO-d$_6$) δ 7.91 (s, 1H), 7.75 (d, J=1.3 Hz, 2H), 7.00 (d, J=8.2 Hz, 1H), 6.78 (dd, J=10.4, 2.1 Hz, 2H), 5.15 (s, 2H), 3.99 (s, 2H), 2.93 (dd, J=16.2, 4.7 Hz, 1H), 2.88-2.75 (m, 1H), 2.63 (dd, J=16.1, 7.4 Hz, 3H), 2.03-1.84 (m, 1H), 1.75-1.65 (m, 1H).

MS (APCI) m/z 432.4 (M+NH4)$^+$

152. 2-[6-[(3-chloro-2,6-difluoro-phenyl)methoxy]tetralin-2-yl]oxyacetic acid

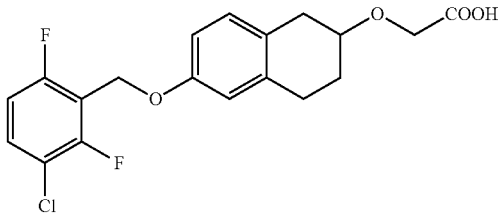 [SMILES: O=C(O)COC1CCc2cc(OCc3c(F)ccc(Cl)c3F)ccc2C1]

$^1$H NMR (400 MHz, DMSO-d$_6$) δ 7.68 (td, J=8.8, 5.7 Hz, 1H), 7.22 (td, J=9.0, 1.7 Hz, 1H), 6.99 (d, J=8.1 Hz, 1H), 6.74 (d, J=8.3 Hz, 2H), 5.07 (d, J=1.3 Hz, 2H), 3.88 (s, 2H), 2.92 (dd, J=16.3, 4.8 Hz, 1H), 2.80 (dt, J=17.1, 6.1 Hz, 1H), 2.71-2.56 (m, 2H), 1.93 (dq, J=12.8, 5.8, 4.3 Hz, 1H), 1.70 (ddt, J=12.5, 8.2, 4.2 Hz, 1H).

MS (APCI) m/z 400.2 (M+NH4)$^+$

153. 2-[6-[[5-chloro-2-(trifluoromethyl)phenyl]methoxy]tetralin-2-yl]oxyacetic acid

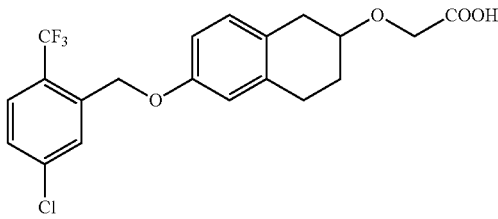 [SMILES: O=C(O)COC1CCc2cc(OCc3cc(Cl)ccc3C(F)(F)F)ccc2C1]

¹H NMR (400 MHz, DMSO-d₆) δ 7.90-7.74 (m, 2H), 7.68-7.55 (m, 1H), 7.00 (d, J=8.3 Hz, 1H), 6.73 (dt, J=14.0, 2.8 Hz, 2H), 5.16 (d, J=8.6 Hz, 2H), 4.00 (s, 2H), 2.93 (dd, J=16.3, 4.8 Hz, 1H), 2.80 (dt, J=16.9, 6.1 Hz, 1H), 2.68-2.53 (m, 2H), 1.92 (d, J=6.7 Hz, 1H), 1.71 (td, J=13.8, 8.0 Hz, 1H).
MS (APCI) m/z 432.2 (M+NH4)⁺

154. 2-[6-[(3-methoxyphenyl)methoxy]tetralin-2-yl]oxyacetic acid

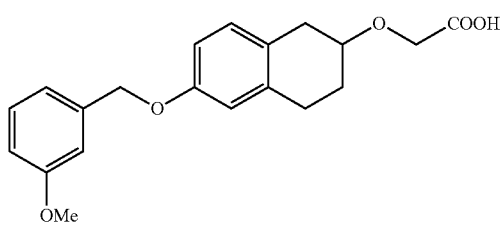 [SMILES: COc1cccc(COc2ccc3c(c2)CCC(OCC(=O)O)C3)c1]

¹H NMR (400 MHz, DMSO-d₆) δ 7.29 (t, J=7.8 Hz, 1H), 7.01-6.92 (m, 3H), 6.86 (ddd, J=8.2, 2.6, 0.9 Hz, 1H), 6.76-6.67 (m, 2H), 5.00 (s, 2H), 3.90 (s, 2H), 3.81 (s, 3H), 2.91 (dd, J=16.2, 4.8 Hz, 1H), 2.78 (dt, J=17.1, 6.1 Hz, 1H), 2.62 (td, J=16.5, 7.5 Hz, 2H), 1.97-1.89 (m, 1H), 1.69 (ddt, J=12.4, 8.3, 4.3 Hz, 1H).
MS (APCI) m/z 360.3 (M+NH4)⁺

155. 2-[6-[(5-fluoro-2-methyl-phenyl)methoxy]tetralin-2-yl]oxyacetic acid

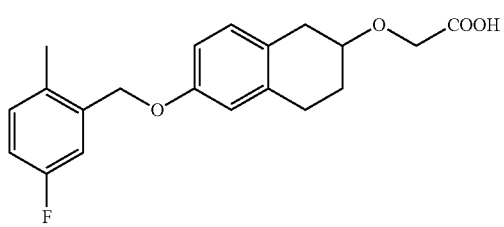 [SMILES: Cc1ccc(F)cc1COc1ccc2c(c1)CCC(OCC(=O)O)C2]

¹H NMR (400 MHz, DMSO-d₆) δ 7.21 (ddd, J=19.3, 9.2, 4.5 Hz, 2H), 7.08-6.95 (m, 2H), 6.80-6.71 (m, 2H), 5.00 (s, 2H), 3.96 (s, 2H), 2.92 (dd, J=16.2, 4.7 Hz, 1H), 2.80 (dt, J=17.1, 6.1 Hz, 1H), 2.64 (td, J=16.4, 7.1 Hz, 2H), 2.26 (s, 3H), 1.98-1.88 (m, 1H), 1.71 (td, J=13.8, 8.1 Hz, 1H).
MS (APCI) m/z 362.3 (M+NH4)⁺

156. 2-[6-[(3,5-dimethylphenyl)methoxy]tetralin-2-yl]oxyacetic acid

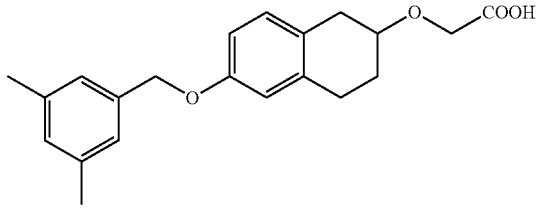 [SMILES: Cc1cc(C)cc(COc2ccc3c(c2)CCC(OCC(=O)O)C3)c1]

¹H NMR (400 MHz, DMSO-d₆) δ 7.23 (d, J=7.7 Hz, 1H), 7.05-6.93 (m, 3H), 6.77-6.68 (m, 2H), 4.94 (s, 2H), 4.03 (s, 2H), 2.92 (dd, J=16.2, 4.6 Hz, 1H), 2.79 (dt, J=17.0, 6.2 Hz, 1H), 2.63 (dt, J=15.9, 8.0 Hz, 2H), 2.25 (s, 6H), 1.94 (d, J=11.9 Hz, 1H), 1.71 (h, J=8.0 Hz, 1H).
MS (APCI) m/z 358.3 (M+NH4)⁺

157. 2-[6-[(2-fluoro-6-methoxy-phenyl)methoxy]tetralin-2-yl]oxyacetic acid

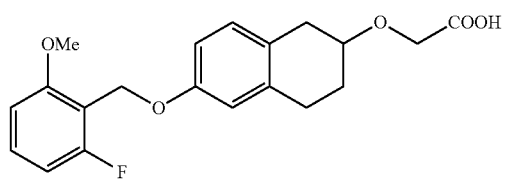 [SMILES: COc1cccc(F)c1COc1ccc2c(c1)CCC(OCC(=O)O)C2]

¹H NMR (400 MHz, DMSO-d₆) δ 7.40 (td, J=8.5, 7.0 Hz, 1H), 6.97 (d, J=9.2 Hz, 1H), 6.91 (d, J=8.5 Hz, 1H), 6.83 (t, J=8.8 Hz, 1H), 6.74-6.68 (m, 2H), 4.96 (s, 2H), 3.98 (s, 2H), 3.81 (s, 3H), 2.90 (d, J=4.8 Hz, 1H), 2.73-2.56 (m, 2H), 2.37-2.31 (m, 1H), 1.92 (d, J=12.7 Hz, 1H), 1.71 (dt, J=13.5, 7.1 Hz, 1H).
MS (APCI) 378.2 m/z (M+NH4)⁺

158. 2-[6-[[2-fluoro-6-(trifluoromethyl)phenyl]methoxy]tetralin-2-yl]oxyacetic acid

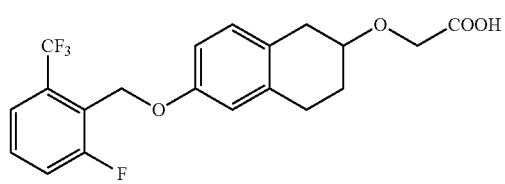 [SMILES: O=C(O)COC1CCc2cc(OCc3c(F)cccc3C(F)(F)F)ccc2C1]

¹H NMR (400 MHz, DMSO-d₆) δ 7.75-7.58 (m, 3H), 7.00 (d, J=8.4 Hz, 1H), 6.74 (d, J=7.3 Hz, 2H), 5.08 (s, 2H), 4.03 (s, 2H), 2.94 (dd, J=16.5, 4.8 Hz, 1H), 2.81 (dt, J=17.1, 6.2 Hz, 1H), 2.65 (dt, J=16.0, 8.3 Hz, 2H), 2.00-1.89 (m, 1H), 1.72 (dq, J=14.0, 8.0 Hz, 1H).
MS (APCI) m/z 416.3 (M+NH4)⁺

159. 2-[6-[(2,6-difluorophenyl)methoxy]tetralin-2-yl]oxyacetic acid

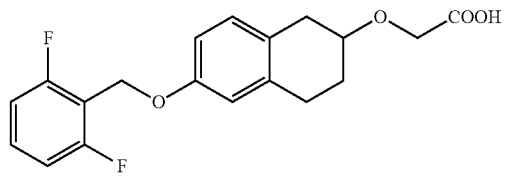 [SMILES: O=C(O)COC1CCc2cc(OCc3c(F)cccc3F)ccc2C1]

¹H NMR (400 MHz, DMSO-d₆) δ 7.56-7.43 (m, 1H), 7.14 (t, J=8.0 Hz, 2H), 6.99 (d, J=8.2 Hz, 1H), 6.76 (d, J=2.7 Hz, 1H), 6.74 (s, 1H), 5.03 (s, 2H), 4.02 (s, 2H), 2.93 (dd, J=16.3, 4.7 Hz, 1H), 2.80 (dt, J=17.2, 6.2 Hz, 1H), 2.65 (td, J=15.9, 15.3, 7.6 Hz, 2H), 1.98-1.89 (m, 1H), 1.71 (h, J=7.9 Hz, 1H). MS (APCI) m/z 366.2 (M+NH4)⁺

160. 2-[6-[(2-fluoro-5-methyl-phenyl)methoxy]tetralin-2-yl]oxyacetic acid

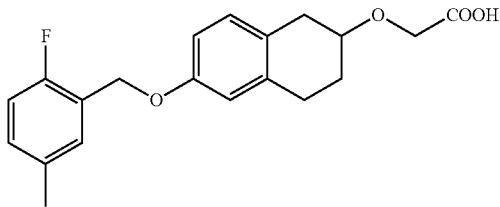 [SMILES: Cc1ccc(F)c(COc2ccc3c(c2)CCC(OCC(=O)O)C3)c1]

¹H NMR (400 MHz, DMSO-d₆) δ 7.70 (s, 1H), 7.30 (dd, J=7.2, 2.3 Hz, 4H), 7.19 (ddd, J=7.8, 5.1, 2.3 Hz, 4H), 7.09 (dd, J=10.1, 8.4 Hz, 5H), 6.97 (d, J=8.3 Hz, 4H), 6.76-6.66 (m, 7H), 4.99 (s, 7H), 3.87 (s, 7H), 2.91 (dd, J=16.2, 4.8 Hz, 4H), 2.79 (dt, J=17.0, 6.1 Hz, 5H), 2.69-2.56 (m, 8H), 2.27 (s, 9H), 1.92 (ddt, J=9.2, 6.4, 2.5 Hz, 4H), 1.69 (ddt, J=12.5, 8.3, 4.3 Hz, 4H).

MS (APCI) m/z 362.3 (M+NH4)⁺

161. 2-[6-[[2-fluoro-5-(trifluoromethoxy)phenyl]methoxy]tetralin-2-yl]oxyacetic acid

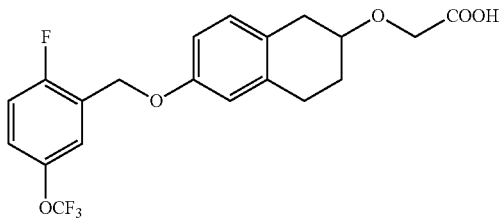 [SMILES: O=C(O)COC1CCc2cc(OCc3cc(OC(F)(F)F)ccc3F)ccc2C1]

¹H NMR (400 MHz, DMSO-d₆) δ 7.30 (dd, J=7.2, 2.3 Hz, 1H), 7.19 (ddd, J=7.8, 5.1, 2.3 Hz, 1H), 7.09 (dd, J=10.1, 8.4 Hz, 1H), 6.97 (d, J=8.3 Hz, 1H), 6.80-6.68 (m, 2H), 4.99 (s, 2H), 3.87 (s, 2H), 2.91 (dd, J=16.2, 4.8 Hz, 1H), 2.79 (dt, J=17.0, 6.1 Hz, 1H), 2.71-2.53 (m, 2H), 2.27 (s, 3H), 1.93 (ddt, J=13.0, 6.4, 4.1 Hz, 1H), 1.69 (ddt, J=12.4, 8.3, 4.3 Hz, 1H).

MS (APCI) m/z 432.3 (M+NH4)⁺

162. 2-[6-[(2,4-dichlorophenyl)methoxy]tetralin-2-yl]oxyacetic acid

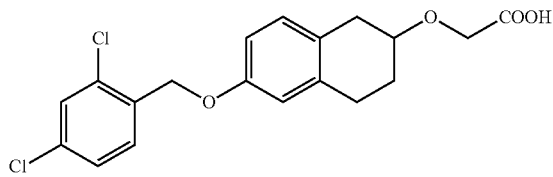 [SMILES: O=C(O)COC1CCc2cc(OCc3ccc(Cl)cc3Cl)ccc2C1]

¹H NMR (400 MHz, DMSO-d₆) δ 7.64 (d, J=2.1 Hz, 1H), 7.57 (d, J=8.3 Hz, 1H), 7.45 (dd, J=8.3, 2.1 Hz, 1H), 6.99 (d, J=8.3 Hz, 1H), 6.78-6.69 (m, 2H), 5.06 (s, 2H), 4.00 (s, 2H), 2.92 (dd, J=16.3, 4.8 Hz, 1H), 2.80 (dt, J=17.0, 6.1 Hz, 1H), 2.64 (dt, J=15.6, 7.1 Hz, 2H), 1.94 (d, J=10.7 Hz, 1H), 1.71 (td, J=13.9, 8.0 Hz, 1H).

MS (APCI) m/z 398.1 (M+NH4)⁺

163. 2-[6-[(2,5-difluorophenyl)methoxy]tetralin-2-yl]oxyacetic acid

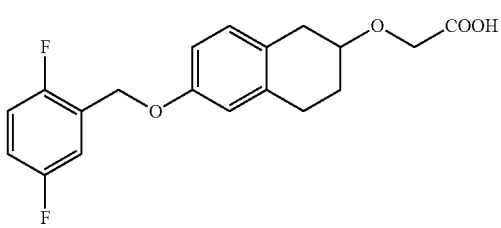 [SMILES: O=C(O)COC1CCc2cc(OCc3cc(F)ccc3F)ccc2C1]

¹H NMR (400 MHz, DMSO-d₆) δ 7.39-7.16 (m, 3H), 6.98 (d, J=8.4 Hz, 1H), 6.79-6.70 (m, 2H), 5.05 (s, 2H), 3.95 (s, 2H), 2.92 (dd, J=16.3, 4.8 Hz, 1H), 2.80 (dt, J=17.2, 6.2 Hz, 1H), 2.63 (dt, J=16.2, 8.4 Hz, 2H), 1.98-1.88 (m, 1H), 1.77-1.63 (m, 1H).

MS (APCI) m/z 366.2 (M+NH4)⁺

164. 2-[6-[(2,5-dichlorophenyl)methoxy]tetralin-2-yl]oxyacetic acid

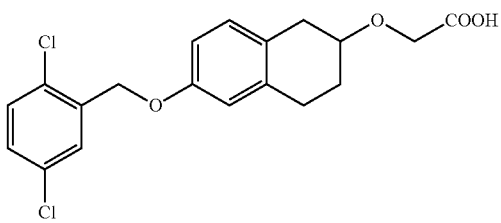 [SMILES: O=C(O)COC1CCc2cc(OCc3cc(Cl)ccc3Cl)ccc2C1]

¹H NMR (500 MHz, DMSO-d₆) δ 7.59 (d, J=2.6 Hz, 1H), 7.53 (d, J=8.5 Hz, 1H), 7.44 (dd, J=8.6, 2.6 Hz, 1H), 6.99 (d, J=8.4 Hz, 1H), 6.76-6.69 (m, 2H), 5.06 (s, 2H), 4.01 (s, 2H), 2.91 (d, J=4.7 Hz, 1H), 2.78 (m, 1H), 2.67-2.60 (m, 2H), 1.90 (m, 1H), 1.76-1.64 (m, 1H).

MS (APCI) m/z 398.2 (M+NH4)⁺

165. 2-[6-[(4-methoxyphenyl)methoxy]tetralin-2-yl]oxyacetic acid

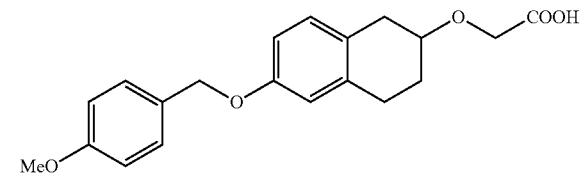

¹H NMR (500 MHz, DMSO-d₆) δ 7.40-7.23 (m, 2H), 6.99-6.86 (m, 3H), 6.74-6.61 (m, 2H), 4.93 (s, 2H), 4.02 (s, 2H), 2.91 (dd, J=16.3, 4.7 Hz, 1H), 2.78 (dt, J=17.0, 6.2 Hz, 1H), 1.92 (dd, J=11.5, 5.6 Hz, 2H), 1.70 (dt, J=13.4, 6.8 Hz, 1H), 1.66 (m, 1H).

MS (APCI) m/z 360.3 (M+NH4)⁺

166. 2-[6-[(5-fluoro-2-methoxy-phenyl)methoxy]tetralin-2-yl]oxyacetic acid

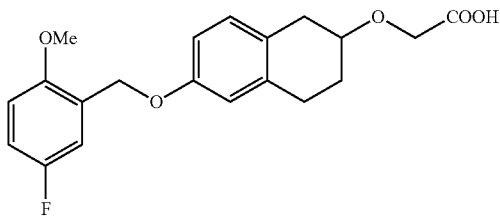 [SMILES: COc1ccc(F)cc1COc1ccc2c(c1)CCC(OCC(=O)O)C2]

$^1$H NMR (500 MHz, DMSO-d$_6$) δ 7.19-7.08 (m, 2H), 6.97 (d, J=8.4 Hz, 1H), 6.77-6.67 (m, 2H), 4.97 (s, 2H), 4.02 (s, 2H), 2.92 (dd, J=16.2, 4.8 Hz, 1H), 2.79 (dt, J=17.2, 6.2 Hz, 1H), 2.63 (td, J=17.8, 16.5, 7.2 Hz, 2H), 1.98-1.83 (m, 1H), 1.75-1.64 (m, 1H).

MS (APCI) m/z 378.3 (M+NH4)$^+$

167. 2-[6-[[2-chloro-6-(trifluoromethyl)phenyl]methoxy]tetralin-2-yl]oxyacetic acid

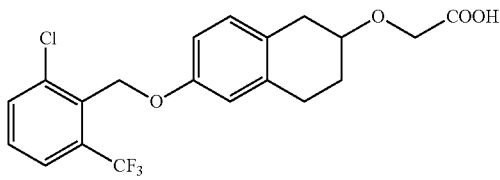 [SMILES: O=C(O)COC1CCc2cc(OCc3c(Cl)cccc3C(F)(F)F)ccc2C1]

$^1$H NMR (500 MHz, DMSO-d$_6$) δ 7.88 (d, J=8.1 Hz, 1H), 7.83-7.77 (m, 1H), 7.66 (t, J=8.0 Hz, 1H), 7.09-6.96 (m, 1H), 6.76 (d, J=7.1 Hz, 2H), 5.12 (s, 2H), 4.02 (s, 2H), 2.94 (dd, J=16.3, 4.8 Hz, 1H), 2.81 (d, J=17.1 Hz, 1H), 2.70-2.62 (m, 2H), 1.96-1.86 (m, 1H), 1.81-1.64 (m, 1H).

MS (APCI) m/z 432.2 (M+NH4)$^+$

168. 2-[6-[[5-fluoro-2-(trifluoromethyl)phenyl]methoxy]tetralin-2-yl]oxyacetic acid

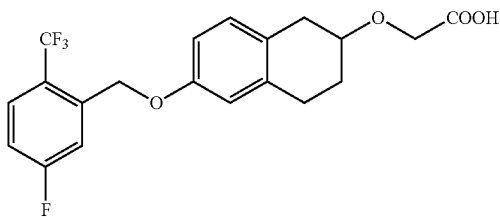 [SMILES: O=C(O)COC1CCc2cc(OCc3cc(F)ccc3C(F)(F)F)ccc2C1]

$^1$H NMR (500 MHz, DMSO-d$_6$) δ 7.86 (dd, J=8.8, 5.4 Hz, 1H), 7.60-7.53 (m, 1H), 7.39 (td, J=8.5, 2.8 Hz, 1H), 6.99 (d, J=8.3 Hz, 1H), 6.81-6.70 (m, 2H), 5.16 (s, 2H), 4.00 (s, 2H), 2.92 (dd, J=16.3, 4.8 Hz, 1H), 2.79 (dt, J=17.0, 6.1 Hz, 1H), 2.69-2.58 (m, 2H), 1.99-1.88 (m, 1H), 1.71 (td, J=13.8, 8.0 Hz, 1H).

MS (APCI) m/z 416.2 (M+NH4)$^+$

169. 2-[6-[(2-chloro-6-fluoro-phenyl)methoxy]tetralin-2-yl]oxyacetic acid

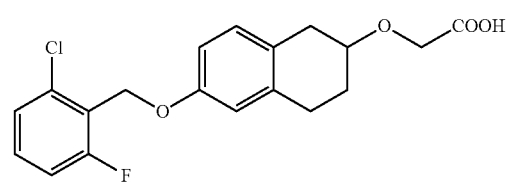

$^1$H NMR (500 MHz, DMSO-d$_6$) δ 7.48 (td, J=8.2, 6.1 Hz, 1H), 7.39 (d, J=8.1 Hz, 1H), 7.28 (t, J=8.8 Hz, 1H), 6.99 (d, J=8.1 Hz, 1H), 6.75 (s, 2H), 5.07 (d, J=1.8 Hz, 2H), 4.03 (s, 2H), 2.93 (dd, J=16.3, 4.8 Hz, 1H), 2.79 (q, J=6.3, 5.4 Hz, 1H), 2.70-2.59 (m, 2H), 1.93 (dd, J=14.7, 8.1 Hz, 1H), 1.72 (tt, J=13.8, 6.6 Hz, 1H).

MS (APCI) m/z 382.2 (M+NH4)$^+$

170. 2-[6-[(2-methoxyphenyl)methoxy]tetralin-2-yl]oxyacetic acid

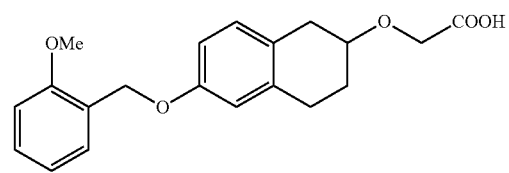 [SMILES: COc1ccccc1COc1ccc2c(c1)CCC(OCC(=O)O)C2]

$^1$H NMR (500 MHz, DMSO-d$_6$) δ 7.32 (ddd, J=18.1, 7.6, 1.8 Hz, 2H), 7.03 (d, 1H), 7.01-6.91 (m, 2H), 6.76-6.66 (m, 2H), 4.97 (s, 2H), 4.00 (s, 2H), 3.8 (s, 3H), 2.92 (dd, J=16.3, 4.8 Hz, 1H), 2.80 (dt, J=17.0, 6.2 Hz, 1H), 2.71-2.59 (m, 2H), 1.97-1.88 (m, 1H), 1.72 (ddt, J=12.5, 8.1, 4.2 Hz, 1H).

MS (APCI) m/z 360.2 (M+NH4)$^+$

171. 2-[6-[(2-chloro-5-fluoro-phenyl)methoxy]tetralin-2-yl]oxyacetic acid

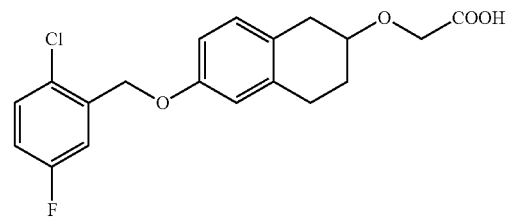 [SMILES: O=C(O)COC1CCc2cc(OCc3cc(F)ccc3Cl)ccc2C1]

$^1$H NMR (500 MHz, DMSO-d$_6$) δ 7.53 (dd, J=8.8, 5.1 Hz, 1H), 7.38 (dd, J=9.3, 3.2 Hz, 1H), 7.23 (td, J=8.5, 3.1 Hz, 1H), 6.99 (d, J=8.4 Hz, 1H), 6.79-6.71 (m, 2H), 5.06 (s, 2H), 4.04 (s, 2H), 2.92 (dd, J=16.3, 4.8 Hz, 1H), 2.80 (dt, J=17.0, 6.2 Hz, 1H), 2.71-2.59 (m, 2H), 1.97-1.88 (m, 1H), 1.72 (ddt, J=12.5, 8.1, 4.2 Hz, 1H).

MS (APCI) m/z 382.2 (M+NH4)$^+$

172. 2-[6-[[2-fluoro-5-(trifluoromethyl)phenyl]methoxy]tetralin-2-yl]oxyacetic acid

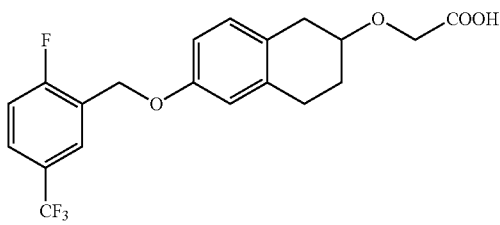 [SMILES: O=C(O)COC1CCc2cc(OCc3cc(C(F)(F)F)ccc3F)ccc2C1]

$^1$H NMR (500 MHz, DMSO-d$_6$) δ 7.92 (d, J=2.4 Hz, 1H), 7.87-7.74 (m, 1H), 7.49 (d, J=9.2 Hz, 1H), 6.99 (d, J=8.3 Hz, 1H), 6.82-6.73 (m, 2H), 5.13 (s, 2H), 4.01 (s, 2H), 3.00-2.91 (m, -1H), 2.90-2.77 (m, 1H), 2.72-2.62 (m, 2H), 1.99-1.91 (m, 1H), 1.71 (dq, J=13.9, 7.6 Hz, 1H).

MS (APCI) m/z 416.3 (M+NH4)$^+$

173. 2-[6-[(3,5-dimethylphenyl)methoxy]tetralin-2-yl]oxyacetic acid

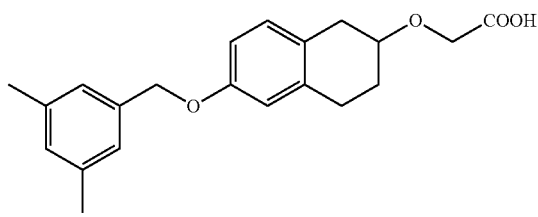 [SMILES: Cc1cc(C)cc(COc2ccc3c(c2)CCC(OCC(=O)O)C3)c1]

$^1$H NMR (500 MHz, DMSO-d$_6$) δ 7.00 (s, 2H), 6.99-6.92 (m, 2H), 6.78-6.67 (m, 2H), 4.92 (s, 2H), 3.99 (s, 2H), 2.91 (dd, J=16.3, 4.8 Hz, 1H), 2.79 (dt, J=17.1, 6.1 Hz, 1H), 2.69-2.54 (m, 2H), 2.25 (s, 6H), 1.97-1.88 (m, 1H), 1.69 (d, J=7.6 Hz, 1H).

MS (APCI) m/z 358.3 (M+NH4)$^+$

174. 2-[6-[(5-chloro-2-fluoro-phenyl)methoxy]tetralin-2-yl]oxyacetic acid

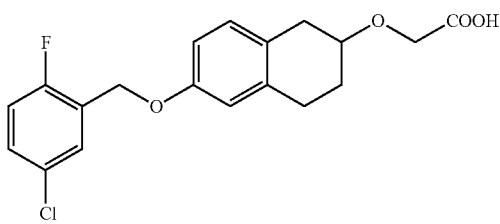

$^1$H NMR (500 MHz, DMSO-d$_6$) δ 7.56 (dd, J=6.3, 2.8 Hz, 1H), 7.45 (ddd, J=8.8, 4.5, 2.7 Hz, 1H), 7.28 (t, J=9.2 Hz, 1H), 6.98 (d, J=8.4 Hz, 1H), 6.78-6.70 (m, 2H), 5.05 (s, 2H), 3.91 (d, J=1.0 Hz, 2H), 2.91 (dd, J=16.3, 4.8 Hz, 1H), 2.79 (dt, J=17.1, 6.1 Hz, 1H), 2.69-2.54 (m, 2H), 1.97-1.88 (m, 1H), 1.69 (ddt, J=12.3, 8.1, 4.3 Hz, 1H).

MS (APCI) m/z 382.2 (M+NH4)$^+$

175. 2-[6-[(2,6-dimethylphenyl)methoxy]tetralin-2-yl]oxyacetic acid

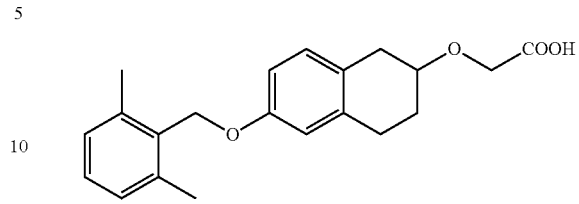

$^1$H NMR (500 MHz, DMSO-d$_6$) δ 7.14 (dd, J=8.1, 7.0 Hz, 1H), 7.05 (d, J=7.6 Hz, 2H), 7.02-6.96 (m, 1H), 6.75 (s, 2H), 4.95 (s, 2H), 4.05 (s, 2H), 2.93 (dd, J=16.2, 4.7 Hz, 1H), 2.81 (dt, J=17.0, 6.1 Hz, 1H), 2.72-2.59 (m, 2H), 2.29 (s, 6H), 1.95 (dd, J=10.9, 4.1 Hz, 1H), 1.78-1.67 (m, 1H).

MS (APCI) m/z 358.3 (M+NH4)$^+$

176. 2-[6-[(5-chloro-2-methoxy-phenyl)methoxy]tetralin-2-yl]oxyacetic acid

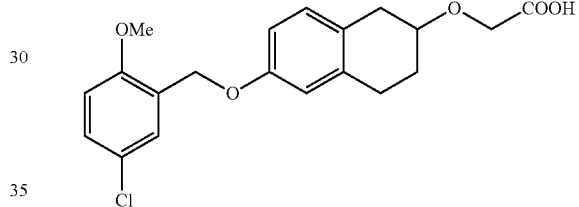

$^1$H NMR (500 MHz, DMSO-d$_6$) δ 7.35 (d, J=7.4 Hz, 2H), 7.09-7.03 (m, 1H), 6.97 (d, J=8.3 Hz, 1H), 6.75-6.67 (m, 2H), 4.96 (s, 2H), 4.03 (s, 2H), 3.80 (s, 3H), 2.92 (dd, J=16.3, 4.7 Hz, 1H), 2.79 (dt, J=17.1, 6.1 Hz, 1H), 2.70-2.58 (m, 2H), 1.93 (dd, J=14.0, 7.3 Hz, 1H), 1.76-1.65 (m, 1H).
MS (APCI) m/z 394.3 (M+NH4)$^+$

General Procedure II for Compounds 177-215

A 4 mL vial was charged with a stir bar to which was added NaH (8 mg, 0.35 mmol). To this NaH was then added a solution of methyl 3-((6-hydroxy-1,2,3,4-tetrahydronaphthalen-2-yl)oxy)propanoate core (30 mg, 0.12 mmol) in dimethyl formamide (300 µl) at 0 degrees and stirred for 30 minutes. After 30 minutes, to this mixture was added a solution of 2-(bromomethyl)-4-methyl-1-(trifluoromethyl)benzene 2 halide monomer (40 mg, 1.4 eq., 0.16 mmol) also in dimethylformamide (200 µl). This was allowed to stir at rt for 2 hours. Upon completion of the first step, to the crude material was added 500 µl of 1M lithium hydroxide and further allowed to be stirred for 1 hour at room temperature. The residues were dissolved in 1:1 DMSO/MeOH and purified by reverse phase HPLC (AA method). Samples were purified by preparative HPLC on a Phenomenex Luna C8(2) 5 um 100 Å AXIA column (30 mm×150 mm). A gradient of ACN (A) and 10 mM ammonium acetate in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain title compounds. Product

177. 3-[6-[[5-methyl-2-(trifluoromethyl)phenyl]methoxy]tetralin-2-yl]oxypropanoic acid

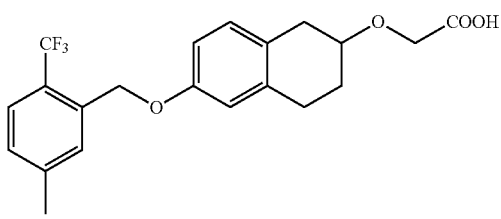 [SMILES: Cc1ccc(C(F)(F)F)c(COc2ccc3c(c2)CCC(OCC(=O)O)C3)c1]

¹H NMR (400 MHz, DMSO-d$_6$) δ 7.65 (d, J=8.0 Hz, 1H), 7.52 (s, 1H), 7.37 (d, J=8.1 Hz, 1H), 6.98 (d, J=8.4 Hz, 1H), 6.79-6.64 (m, 2H), 5.09 (s, 2H), 3.70-3.60 (m, 3H), 2.96-2.89 (m, 1H), 2.78 (dt, J=17.0, 6.2 Hz, 1H), 2.71-2.55 (m, 2H), 2.41 (d, J=5.8 Hz, 2H), 2.39 (s, 3H), 1.89 (m, 2H), 1.69 (dtd, J=13.6, 8.2, 5.6 Hz, 1H).

MS (APCI) m/z 426.3 (M+NH4)$^+$

178. 3-[6-[[2-(trifluoromethyl)phenyl]methoxy]tetralin-2-yl]oxypropanoic acid

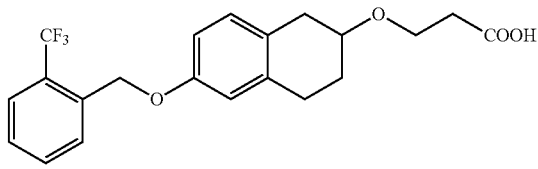 [SMILES: O=C(O)CCOC1CCc2cc(OCc3ccccc3C(F)(F)F)ccc2C1]

¹H NMR (400 MHz, DMSO-d$_6$) δ 7.78 (d, J=7.7 Hz, 1H), 7.76-7.67 (m, 2H), 7.64-7.53 (m, 1H), 6.97 (d, J=8.1 Hz, 1H), 6.76-6.68 (m, 2H), 5.15 (d, J=1.3 Hz, 2H), 3.70-3.59 (m, 3H), 2.91 (dd, J=16.2, 4.9 Hz, 1H), 2.77 (dt, J=17.0, 6.1 Hz, 1H), 2.72-2.55 (m, 2H), 2.36 (d, J=6.5 Hz, 2H), 1.86 (m, 2H), 1.78-1.63 (m, 1H).

MS (APCI) m/z 412.3 (M+NH4)$^+$

179. 3-[6-(o-tolylmethoxy)tetralin-2-yl]oxypropanoic acid

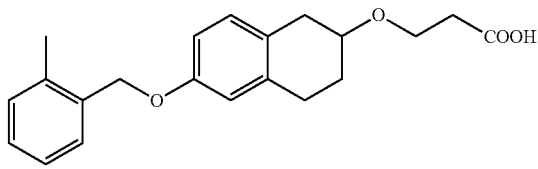 [SMILES: Cc1ccccc1COc1ccc2c(c1)CCC(OCCC(=O)O)C2]

¹H NMR (400 MHz, DMSO-d$_6$) δ 7.40-7.35 (m, 1H), 7.26-7.14 (m, 3H), 6.96 (d, J=8.3 Hz, 1H), 6.77-6.67 (m, 2H), 4.99 (s, 2H), 3.70-3.59 (m, 3H), 2.91 (dd, J=16.3, 4.9 Hz, 1H), 2.78 (dt, J=17.0, 6.2 Hz, 1H), 2.70-2.54 (m, 2H), 2.37 (t, J=6.5 Hz, 2H), 2.29 (s, 3H), 1.94-1.87 (m, 1H), 1.74-1.63 (m, 1H).

MS (APCI) m/z 358.2 (M+NH4)$^+$

180. 3-[6-[(3-fluorophenyl)methoxy]tetralin-2-yl]oxypropanoic acid

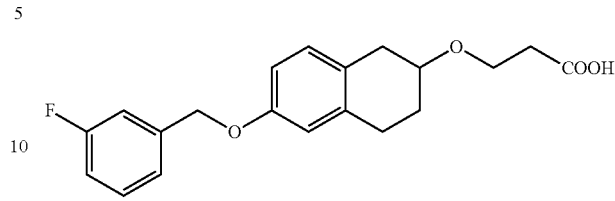

¹H NMR (400 MHz, DMSO-d$_6$) δ 7.42 (td, J=7.9, 6.0 Hz, 1H), 7.28-7.20 (m, 2H), 7.18-7.10 (m, 1H), 6.96 (d, J=8.4 Hz, 1H), 6.78-6.70 (m, 2H), 5.05 (s, 2H), 3.72-3.60 (m, 3H), 2.98-2.88 (m, 1H), 2.77 (dt, J=16.9, 6.2 Hz, 1H), 2.72-2.55 (m, 2H), 2.38 (t, J=6.4 Hz, 2H), 1.88 (m, 1H), 1.68 (dtd, J=13.6, 8.2, 5.6 Hz, 1H).

MS (APCI) m/z 362 3 (M+NH4)$^+$

181. 3-[6-[(3,4-dichlorophenyl)methoxy]tetralin-2-yl]oxypropanoic acid

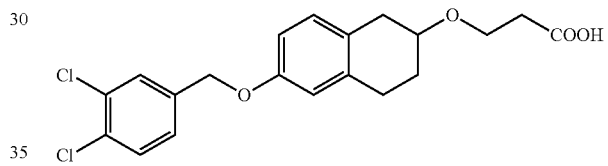

¹H NMR (400 MHz, DMSO-d$_6$) δ 7.69-7.59 (m, 2H), 7.41 (dd, J=8.3, 2.0 Hz, 1H), 6.96 (d, J=8.3 Hz, 1H), 6.79-6.70 (m, 2H), 5.04 (s, 2H), 3.71-3.60 (m, 3H), 2.96-2.88 (m, 1H), 2.77 (dt, J=17.0, 6.2 Hz, 1H), 2.72-2.57 (m, J=2H), 2.35 (t, J=6.5 Hz, 2H), 1.90 (d, J=7.1 Hz, 1H), 1.68 (ddt, J=12.5, 7.9, 4.1 Hz, 1H).

MS (APCI) m/z 412.2 (M+NH4)$^+$

182. 3-[6-[(4-methylsulfanylphenyl)methoxy]tetralin-2-yl]oxypropanoic acid

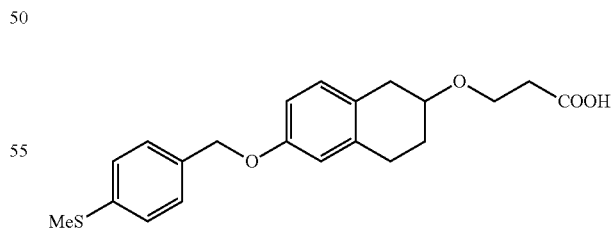

¹H NMR (400 MHz, DMSO-d$_6$) δ 7.41-7.33 (m, 2H), 7.31-7.23 (m, 2H), 6.94 (d, J=8.3 Hz, 1H), 6.75-6.64 (m, 2H), 4.98 (s, 2H), 3.69-3.58 (m, 3H), 2.90 (dd, J=16.3, 4.8 Hz, 1H), 2.76 (dt, J=16.9, 6.2 Hz, 1H), 2.72-2.56 (m, 2H), 2.45 (s, 3H), 2.39 (d, J=6.3 Hz, 2H), 1.89 (d, J=11.7 Hz, 1H), 1.69 (dt, J=13.1, 6.9 Hz, 1H).

MS (APCI) m/z 390.3 (M+NH4)$^+$

183. 3-[6-[[4-(trifluoromethyl)phenyl]methoxy]tetralin-2-yl]oxypropanoic acid

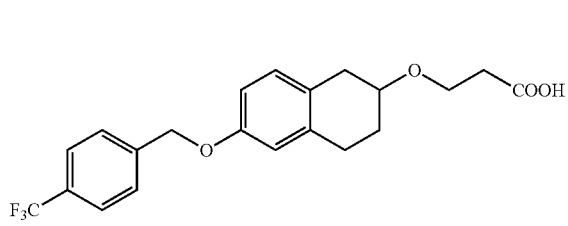 [SMILES: O=C(O)CCOC1CCc2cc(OCc3ccc(C(F)(F)F)cc3)ccc2C1]

¹H NMR (400 MHz, DMSO-d₆) δ 7.73 (d, J=8.1 Hz, 2H), 7.63 (d, J=8.0 Hz, 2H), 6.96 (d, J=8.2 Hz, 1H), 6.79-6.70 (m, 2H), 5.14 (s, 2H), 3.72-3.61 (m, 3H), 3.00-2.88 (m, 1H), 2.84-2.74 (m, 1H), 2.72-2.55 (m, 2H), 2.39 (d, J=6.4 Hz, 2H), 1.97-1.85 (m, 1H), 1.69 (ddt, J=12.5, 7.9, 4.0 Hz, 1H). MS (APCI) m/z 412.2 (M+NH4)⁺

184. 3-[6-[[3-(trifluoromethoxy)phenyl]methoxy]tetralin-2-yl]oxypropanoic acid

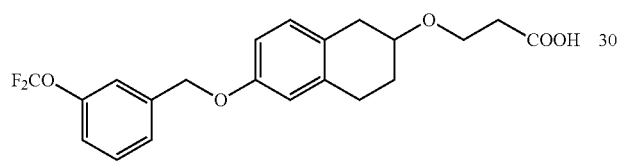

¹H NMR (400 MHz, DMSO-d₆) δ 7.53 (d, J=7.8 Hz, 1H), 7.50-7.43 (m, 1H), 7.39 (s, 1H), 7.29 (ddt, J=8.1, 2.4, 1.2 Hz, 1H), 6.96 (d, J=8.3 Hz, 1H), 6.78-6.69 (m, 2H), 5.09 (s, 2H), 3.71-3.59 (m, 3H), 2.96-2.88 (m, 1H), 2.84-2.74 (m, 1H), 2.72-2.55 (m, 2H), 2.35 (t, J=6.5 Hz, 2H), 1.96-1.87 (m, 1H), 1.76-1.61 (m, 1H). MS (APCI) m/z 428.3 (M+NH4)⁺

185. 3-[6-[[4-(trifluoromethoxy)phenyl]methoxy]tetralin-2-yl]oxypropanoic acid

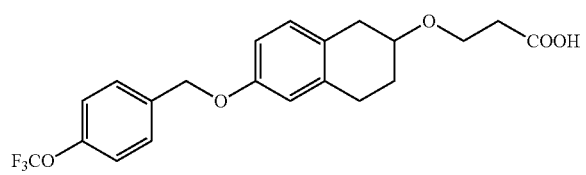 [SMILES: O=C(O)CCOC1CCc2cc(OCc3ccc(OC(F)(F)F)cc3)ccc2C1]

¹H NMR (400 MHz, DMSO-d₆) δ 7.61-7.49 (m, 2H), 7.44-7.35 (m, 2H), 6.96 (d, J=8.2 Hz, 1H), 6.78-6.69 (m, 2H), 5.06 (s, 2H), 3.70-3.61 (m, 3H), 2.96-2.88 (m, 1H), 2.84-2.73 (m, 1H), 2.72-2.56 (m, 2H), 2.40 (d, J=6.3 Hz, 2H), 1.90 (d, J=12.9 Hz, 1H), 1.68 (dtd, J=13.5, 8.1, 5.5 Hz, 1H). MS (APCI) m/z 428.3 (M+NH4)⁺

186. 3-[6-[(2,3-difluorophenyl)methoxy]tetralin-2-yl]oxypropanoic acid

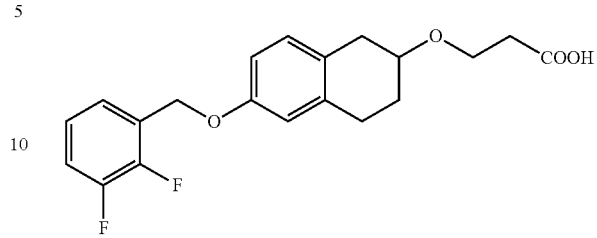

¹H NMR (400 MHz, DMSO-d₆) δ 7.46-7.39 (m, 1H), 7.39-7.32 (m, 1H), 7.23 (tdd, J=8.0, 5.0, 1.5 Hz, 1H), 6.97 (d, J=8.3 Hz, 1H), 6.80-6.71 (m, 2H), 5.10 (d, J=1.1 Hz, 2H), 3.70-3.60 (m, 3H), 2.91 (dd, J=16.2, 4.9 Hz, 1H), 2.78 (dt, J=17.1, 6.2 Hz, 1H), 2.69-2.56 (m, 2H), 2.35 (t, J=6.5 Hz, 2H), 1.97-1.85 (m, 1H), 1.77-1.61 (m, 1H). MS (APCI) m/z 380.2 (M+NH4)⁺

187. 3-[6-[(3-chlorophenyl)methoxy]tetralin-2-yl]oxypropanoic acid

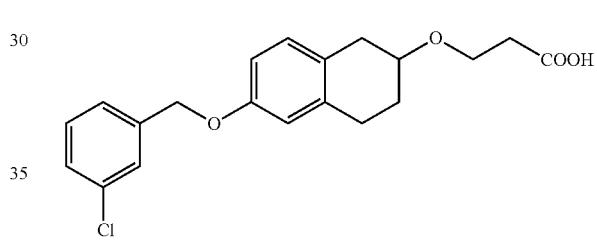

¹H NMR (400 MHz, DMSO-d₆) δ 7.51-7.43 (m, 1H), 7.44-7.36 (m, 3H), 6.96 (d, J=8.4 Hz, 1H), 6.77-6.69 (m, 2H), 5.05 (s, 2H), 3.70-3.59 (m, 3H), 2.95-2.88 (m, 1H), 2.77 (dt, J=16.9, 6.2 Hz, 1H), 2.72-2.55 (m, 2H), 2.37 (t, J=6.4 Hz, 2H), 1.90 (d, J=5.5 Hz, 0H), 1.75-1.65 (m, 1H). MS (APCI) m/z 378.3 (M+NH4)⁺

188. 3-[6-[(2-chlorophenyl)methoxy]tetralin-2-yl]oxypropanoic acid

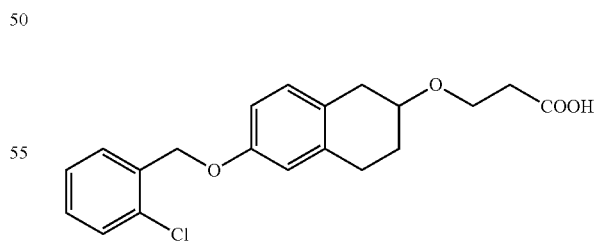

¹H NMR (400 MHz, DMSO-d₆) δ 7.55 (dd, J=4.3, 2.0 Hz, 1H), 7.54-7.46 (m, 1H), 7.46-7.32 (m, 2H), 6.97 (d, J=8.4 Hz, 1H), 6.79-6.69 (m, 2H), 5.07 (8, 2H), 3.70-3.59 (m, 3H), 2.91 (dd, J=16.2, 4.8 Hz, 1H), 2.78 (dt, J=17.0, 6.2 Hz, 1H), 2.72-2.55 (m, 2H), 2.38 (t, J=6.4 Hz, 2H), 1.92 (d, J=7.9 Hz, 0H), 1.77-1.64 (m, 1H). MS (APCI) m/z 378.2 (M+NH4)⁺

189. 3-[6-[(2,3-dichlorophenyl)methoxy]tetralin-2-yl]oxypropanoic acid

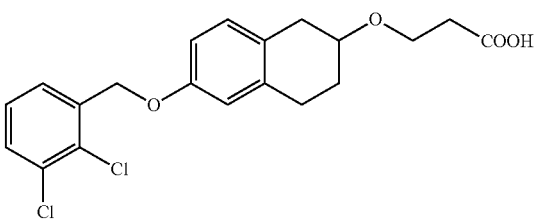 [SMILES: O=C(O)CCOC1CCc2cc(OCc3cccc(F)c3F)ccc2C1]

$^1$H NMR (400 MHz, DMSO-d$_6$) δ 7.62 (dd, J=8.0, 1.6 Hz, 1H), 7.53 (dd, J=7.8, 1.6 Hz, 1H), 7.39 (t, J=7.9 Hz, 1H), 6.98 (d, J=8.2 Hz, 1H), 6.78-6.70 (m, 2H), 5.11 (s, 2H), 3.72-3.58 (m, 3H), 2.91 (dd, J=16.2, 4.8 Hz, 1H), 2.78 (dt, J=17.0, 6.3 Hz, 1H), 2.72-2.55 (m, 2H), 2.36 (d, J=6.6 Hz, 2H), 1.97-1.85 (m, 1H), 1.69 (ddt, J=12.4, 7.9, 4.1 Hz, 1H).

MS (APCI) m/z 412.2 (M+NH4)$^+$

190. 3-[6-[[2-(trifluoromethoxy)phenyl]methoxy]tetralin-2-yl]oxypropanoic acid

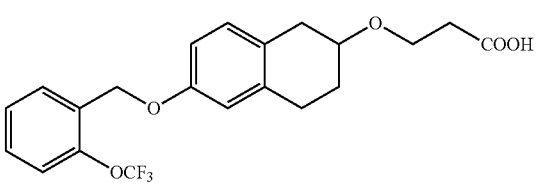 [SMILES: O=C(O)CCOC1CCc2cc(OCc3ccccc3OC(F)(F)F)ccc2C1]

$^1$H NMR (400 MHz, DMSO-d$_6$) δ 7.61 (dd, J=7.6, 1.8 Hz, 1H), 7.50 (td, J=7.7, 1.9 Hz, 1H), 7.47-7.38 (m, 2H), 6.97 (d, J=8.3 Hz, 1H), 6.76-6.69 (m, 2H), 5.05 (s, 2H), 3.71-3.61 (m, 3H), 2.91 (dd, J=16.3, 4.8 Hz, 1H), 2.77 (dt, J=17.0, 6.2 Hz, 1H), 2.73-2.55 (m, 2H), 2.37 (t, J=6.5 Hz, 2H), 1.76-1.62 (m, 1H).

MS (APCI) m/z 428.3 (M+NH4)$^+$

191. 3-[6-[(4-chlorophenyl)methoxy]tetralin-2-yl]oxypropanoic acid

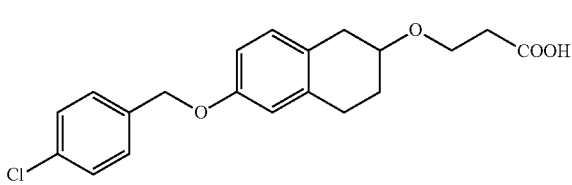 [SMILES: O=C(O)CCOC1CCc2cc(OCc3ccc(Cl)cc3)ccc2C1]

$^1$H NMR (400 MHz, DMSO-d$_6$) δ 7.43 (s, 4H), 6.95 (d, J=8.3 Hz, 1H), 6.76-6.66 (m, 2H), 5.02 (s, 2H), 3.71-3.60 (m, 3H), 2.90 (dd, J=16.2, 4.9 Hz, 1H), 2.76 (dt, J=17.0, 6.2 Hz, 1H), 2.70-2.56 (m, 1H), 2.38 (t, J=6.4 Hz, 2H), 1.95-1.86 (m, 1H), 1.77-1.62 (m, 1H).

MS (APCI) m/z 378.2 (M+NH4)$^+$

192. 3-[6-[(4-tert-butylphenyl)methoxy]tetralin-2-yl]oxypropanoic acid

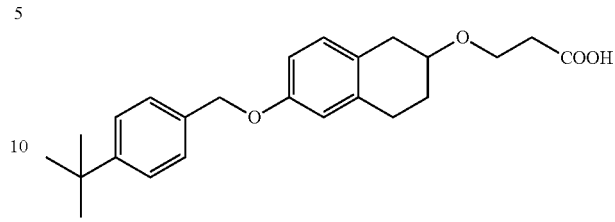

$^1$H NMR (400 MHz, DMSO-d$_6$) δ 7.39 (d, J=8.5 Hz, 2H), 7.33 (d, J=8.5 Hz, 2H), 6.95 (d, J=8.2 Hz, 1H), 6.78-6.67 (m, 2H), 4.97 (s, 2H), 3.70-3.60 (m, 3H), 2.90 (dd, J=16.1, 4.9 Hz, 1H), 2.77 (dt, J=16.9, 6.1 Hz, 1H), 2.74-2.56 (m, 2H), 2.39 (t, J=6.4 Hz, 2H), 1.90 (d, J=9.1 Hz, 1H), 1.76-1.61 (m, 1H), 1.26 (s, 9H).

MS (APCI) m/z 400.3 (M+NH4)$^+$

193. 3-[6-[[3-(trifluoromethyl)phenyl]methoxy]tetralin-2-yl]oxypropanoic acid

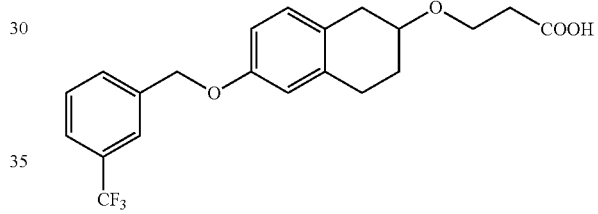

$^1$H NMR (400 MHz, DMSO-d$_6$) δ 7.79-7.58 (m, 4H), 6.97 (d, J=8.3 Hz, 1H), 6.80-6.71 (m, 2H), 5.13 (s, 2H), 3.71-3.59 (m, 3H), 2.91 (dd, J=16.5, 4.9 Hz, 1H), 2.84-2.74 (m, 1H), 2.70-2.56 (m, 2H), 2.37 (t, J=6.4 Hz, 2H), 1.90 (d, J=7.6 Hz, 1H), 1.76-1.64 (m, 1H).

MS (APCI) m/z 412.3 (M+NH4)$^+$

194. 3-[6-[(4-fluorophenyl)methoxy]tetralin-2-yl]oxypropanoic acid

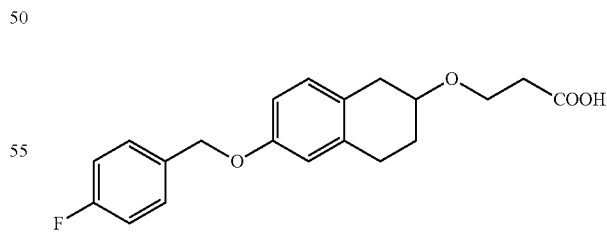

$^1$H NMR (400 MHz, DMSO-d$_6$) δ 7.51-7.43 (m, 2H), 7.27-7.14 (m, 2H), 6.95 (d, J=8.2 Hz, 1H), 6.78-6.65 (m, 2H), 5.00 (s, 2H), 3.73-3.58 (m, 3H), 2.90 (dd, J=16.2, 4.9 Hz, 1H), 2.77 (dt, J=17.0, 6.2 Hz, 1H), 2.72-2.56 (m, 1H), 2.34 (t, J=6.5 Hz, 2H), 1.98-1.88 (m, 1H), 1.73-1.62 (m, 1H).

MS (APCI) m/z 362.2 (M+NH4)$^+$

195. 2-[6-[[5-methyl-2-(trifluoromethyl)phenyl]methoxy]tetralin-2-yl]oxyacetic acid

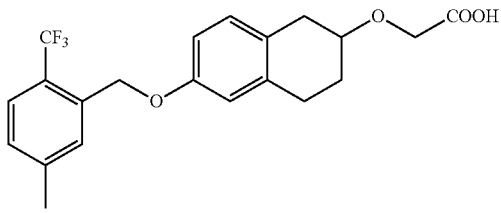 [SMILES: Cc1ccc(C(F)(F)F)c(COc2ccc3c(c2)CCC(OCC(=O)O)C3)c1]

¹H NMR (400 MHz, DMSO-d$_6$) 7.65 (d, J=8.0 Hz, 1H), 7.53 (d, J=1.6 Hz, 1H), 7.37 (d, J=8.1 Hz, 1H), 6.98 (d, J=8.3 Hz, 1H), 6.76-6.69 (m, 2H), 5.09 (s, 2H), 3.89 (s, 2H), 3.78 (d, J=7.3 Hz, 1H), 2.92 (dd, J=16.2, 4.8 Hz, 1H), 2.79 (dt, J=17.1, 6.0 Hz, 1H), 2.71-2.59 (m, 2H), 2.38 (s, 3H), 1.94 (d, J=7.0 Hz, 1H), 1.70 (tt, J=13.8, 6.9 Hz, 1H).

MS (APCI) m/z 412.3 (M+NH4)$^+$

196. 2-[6-[[2-(trifluoromethyl)phenyl]methoxy]tetralin-2-yl]oxyacetic acid

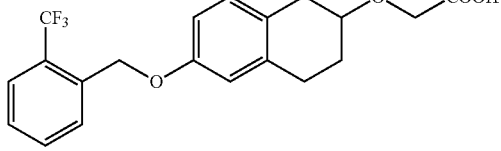

¹H NMR (400 MHz, DMSO-d$_6$) δ 7.78 (d, J=7.8 Hz, 1H), 7.76-7.66 (m, 2H), 7.57 (s, 1H), 6.99 (d, J=8.1 Hz, 1H), 6.76-6.65 (m, 2H), 5.15 (s, 2H), 4.00 (s, 2H), 3.78 (d, J=7.3 Hz, 1H), 2.95 (s, 1H), 2.79 (s, 1H), 2.72-2.62 (m, 2H), 1.92 (s, 1H), 1.73 (8, 1H).

MS (APCI) m/z 398.3 (M+NH4)$^+$

197. 2-[6-(o-tolylmethoxy)tetralin-2-yl]oxyacetic acid

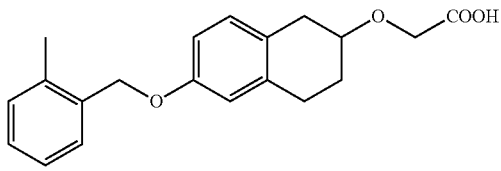

¹H NMR (400 MHz, DMSO-d$_6$) δ 7.36 (dd, J=7.3, 1.4 Hz, 1H), 7.28-7.15 (m, 3H), 6.97 (d, J=8.2 Hz, 1H), 6.79-6.71 (m, 2H), 4.99 (s, 2H), 3.80 (s, 2H), 3.77 (t, J=3.9 Hz, 1H), 2.91 (dd, J=16.2, 4.8 Hz, 1H), 2.80 (dt, J=17.1, 6.0 Hz, 1H), 2.62 (ddd, J=23.2, 12.3, 4.9 Hz, 2H), 2.29 (s, 3H), 2.03-1.89 (m, 1H), 1.68 (ddt, J=12.3, 8.2, 4.2 Hz, 1H).

MS (APCI) m/z 344.3 (M+NH4)$^+$

198. 2-[6-[(3-fluorophenyl)methoxy]tetralin-2-yl]oxyacetic acid

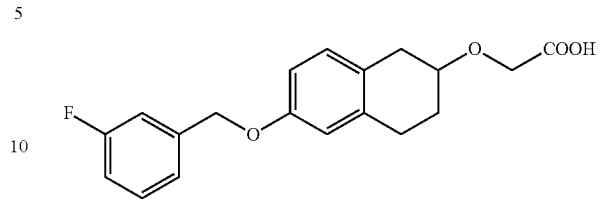

¹H NMR (400 MHz, DMSO-d$_6$) δ 7.42 (td, J=8.0, 6.0 Hz, 1H), 7.32-7.19 (m, 2H), 7.19-7.07 (m, 1H), 6.96 (d, J=8.3 Hz, 1H), 6.78-6.67 (m, 2H), 5.05 (s, 2H), 3.87 (s, 2H), 3.78 (td, J=4.4, 4.0, 2.3 Hz, 1H), 2.99-2.89 (m, 1H), 2.78 (dt, J=17.1, 6.1 Hz, 1H), 2.72-2.56 (m, 2H), 1.93 (dq, J=9.1, 6.4, 5.9 Hz, 1H), 1.68 (dtd, J=13.8, 8.5, 5.6 Hz, 1H). MS (APCI) m/z 348.2 (M+NH4)$^+$

199. 2-[6-[(3,4-dichlorophenyl)methoxy]tetralin-2-yl]oxyacetic acid

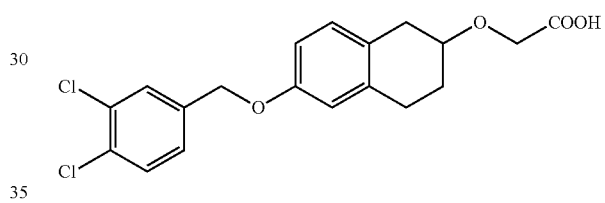

¹H NMR (400 MHz, DMSO-d$_6$) δ 7.72-7.59 (m, 2H), 7.41 (dd, J=8.3, 2.0 Hz, 1H), 6.96 (d, J=8.4 Hz, 1H), 6.79-6.68 (m, 2H), 5.04 (s, 2H), 3.77 (s, 3H), 2.90 (dd, J=16.2, 4.8 Hz, 1H), 2.78 (dt, J=17.0, 6.0 Hz, 1H), 2.71-2.56 (m, 2H), 1.99-1.90 (m, 1H), 1.67 (ddt, J=12.5, 8.3, 4.3 Hz, 1H).

MS (APCI) m/z 398.2 (M+NH4)$^+$

200. 2-[6-[[2-methyl-3-(trifluoromethyl)phenyl]methoxy]tetralin-2-yl]oxyacetic acid

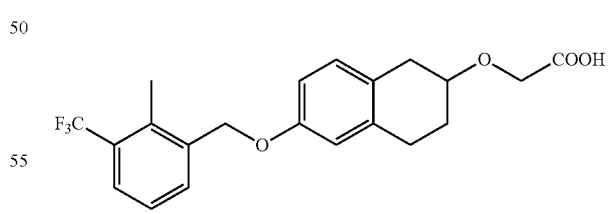

¹H NMR (400 MHz, DMSO-d$_6$) δ 7.75-7.62 (m, 2H), 7.41 (t, J=7.8 Hz, 1H), 6.98 (d, J=8.2 Hz, 1H), 6.77 (d, J=8.4 Hz, 2H), 5.10 (s, 2H), 3.85 (s, 2H), 3.78 (ddq, J=8.7, 4.9, 2.6, 1.8 Hz, 1H), 2.92 (dd, J=16.2, 4.8 Hz, 1H), 2.80 (dt, J=17.0, 6.1 Hz, 1H), 2.65 (ddd, J=16.3, 8.9, 5.1 Hz, 2H), 2.40 (d, J=1.7 Hz, 3H), 2.02-1.89 (m, 1H), 1.70 (ddt, J=12.5, 8.3, 4.3 Hz, 1H).

MS (APCI) m/z 412.3 (M+NH4)$^+$

201. 2-[6-[(4-methylsulfanylphenyl)methoxy]tetralin-2-yl]oxyacetic acid

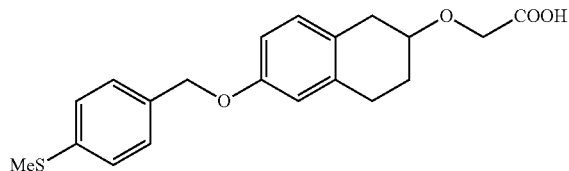 [SMILES: CSc1ccc(COc2ccc3c(c2)CCC(OCC(=O)O)C3)cc1]

¹H NMR (400 MHz, DMSO-d₆) δ 7.42-7.33 (m, 2H), 7.31-7.23 (m, 2H), 6.95 (d, J=8.3 Hz, 1H), 6.76-6.66 (m, 2H), 4.98 (s, 2H), 2.89 (dd, J=16.2, 4.8 Hz, 1H), 2.77 (dt, J=16.8, 5.9 Hz, 1H), 2.71-2.56 (m, 2H), 2.45 (s, 3H), 2.00-1.90 (m, 1H), 1.72-1.61 (m, 1H).

MS (APCI) m/z 376.2 (M+NH4)⁺

202. 2-[6-[[4-(trifluoromethyl)phenyl]methoxy]tetralin-2-yl]oxyacetic acid

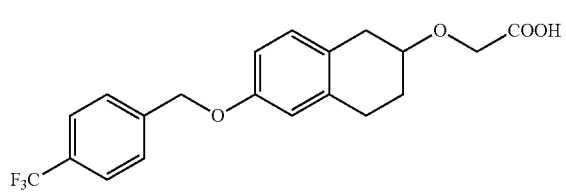 [SMILES: O=C(O)COC1CCc2cc(OCc3ccc(C(F)(F)F)cc3)ccc2C1]

¹H NMR (400 MHz, DMSO-d₆) δ 7.73 (d, J=8.1 Hz, 2H), 7.63 (d, J=8.1 Hz, 2H), 6.97 (d, J=8.3 Hz, 1H), 6.80-6.70 (m, 2H), 5.14 (s, 2H), 3.85 (s, 2H), 3.82-3.76 (m, 1H), 2.91 (dd, J=16.2, 4.8 Hz, 1H), 2.79 (dt, J=17.1, 6.1 Hz, 1H), 2.62 (td, J=17.0, 16.3, 7.5 Hz, 2H), 1.92 (dt, J=9.4, 2.8 Hz, 1H), 1.69 (ddt, J=12.6, 8.3, 4.3 Hz, 1H).

MS (APCI) m/z 398.2 (M+NH4)⁺

203. 2-[6-[[4-(trifluoromethoxy)phenyl]methoxy]tetralin-2-yl]oxyacetic acid

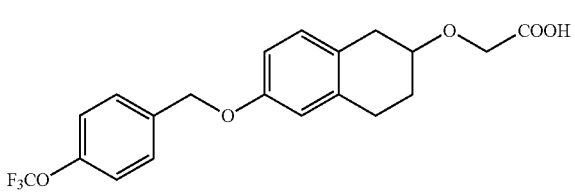 [SMILES: O=C(O)COC1CCc2cc(OCc3ccc(OC(F)(F)F)cc3)ccc2C1]

¹H NMR (400 MHz, DMSO-d₆) δ 7.60-7.52 (m, 2H), 7.40-7.34 (m, 2H), 6.97 (d, J=8.3 Hz, 1H), 6.81-6.68 (m, 2H), 5.06 (s, 2H), 3.87 (s, 2H), 3.77 (s, 1H), 2.99-2.88 (m, 1H), 2.79 (dt, J=17.0, 6.1 Hz, 1H), 2.63 (dt, J=16.3, 7.8 Hz, 2H), 1.99-1.89 (m, 1H), 1.74-1.61 (m, 1H).

MS (APCI) m/z 414.2 (M+NH4)⁺

204. 2-[6-[(2,3-difluorophenyl)methoxy]tetralin-2-yl]oxyacetic acid

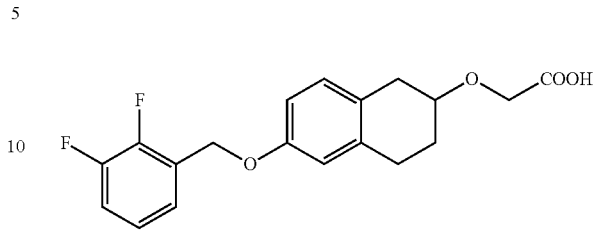

¹H NMR (400 MHz, DMSO-d₆) δ 7.50-7.30 (m, 2H), 7.22 (tdd, J=8.0, 5.0, 1.5 Hz, 1H), 6.98 (d, J=8.3 Hz, 1H), 6.79-6.69 (m, 2H), 5.11 (d, J=1.2 Hz, 2H), 3.88 (s, 2H), 3.79 (td, J=4.2, 2.2 Hz, 1H), 2.92 (dd, J=16.2, 4.8 Hz, 1H), 2.80 (dt, J=17.0, 6.1 Hz, 1H), 2.71-2.57 (m, 2H), 2.00-1.88 (m, 1H), 1.69 (dtd, J=13.7, 8.3, 5.6 Hz, 1H).

MS (APCI) m/z 366.2 (M+NH4)⁺

205. 2-[6-[(3-chlorophenyl)methoxy]tetralin-2-yl]oxyacetic acid

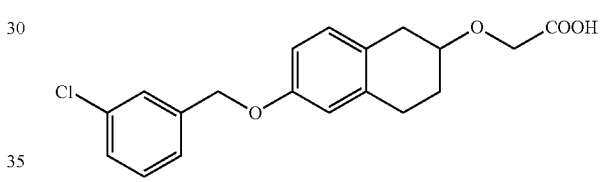

¹H NMR (400 MHz, DMSO-d₆) δ 7.67-7.57 (m, 1H), 7.50 (td, J=7.7, 1.8 Hz, 1H), 7.42 (t, J=7.5 Hz, 2H), 6.98 (d, J=8.4 Hz, 1H), 6.73 (dd, J=10.9, 2.6 Hz, 2H), 5.06 (s, 2H), 4.02 (s, 2H), 3.78 (s, 1H), 2.93 (dd, J=16.3, 4.8 Hz, 1H), 2.80 (dt, J=16.7, 6.3 Hz, 1H), 2.63 (dd, J=16.2, 6.9 Hz, 2H), 1.94 (d, J=12.0 Hz, 1H), 1.72 (dt, J=13.6, 7.1 Hz, 1H).

MS (APCI) m/z 364.2 (M+NH4)⁺

206. 2-[6-[(2-chlorophenyl)methoxy]tetralin-2-yl]oxyacetic acid

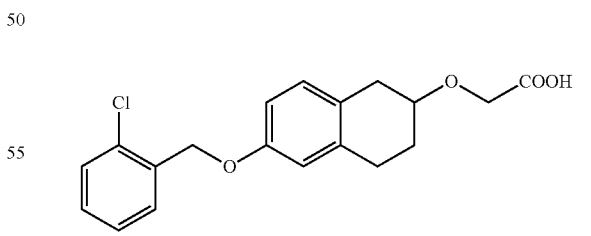

¹H NMR (400 MHz, DMSO-d₆) δ 7.55 (dd, J=4.2, 2.0 Hz, 1H), 7.49 (dd, J=4.4, 2.7 Hz, 1H), 7.41-7.36 (m, 2H), 6.98 (d, J=8.2 Hz, 1H), 6.79-6.70 (m, 2H), 5.07 (s, 2H), 3.82 (s, 2H), 3.78 (d, J=3.3 Hz, 1H), 2.91 (dd, J=16.3, 4.8 Hz, 1H), 2.80 (dt, J=16.9, 6.0 Hz, 1H), 2.72-2.56 (m, 2H), 2.01-1.88 (m, 1H), 1.69 (ddt, J=12.3, 8.2, 4.3 Hz, 1H).

MS (APCI) m/z 364.2 (M+NH4)⁺

207. 2-[6-[(2,3-dichlorophenyl)methoxy]tetralin-2-yl]oxyacetic acid

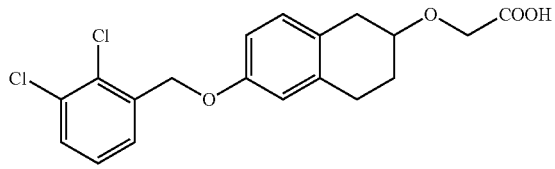 [SMILES: O=C(O)COC1CCc2cc(OCc3cccc(Cl)c3Cl)ccc2C1]

¹H NMR (400 MHz, DMSO-d₆) 7.62 (dd, J=8.0, 1.6 Hz, 1H), 7.53 (dd, J=7.8, 1.6 Hz, 1H), 7.39 (t, J=7.9 Hz, 1H), 6.98 (d, J=8.2 Hz, 1H), 6.79-6.71 (m, 2H), 5.12 (s, 2H), 3.78 (s, 3H), 2.91 (dd, J=16.3, 4.8 Hz, 1H), 2.88-2.76 (m, 1H), 2.73-2.58 (m, 2H), 1.93 (d, J=12.8 Hz, 1H), 1.76-1.61 (m, 1H).

MS (APCI) m/z 398.2 (M+NH4)⁺

208. 2-[6-[[2-(trifluoromethoxy)phenyl]methoxy]tetralin-2-yl]oxyacetic

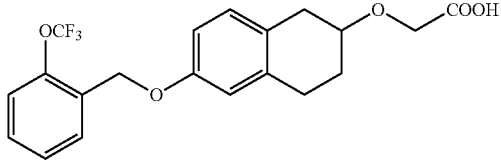 [SMILES: O=C(O)COC1CCc2cc(OCc3ccccc3OC(F)(F)F)ccc2C1]

¹H NMR (400 MHz, DMSO-d₆) δ 7.67-7.57 (m, 1H), 7.50 (td, J=7.7, 1.8 Hz, 1H), 7.42 (t, J=7.5 Hz, 2H), 6.98 (d, J=8.4 Hz, 1H), 6.73 (dd, J=10.9, 2.6 Hz, 2H), 5.06 (s, 2H), 4.02 (s, 2H), 3.78 (s, 1H), 2.93 (dd, J=16.3, 4.8 Hz, 1H), 2.80 (dt, J=16.7, 6.3 Hz, 1H), 2.63 (dd, J=16.2, 6.9 Hz, 2H), 1.94 (d, J=12.0 Hz, 1H), 1.72 (dt, J=13.6, 7.1 Hz, 1H).

MS (APCI) m/z 414.3 (M+NH4)⁺

209. 2-[6-[(4-chlorophenyl)methoxy]tetralin-2-yl]oxyacetic acid

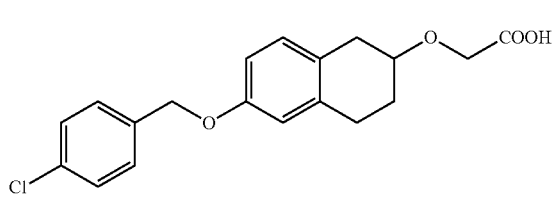 [SMILES: O=C(O)COC1CCc2cc(OCc3ccc(Cl)cc3)ccc2C1]

¹H NMR (400 MHz, DMSO-d₆) δ 7.43 (d, J=1.1 Hz, 4H), 6.96 (d, J=8.3 Hz, 1H), 6.78-6.67 (m, 2H), 5.02 (s, 2H), 3.79 (s, 3H), 2.97-2.88 (m, 1H), 2.85-2.75 (m, 1H), 2.62 (dt, J=20.9, 7.7 Hz, 2H), 1.98-1.89 (m, 1H), 1.68 (ddt, J=12.4, 8.3, 4.3 Hz, 1H).

MS (APCI) m/z 364.2 (M+NH4)⁺

210. 2-[6-[(2,6-dichlorophenyl)methoxy]tetralin-2-yl]oxyacetic acid

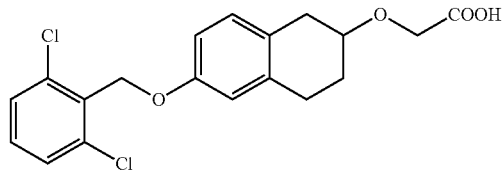 [SMILES: O=C(O)COC1CCc2cc(OCc3c(Cl)cccc3Cl)ccc2C1]

¹H NMR (400 MHz, DMSO-d₆) δ 7.54 (d, J=1.2 Hz, 1H), 7.48-7.43 (m, 1H), 7.00 (d, J=8.8 Hz, 1H), 6.77 (d, J=7.1 Hz, 2H), 5.16 (s, 2H), 3.95 (s, 2H), 3.79 (s, 1H), 2.94 (dd, J=16.3, 4.8 Hz, 1H), 2.90-2.76 (m, 1H), 2.63 (dd, J=16.4, 7.3 Hz, 2H), 1.93 (s, 1H), 1.80-1.60 (m, 1H).

MS (APCI) m/z 398.2 (M+NH4)⁺

211. 2-[6-[(4-tert-butylphenyl)methoxy]tetralin-2-yl]oxyacetic acid

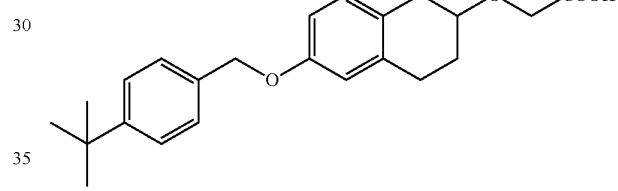

¹H NMR (400 MHz, DMSO-d₆) δ 7.43-7.31 (m, 3H), 6.95 (d, J=8.3 Hz, 1H), 6.71 (dd, J=11.1, 3.1 Hz, 2H), 4.98 (s, 2H), 3.88 (s, 2H), 2.91 (dd, J=16.2, 4.4 Hz, 1H), 2.79 (dt, J=17.0, 6.1 Hz, 1H), 2.61 (t, J=7.9 Hz, 2H), 1.91 (d, J=7.3 Hz, 1H), 1.75-1.65 (m, 1H), 1.26 (s, 9H).

MS (APCI) m/z 386.3 (M+NH4)⁺

212. 2-[6-[(3,4-difluorophenyl)methoxy]tetralin-2-yl]oxyacetic acid

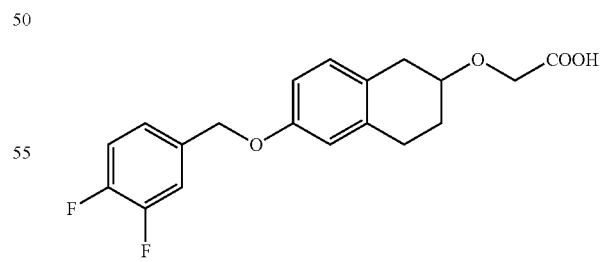

¹H NMR (400 MHz, DMSO-d₆) δ 7.55-7.36 (m, 2H), 7.33-7.22 (m, 1H), 6.97 (d, J=8.2 Hz, 1H), 6.77-6.68 (m, 2H), 5.02 (s, 2H), 3.88 (s, 2H), 3.78 (s, 1H), 2.91 (dd, J=16.2, 4.9 Hz, 1H), 2.79 (dt, J=17.0, 6.1 Hz, 1H), 2.62 (td, J=16.7, 7.4 Hz, 2H), 1.98-1.90 (m, 1H), 1.75-1.61 (m, 1H).

MS (APCI) m/z 366.2 (M+NH4)⁺

213. 2-[6-[[3-(trifluoromethyl)phenyl]methoxy]tetralin-2-yl]oxyacetic acid

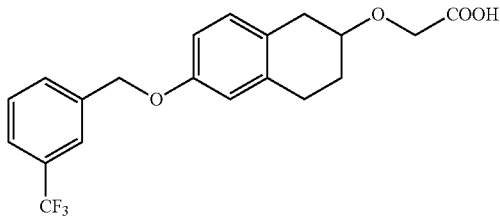 [SMILES: O=C(O)COC1CCc2cc(OCc3cccc(C(F)(F)F)c3)ccc2C1]

¹H NMR (400 MHz, DMSO-d₆) δ 7.75 (d, J=9.9 Hz, 1H), 7.69 (s, 1H), 7.67-7.61 (m, 1H), 6.98 (d, J=8.4 Hz, 1H), 6.80-6.72 (m, 2H), 5.13 (s, 2H), 3.98 (s, 2H), 3.78 (s, 1H), 2.92 (dd, J=16.2, 4.8 Hz, 1H), 2.79 (dt. J=16.9, 6.2 Hz, 1H), 2.71-2.59 (m, 2H), 1.92 (s, 1H), 1.70 (ddd, J=13.7, 11.0, 6.8 Hz, 1H).

MS (APCI) m/z 398.2 (M+NH4)⁺

214. 2-[6-[(4-fluorophenyl)methoxy]tetralin-2-yl]oxyacetic acid

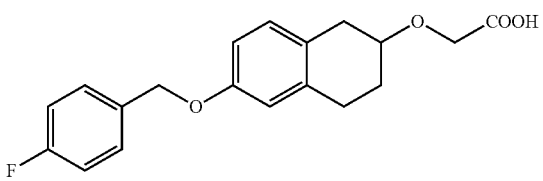 [SMILES: O=C(O)COC1CCc2cc(OCc3ccc(F)cc3)ccc2C1]

¹H NMR (400 MHz, DMSO-d₆) δ 7.52-7.43 (m, 2H), 7.25-7.16 (m, 2H), 6.96 (d, J=8.4 Hz, 1H), 6.77-6.68 (m, 2H), 5.00 (s, 2H), 3.85 (s, 2H), 3.76 (s, 1H), 2.91 (dd, J=16.1, 4.8 Hz, 1H), 2.84-2.75 (m, 1H), 2.62 (td, J=17.2, 16.3, 7.2 Hz, 2H), 1.98-1.88 (m, 1H), 1.69 (ddt, J=12.5, 8.2, 4.3 Hz, 1H).

MS (APCI) m/z 348.2 (M+NH4)⁺

215. 2-[6-[(2-fluorophenyl)methoxy]tetralin-2-yl]oxyacetic acid

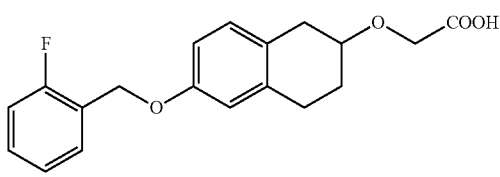 [SMILES: O=C(O)COC1CCc2cc(OCc3ccccc3F)ccc2C1]

¹H NMR (400 MHz, DMSO-d₆) δ 7.51 (td, J=7.5, 1.8 Hz, 1H), 7.40 (tdd, J=7.8, 5.5, 1.9 Hz, 1H), 7.29-7.18 (m, 2H), 6.97 (d, J=8.3 Hz, 1H), 6.79-6.69 (m, 2H), 5.05 (s, 2H), 3.83 (s, 2H), 3.77 (d, J=7.6 Hz, 1H), 2.96-2.89 (m, 1H), 2.87-2.76 (m, 1H), 2.62 (td. J=16.6, 14.7, 7.4 Hz, 2H), 2.00-1.90 (m, 1H), 1.74-1.63 (m, 1H).

MS (APCI) m/z 348.2 (M+NH4)⁺

216. 2-[[6-[(2-chloro-6-ethyl-phenyl)methoxy]tetralin-2-yl]amino]-N-methoxy-N-methyl-acetamide

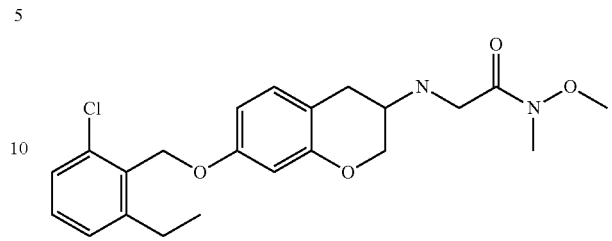

A mixture of 2-((6-((2-chloro-6-ethylbenzyl)oxy)-1,2,3,4-tetrahydronaphthalen-2-yl)amino)acetic acid (0.235 g, 0.629 mmol), N,O-dimethylhydroxylamine hydrochloride (0.074 g, 0.754 mmol), EDC (0.145 g, 0.754 mmol), HOBT (0.116 g, 0.754 mmol), TEA (0.105 ml, 0.754 mmol) and N-methylmorpholine (0.014 ml, 0.126 mmol) in 10 ml DCM was stirred overnight at room temperature and subsequently concentrated under vacuum. The residue was purified by chromatography (silica gel) giving the desired compound with a yield of 98 mg.

¹H NMR (300 MHz, Methanol-d₄) δ 7.35-7.20 (m, 3H), 7.10-7.00 (m, 1H), 6.80-6.72 (m, 2H), 5.18 (s, 2H), 3.78 (s, 3H), 3.72 (s, 2H), 3.22 (s, 3H), 3.10-2.80 (m, 4H), 2.75 (q, 2H), 2.65-2.50 (m, 1H), 2.18-2.08 (m, 3H), 1.70-1.55 (m, 1H), 1.22 (t, 3H)

217. 1-[6-[(2-chloro-6-ethyl-phenyl)methoxy]tetralin-2-yl]-N-methoxy-N-methyl-azetidine-3-carboxamide

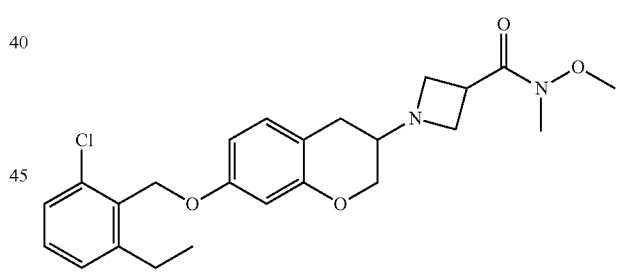

A mixture of N,O-dimethylhydroxylamine hydrochloride (0.195 g, 2.000 mmol) and N-ethyl-N-isopropylpropan-2-amine (0.517 g, 4.00 mmol) in 6 ml DMF was added to a solution of 1-(6-((2-chloro-6-ethylbenzyl)oxy)-1,2,3,4-tetrahydronaphthalen-2-yl)azetidine-3-carboxylic acid (0.4 g, 1.000 mmol) and 2-(3H-[1,2,3]triazolo[4,5-b]pyridin-3-yl)-1,1,3,3-tetramethyluronium hexafluorophosphate(V) (0.761 g, 2.000 mmol). The reaction mixture was stirred over night at room temperature, the concentrated under vacuum and subsequently purified to afford 214 mg of the desired product as off-white solid.

¹H NMR (400 MHz, Methanol-d₄) δ 7.30-7.15 (m, 3H), 7.00-6.95 (m, 1H), 6.80-6.70 (m, 2H), 5.10 (s, 2H), 3.78 (s, 2H), 3.70 (s, 3H), 3.18 (s, 3H), 2.90-2.70 (m, 5H), 2.65-2.55 (m, 1H), 2.42-2.32 (m, 1H), 1.95-1.85 (m, 1H), 1.50-1.35 (m, 1H), 1.20 (t, 3H)

218. 2-[[6-[(2-chloro-6-ethyl-phenyl)methoxy]tetralin-2-yl]amino]-N-methoxy-acetamide

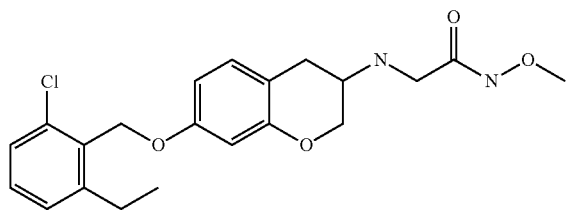 [SMILES: CCc1cccc(Cl)c1COc1ccc2c(c1)OCC(NCC(=O)NOC)C2]

Compound 218 was prepared as described for Compound 216 using O-methylhydroxylamine hydrochloride instead of N,O-dimethylhydroxylamine hydrochloride.

$^1$H NMR (300 MHz, DMSO-d$_6$) δ 7.40-7.22 (m, 3H), 7.10-7.00 (m, 1H), 6.85-6.80 (m, 2H), 5.10 (s, 2H), 3.75 (s, 2H), 3.65 (s, 3H), 3.15-3.00 (m, 1H), 2.90-2.75 (m, 2H), 3.70 (q, 2H), 2.65-2.50 (m, 1H), 2.30-2.15 (m, 1H), 1.85-1.65 (m, 1H), 1.12 (t, 3H)

219. 1-[6-[(2-chloro-6-ethyl-phenyl)methoxy]tetralin-2-yl]-N-methoxy-azetidine-3-carboxamide

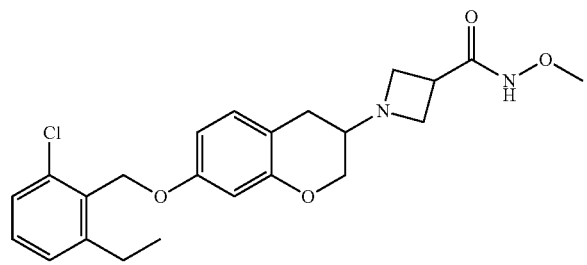 [SMILES: CCc1cccc(Cl)c1COc1ccc2c(c1)OCC(N1CC(C(=O)NOC)C1)C2]

Compound 219 was prepared as described for Compound 217 using O-methylhydroxylamine hydrochloride instead of N,O-dimethylhydroxylamine hydrochloride.

$^1$H NMR (400 MHz, Methanol-d$_4$) δ 7.30-7.15 (m, 3H), 7.00-6.95 (m, 1H), 6.80-6.70 (m, 2H), 5.10 (s, 2H), 3.75-3.60 (m, 5H), 3.55-3.40 (s, br, 1H), 3.25-3.15 (m, 1H), 2.90-2.60 (m, 6H), 2.42-2.32 (m, 1H), 1.95-1.85 (m, 1H), 1.50-1.35 (m, 1H), 1.20 (t, 3H)

220. 5-[[[6-[(2-chloro-6-ethyl-phenyl)methoxy]tetralin-2-yl]amino]methyl]isoxazol-3-one

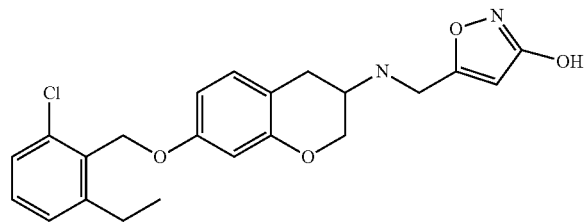 [SMILES: CCc1cccc(Cl)c1COc1ccc2c(c1)OCC(NCc1cc(O)no1)C2]

To a solution of 6-((2-chloro-6-ethylbenzyl)oxy)-3,4-dihydronaphthalen-2(1H)-one (0.2483 g, 0.789 mmol) 10 ml DCM was added 5-(aminomethyl)isoxazol-3(2H)-one hydrobromide (0.308 g, 1.577 mmol) and acetic acid (0.047 g, 0.789 mmol). After stirring at RT for 4 h. sodium triacetoxyhydroborate (0.201 g, 0.946 mmol) was added to the solution. The reaction mixture was further stirred overnight at RT and concentrated under vacuum. The crude product was purified by chromatography (silica gel) affording the desired product.

$^1$H NMR (300 MHz, Methanol-d$_4$) δ 7.35-7.20 (m, 3H), 7.15-7.05 (m, 1H), 6.90-6.80 (m, 2H), 6.22 (s, 1H), 5.18 (s, 2H), 4.25 (s, 2H), 3.65-3.50 (m, 1H), 3.25-3.20 (m, 4H), 3.00-2.80 (m, 3H), 2.75 (q, 2H), 2.50-2.35 (m, 1H), 1.95-1.80 (m, 1H), 1.22 (t, 3H)

221 1-[6-bromo-7-[(2,6-dichlorophenyl)methoxy]chroman-3-yl]azetidine-3-carboxylic acid

221.1 6-bromo-7-hydroxychroman-3-one (Regioisomers Mixture)

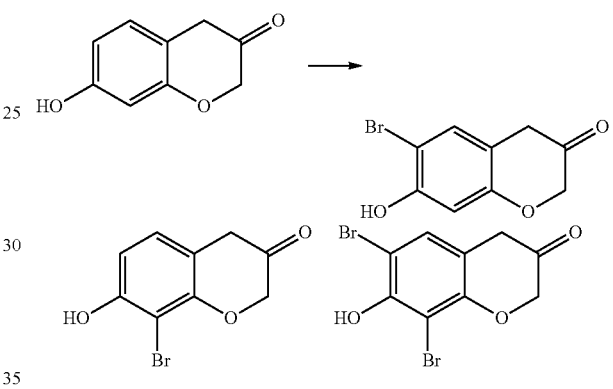

Bromine (3.1 mmol, 487 mg) was added dropwise at 5° C. to a solution of 7-hydroxychroman-3-one (3.1 mmol, 500 mg) and sodium acetate (6.1 mmol, 500 mg, 80% in acetic acid (10 ml). The mixture was stirred at 0° C. for 2 h and then 12 h at rt. It was poured onto cold 5% aq. K$_2$CO$_3$ (20 ml) and extracted three-times with ethyl acetate (20 ml each); the organic phases were combined and washed with water three-times (20 ml each) and dried upon Na2SO$_4$, filtered and evaporated. It was purified on silica gel (eluent: 5-100% EtOAc in heptane).

yield: 180 mg (the mixture of regioisomeres was used in the next step without further purification).

221.2 1-[6-bromo-7-[(2,6-dichlorophenyl)methoxy]chroman-3-yl]azetidine-3-carboxylic acid

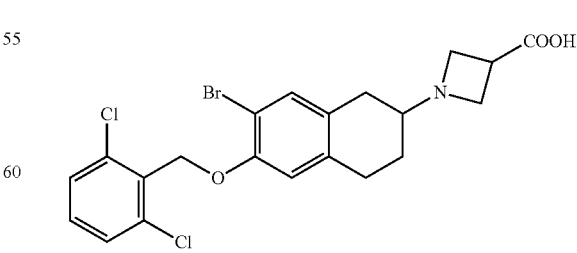

Compound 221 was prepared subsequently as described for compound 1
ESI-MS: [M+H+]=488.0.

222. 1-[7-[(2,6-dichlorophenyl)methoxy]-6-methyl-chroman-3-yl]azetidine-3-carboxylic acid 222.1 Methyl 1-(7-((2,6-dichlorobenzyl)oxy)-6-methylchroman-3-yl)azetidine-3-carboxylate

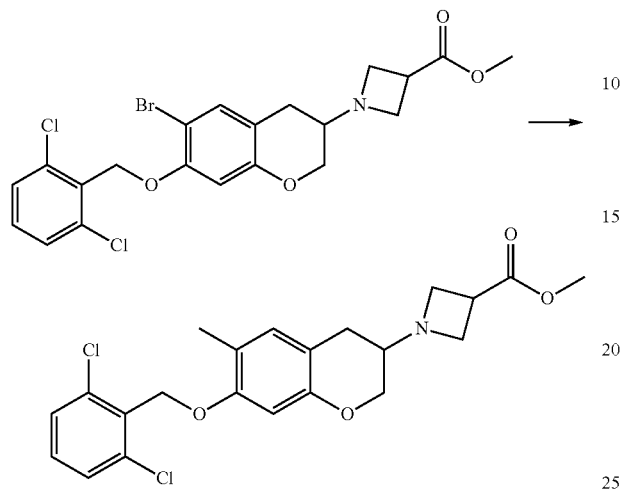

Prepared from methyl 1-(6-bromo-7-((2,6-dichlorobenzyl)oxy)chroman-3-yl)azetidine-3-carboxylate according to J. R. Merritt et al, Journal of Medicinal Chemistry, 52(5), 1295-1301; 2009 (intermediate 7j, s, supporting information S4): Pd catalyzed methylation using trimethylboroxine.

222.2 1-[7-[(2,6-dichlorophenyl)methoxy]-6-methyl-chroman-3-yl]azetidine-3-carboxylic acid

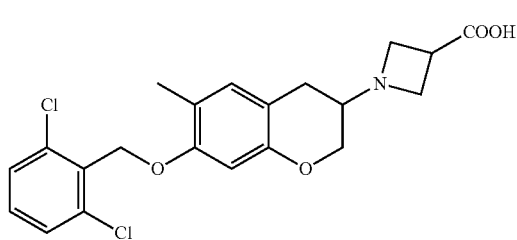 [SMILES: Cc1cc2c(cc1OCc1c(Cl)cccc1Cl)OCC(N1CC(C(=O)O)C1)C2]

Compound 222 was prepared subsequently from 222.1 by hydrolysis of methylester
ESI-MS: 424.1, [M+]=422.1, 402.2.

223 1-[7-[(2,6-dichlorophenyl)methoxy]-6-fluoro-chroman-4-yl]azetidine-3-carboxylic acid

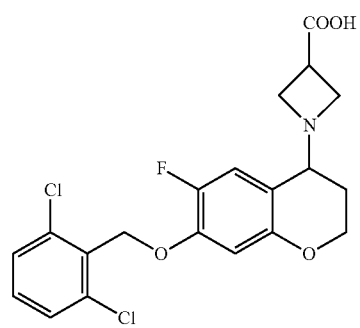 [SMILES: O=C(O)C1CN(C2CCOc3cc(OCc4c(Cl)cccc4Cl)c(F)cc32)C1]

Compound 223 was prepared as described for compound 1 starting from commercially available from 6-fluoro-7-hydroxychroman-4-one
ESI-MS: 428.2, [M+]=426.2, 325.2.

224 2-[1-[7-[(2,6-dichlorophenyl)methoxy]isochroman-4-yl]azetidin-3-yl]acetic acid

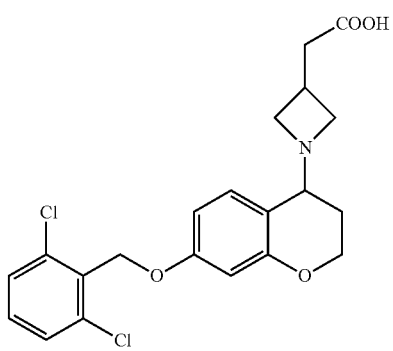 [SMILES: O=C(O)CC1CN(C2CCOc3cc(OCc4c(Cl)cccc4Cl)ccc32)C1]

Compound 224 was prepared as described for compound 1 starting from methyl 2-(azetidin-3-yl)acetate hydrochloride and 7-hydroxyisochroman-4-one
ESI-MS: 424.20, [M+]=422.2.

225 1-[8-[(2,6-dichlorophenyl)methoxy]chroman-3-yl]azetidine-3-carboxylic acid

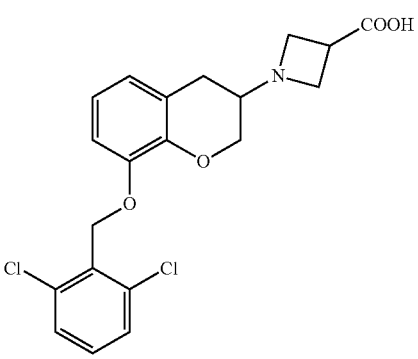 [SMILES: O=C(O)C1CN(C2COc3c(cccc3OCc3c(Cl)cccc3Cl)C2)C1]

Compound 225 was prepared as described for compound 1 starting from 8-methoxychroman-3-one
ESI-MS: 410.20, [M+]=408.20.

226 1-(7-phenethyloxychroman-3-yl)azetidine-3-carboxylic acid

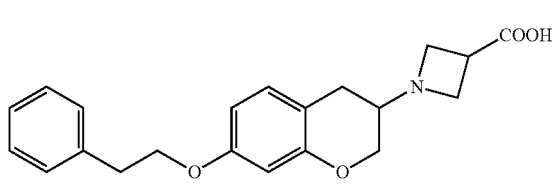 [SMILES: O=C(O)C1CN(C2COc3cc(OCCc4ccccc4)ccc3C2)C1]

Compound 226 was prepared as described for compound 69
ESI-MS: [M+H+]=354.25.

227 1-[7-[2-(2-chlorophenyl)ethoxy]chroman-3-yl]azetidine-3-carboxylic acid

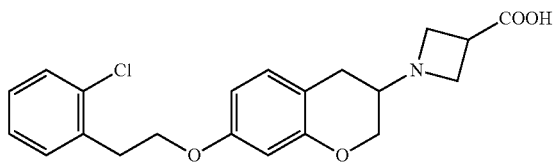 [SMILES: O=C(O)C1CN(C2COc3cc(OCCc4ccccc4Cl)ccc3C2)C1]

Compound 227 was prepared as described for compound 69
ESI-MS: [2M+H+]=775.30; [M+H+]=388.20.

228 1-[7-[2-(4-chlorophenyl)ethoxy]chroman-3-yl]azetidine-3-carboxylic acid

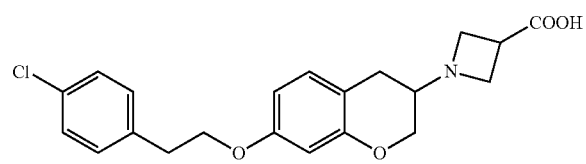 [SMILES: O=C(O)C1CN(C2COc3cc(OCCc4ccc(Cl)cc4)ccc3C2)C1]

Compound 228 was prepared as described for compound 69
ESI-MS: [M+H+]=388.20.

229 1-[7-(2,6-dichlorophenoxy)chroman-3-yl]azetidine-3-carboxylic acid

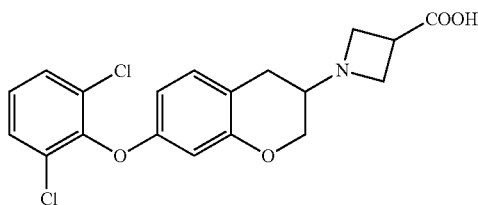 [SMILES: O=C(O)C1CN(C2COc3cc(Oc4c(Cl)cccc4Cl)ccc3C2)C1]

229.1 Methyl 1-(7-(2,6-dichlorophenoxy)chroman-3-yl)azetidine-3-carboxylate

Potassium carbonate (0.18 mmol, 25 mg) was added to a solution of methyl 1-(7-hydroxychroman-3-yl)azetidine-3-carboxylate (0.1 mol, 30 mg) and 1,3-dichloro-2-fluorobenzene (0.11, 19 mg) in DMF (4 ml). It was then heated for 22 h at 100° C. in the microwave (Biotage). At room temperature, the reaction mixture was diluted with ethyl acetate (20 ml) and then poured into cold 5% aq. K2CO3 (80 mL) and extracted three-times with ethyl acetate (80 mL each). The organic phases were combined and washed with 50 mL water, dried with Na2SO4, filtered and evaporated. The residue was passed through a WATERS XBRIDGE C18 OBD column (HPLC) with a gradient [water/acetonitrile (80/20 to 0/100)]/0.1% TFA (see also WO 2012/004378)
Yield 10 mg (22%).

229.2 1-(7-(2,6-dichlorophenoxy)chroman-3-yl)azetidine-3-carboxylic acid

The methyl ester was saponified using 2N aqueous NaOH in standard conditions; yield 52%, 90% purity
ESI-MS: 396.10, [M+]=394.15.

230 1-[7-(cyclobutylmethoxy)chroman-3-yl]azetidine-3-carboxylic acid

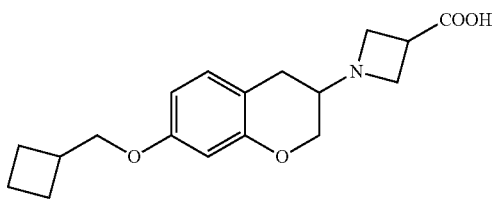 [SMILES: O=C(O)C1CN(C2COc3cc(OCC4CCC4)ccc3C2)C1]

Compound 230 was prepared as described in analogy to compound 1
1H NMR (600 MHz, DMSO-d6) δ 6.98 (d, 1H), 6.52 (dd, 1H), 6.39 (dd, 1H), 4.29-4.06 (m br., 6H), 3.88 (dt, 2H), 3.52 (t, 2H), 3.04 (dd, 1H), 2.67 (hept, 2H), 2.05 (dddd, 2H), 1.89 (m sym., 2H), 1.79 (m sym., 2H).

231 1-[7-(cyclopropylmethoxy)chroman-3-yl]azetidine-3-carboxylic acid

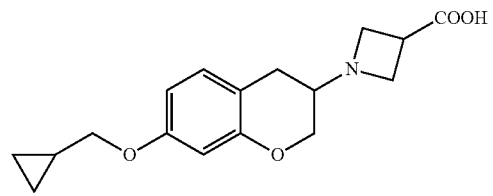 [SMILES: O=C(O)C1CN(C2COc3cc(OCC4CC4)ccc3C2)C1]

Compound 231 was prepared as described in analogy to compound 1
1H NMR (600 MHz, DMSO-d6) δ 6.96 (d, 1H), 6.51 (m sym., 1H), 6.36 (s, 1H), 4.09 (s br., 6H), 3.73 (q, 3H), 2.96 (m br., 1H), 2.59 (m sym., 1H), 1.15 (td, 1H), 0.54 (dt, 2H), 0.27 (dt, 2H).

232 1-(8-phenethyloxychroman-3-yl)azetidine-3-carboxylic acid

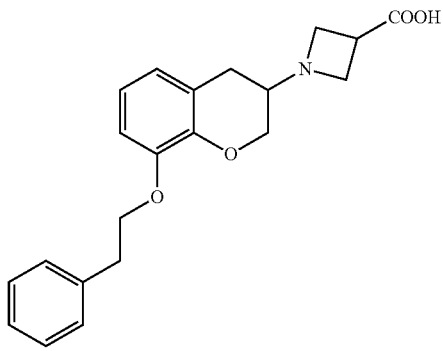 [SMILES: O=C(O)C1CN(C2COc3c(cccc3OCCc3ccccc3)C2)C1]

Compound 232 was prepared as described for compound 69 starting from 8-methoxychroman-3-one 1H NMR (600 MHz, DMSO-d6) δ 7.30 (sext., 4H), 7.20 (t, 1H), 6.75 (d, 1H), 6.68 (t, 1H), 6.58 (d, 1H), 4.10 (oct., 2H), 3.99 (d, 1H), 3.78-2.97 [m, incl. 3.70 (m sym., 1H), 3.18 (td, 2H), 3.05 (t, 2H), & H2O], 2.85 (quint., 1H), 2.76 (m, 1H), 2.39 (m, 1H), 1.32-1.08 (m br., 2H); other aliphatic H were partly covered by DMSO.

ESI-MS: [M+H+]=354.20.

233 ((7-((2-chloro-6-ethylbenzyl)oxy)chroman-3-yl)oxy)acetic acid

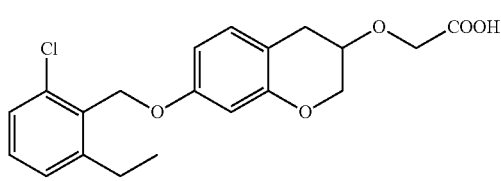 [SMILES: CCc1cccc(Cl)c1COc1ccc2c(c1)OCC(OCC(=O)O)C2]

233.1 7-((2-chloro-6-ethylbenzyl)oxy)chroman-3-ol

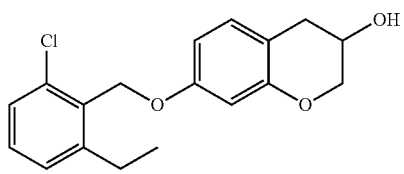 [SMILES: CCc1cccc(Cl)c1COc1ccc2c(c1)OCC(O)C2]

2-(bromomethyl)-1-chloro-3-ethylbenzene (141 mg, 0.6 mmol) was added to a suspension of chroman-3,7-diol (100 mg, 0.6 mmol) and potassium carbonate (332 mg, 2.4 mmol) in acetone. The mixture was heated 1.5 h to reflux, subsequently concentrated under vacuum and the residue distributed between water and ethyl acetate. The organic layer was dried (MgSO₄), filtered and purified by chromatography (silica gel) to afford 103 mg of desired product.

233.2 Ethyl 2-((7-((2-chloro-6-ethylbenzyl)oxy)chroman-3-yl)oxy)acetate

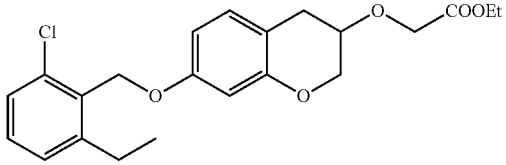 [SMILES: CCOC(=O)COC1COc2cc(OCc3c(Cl)cccc3CC)ccc2C1]

7-((2-chloro-6-ethylbenzyl)oxy)chroman-3-ol (90 mg, 0.3 mmol) in 1.5 ml DMF was added to a suspension of sodium hydride in 0.5 ml DMF. After stirring for 40 min at RT ethyl 2-bromoacetate (71 mg, 0.4 mmol) was added and the resulting mixture stirred for further 2 h at 40° C. The reaction was concentrated under vacuum and distributed among ethyl acetate and sat. ammonium chloride. The organic layer was dried, filtered, concentrated under vacuum and the residue purified by chromatography (silica gel), affording 86 mg of desired product.

233.3 2-((7-((2-chloro-6-ethylbenzyl)oxy)chroman-3-yl)oxy)acetic acid

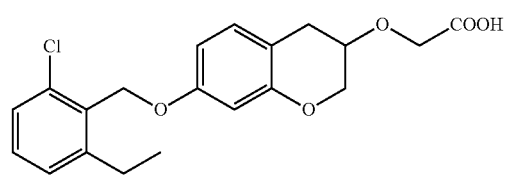 [SMILES: CCc1cccc(Cl)c1COc1ccc2c(c1)OCC(OCC(=O)O)C2]

The ethyl ester (83 mg) was saponified using 2N aqueous NaOH in standard conditions; yield 67 mg ¹H NMR (600 MHz, DMSO-d₆) δ 7.39-7.33 (m, 2H), 7.28 (dd, J=6.0, 3.0 Hz, 1H), 6.98 (d, J=8.4 Hz, 1H), 6.56-6.53 (m, 1H), 6.47 (d, J=2.6 Hz, 1H), 5.08 (s, 2H), 4.15 (s, 2H), 4.13-4.08 (m, 2H), 3.99-3.94 (m, 1H), 2.97 (dd, J=16.2, 4.7 Hz, 1H), 2.76-2.71 (m, 1H), 2.71 (q, J=7.5 Hz, 3H), 1.16 (t, J=7.5 Hz, 4H).

234 2-((7-((3-chloro-2,6-difluorobenzyl)oxy)chroman-3-yl)oxy)acetic acid

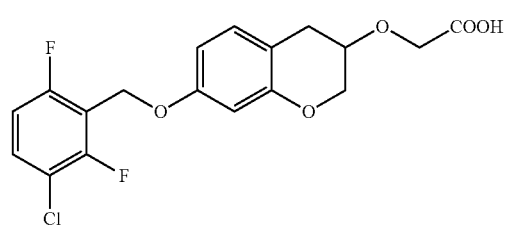 [SMILES: O=C(O)COC1COc2cc(OCc3c(F)ccc(Cl)c3F)ccc2C1]

Compound 234 was prepared in analogy to compound 233

¹H NMR (600 MHz, DMSO-d₆) δ 7.73 (td, J=8.7, 5.7 Hz, 1H), 7.27 (td, J=8.9, 1.6 Hz, 1H), 6.98 (d, J=8.4 Hz, 1H), 6.52 (dd, J=8.3, 2.6 Hz, 1H), 6.44 (d, J=2.6 Hz, 1H), 5.07 (s, 2H), 4.14 (s, 2H), 4.11-4.06 (m, 2H), 3.95 (qd, J=4.7, 2.8 Hz, 1H), 2.95 (dd, J=16.3, 4.7 Hz, 1H), 2.72 (dd, J=16.4, 5.0 Hz, 1H).

235 ((7-((2-fluoro-6-cyclopropylbenzyl)oxy)chroman-3-yl)oxy)acetic acid

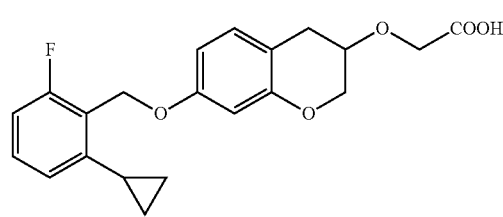 [SMILES: O=C(O)COC1COc2cc(OCc3c(F)cccc3C3CC3)ccc2C1]

Compound 235 was prepared in analogy to compound 233

¹H NMR (600 MHz, DMSO-d₆) δ 7.32 (td, J=8.0, 6.0 Hz, 1H), 7.05 (ddd, J=9.5, 8.2, 1.1 Hz, 1H), 6.97 (d, J=8.3 Hz, 1H), 6.85 (dd, J=7.8, 0.9 Hz, 1H), 6.55 (dd, J=8.4, 2.6 Hz, 1H), 6.47 (d, J=2.6 Hz, 1H), 5.15 (s, 2H), 4.13 (s, 2H), 4.12-4.06 (m, 2H), 3.95 (qd, J=4.7, 2.9 Hz, 1H), 2.99-2.92

(m, 1H), 2.72 (dd, J=16.3, 5.0 Hz, 1H), 2.04 (tt, J=8.4, 5.3 Hz, 1H), 0.96-0.91 (m, 2H), 0.71-0.66 (m, 2H).

236 2-((6-((2-chloro-6-ethylbenzyl)oxy)-1,2,3,4-tetrahydronaphthalen-2-yl)amino)acetohydroxamic acid

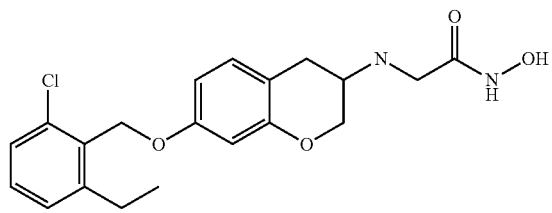 [SMILES: CCc1cccc(Cl)c1COc1ccc2c(c1)OCC(NCC(=O)NO)C2]

236.1 3-(6-((2-chloro-6-ethylbenzyl)oxy)-1,2,3,4-tetrahydronaphthalen-2-yl)oxazolidine-2, 5-dione

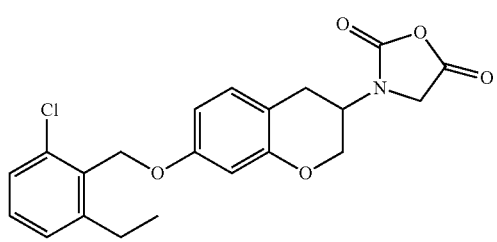 [SMILES: CCc1cccc(Cl)c1COc1ccc2c(c1)OCC(N1CC(=O)OC1=O)C2]

To a solution of 2-((6-((2-chloro-6-ethylbenzyl)oxy)-1,2,3,4-tetrahydronaphthalen-2-yl)amino)acetic acid (0.57 g, 1.525 mmol) in 10 ml THF was added under nitrogen bis(trichloromethyl) carbonate (0.181 g, 0.610 mmol) and stirred for 4 h at 50° C. The reaction mixture was concentrated. The residue was for the next step directly.

236.2 2-((6-((2-chloro-6-ethylbenzyl)oxy)-1,2,3,4-tetrahydronaphthalen-2-yl)amino)acetohydroxamic acid

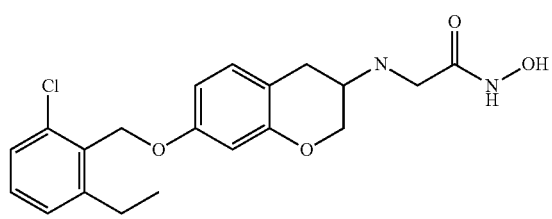 [SMILES: CCc1cccc(Cl)c1COc1ccc2c(c1)OCC(NCC(=O)NO)C2]

Hydroxylamine hydrochloride (0.318 g, 4.58 mmol) and triethylamine (0.309 g, 3.05 mmol) were added to a solution of 3-(6-((2-chloro-6-ethylbenzyl)oxy)-1,2,3,4-tetrahydronaphthalen-2-yl)oxazolidine-2,5-dione 10 ml DMF and the resulting mixture, was stirred overnight at 50° C. The reaction was concentrated under vacuum and the crude product was purified by chromatography (silica gel) affording 38.8 mg of desired product.

$^1$H NMR (300 MHz, Methanol-$d_4$) δ 7.35-7.20 (m, 3H), 7.10-7.00 (m, 1H), 6.80-6.72 (m, 2H), 5.18 (s, 2H), 3.87 (s, 1H), 3.65-3.50 (m, 1H), 3.28-3.15 (m, 1H), 3.00-2.65 (m, 5H), 2.40-2.25 (m, 1H), 1.95-1.75 (m, 1H), 1.22 (t, 3H).

237 2-((7-(4-(benzyloxy)phenyl)chroman-3-yl)amino)acetic acid

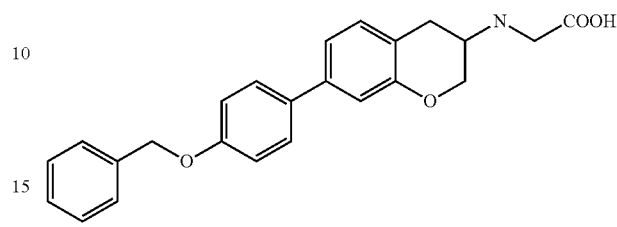

Compound 237 was prepared as described for compound 54.1 using methyl 2-aminoacetate hydrochloride instead of methylazetine-3-carboxylate hydrochloride.

$^1$H NMR (600 MHz, DMSO-$d_6$) δ 7.58-7.53 (m, 2H), 7.49-7.44 (m, 2H), 7.40 (dd, J=8.3, 6.8 Hz, 2H), 7.36-7.31 (m, 1H), 7.13-7.08 (m, 2H), 7.08-7.04 (m, 2H), 6.97 (d, J=1.6 Hz, 1H), 5.14 (s, 2H), 4.24 (ddd, J=10.7, 2.9, 1.6 Hz, 1H), 3.87 (dd, J=10.8, 7.5 Hz, 1H), 3.01 (dd, J=16.1, 5.2 Hz, 1H), 2.67 (dd, J=16.3, 7.7 Hz, 1H).

238 2-((7-(4-(benzyloxy)phenyl)chroman-3-yl)(methyl)amino)acetic acid

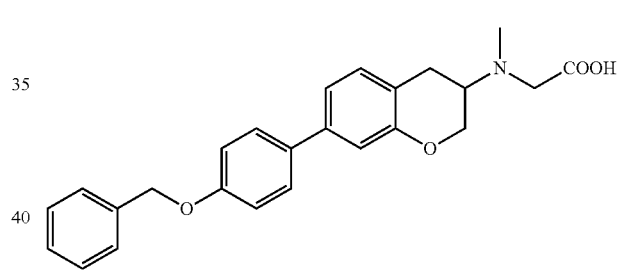

Compound 238 was prepared as described for compound 54.1 using methyl 2-(methylamino)acetate hydrochloride instead of methylazetine-3-carboxylate hydrochloride.

$^1$H NMR (600 MHz, DMSO-$d_6$) δ 7.56-7.52 (m, 2H), 7.49-7.44 (m, 2H), 7.40 (dd, J=8.4, 6.8 Hz, 2H), 7.36-7.31 (m, 1H), 7.13 (d, J=7.9 Hz, 1H), 7.10-7.03 (m, 3H), 6.96 (d, J=1.8 Hz, 1H), 5.14 (s, 2H), 4.29 (dt, J=10.6, 2.6 Hz, 1H), 3.91 (dd, J=10.9, 8.1 Hz, 1H), 3.20-3.15 (m, 1H), 2.91 (ddd, J=16.3, 5.0, 1.7 Hz, 1H), 2.79 (dd, J=16.1, 8.8 Hz, 1H), 2.43 (s, 3H).

Pure enantiomers of ((7-((2-chloro-6-ethylbenzyl)oxy)chroman-3-yl)oxy)acetic acid (Compounds 239 and 240)

Compounds 239 and 240 are the pure enantiomers of compound 233. The racemate was separated as ethyl esters by SFC and subsequently hydrolyzed to the free acid.

Separation of rac-ethyl 2-((6-((2-chloro-6-ethylbenzyl)oxy)-1,2,3,4-tetrahydronaphthalen-2-yl)oxy)acetate by preparative SFC:

Two peaks were separated on a YMC Amylose-C column (20×250, 5 μm), at a total flow of 100 ml/min, isocratic, at 30° C. ($t_R$ [min]=3.3, 3.8). The mobile phase consisted of 90% CO$_2$ and 10% modifier which was methanol with addition of 0.2% aqueous ammonia solution.
Enantiomer 1 (Peak A, Compound 239.1) was Hydrolyzed to Enantiomerically Pure acid as Described for Compound 233

$^1$H NMR (600 MHz, Chloroform-d) δ 7.29 (dd, J=8.0, 1.4 Hz, 1H), 7.24 (t, J=7.8 Hz, 1H), 7.17 (dd, J=7.6, 1.4 Hz, 1H), 7.04 (d, J=8.3 Hz, 1H), 6.83 (dd, J=8.4, 2.7 Hz, 1H), 6.77 (d, J=2.6 Hz, 1H), 5.14 (s, 2H), 4.24 (d, J=16.4 Hz, 1H), 4.21 (d, J=16.4 Hz, 1H), 3.96-3.91 (m, 1H), 3.10-3.05 (m, 1H), 2.96 (dt, J=17.0, 6.0 Hz, 1H), 2.86-2.79 (m, 2H), 2.76 (q, J=7.6 Hz, 2H), 2.14-2.08 (m, 1H), 1.96-1.88 (m, 1H), 1.24 (t, J=7.6 Hz, 3H).

Enantiomer 2 (Peak B, Compound 240.1) was Hydrolyzed to Enantiomerically Pure acid as Described for Compound 233

$^1$H NMR (600 MHz, Chloroform-d) δ 7.29 (dd, J=8.0, 1.4 Hz, 1H), 7.24 (t, J=7.8 Hz, 1H), 7.17 (dd, J=7.6, 1.4 Hz, 1H), 7.04 (d, J=8.4 Hz, 1H), 6.84 (dd, J=8.4, 2.7 Hz, 1H), 6.77 (d, J=2.6 Hz, 1H), 5.14 (s, 2H), 4.25 (d, J=16.5 Hz, 1H), 4.21 (d, J=16.4 Hz, 1H), 3.96-3.91 (m, 1H), 3.08 (dd, J=16.0, 4.9 Hz, 1H), 2.99-2.92 (m, 1H), 2.86-2.79 (m, 2H), 2.76 (q, J=7.6 Hz, 2H), 2.14-2.08 (m, 1H), 1.95-1.88 (m, 1H), 1.24 (t, J=7.6 Hz, 3H).

TABLE 1

| No | Name | S1P5 EC50 range # | S1P1 EC50 | S1P3 EC50 | S1P4 EC50 |
|---|---|---|---|---|---|
| 1 | 1-(7-((2,6-dichlorobenzyl)oxy)chroman-3-yl)azetidine-3-carboxylic acid | A | >1 μM | >1 μM | >1 μM |
| 2 | 1-(6-((2-chloro-6-ethylbenzyl)oxy)-1,2,3,4-tetrahydronaphthalen-2-yl)azetidine-3-carboxylic acid | | | | |
| 3 | 1-(7-((2-fluorobenzyl)oxy)chroman-3-yl)azetidine-3-carboxylic acid | D | >1 μM | | >1 μM |
| 4 | 1-(6-((2,6-dichlorobenzyl)oxy)-1,2,3,4-tetrahydronaphthalen-2-yl)azetidine-3-carboxylic acid | A | >1 μM | >1 μM | |
| 5 | 1-((6-((2-chloro-6-ethylbenzyl)oxy)-1,2,3,4-tetrahydronaphthalen-2-yl)amino)cyclopropanecarboxylic acid | A | >1 μM | >1 μM | <1 μM |
| 6 | 3-((6-((2-chloro-6-ethylbenzyl)oxy)-1,2,3,4-tetrahydronaphthalen-2-yl)amino)propanoic acid | A | <1 μM | >1 μM | |
| 7 | 3-((6-(benzyloxy)-1,2,3,4-tetrahydronaphthalen-2-yl)amino)propanoic acid | B | >1 μM | >1 μM | |
| 8 | 3-((6-((2-chlorobenzyl)oxy)-1,2,3,4-tetrahydronaphthalen-2-yl)amino)propanoic acid | A | >1 μM | >1 μM | <1 μM |
| 9 | 3-((6-((2,6-dichlorobenzyl)oxy)-1,2,3,4-tetrahydronaphthalen-2-yl)amino)propanoic acid | A | >1 μM | >1 μM | |
| 10 | 3-((7-((2,6-dichlorobenzyl)oxy)-1,2,3,4-tetrahydronaphthalen-2-yl)amino)propanoic acid | D | >1 μM | >1 μM | |
| 11 | 3-((6-((4-chlorobenzyl)oxy)-1,2,3,4-tetrahydronaphthalen-2-yl)amino)propanoic acid | D | >1 μM | >1 μM | |
| 12 | 3-((6-((2,6-dichlorophenyl)ethynyl)-1,2,3,4-tetrahydronaphthalen-2-yl)amino)propanoic acid | A | >1 μM | >1 μM | <1 μM |
| 13 | 3-((6-((2,6-dichlorophenyl)ethynyl)-1,2,3,4-tetrahydronaphthalen-2-yl)(methyl)amino)propanoic acid | A | >1 μM | >1 μM | <1 μM |
| 14 | 3-((6-((3,5-difluorophenyl)ethynyl)-1,2,3,4-tetrahydronaphthalen-2-yl)amino)propanoic acid | A | >1 μM | >1 μM | <1 μM |
| 15 | 3-((6-((3,5-difluorophenyl)ethynyl)-1,2,3,4-tetrahydronaphthalen-2-yl)(methyl)amino)propanoic acid | A | >1 μM | >1 μM | <1 μM |
| 16 | 3-((6-((2-chlorobenzyl)oxy)-1,2,3,4-tetrahydronaphthalen-2-yl)(methyl)amino)propanoic acid | C | >1 μM | >1 μM | <1 μM |
| 17 | 3-((6-((2-chloro-6-ethylbenzyl)oxy)-1,2,3,4-tetrahydronaphthalen-2-yl)(methyl)amino)propanoic acid | A | <1 μM | >1 μM | <1 μM |
| 18 | (E)-3-((6-(2,6-dichlorostyryl)-1,2,3,4-tetrahydronaphthalen-2-yl)amino)-propanoic acid | A | <1 μM | >1 μM | <1 μM |
| 19 | (E)-3-((6-styryl-1,2,3,4-tetrahydronaphthalen-2-yl)amino)propanoic acid | B | >1 μM | >1 μM | <1 μM |
| 20 | (E)-3-((6-(3-chlorostyryl)-1,2,3,4-tetrahydronaphthalen-2-yl)amino)-propanoic acid | A | >1 μM | >1 μM | <1 μM |

TABLE 1-continued

| No | Name | S1P5 EC50 range # | S1P1 EC50 | S1P3 EC50 | S1P4 EC50 |
|---|---|---|---|---|---|
| 21 | 3-((6-((2-chloro-6-cyclopropylbenzyl)oxy)-1,2,3,4-tetrahydronaphthalen-2-yl)amino)propanoic acid | D | >1 μM | >1 μM | >1 μM |
| 22 | methyl 2-(((2-chloro-6-ethylbenzyl)(6-((2-chloro-6-ethylbenzyl)oxy)-1,2,3,4-tetrahydronaphthalen-2-yl)amino)methyl)acrylate | D | >1 μM | >1 μM | >1 μM |
| 23 | 1-(7-((2-chloro-6-ethylbenzyl)oxy)chroman-3-yl)azetidine-3-carboxylic acid | A | >1 μM | >1 μM | <1 μM |
| 24 | 1-(7-((3-chlorobenzyl)oxy)chroman-3-yl)azetidine-3-carboxylic acid | D | >1 μM | >1 μM | >1 μM |
| 25 | 1-(7-((2-chloro-6-cyclopropylbenzyl)oxy)chroman-3-yl)azetidine-3-carboxylic acid | A | >1 μM | >1 μM | <1 μM |
| 26 | 1-(7-((2,3-difluorophenyl)ethynyl)chroman-3-yl)azetidine-3-carboxylic acid | B | >1 μM | | >1 μM |
| 27 | 1-(7-((3,5-difluorophenyl)ethynyl)chroman-3-yl)azetidine-3-carboxylic acid | A | >1 μM | >1 μM | <1 μM |
| 28 | 2-((6-((3,5-difluorophenyl)ethynyl)-1,2,3,4-tetrahydronaphthalen-2-yl)amino)acetic acid | A | >1 μM | >1 μM | <1 μM |
| 29 | 2-((6-((2,6-dichlorophenyl)ethynyl)-1,2,3,4-tetrahydronaphthalen-2-yl)amino)acetic acid | A | >1 μM | >1 μM | <1 μM |
| 30 | 2-((6-(cyclohexylethynyl)-1,2,3,4-tetrahydronaphthalen-2-yl)amino)acetic acid | A | >1 μM | >1 μM | <1 μM |
| 31 | 1-(6-((2,6-dichlorobenzyl)oxy)-1,2,3,4-tetrahydronaphthalen-2-yl)piperidine-4-carboxylic acid | A | <1 μM | >1 μM | <1 μM |
| 32 | 3-((6-((2,6-dichlorobenzyl)oxy)-1,2,3,4-tetrahydronaphthalen-2-yl)amino)bicyclo[1.1.1]pentane-1-carboxylic acid | A | >1 μM | >1 μM | <1 μM |
| 33 | 2-((6-((2,6-dichlorobenzyl)oxy)-1,2,3,4-tetrahydronaphthalen-2-yl)amino)propanoic acid | A | >1 μM | >1 μM | <1 μM |
| 34 | 2-((7-((2-chloro-6-ethylbenzyl)oxy)chroman-3-yl)amino)acetic acid | A | >1 μM | >1 μM | <1 μM |
| 35 | 2-((7-((2,6-dichlorobenzyl)oxy)chroman-3-yl)amino)acetic acid | C | >1 μM | >1 μM | <1 μM |
| 36 | 2-(6-((2,6-dichlorobenzyl)oxy)-1,2,3,4-tetrahydronaphthalen-2-yl)-2-azabicyclo[3.1.0]hexane-1-carboxylic acid | C | >1 μM | | >1 μM |
| 37 | 2-(6-((2,6-dichlorobenzyl)oxy)-1,2,3,4-tetrahydronaphthalen-2-yl)amino)-3-methylbutanoic acid | C | >1 μM | | >1 μM |
| 38 | 1-(7-((2,5-difluorophenyl)ethynyl)chroman-3-yl)azetidine-3-carboxylic acid | A | >1 μM | >1 μM | <1 μM |
| 39 | 1-(7-(cyclohexylethynyl)chroman-3-yl)azetidine-3-carboxylic acid | C | >1 μM | | >1 μM |
| 40 | 1-(7-((3-chlorophenyl)ethynyl)chroman-3-yl)azetidine-3-carboxylic acid | B | >1 μM | >1 μM | <1 μM |
| 41 | 1-(7-((2-(trifluoromethyl)phenyl)ethynyl)chroman-3-yl)azetidine-3-carboxylic acid | B | >1 μM | >1 μM | >1 μM |
| 42 | 1-(7-((2-(difluoromethoxy)phenyl)ethynyl)chroman-3-yl)azetidine-3-carboxylic acid | B | >1 μM | >1 μM | >1 μM |
| 43 | 1-(7-((3-(methyl)phenyl)ethynyl)chroman-3-yl)azetidine-3-carboxylic acid | C | >1 μM | | <1 μM |
| 44 | 1-(7-((2,6-dichlorophenyl)ethynyl)chroman-3-yl)azetidine-3-carboxylic acid | B | >1 μM | >1 μM | >1 μM |
| 45 | 1-(7-((4-ethoxyphenyl)ethynyl)chroman-3-yl)azetidine-3-carboxylic acid | C | <1 μM | | >1 μM |
| 46 | 1-(7-((4-chlorobenzyl)oxy)chroman-3-yl)azetidine-3-carboxylic acid | D | >1 μM | | >1 μM |
| 47 | 1-(7-((2,6-difluorophenyl)ethynyl)chroman-3-yl)azetidine-3-carboxylic acid | B | >1 μM | >1 μM | <1 μM |

TABLE 1-continued

| No | Name | S1P5 EC50 range # | S1P1 EC50 | S1P3 EC50 | S1P4 EC50 |
|---|---|---|---|---|---|
| 48 | 3-((7-((2,6-dichlorobenzyl)oxy)chroman-3-yl)amino)-bicyclo[1.1.1]pentane-1-carboxylic acid | B | >1 μM | >1 μM | >1 μM |
| 49 | 1-(((7-((2,6-dichlorobenzyl)oxy)chroman-3-yl)amino)methyl)cyclopropanecarboxylic acid | C | >1 μM | | <1 μM |
| 50 | 1-(7-((2,6-dichlorobenzyl)oxy)chroman-3-yl)pyrrolidine-3-carboxylic acid | A | >1 μM | >1 μM | >1 μM |
| 51 | 1-(7-((2,3-difluorobenzyl)oxy)chroman-3-yl)azetidine-3-carboxylic acid | | >1 μM | | >1 μM |
| 52 | 1-(7-((2,5-dichlorobenzyl)oxy)chroman-3-yl)azetidine-3-carboxylic acid | D | >1 μM | | >1 μM |
| 53 | 1-(7-((2-fluoro-6-methylbenzyl)oxy)chroman-3-yl)azetidine-3-carboxylic acid | C | >1 μM | | >1 μM |
| 54 | 1-(7-(4-((4-chlorobenzyl)oxy)phenyl)chroman-3-yl)azetidine-3-carboxylic acid | A | >1 μM | >1 μM | >1 μM |
| 55 | 1-(7-(4-(cyclohexylmethoxy)phenyl)chroman-3-yl)azetidine-3-carboxylic acid | A | <1 μM | >1 μM | >1 μM |
| 56 | 1-(7-(4-((2,3-difluorobenzyl)oxy)phenyl)chroman-3-yl)azetidine-3-carboxylic acid | B | <1 μM | >1 μM | >1 μM |
| 57 | 1-(7-((4-(trifluoromethyl)benzyl)oxy)chroman-3-yl)azetidine-3-carboxylic acid | D | >1 μM | | >1 μM |
| 58 | 1-(7-((3-methylbenzyl)oxy)chroman-3-yl)azetidine-3-carboxylic acid | D | >1 μM | | >1 μM |
| 59 | 1-(7-((3-(trifluoromethyl)benzyl)oxy)chroman-3-yl)azetidine-3-carboxylic acid | C | >1 μM | | <1 μM |
| 60 | 1-(7-((2,6-difluorobenzyl)oxy)chroman-3-yl)azetidine-3-carboxylic acid | | >1 μM | | >1 μM |
| 61 | 1-(7-((2-chloro-6-fluorobenzyl)oxy)chroman-3-yl)azetidine-3-carboxylic acid | C | >1 μM | | >1 μM |
| 62 | 1-(7-((2-(trifluoromethyl)benzyl)oxy)chroman-3-yl)azetidine-3-carboxylic acid | B | >1 μM | | >1 μM |
| 63 | 1-(7-((2-chlorobenzyl)oxy)chroman-3-yl)azetidine-3-carboxylic acid | C | >1 μM | | >1 μM |
| 64 | 1-(7-((2-ethylbenzyl)oxy)chroman-3-yl)azetidine-3-carboxylic acid | B | >1 μM | >1 μM | <1 μM |
| 65 | 1-(7-((2-ethyl-6-fluorobenzyl)oxy)chroman-3-yl)azetidine-3-carboxylic acid | A | >1 μM | >1 μM | <1 μM |
| 66 | 1-(7-((2-fluoro-6-(trifluoromethyl)benzyl)oxy)chroman-3-yl)azetidine-3-carboxylic acid | B | >1 μM | >1 μM | <1 μM |
| 67 | 1-(7-((2-cyclopropyl-6-fluorobenzyl)oxy)chroman-3-yl)azetidine-3-carboxylic acid | A | >1 μM | >1 μM | <1 μM |
| 68 | 1-(7-((2,4-dichlorobenzyl)oxy)chroman-3-yl)azetidine-3-carboxylic acid | C | >1 μM | >1 μM | >1 μM |
| 69 | 1-(7-((2,6-dichlorophenethoxy)chroman-3-yl)azetidine-3-carboxylic acid | B | >1 μM | >1 μM | <1 μM |
| 70 | 1-((6-((2,6-dichlorobenzyl)oxy)isochroman-1-yl)methyl)piperidine-4-carboxylic acid | B | >1 μM | >1 μM | <1 μM |
| 71 | 1-(7-((2-chloro-6-methylbenzyl)oxy)chroman-3-yl)azetidine-3-carboxylic acid | C | >1 μM | | >1 μM |
| 72 | 2-((7-((2-ethyl-6-fluorobenzyl)oxy)chroman-3-yl)(methyl)amino)acetic acid | A | >1 μM | | <1 μM |
| 73 | 2-((6-((2-chloro-6-ethylbenzyl)oxy)-1,2,3,4-tetrahydronaphthalen-2-yl)amino)acetic acid | A | <1 μM | >1 μM | <1 μM |
| 74 | 1-(6-((2,6-dichlorobenzyl)oxy)-1,2,3,4-tetrahydronaphthalen-2-yl)pyrrolidine-3-carboxylic acid | A | >1 μM | >1 μM | <1 μM |
| 75 | 2-((6-((2,6-dichlorobenzyl)oxy)-1,2,3,4-tetrahydronaphthalen-2-yl)amino)acetic acid | A | >1 μM | >1 μM | <1 μM |
| 76 | 1-(((6-((2-chloro-6-ethylbenzyl)oxy)-1,2,3,4-tetrahydronaphthalen-2- | A | <1 μM | | <1 μM |

TABLE 1-continued

| No | Name | S1P5 EC50 range # | S1P1 EC50 | S1P3 EC50 | S1P4 EC50 |
|---|---|---|---|---|---|
| | yl)amino)methyl)cyclopropanecarboxylic acid | | | | |
| 77 | (1s,3s)-3-((6-((2,6-dichlorobenzyl)oxy)-1,2,3,4-tetrahydronaphthalen-2-yl)amino)cyclobutanecarboxylic acid | A | <1 μM | >1 μM | <1 μM |
| 78 | 2-(1-(6-((2,6-dichlorobenzyl)oxy)-1,2,3,4-tetrahydronaphthalen-2-yl)azetidin-3-yl)acetic acid | A | >1 μM | >1 μM | <1 μM |
| 79 | (1r,3r)-3-((6-((2,6-dichlorobenzyl)oxy)-1,2,3,4-tetrahydronaphthalen-2-yl)amino)cyclobutanecarboxylic acid | A | <1 μM | >1 μM | <1 μM |
| 80 | 2-(1-(6-((2,6-dichlorobenzyl)oxy)-1,2,3,4-tetrahydronaphthalen-2-yl)pyrrolidin-3-yl)acetic acid | B | >1 μM | >1 μM | <1 μM |
| 81 | 1-(7-(3,5-difluorophenethyl)chroman-3-yl)azetidine-3-carboxylic acid | D | >1 μM | >1 μM | >1 μM |
| 82 | 3-(8-((2-chloro-6-ethylbenzyl)oxy)-5,6-dihydro-2H-naphtho[1,2-b][1,4]oxazin-4(3H,4aH,10bH)-yl)propanoic acid | A | <1 μM | >1 μM | <1 μM |
| 84 | 1-[7-[(4-fluoro-3-methyl-phenyl)methoxy]chroman-3-yl]azetidine-3-carboxylic acid | D | >1 μM | | >1 μM |
| 85 | 1-[7-[[4-fluoro-3-(trifluoromethyl)phenyl]methoxy]chroman-3-yl]azetidine-3-carboxylic acid | D | >1 μM | | >1 μM |
| 86 | 1-[7-[(2-fluoro-3-methoxy-phenyl)methoxy]chroman-3-yl]azetidine-3-carboxylic acid | D | >1 μM | | >1 μM |
| 87 | 1-[7-[(3-fluoro-5-methyl-phenyl)methoxy]chroman-3-yl]azetidine-3-carboxylic acid | D | >1 μM | | >1 μM |
| 88 | 1-[7-[(2-fluoro-4-methyl-phenyl)methoxy]chroman-3-yl]azetidine-3-carboxylic acid | D | >1 μM | | >1 μM |
| 89 | 1-[7-[(4-cyano-2-fluoro-phenyl)methoxy]chroman-3-yl]azetidine-3-carboxylic acid | D | >1 μM | | >1 μM |
| 90 | 1-[7-[[3-fluoro-5-(trifluoromethyl)phenyl]methoxy]chroman-3-yl]azetidine-3-carboxylic acid | B | >1 μM | | <1 μM |
| 91 | 1-[7-[[5-fluoro-2-(trifluoromethyl)phenyl]methoxy]chroman-3-yl]azetidine-3-carboxylic acid | C | >1 μM | | >1 μM |
| 92 | 1-[7-[(4-fluoro-3-methoxy-phenyl)methoxy]chroman-3-yl]azetidine-3-carboxylic acid | D | >1 μM | | >1 μM |
| 93 | 1-[7-[2-(4-fluorophenoxy)ethoxy]chroman-3-yl]azetidine-3-carboxylic acid | D | >1 μM | | >1 μM |
| 94 | 1-[7-[[2-fluoro-3-(trifluoromethyl)phenyl]methoxy]chroman-3-yl]azetidine-3-carboxylic acid | D | >1 μM | | >1 μM |
| 95 | 1-[7-[(3-fluoro-4-methoxy-phenyl)methoxy]chroman-3-yl]azetidine-3-carboxylic acid | D | >1 μM | | >1 μM |
| 96 | 1-[7-[(3-fluoro-2-methyl-phenyl)methoxy]chroman-3-yl]azetidine-3-carboxylic acid | C | >1 μM | | >1 μM |
| 97 | 1-[7-[2-(3-fluorophenoxy)ethoxy]chroman-3-yl]azetidine-3-carboxylic acid | D | >1 μM | | >1 μM |
| 98 | 1-[7-[(2-fluoro-5-methoxy-phenyl)methoxy]chroman-3-yl]azetidine-3-carboxylic acid | D | >1 μM | | >1 μM |
| 99 | 1-[7-[3-(3-fluorophenyl)propoxy]chroman-3-yl]azetidine-3-carboxylic acid | D | >1 μM | | >1 μM |
| 100 | 1-[7-[(3-fluoro-5-methoxy-phenyl)methoxy]chroman-3-yl]azetidine-3-carboxylic acid | D | >1 μM | | >1 μM |
| 101 | 1-[7-[(2-fluoro-6-methoxy-phenyl)methoxy]chroman-3-yl]azetidine-3-carboxylic acid | D | >1 μM | | >1 μM |
| 102 | 1-[7-[4-(3-fluorophenoxy)butoxy]chroman-3-yl]azetidine-3-carboxylic acid | D | >1 μM | | >1 μM |
| 103 | 1-[7-[[3-fluoro-4-(trifluoromethyl)phenyl]methoxy]chroman-3-yl]azetidine-3-carboxylic acid | D | >1 μM | | >1 μM |

TABLE 1-continued

| No | Name | S1P5 EC50 range # | S1P1 EC50 | S1P3 EC50 | S1P4 EC50 |
|---|---|---|---|---|---|
| 104 | 1-[7-[[2-fluoro-5-(trifluoromethoxy)phenyl]methoxy]chroman-3-yl]azetidine-3-carboxylic acid | C | >1 μM | | >1 μM |
| 105 | 1-[7-[(2-fluoro-3-methyl-phenyl)methoxy]chroman-3-yl]azetidine-3-carboxylic acid | D | >1 μM | | >1 μM |
| 106 | 1-[7-[[2-fluoro-4-(trifluoromethyl)phenyl]methoxy]chroman-3-yl]azetidine-3-carboxylic acid | D | >1 μM | | >1 μM |
| 107 | 1-[7-[1-(2-fluorophenyl)ethoxy]chroman-3-yl]azetidine-3-carboxylic acid | D | >1 μM | | >1 μM |
| 108 | 1-[7-[(6-fluoro-2-quinolyl)methoxy]chroman-3-yl]azetidine-3-carboxylic acid | D | >1 μM | | >1 μM |
| 109 | 1-(7-(cyclohexylmethoxy)chroman-3-yl)azetidine-3-carboxylic acid | C | >1 μM | | >1 μM |
| 110 | 1-(7-((2,6-dichlorobenzyl)oxy)chroman-3-yl)piperidine-4-carboxylic acid | B | >1 μM | | <1 μM |
| 111 | 1-(7-((2-chloro-6-ethylbenzyl)oxy)chroman-3-yl)piperidine-4-carboxylic acid | A | <1 μM | | <1 μM |
| 112 | 1-(7-benzyloxychroman-3-yl)piperidine-4-carboxylic acid | D | >1 μM | | <1 μM |
| 113 | 2-[[7-(cyclohexylmethoxy)chroman-3-yl]amino]acetic acid | C | >1 μM | | >1 μM |
| 114 | 2-[[7-[2-(2,6-dichlorophenyl)ethoxy]chroman-3-yl]amino]acetic acid | D | >1 μM | | >1 μM |
| 115 | 2-(1-((7-((2-chloro-6-ethylbenzyl)oxy)chroman-3-yl)amino)cyclopentyl) acetic acid | A | >1 μM | | <1 μM |
| 116 | 2-(1-((7-((2-chloro-6-ethylbenzyl)oxy)chroman-3-yl)amino)cyclobutyl)acetic acid | A | >1 μM | | <1 μM |
| 117 | 2-(1-((7-((2-ethyl-6-fluorobenzyl)oxy)chroman-3-yl)amino)cyclopentyl) acetic acid | A | >1 μM | | <1 μM |
| 118 | 2-(1-((7-((2-ethyl-6-fluorobenzyl)oxy)chroman-3-yl)amino)cyclobutyl)acetic acid | A | >1 μM | | <1 μM |
| 119 | 1-((7-((2,6-dichlorobenzyl)oxy)chroman-3-yl)amino)cyclobutane-1-carboxylic acid | D | >1 μM | | >1 μM |
| 120 | 1-((7-((2-chloro-6-ethylbenzyl)oxy)chroman-3-yl)amino)cyclobutane-1-carboxylic acid | B | <1 μM | | <1 μM |
| 121 | 3-((7-((2-chloro-6-ethylbenzyl)oxy)chroman-3-yl)amino)bicyclo[1.1.1]pentane-1-carboxylic acid | C | >1 μM | | <1 μM |
| 122 | 3-((7-((2-ethyl-6-fluorobenzyl)oxy)chroman-3-yl)amino)bicyclo[1.1.1]pentane-1-carboxylic acid | B | >1 μM | | <1 μM |
| 123 | 2-((7-((2,6-dichlorobenzyl)oxy)chroman-3-yl)(methyl)amino)acetic acid | B | >1 μM | | <1 μM |
| 124 | 2-((7-((2-chloro-6-ethylbenzyl)oxy)chroman-3-yl)(methyl)amino)acetic acid | A | >1 μM | | <1 μM |
| 125 | 2-(1-(7-((2-chloro-6-ethylbenzyl)oxy)chroman-3-yl)pyrrolidin-3-yl)acetic acid | A | >1 μM | | <1 μM |
| 126 | 2-((7-((2-fluoro-6-ethylbenzyl)oxy)chroman-3-yl)amino)acetic acid | A | >1 μM | | <1 μM |
| 127 | 1-(7-((2-ethyl-6-fluorobenzyl)oxy)chroman-3-yl)pyrrolidine-3-carboxylic acid | A | >1 μM | | <1 μM |
| 128 | 1-(7-((2-chloro-6-ethylbenzyl)oxy)chroman-3-yl)pyrrolidine-3-carboxylic acid | A | >1 μM | | <1 μM |
| 129 | 2-(1-((7-((2-ethyl-6-fluorobenzyl)oxy)chroman-3-yl)amino)cyclopropyl) acetic acid | A | >1 μM | | >1 μM |
| 130 | 2-(1-(7-((2-ethyl-6-fluorobenzyl)oxy)chroman-3-yl)pyrrolidin-3-yl)acetic acid | A | >1 μM | | <1 μM |

TABLE 1-continued

| No | Name | S1P5 EC50 range # | S1P1 EC50 | S1P3 EC50 | S1P4 EC50 |
|---|---|---|---|---|---|
| 131 | (7-(4-((2,3-difluorobenzyl)oxy)phenyl)chroman-3-yl)glycine | A | <1 μM | | >1 μM |
| 132 | (7-((4-((3-chlorobenzyl)oxy)benzyl)oxy)chroman-3-yl)glycine | A | >1 μM | | >1 μM |
| 133 | 2-((7-(4-((2,3-difluorobenzyl)oxy)phenyl)chroman-3-yl)(methyl)amino)acetic acid | A | <1 μM | | >1 μM |
| 134 | 2-((7-(4-((3-chlorobenzyl)oxy)phenyl)chroman-3-yl)(methyl)amino)acetic acid | A | >1 μM | | >1 μM |
| 135 | 2-((7-(4-((4-chlorobenzyl)oxy)phenyl)chroman-3-yl)(methyl)amino)acetic acid | B | >1 μM | | >1 μM |
| 136 | (S)-5-(((7-((2-ethyl-6-fluorobenzyl)oxy)chroman-3-yl)amino)methyl)isoxazol-3-ol | A | >1 μM | | <1 μM |
| 137 | (S)—N-(3-((tert-butyldimethylsilyl)oxy)isoxazol-5-yl)methyl)-7-((2-chloro-6-ethylbenzyl)oxy)chroman-3-amine | A | >1 μM | | <1 μM |
| 138 | (S)-1-(7-((2,6-dichlorobenzyl)oxy)chroman-3-yl)-3-methylazetidine-3-carboxylic acid | A | >1 μM | | >1 μM |
| 139 | (S)-1-(7-((2-ethyl-6-fluorobenzyl)oxy)chroman-3-yl)-3-methylazetidine-3-carboxylic acid | A | >1 μM | | <1 μM |
| 140 | (S)-1-(7-((2,6-dichlorobenzyl)oxy)chroman-3-yl)-3-ethylazetidine-3-carboxylic acid | D | >1 μM | | >1 μM |
| 141 | (S)-1-(7-((2,6-dichlorobenzyl)oxy)chroman-3-yl)-3-propylazetidine-3-carboxylic acid | D | >1 μM | | >1 μM |
| 142 | 2-((6-((2-chloro-6-ethylbenzyl)oxy)-1,2,3,4-tetrahydronaphthalen-2-yl)oxy)acetic acid | A | >1 μM | | >1 μM |
| 143 | 2-((6-((2-chloro-6-cyclopropylbenzyl)oxy)-1,2,3,4-tetrahydronaphthalen-2-yl)oxy)acetic acid | A | >1 μM | | >1 μM |
| 144 | 1-(7-((2,6-dichlorobenzyl)oxy)chroman-3-yl)azetidine-3-carboxylic acid, enantiomer 1 | B | >1 μM | | >1 μM |
| 145 | 1-(7-((2,6-dichlorobenzyl)oxy)chroman-3-yl)azetidine-3-carboxyiic acid, enantiomer 2 | C | >1 μM | | >1 μM |
| 146 | 1-(7-((2-ethyl-6-fluorobenzyl)oxy)chroman-3-yl)azetidine-3-carboxylic acid, enantiomer 1 | A | >1 μM | | <1 μM |
| 147 | 1-(7-((2-ethyl-6-fluorobenzyl)oxy)chroman-3-yl)azetidine-3-carboxylic acid, enantiomer 2 | A | >1 μM | | <1 μM |
| 148 | 1-(7-((2-methoxy-4-propylbenzyl)oxy)chroman-3-yl)azetidine-3-carboxylic acid | D | >1 μM | | >1 μM |
| 149 | 2-((6-((2,6-difluoro-3-methylbenzyl)oxy)-1,2,3,4-tetrahydronaphthalen-2-yl)oxy)acetic acid | D | >1 μM | | >1 μM |
| 150 | 2-((6-((2-fluoro-3-methyl-6-chlorobenzyl)oxy)-1,2,3,4-tetrahydronaphthalen-2-yl)oxy)acetic acid | D | >1 μM | | >1 μM |
| 151 | 2-((6-((2-chloro-5-(trifluoromethyl)benzyl)oxy)-1,2,3,4-tetrahydronaphthalen-2-yl)oxy)acetic acid | D | >1 μM | | >1 μM |
| 152 | 2-((6-((2,6-difluoro-3-chlorobenzyl)oxy)-1,2,3,4-tetrahydronaphthalen-2-yl)oxy)acetic acid | A | >1 μM | >1 μM | >1 μM |
| 153 | 2-((6-((2-(trifluoromethyl)-5-chlorobenzyl)oxy)-1,2,3,4-tetrahydronaphthalen-2-yl)oxy)acetic acid | | >1 μM | | |
| 154 | 2-((6-((3-methoxybenzyl)oxy)-1,2,3,4-tetrahydronaphthalen-2-yl)oxy)acetic acid | D | >1 μM | | >1 μM |
| 155 | 2-((6-((2-methyl-5-fluorobenzyl)oxy)-1,2,3,4-tetrahydronaphthalen-2-yl)oxy)acetic acid | D | >1 μM | | >1 μM |
| 156 | 2-((6-((3,5-dimethylbenzyl)oxy)-1,2,3,4-tetrahydronaphthalen-2-yl)oxy)acetic acid | D | >1 μM | | >1 μM |
| 157 | 2-((6-((2-fluoro-6-methoxybenzyl)oxy)-1,2,3,4-tetrahydronaphthalen-2-yl)oxy)acetic acid | D | >1 μM | | >1 μM |

TABLE 1-continued

| No | Name | S1P5 EC50 range # | S1P1 EC50 | S1P3 EC50 | S1P4 EC50 |
|---|---|---|---|---|---|
| 158 | 2-((6-((2-fluoro-6-(trifluoromethyl)benzyl)oxy)-1,2,3,4-tetrahydronaphthalen-2-yl)oxy)acetic acid | D | >1 μM | | >1 μM |
| 159 | 2-((6-((2,6-difluorobenzyl)oxy)-1,2,3,4-tetrahydronaphthalen-2-yl)oxy)acetic acid | D | >1 μM | | >1 μM |
| 160 | 2-((6-((2-fluoro-5-methylbenzyl)oxy)-1,2,3,4-tetrahydronaphthalen-2-yl)oxy)acetic acid | C | >1 μM | | >1 μM |
| 161 | 2-((6-((2-fluoro-5-(trifluoromethoxy)benzyl)oxy)-1,2,3,4-tetrahydronaphthalen-2-yl)oxy)acetic acid | B | >1 μM | >1 μM | >1 μM |
| 162 | 2-((6-((2,4-dichlorobenzyl)oxy)-1,2,3,4-tetrahydronaphthalen-2-yl)oxy)acetic acid | D | >1 μM | | >1 μM |
| 163 | 2-((6-((2,5-difluorobenzyl)oxy)-1,2,3,4-tetrahydronaphthalen-2-yl)oxy)acetic acid | C | >1 μM | | >1 μM |
| 164 | 2-((6-((2,5-dichlorobenzyl)oxy)-1,2,3,4-tetrahydronaphthalen-2-yl)oxy)acetic acid | D | >1 μM | | >1 μM |
| 165 | 2-((6-((4-methoxybenzyl)oxy)-1,2,3,4-tetrahydronaphthalen-2-yl)oxy)acetic acid | D | >1 μM | | >1 μM |
| 166 | 2-((6-((2-methoxy-5-fluorobenzyl)oxy)-1,2,3,4-tetrahydronaphthalen-2-yl)oxy)acetic acid | C | >1 μM | | >1 μM |
| 167 | 2-((6-((2-chloro-6-(trifluoromethyl)benzyl)oxy)-1,2,3,4-tetrahydronaphthalen-2-yl)oxy)acetic acid | A | >1 μM | >1 μM | >1 μM |
| 168 | 2-((6-((2-(trifluoromethyl)-5-fluorobenzyl)oxy)-1,2,3,4-tetrahydronaphthalen-2-yl)oxy)acetic acid | A | >1 μM | >1 μM | <1 μM |
| 169 | 2-((6-((2-chloro-6-fluorobenzyl)oxy)-1,2,3,4-tetrahydronaphthalen-2-yl)oxy)acetic acid | C | >1 μM | | >1 μM |
| 170 | 2-((6-((2-methoxybenzyl)oxy)-1,2,3,4-tetrahydronaphthalen-2-yl)oxy)acetic acid | D | >1 μM | | >1 μM |
| 171 | 2-((6-((2-chloro-5-fluorobenzyl)oxy)-1,2,3,4-tetrahydronaphthalen-2-yl)oxy)acetic acid | D | >1 μM | | >1 μM |
| 172 | 2-((6-((2-fluoro-5-(trifluoromethyl)benzyl)oxy)-1,2,3,4-tetrahydronaphthalen-2-yl)oxy)acetic acid | D | >1 μM | | >1 μM |
| 174 | 2-((6-((2-fluoro-5-chlorobenzyl)oxy)-1,2,3,4-tetrahydronaphthalen-2-yl)oxy)acetic acid | D | >1 μM | | >1 μM |
| 175 | 2-((6-((2,6-dimethylbenzyl)oxy)-1,2,3,4-tetrahydronaphthalen-2-yl)oxy)acetic acid | B | >1 μM | >1 μM | >1 μM |
| 176 | 2-((6-((2-methoxy-5-chlorobenzyl)oxy)-1,2,3,4-tetrahydronaphthalen-2-yl)oxy)acetic acid | D | >1 μM | | >1 μM |
| 177 | 3-((6-((2-(trifluoromethyl)-5-methylbenzyl)oxy)-1,2,3,4-tetrahydronaphthalen-2-yl)oxy)propanoic acid | D | >1 μM | | >1 μM |
| 178 | 3-((6-((2-(trifluoromethyl)benzyl)oxy)-1,2,3,4-tetrahydronaphthalen-2-yl)oxy)propanoic acid | D | >1 μM | | |
| 179 | 3-((6-((2-methylbenzyl)oxy)-1,2,3,4-tetrahydronaphthalen-2-yl)oxy)propanoic acid | D | >1 μM | | >1 μM |
| 180 | 3-((6-((3-fluorobenzyl)oxy)-1,2,3,4-tetrahydronaphthalen-2-yl)oxy)propanoic acid | D | >1 μM | | >1 μM |
| 181 | 3-((6-((3,4-dichlorobenzyl)oxy)-1,2,3,4-tetrahydronaphthalen-2-yl)oxy)propanoic acid | D | >1 μM | | >1 μM |
| 182 | 3-((6-((4-methylthiobenzyl)oxy)-1,2,3,4-tetrahydronaphthalen-2-yl)oxy)propanoic acid | D | >1 μM | | >1 μM |
| 183 | 3-((6-((4-(trifluoromethyl)benzyl)oxy)-1,2,3,4-tetrahydronaphthalen-2-yl)oxy)propanoic acid | D | >1 μM | | >1 μM |
| 184 | 3-((6-((3-(trifluoromethoxy)benzyl)oxy)-1,2,3,4-tetrahydronaphthalen-2-yl)oxy)propanoic acid | D | >1 μM | | >1 μM |
| 185 | 3-((6-((4-(trifluoromethoxy)benzyl)oxy)-1,2,3,4-tetrahydronaphthalen-2-yl)oxy)propanoic acid | D | >1 μM | | >1 μM |

TABLE 1-continued

| No | Name | S1P5 EC50 range # | S1P1 EC50 | S1P3 EC50 | S1P4 EC50 |
|---|---|---|---|---|---|
| 186 | 3-((6-((2,3-difluorobenzyl)oxy)-1,2,3,4-tetrahydronaphthalen-2-yl)oxy)propanoic acid | D | >1 μM | | >1 μM |
| 187 | 3-((6-((3-chlorobenzyl)oxy)-1,2,3,4-tetrahydronaphthalen-2-yl)oxy)propanoic acid | | >1 μM | | >1 μM |
| 188 | 3-((6-((2-chlorobenzyl)oxy)-1,2,3,4-tetrahydronaphthalen-2-yl)oxy)propanoic acid | D | >1 μM | | >1 μM |
| 189 | 3-((6-((2,3-dichlorobenzyl)oxy)-1,2,3,4-tetrahydronaphthalen-2-yl)oxy)propanoic acid | D | >1 μM | | >1 μM |
| 190 | 3-((6-((2-(trifluoromethoxy)benzyl)oxy)-1,2,3,4-tetrahydronaphthalen-2-yl)oxy)propanoic acid | D | >1 μM | | >1 μM |
| 191 | 3-((6-((4-chlorobenzyl)oxy)-1,2,3,4-tetrahydronaphthalen-2-yl)oxy)propanoic acid | D | >1 μM | | >1 μM |
| 192 | 3-((6-((4-tert-butyl)benzyl)oxy)-1,2,3,4-tetrahydronaphthalen-2-yl)oxy)propanoic acid | D | >1 μM | | >1 μM |
| 193 | 3-((6-((3-trifluoromethyl)benzyl)oxy)-1,2,3,4-tetrahydronaphthalen-2-yl)oxy)propanoic acid | | >1 μM | | <1 μM |
| 194 | 3-((6-((4-fluorobenzyl)oxy)-1,2,3,4-tetrahydronaphthalen-2-yl)oxy)propanoic acid | D | >1 μM | | >1 μM |
| 195 | 2-((6-((2-(trifluoromethyl)-5-methylbenzyl)oxy)-1,2,3,4-tetrahydronaphthalen-2-yl)oxy)acetic acid | D | >1 μM | | >1 μM |
| 196 | 2-((6-((2-(trifluoromethyl)benzyl)oxy)-1,2,3,4-tetrahydronaphthalen-2-yl)oxy)acetic acid | C | >1 μM | | >1 μM |
| 197 | 2-((6-((2-methylbenzyl)oxy)-1,2,3,4-tetrahydronaphthalen-2-yl)oxy)acetic acid | | >1 μM | | <1 μM |
| 198 | 2-((6-((3-fluorobenzyl)oxy)-1,2,3,4-tetrahydronaphthalen-2-yl)oxy)acetic acid | D | >1 μM | | >1 μM |
| 199 | 2-((6-((3,4-dichlorobenzyl)oxy)-1,2,3,4-tetrahydronaphthalen-2-yl)oxy)acetic acid | D | >1 μM | | >1 μM |
| 200 | 2-((6-((2-methyl-3-(trifluoromethyl)benzyl)oxy)-1,2,3,4-tetrahydronaphthalen-2-yl)oxy)acetic acid | D | >1 μM | | >1 μM |
| 201 | 2-((6-((4-methylthiobenzyl)oxy)-1,2,3,4-tetrahydronaphthalen-2-yl)oxy)acetic acid | D | >1 μM | | >1 μM |
| 202 | 2-((6-((4-(trifluoromethyl)benzyl)oxy)-1,2,3,4-tetrahydronaphthalen-2-yl)oxy)acetic acid | | >1 μM | | >1 μM |
| 203 | 2-((6-((4-(trifluoromethoxy)benzyl)oxy)-1,2,3,4-tetrahydronaphthalen-2-yl)oxy)acetic acid | D | >1 μM | | >1 μM |
| 204 | 2-((6-((2,3-difluorobenzyl)oxy)-1,2,3,4-tetrahydronaphthalen-2-yl)oxy)acetic acid | D | >1 μM | | >1 μM |
| 205 | 2-((6-((3-chlorobenzyl)oxy)-1,2,3,4-tetrahydronaphthalen-2-yl)oxy)acetic acid | C | >1 μM | | >1 μM |
| 206 | 2-((6-((2-chlorobenzyl)oxy)-1,2,3,4-tetrahydronaphthalen-2-yl)oxy)acetic acid | D | >1 μM | | >1 μM |
| 207 | 2-((6-((2,3-dichlorobenzyl)oxy)-1,2,3,4-tetrahydronaphthalen-2-yl)oxy)acetic acid | D | F | | F |
| 208 | 2-((6-((2-(trifluoromethoxy)benzyl)oxy)-1,2,3,4-tetrahydronaphthalen-2-yl)oxy)acetic acid | C | >1 μM | | >1 μM |
| 209 | 2-((6-((4-chlorobenzyl)oxy)-1,2,3,4-tetrahydronaphthalen-2-yl)oxy)acetic acid | D | >1 μM | | >1 μM |
| 210 | 2-((6-((2,6-dichlorobenzyl)oxy)-1,2,3,4-tetrahydronaphthalen-2-yl)oxy)acetic acid | C | >1 μM | >1 μM | >1 μM |
| 211 | 2-((6-((4-(tert-butyl)benzyl)oxy)-1,2,3,4-tetrahydronaphthalen-2-yl)oxy)acetic acid | B | >1 μM | >1 μM | >1 μM |
| 212 | 2-((6-((3,4-difluorobenzyl)oxy)-1,2,3,4-tetrahydronaphthalen-2-yl)oxy)acetic acid | D | >1 μM | | >1 μM |
| 213 | 2-((6-((3-(trifluoromethyl)benzyl)oxy)-1,2,3,4-tetrahydronaphthalen-2-yl)oxy)acetic acid | B | >1 μM | >1 μM | <1 μM |
| 214 | 2-((6-((4-fluorobenzyl)oxy)-1,2,3,4-tetrahydronaphthalen-2-yl)oxy)acetic acid | D | >1 μM | | >1 μM |
| 215 | 2-((6-((2-fluorobenzyl)oxy)-1,2,3,4-tetrahydronaphthalen-2-yl)oxy)acetic acid | D | >1 μM | | |

TABLE 1-continued

| No | Name | S1P5 EC50 range # | S1P1 EC50 | S1P3 EC50 | S1P4 EC50 |
|---|---|---|---|---|---|
| 216 | 2-((6-((2-chloro-6-ethylbenzyl)oxy)-1,2,3,4-tetrahydronaphthalen-2-yl)amino)-1-(N-methylmethoxyamino)-1-ethanone | A | >1 µM | >1 µM | >1 µM |
| 217 | (1-(6-((2-chloro-6-ethylbenzyl)oxy)-1,2,3,4-tetrahydronaphthalen-2-yl)-3-azetidinyl)(N-methylmethoxyamino)formaldehyde | C | >1 µM | | >1 µM |
| 218 | 2-((6-((2-chloro-6-ethylbenzyl)oxy)-1,2,3,4-tetrahydronaphthalen-2-yl)amino)-1-(methoxyamino)-1-ethanone | C | >1 µM | >1 µM | >1 µM |
| 219 | (1-(6-((2-chloro-6-ethylbenzyl)oxy)-1,2,3,4-tetrahydronaphthalen-2-yl)-3-azetidinyl)(methoxyamino)formaldehyde | B | >1 µM | >1 µM | >1 µM |
| 220 | 5-(((6-((2-chloro-6-ethylbenzyl)oxy)-1,2,3,4-tetrahydronaphthalen-2-yl)amino)methyl)-2H-isoxazol-3-one | A | <1 µM | >1 µM | <1 µM |
| 221 | 1-(6-bromo-7-((2,6-dichlorobenzyl)oxy)chroman-3-yl)azetidine-3-carboxylic acid | B | >1 µM | | >1 µM |
| 222 | 1-(6-methyl-7-((2,6-dichlorobenzyl)oxy)chroman-3-yl)azetidine-3-carboxylic acid | B | >1 µM | | >1 µM |
| 223 | 1-(6-fluoro-7-((2,6-dichlorobenzyl)oxy)chroman-4-yl)azetidine-3-carboxylic acid | A | >1 µM | | >1 µM |
| 224 | 2-(1-(7-((2,6-dichlorobenzyl)oxy)isochroman-4-yl)azetidin-3-yl)acetic acid | C | >1 µM | | >1 µM |
| 225 | 1-(8-((2,6-dichlorobenzyl)oxy)chroman-3-yl)azetidine-3-carboxylic acid | D | >1 µM | | >1 µM |
| 226 | 1-(7-(phenethoxy)chroman-3-yl)azetidine-3-carboxylic acid | D | >1 µM | | >1 µM |
| 227 | 1-(7-(2-chlorophenethoxy)chroman-3-yl)azetidine-3-carboxylic acid | D | >1 µM | | >1 µM |
| 228 | 1-(7-(4-chlorophenethoxy)chroman-3-yl)azetidine-3-carboxylic acid | D | >1 µM | | >1 µM |
| 229 | 1-(7-(2,6-dichlorophenoxy)chroman-3-yl)azetidine-3-carboxylic acid | D | >1 µM | | >1 µM |
| 230 | 1-(7-(cyclobutylmethoxy)chroman-3-yl)azetidine-3-carboxylic acid | D | >1 µM | | >1 µM |
| 231 | 1-(7-(cyclopropylmethoxy)chroman-3-yl)azetidine-3-carboxylic acid | D | >1 µM | | >1 µM |
| 232 | 1-(8-(phenethoxy)chroman-3-yl)azetidine-3-carboxylic acid | | | | |
| 233 | ((7-((2-chloro-6-ethylbenzyl)oxy)chroman-3-yl)oxy)acetic acid | A | >1 µM | | >1 µM |
| 234 | ((7-((2,6-difluoro-3-chlorobenzyl)oxy)chroman-3-yl)oxy)acetic acid | D | >1 µM | | >1 µM |
| 235 | ((7-((2-fluoro-6-cyclopropylbenzyl)oxy)chroman-3-yl)oxy)acetic acid | | | | |
| 236 | 2-((6-((2-chloro-6-ethylbenzyl)oxy)-1,2,3,4-tetrahydronaphthalen-2-yl)amino)acetohydroxamic acid | A | >1 µM | >1 µM | <1 µM |
| 237 | 2-((7-(4-(benzyloxy)phenyl)chroman-3-yl)amino)acetic acid | A | >1 µM | | >1 µM |
| 238 | 2-((7-(4-(benzyloxy)phenyl)chroman-3-yl)(methyl)amino)acetic acid | B | <1 µM | >1 µM | >1 µM |
| 239 | ((7-((2-chloro-6-ethylbenzyl)oxy)chroman-3-yl)oxy)acetic acid, enantiomer 1 | C | >1 µM | | >1 µM |
| 240 | ((7-((2-chloro-6-ethylbenzyl)oxy)chroman-3-yl)oxy)acetic acid, enantiomer 2 | B | >1 µM | | >1 µM |

A: EC50 ≤10 nM B: EC50 = 10 nM < EC50 ≤ 100 nM C: EC50 = 100 nM < EC50 ≤ 1 µM D: EC50 = 1 µM EC50 < EC50 ≤ 10 µM

4. Assessment of Agonist Potency

Agonistic activity was measured using the method described below. The results are shown in table 1.

Intracellular $Ca^{2+}$ Release

Agonist potency and intrinsic activity was assessed by measurement of intracellular $Ca^{2+}$ release. Recombinant CHO-K1 cells (Euroscreen, Brussels, Belgium) expressing human S1PR5, S1PR1, S1PR3 or S1PR4 receptors, aequorin, and GTP binding protein Gq/i5 were cultured using a medium containing nutrient mixture F-12 Ham (Sigma-Aldrich) with 10% FBS, and 100 µg/mL gentamicin and equilibrated at 5% $CO_2$.

15.000 cells in 20 µL medium were seeded into Biocoat poly-D-Lysine coated 384 well plates (Becton Dickinson #35-6663) and grown to ~95% confluency after 24 h.

Culture medium was replaced by an assay buffer consisting of HBBS with $Ca^{2+}$ and $Mg^{2+}$ (Invitrogen #14025-050), 20 mmol/L Hepes (Sigma-Aldrich #H-3375), 2.5 mmol/L probenecid (Sigma-Aldrich #P-8761, and 0.1% BSA (Sigma-Aldrich #A-7030) pH 7.4. The Calcium 5 no-wash FLIPR assay kit (Molecular Devices #5000625) was performed as described in the kit instructions. Cells were incubated with Calcium 5 dye for 1 h at 37° C., 5% $CO_{02}$ in the dark. After 45 min adaptation to RT assessment of agonist stimulation of intracellular $Ca^{2+}$ release was performed by addition of test compounds at concentrations obtained by serial dilution. Phospho-fingolimod was used as positive control. Antagonists were pre-incubated for 10 min with cells before addition of the agonist (phospho-fingolimod at $EC_{80}$). Measurements were performed using a fluorometric imaging plate reader FLIPR®tetra (Molecular Devices). Agonist at the human S1P receptors were characterized by deducing $EC_{50}$ (potency) values from a nonlinear fit to the measured fluorescence raw data after normalization to the reference agonist (phospho-fingolimod) curve.

The invention claimed is:
1. A compound of formula (I):

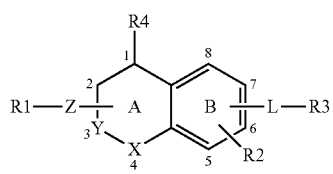

(I)

or a pharmaceutically acceptable salt, solvate, tautomer, stereoisomer or N-oxide thereof, wherein X and Y are independently selected from the group consisting of O, $CH_2$ and CH—Z—R1, with the proviso that at most one of X and Y is O and at most one of X and Y is CH—Z—R1;

Z—R1 and R4 are selected from:
(1) Z is attached to ring A at atom 1, 2, 3 or 4 and selected from the group consisting of —O—, —NR5- and —NR5—$CH_2$— whereby NR5 is attached to R1 and $CH_2$ is attached to ring A;

wherein R5 is selected from the group consisting of H, (C1-4)alkyl, (C1-4)alkyl substituted with one or more fluor atoms and benzyl optionally substituted with one or more substituents selected from the group consisting of a halogen atom, (C1-4)alkyl optionally substituted with one or more halogen atoms, and (C1-4)alkoxy optionally substituted with one or more halogen atoms;

R1 is selected from the group consisting of:
—(C1-6)alkylene-R6 wherein one or more carbon atoms in the alkylene group, each independently, are optionally substituted with one or more halogen atoms, with $(CH_2)_2$ to form a cyclopropyl moiety, with $(CH_2)_3$ to form a cyclobutyl moiety or with $(CH_2)_4$ to form a cyclopentyl moiety;
—(C3-6)cycloalkylene-R6, optionally substituted with (C1-4)alkyl or with (C1-4)alkyl substituted with one or more fluor atoms, and wherein one carbon atom in the (C3-6)cycloalkylene can optionally be replaced by oxygen;
—(C1-3)alkylene—(C3-6)cycloalkylene-R6, whereby said (C3-6)cycloalkylene is optionally substituted with (C1-4)alkyl or with (C1-4)alkyl substituted with one or more fluor atoms;
—(C3-6)cycloalkylene—(C1-3)alkylene-R6, whereby said (C3-6)cycloalkylene is optionally substituted with (C1-4)alkyl or with (C1-4)alkyl substituted with one or more fluor atoms; and
—C(O)—(C1-4)alkylene-R6; and R4 is hydrogen; or
(2) Z is NR5 and attached to ring A at atom 1, 2, 3 or 4, and NR5 and R1 together form a group selected from —(C3-8)-heterocycloalkylene-R6, optionally substituted with (C1-4)alkyl or with (C1-4)alkyl substituted with one or more fluor atoms and —(C3-8)heterocycloalkylene—(C1-3)-alkylene-R6, optionally substituted with (C1-4)alkyl or with (C1-4)alkyl substituted with one or more fluor atoms; and R4 is hydrogen; or
(3) Z is NR5 and is attached to ring A at atom 2, and NR5 and R4 together form a group selected from pyrrolidine, pyrazolidine, imidazolidine, oxazolidine, isoxazolidine, thiazolidine, isothiazolidine, piperidine, piperazine, 1,2-diazinane, 1,3-diazinane, morpholine, 1,3-oxazinane, 1,2-oxazinane, thiomorpholine, 1,3-thiazinane and 1,2-thiazinane, and R1 is as defined above;

R2 is hydrogen or one or more substituents independently selected from the group consisting of a halogen atom, (C1-4)alkyl optionally substituted with one or more halogen atoms, and (C1-4)alkoxy optionally substituted with one or more halogen atoms;

R6 is selected from the group consisting of —OH, —COOH, —$OPO_3H_2$, —CO—O—(C1-4)alkyl, —CO—NH—OH, —CO—NH—O—(C1-4)alkyl, —CO—N($CH_3$)—O—(C1-4)alkyl, -isoxazol-3-one, 3-isoxazolol -dihydro-2-furanone and -tetrazol-5-yl;

L is a group —W—$(CH_2)$p-T- wherein:
W is attached to ring B at atom 5, 6, 7 or 8 and
W is selected from the group consisting of —O—, —CO—, —S—, —SO—, —$SO_2$—, —NH—, —CH=CH—, —C($CF_3$)=CH—, CH=C ($CF_3$)—, —C≡C—, —$CH_2$—O—, —O—CO—, —CO—O—, —CO—NH—, —NH—CO— and —O—$CH_2$-phenyl-, or W is —$(CH_2)$n- wherein n is 1 or 2 and one or both C atoms of $(CH_2)$n are optionally substituted with one or two fluoro atoms, or W is selected from the group consisting of phenyl, pyridyl, thienyl, thiazolyl and (C3-7)cycloalkylene, each optionally substituted with one or more substituents independently selected from the group consisting of:
a halogen atom,
hydroxy,
cyano,
(C1-4)alkyl optionally substituted with one or more halogen atoms,
(C1-4)alkoxy optionally substituted with one or more halogen atoms,
(C3-6)cycloalkyl optionally substituted with one or more halogen atoms and
phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms;

p is an integer from 0 to 5 and one or more C atoms of $(CH_2)$p are optionally substituted with one or two methyl groups, ethyl groups or fluoro atoms;

T is absent or attached to R3 and selected from the group consisting of —O—, —S—, —SO—, —$SO_2$—,—NH—, —CO—, —C=C—,C≡C—, cyclopropylene, —$(CH_2)$m- and —O—$(CH_2)$m- wherein m is an integer from 1 to 5 and one or more C atoms of $(CH_2)$m are optionally substituted with one or two fluoro atoms;

R3 is selected from the group consisting of:
  (C3-8)alkyl, (C3-8)alkenyl or (C3-8)alkynyl wherein one or more carbon atoms in the alkyl, alkenyl or alkynyl group are optionally substituted with one or more halogen atoms;
  (C3-6)cycloalkyl, (C4-6)cycloalkenyl or an 8-10 membered bicyclic group, each optionally substituted with one or more substituents independently selected from the group consisting of a halogen atom, (C1-4)alkyl optionally substituted with one or more fluoro atoms and (C1-4)alkoxy optionally substituted with one or more fluoro atoms,
  phenyl, biphenyl, naphthyl, pyridyl, thienyl or thiazolyl optionally substituted with one or more substituents independently selected from the group consisting of:
    a halogen atom,
    cyano,
    (C1-4)alkyl optionally substituted with one or more fluoro atoms,
    (C1-4)alkoxy optionally substituted with one or more fluoro atoms,
    —S—(C1-4)-alkyl,
    —SF$_5$, and
    (C3-6)cycloalkyl optionally substituted with phenyl whereby said phenyl is optionally substituted with a substituent selected from the group consisting of (C1-4)alkyl and a halogen atom.

2. The compound according to claim 1 wherein one of X and Y is O.

3. The compound according to claim 1 wherein Z is selected from the group consisting of —NR5- and —O—.

4. The compound according to claim 1 wherein R3 is unsubstituted (C3-6)cycloalkyl or phenyl, biphenyl, naphthyl, pyridyl, thienyl or thiazolyl substituted with one or more substituents independently selected from the group consisting of:
  a halogen atom,
  cyano,
  (C1-4)alkyl optionally substituted with one or more fluoro atoms,
  (C1-4)alkoxy optionally substituted with one or more fluoro atoms,
  —S—(C1-4)-alkyl,
  —SF$_5$, and
  (C3-6)cycloalkyl optionally substituted with phenyl whereby said phenyl is optionally substituted with a substituent selected from the group consisting of (C1-4)alkyl and a halogen atom,
wherein said one or more substituents are at one or more of the ortho and meta positions with respect to L.

5. The compound according to claim 1 wherein Z is attached to ring A at atom 1 or 2.

6. The compound according to claim 1 wherein Z is attached to ring A at atom 2 or 3.

7. The compound according to claim 1 wherein L is attached to ring B at atom 5, 6 or 7, and selected from the group consisting of —O—(CH$_2$)p-, —CH=CH—, —C≡C—, —O—SO$_2$—, —O—, —CO—, -Ph-(CH$_2$)m-, -Ph-O—(CH$_2$)m-, and —O—CH$_2$-Ph-O—CH$_2$—, wherein Ph is phenyl, p is an integer from 1 to 4 and m is an integer from 1 to 5.

8. The compound according to claim 1 wherein R3 is selected from the group consisting of:
  (C3-6)alkyl, wherein one or more carbon atoms in the alkyl group are optionally substituted with one or more fluoro atoms;
  (C3-6)cycloalkyl optionally substituted with one or more substituents selected from the group consisting of a halogen atom and (C1-4)alkyl,
  phenyl, optionally substituted with one to three substituents independently selected from the group consisting of:
    a halogen atom,
    cyano,
    (C1-4)alkyl optionally substituted with one or more fluoro atoms,
    (C1-4)alkoxy optionally substituted with one or more fluoro atoms,
    —S—(C1-4)-alkyl,
    —SF$_5$, and
    (C3-6)cycloalkyl.

9. The compound according to claim 1 wherein
R1 is selected from the group consisting of:
  —(C1-6)alkylene-R6 wherein one carbon atom in the alkylene group is optionally substituted with (CH$_2$)$_2$ to form a cyclopropyl moiety, with (CH$_2$)$_3$ to form a cyclobutyl moiety or with (CH$_2$)$_4$ to form a cyclopentyl moiety,
  —(C3-6)cycloalkylene-R6, and
  —(C3-6)cycloalkylene—(C1-3)alkylene-R6 and
R5 is selected from the group consisting of H, (C1-4)alkyl and benzyl optionally substituted with one or more substituents selected from the group consisting of a halogen atom and (C1-4)alkyl; or
NR5 and R1 together form a group -D wherein -D is selected from the group consisting of —(C3-6)heterocycloalkylene-R6, optionally substituted with (C1-4)alkyl; and —(C3-6)heterocycloalkylene-(C1-3)alkylene-R6, optionally substituted with (C1-4)alkyl.

10. The compound according to claim 1 selected from the group consisting of:
  1-(7-((2,6-dichlorobenzyl)oxy)chroman-3-yl)azetidine-3-carboxylic acid;
  1-(6-((2-chloro-6-ethylbenzyl)oxy)-1,2,3,4-tetrahydronaphthalen-2-yl)azetidine-3-carboxylic acid;
  1-(7((2-fluorobenzyl)oxy)chroman-3-yl)azetidine-3-carboxylic acid;
  1-(6-((2,6-dichlorobenzyl)oxy)-1,2,3,4-tetrahydronaphthalen-2-yl)azetidine-3-carboxylic acid;
  1-((6-((2-chloro-6-ethylbenzyl)oxy)-1,2,3,4-tetrahydronaphthalen-2-yl)amino)cyclopropanecarboxylic acid;
  3-((6-((2-chloro-6-ethylbenzyl)oxy)-1,2,3,4-tetrahydronaphthalen-2-yl)amino)propanoic acid;
  3-((6-(benzyloxy)-1,2,3,4-tetrahydronaphthalen-2-yl)amino)propanoic acid;
  3-((6-((2-chlorobenzyl)oxy)-1,2,3,4-tetrahydronaphthalen-2-yl)amino)propanoic acid;
  3-((6-((2,6-dichlorobenzyl)oxy)-1,2,3,4-tetrahydronaphthalen-2-yl)amino)propanoic acid;
  3-((7-((2,6-dichlorobenzyl)oxy)-1,2,3,4-tetrahydronaphthalen-2-yl)amino)propanoic acid;
  3-((6-((4-chlorobenzyl)oxy)-1,2,3,4-tetrahydronaphthalen-2-yl)amino)propanoic acid;
  3-((6-((2,6-dichlorophenyl)ethynyl)-1,2,3,4-tetrahydronaphthalen-2-yl)amino)propanoic acid;
  3-((6-((2,6-dichlorophenyl)ethynyl)-1,2,3,4-tetrahydronaphthalen-2-yl)(methyl)amino)propanoic acid;
  3-((6-((3,5-difluorophenyl)ethynyl)-1,2,3,4-tetrahydronaphthalen-2-yl)amino)propanoic acid;
  3-((6-((3,5-difluorophenyl)ethynyl)-1,2,3,4-tetrahydronaphthalen-2-yl)(methyl)amino)propanoic acid;

3-((6-((2-chlorobenzyl)oxy)-1,2,3,4-tetrahydronaphthalen-2-yl)(methyl)amino)propanoic acid;
3-((6-((2-chloro-6-ethylbenzyl)oxy)-1,2,3,4-tetrahydronaphthalen-2-yl)(methyl)amino)propanoic acid;
3-((6-(2,6-dichlorostyryl)-1,2,3,4-tetrahydronaphthalen-2-yl)amino)-propanoic acid;
(E)-3-((6-(2,6-dichlorostyryl)-1,2,3,4-tetrahydronaphthalen-2-yl)amino)-propanoic acid;
3((6-styryl-1,2,3,4-tetrahydronaphthalen-2-yl)amino)propanoic acid;
(E)-3-((6-styryl-1,2,3,4-tetrahydronaphthalen-2-yl)amino)propanoic acid;
3-((6-(3-chlorostyryl)-1,2,3,4-tetrahydronaphthalen-2-yl)amino)-propanoic acid;
(E)-3-((6-(3-chlorostyryl)-1,2,3,4-tetrahydronaphthalen-2-yl)amino)-propanoic acid;
3-((6-((2-chloro-6-cyclopropylbenzyl)oxy)-1,2,3,4-tetrahydronaphthalen-2-yl)amino)propanoic acid;
methyl 2-(((2-chloro-6-ethylbenzyl)(6-((2-chloro-6-ethylbenzyl)oxy)-1,2,3,4-tetrahydronaphthalen-2-yl)amino)methyl)acrylate;
1-(7-((2-chloro-6-ethylbenzyl)oxy)chroman-3-yl)azetidine-3-carboxylic acid;
1-(7-((3-chlorobenzyl)oxy)chroman-3-yl)azetidine-3-carboxylic acid;
1-(7-((2-chloro-6-cyclopropylbenzyl)oxy)chroman-3-yl)azetidine-3-carboxylic acid;
1-(7((2,3-difluorophenyl)ethynyl)chroman-3-yl)azetidine-3-carboxylic acid;
1-(7-((3,5-difluorophenyl)ethynyl)chroman-3-yl)azetidine-3-carboxylic acid;
2-((6-((3,5-difluorophenyl)ethynyl)-1,2,3,4-tetrahydronaphthalen-2-yl)amino)acetic acid;
2-((6-((2,6-dichlorophenyl)ethynyl)-1,2,3,4-tetrahydronaphthalen-2-yl)amino)acetic acid;
2-((6-(cyclohexylethynyl)-1,2,3,4-tetrahydronaphthalen-2-yl)amino)acetic acid;
1-(6-((2,6-dichlorobenzyl)oxy)-1,2,3,4-tetrahydronaphthalen-2-yl)piperidine-4-carboxylic acid;
3-((6-((2,6-dichlorobenzyl)oxy)-1,2,3,4-tetrahydronaphthalen-2-yl)amino)bicyclo[1.1.1]pentane-1-carboxylic acid;
2-((6-((2,6-dichlorobenzyl)oxy)-1,2,3,4-tetrahydronaphthalen-2-yl)amino)propanoic acid;
2-((7-((2-chloro-6-ethylbenzyl)oxy)chroman-3-yl)amino) acetic acid;
2-((7-((2,6-dichlorobenzyl)oxy)chroman-3-yl)amino) acetic acid;
2-(6-((2,6-dichlorobenzyl)oxy)-1,2,3,4-tetrahydronaphthalen-2-yl)-2-azabicyclo[3.1.0]hexane-1-carboxylic acid;
2-((6-((2,6-dichlorobenzyl)oxy)-1,2,3,4-tetrahydronaphthalen-2-yl)amino)-3-methylbutanoic acid;
1-(7-((2,5-difluorophenyl)ethynyl)chroman-3-yl)azetidine-3-carboxylic acid;
1-(7-(cyclohexylethynyl)chroman-3-yl)azetidine-3-carboxylic acid;
1-(7((3-chlorophenyl)ethynyl)chroman-3-yl)azetidine-3-carboxylic acid;
1-(7((2-(trifluoromethyl)phenyl)ethynyl)chroman-3-yl)azetidine-3-carboxylic acid;
1-(7-((2-(difluoromethoxy)phenyl)ethynyl)chroman-3-yl)azetidine-3-carboxylic acid;
1-(7-((3-(methyl)phenyl)ethynyl)chroman-3-yl)azetidine-3-carboxylic acid;
1-(7-((2,6-dichlorophenyl)ethynyl)chroman-3-yl)azetidine-3-carboxylic acid;
1-(7-((4-ethoxyphenyl)ethynyl)chroman-3-yl)azetidine-3-carboxylic acid;
1-(7-((4-chlorobenzyl)oxy)chroman-3-yl)azetidine-3-carboxylic acid;
1-(7((2,6-difluorophenyl)ethynyl)chroman-3-yl)azetidine-3-carboxylic acid;
3-((7-((2,6-dichlorobenzyl)oxy)chroman-3-yl)amino)-bicyclo[1.1.1]pentane-1-carboxylic acid;
1-(((7-((2,6-dichlorobenzyl)oxy)chroman-3-yl)amino) methyl)cyclopropanecarboxylic acid;
1-(7-((2,6-dichlorobenzyl)oxy)chroman-3-yl)pyrrolidine-3-carboxylic acid;
1-(7-((2,3-difluorobenzyl)oxy)chroman-3-yl)azetidine-3-carboxylic acid;
1-(7-((2,5-dichlorobenzyl)oxy)chroman-3-yl)azetidine-3-carboxylic acid;
1-(7-((2-fluoro-6-methylbenzyl)oxy)chroman-3-yl)azetidine-3-carboxylic acid;
1-(7-(4-((4-chlorobenzyl)oxy)phenyl)chroman-3-yl)azetidine-3-carboxylic acid;
1-(7-(4-(cyclohexylmethoxy)phenyl)chroman-3-yl)azetidine-3-carboxylic acid;
1-(7-(4-((2,3-difluorobenzyl)oxy)phenyl)chroman-3-yl)azetidine-3-carboxylic acid;
1-(7-((4-(trifluoromethyl)benzyl)oxy)chroman-3-yl)azetidine-3-carboxylic acid;
1-(7-((3-methylbenzyl)oxy)chroman-3-yl)azetidine-3-carboxylic acid;
1-(7-((3-(trifluoromethyl)benzyl)oxy)chroman-3-yl)azetidine-3-carboxylic acid;
1-(7-((2,6-difluorobenzyl)oxy)chroman-3-yl)azetidine-3-carboxylic acid;
1-(7-((2-chloro-6-fluorobenzyl)oxy)chroman-3-yl)azetidine-3-carboxylic acid;
1-(7-((2-(trifluoromethyl)benzyl)oxy)chroman-3-yl)azetidine-3-carboxylic acid;
1-(7-((2-chlorobenzyl)oxy)chroman-3-yl)azetidine-3-carboxylic acid;
1-(7-((2-ethylbenzyl)oxy)chroman-3-yl)azetidine-3-carboxylic acid;
1-(7-((2-ethyl-6-fluorobenzyl)oxy)chroman-3-yl)azetidine-3-carboxylic acid;
1-(7-((2-fluoro-6-(trifluoromethyl)benzyl)oxy)chroman-3-yl)azetidine-3-carboxylic acid;
1-(7-((2-cyclopropyl-6-fluorobenzyl)oxy)chroman-3-yl) azetidine-3-carboxylic acid;
1-(7-((2,4-dichlorobenzyl)oxy)chroman-3-yl)azetidine-3-carboxylic acid;
1-(7-(2,6-dichlorophenethoxy)chroman-3-yl)azetidine-3-carboxylic acid;
1-((6-((2,6-dichlorobenzyl)oxy)isochroman-1-yl)methyl) piperidine-4-carboxylic acid;
1-(7-((2-chloro-6-methylbenzyl)oxy)chroman-3-yl)azetidine-3-carboxylic acid;
2-((7-((2-ethyl-6-fluorobenzyl)oxy)chroman-3-yl) (methyl)amino)acetic acid;
2-((6-((2-chloro-6-ethylbenzyl)oxy)-1,2,3,4-tetrahydronaphthalen-2-yl)amino)acetic acid;
1-(6-((2,6-dichlorobenzyl)oxy)-1,2,3,4-tetrahydronaphthalen-2-yl)pyrrolidine-3-carboxylic acid;
2-((6-((2,6-dichlorobenzyl)oxy)-1,2,3,4-tetrahydronaphthalen-2-yl)amino)acetic acid;
1-(((6-((2-chloro-6-ethylbenzyl)oxy)-1,2,3,4-tetrahydronaphthalen-2-yl)amino)methyl)cyclopropanecarboxylic acid;
3-((6-((2,6-dichlorobenzyl)oxy)-1,2,3,4-tetrahydronaphthalen-2-yl)amino)cyclobutanecarboxylic acid;

(1s,3s)-3-((6-((2,6-dichlorobenzyl)oxy)-1,2,3,4-tetrahydronaphthalen-2-yl)amino)cyclobutanecarboxylic acid;
2-(1-(6-((2,6-dichlorobenzyl)oxy)-1,2,3,4-tetrahydronaphthalen-2-yl)azetidin-3-yl)acetic acid;
(1r,3r)-3-((6-((2,6-dichlorobenzyl)oxy)-1,2,3,4-tetrahydronaphthalen-2-yl)amino)cyclobutanecarboxylic acid;
2-(1 -(6-((2,6-dichlorobenzyl)oxy)-1,2,3,4-tetrahydronaphthalen-2-yl)pyrrolidin-3-yl)acetic acid;
1-(7-(3,5-difluorophenethyl)chroman-3-yl)azetidine-3-carboxylic acid;
3-(8-((2-chloro-6-ethylbenzyl)oxy)-5,6-dihydro-2H-naphtho[1,2-b][1,4]oxazin-4(3H,4aH,10bH)-yl)propanoic acid;
1-[7-[(4-fluoro-3-methyl-phenyl)methoxy]chroman-3-yl]azetidine-3-carboxylic acid;
1-[7-[[4-fluoro-3-(trifluoromethyl)phenyl]methoxy]chroman-3-yl]azetidine-3-carboxylic acid;
1-[7-[(2-fluoro-3-methoxy-phenyl)methoxy]chroman-3-yl]azetidine-3-carboxylic acid;
1-[7-[(3-fluoro-5-methyl-phenyl)methoxy]chroman-3-yl]azetidine-3-carboxylic acid;
1-[7[(2-fluoro-4-methyl-phenyl)methoxy]chroman-3-yl]azetidine-3-carboxylic acid;
1-[7-[(4-cyano-2-fluoro-phenyl)methoxy]chroman-3-yl]azetidine-3-carboxylic acid;
1-[7-[[3-fluoro-5-(trifluoromethyl)phenyl]methoxy]chroman-3-yl]azetidine-3-carboxylic acid;
1-[7-[[5-fluoro-2-(trifluoromethyl)phenyl]methoxy]chroman-3-yl]azetidine-3-carboxylic acid;
1[7-[(4-fluoro-3-methoxy-phenyl)methoxy]chroman-3-yl]azetidine-3-carboxylic acid;
1-[7-[2-(4-fluorophenoxy)ethoxy]chroman-3-yl]azetidine-3-carboxylic acid;
1-[7-[[2-fluoro-3-(trifluoromethyl)phenyl]methoxy]chroman-3-yl]azetidine-3-carboxylic acid;
1-[7-[(3-fluoro-4-methoxy-phenyl)methoxy]chroman-3-yl]azetidine-3-carboxylic acid;
1-[7-[(3-fluoro-2-methyl-phenyl)methoxy]chroman-3-yl]azetidine-3-carboxylic acid;
1-[7-[2-(3-fluorophenoxy)ethoxy]chroman-3-yl]azetidine-3-carboxylic acid;
1-[7-[(2-fluoro-5-methoxy-phenyl)methoxy]chroman-3-yl]azetidine-3-carboxylic acid;
1-[7-[3-(3-fluorophenyl)propoxy]chroman-3-yl]azetidine-3-carboxylic acid;
1-[7-[(3-fluoro-5-methoxy-phenyl)methoxy]chroman-3-yl]azetidine-3-carboxylic acid;
1-[7-[(2-fluoro-6-methoxy-phenyl)methoxy]chroman-3-yl]azetidine-3-carboxylic acid;
1-[7-[4-(3-fluorophenoxy)butoxy]chroman-3-yl]azetidine-3-carboxylic acid;
1-[7-[[3-fluoro-4-(trifluoromethyl)phenyl]methoxy]chroman-3-yl]azetidine-3-carboxylic acid;
1-[7-[[2-fluoro-5-(trifluoromethoxy)phenyl]methoxy]chroman-3-yl]azetidine-3-carboxylic acid;
1-[7-[(2-fluoro-3-methyl-phenyl)methoxy]chroman-3-yl]azetidine-3-carboxylic acid;
1[7-[[2-fluoro-4-(trifluoromethyl)phenyl]methoxy]chroman-3-yl]azetidine-3-carboxylic acid;
1-[7-[1-(2-fluorophenyl)ethoxy]chroman-3-yl]azetidine-3-carboxylic acid;
1-[7-[(6-fluoro-2-quinolyl)methoxy]chroman-3-yl]azetidine-3-carboxylic acid;
1-(7-(cyclohexylmethoxy)chroman-3-yl)azetidine-3-carboxylic acid;
1-(7-((2,6-dichlorobenzyl)oxy)chroman-3-yl)piperidine-4-carboxylic acid;
1-(7-((2-chloro-6-ethylbenzyl)oxy)chroman-3-yl)piperidine-4-carboxylic acid;
1-(7-benzyloxychroman-3-yl)piperidine-4-carboxylic acid;
2-[[7-(cyclohexylmethoxy)chroman-3-yl]amino]acetic acid;
2-[[7-[2-(2,6-dichlorophenyl)ethoxy]chroman-3-yl]amino]acetic acid;
2-(1-((7-((2-chloro-6-ethylbenzyl)oxy)chroman-3-yl)amino)cyclopentyl) acetic acid;
2-(1-((7-((2-chloro-6-ethylbenzyl)oxy)chroman-3-yl)amino)cyclobutyl)acetic acid;
2-(1-((7-((2-ethyl-6-fluorobenzyl)oxy)chroman-3-yl)amino)cyclopentyl) acetic acid;
2-(1-((7-((2-ethyl-6-fluorobenzyl)oxy)chroman-3-yl)amino)cyclobutyl)acetic acid;
1-((7-((2,6-dichlorobenzyl)oxy)chroman-3-yl)amino)cyclobutane-1-carboxylic acid;
1-((7-((2-chloro-6-ethylbenzyl)oxy)chroman-3-yl)amino)cyclobutane-1-carboxylic acid;
3-((7-((2-chloro-6-ethylbenzyl)oxy)chroman-3-yl)amino)bicyclo[1.1.1]pentane-1-carboxylic acid;
3-((7-((2-ethyl-6-fluorobenzyl)oxy)chroman-3-yl)amino)bicyclo[1.1.1]pentane-1-carboxylic acid;
2-((7-((2,6-dichlorobenzyl)oxy)chroman-3-yl)(methyl)amino)acetic acid;
2-((7-((2-chloro-6-ethylbenzyl)oxy)chroman-3-yl)(methyl)amino)acetic acid;
2-(1-(7-((2-chloro-6-ethylbenzyl)oxy)chroman-3-yl)pyrrolidin-3-yl)acetic acid;
2-((7-((2-fluoro-6-ethylbenzyl)oxy)chroman-3-yl)amino) acetic acid;
1-(7-((2-ethyl-6-fluorobenzyl)oxy)chroman-3-yl)pyrrolidine-3-carboxylic acid;
1-(7-((2-chloro-6-ethylbenzyl)oxy)chroman-3-yl)pyrrolidine-3-carboxylic acid;
2-(1-((7-((2-ethyl-6-fluorobenzyl)oxy)chroman-3-yl)amino)cyclopropyl) acetic acid;
2-(1-(7-((2-ethyl-6-fluorobenzyl)oxy)chroman-3-yl)pyrrolidin-3-yl)acetic acid;
(7-(4((2,3-difluorobenzyl)oxy)phenyl)chroman-3-yl)glycine;
(7-((4-((3-chlorobenzyl)oxy)benzyl)oxy)chroman-3-yl) glycine;
2-((7-(4-((2,3-difluorobenzyl)oxy)phenyl)chroman-3-yl)(methyl)amino)acetic acid;
2-((7-(4-((3-chlorobenzyl)oxy)phenyl)chroman-3-yl) (methyl)amino)acetic acid;
2-((7-(4-((4-chlorobenzyl)oxy)phenyl)chroman-3-yl) (methyl)amino)acetic acid;
5-(((7-((2-ethyl-6-fluorobenzyl)oxy)chroman-3-yl) amino) methyl)isoxazol-3-ol;
(S)-5(((7-((2-ethyl-6-fluorobenzyl)oxy)chroman-3-yl) amino) methyl)isoxazol-3-ol;
N—(3-((3-((tert-butyldimethylsilyl)oxy)isoxazol-5-yl) methyl)-7((2-chloro-6-ethylbenzyl)oxy)chroman-3-amine;
(S)—N—(3-((tert-butyldimethylsilyl)oxy)isoxazol-5-yl) methyl)-7-((2-chloro-6-ethylbenzyl)oxy)chroman-3-amine;
1-(7-((2,6-dichlorobenzyl)oxy)chroman-3-yl)-3-methylazetidine-3-carboxylic acid;
(S)-1-(7-((2,6-dichlorobenzyl)oxy)chroman-3-yl)-3-methylazetidine-3-carboxylic acid;
1-(7-((2-ethyl-6-fluorobenzyl)oxy)chroman-3-yl)-3-methylazetidine-3-carboxylic acid;

(S)-1-(7-((2-ethyl-6-fluorobenzyl)oxy)chroman-3-yl)-3-methylazetidine-3-carboxylic acid;
1-(7-((2,6-dichlorobenzyl)oxy)chroman-3-yl)-3-ethylazetidine-3-carboxylic acid;
(S)-1-(7-((2,6-dichlorobenzyl)oxy)chroman-3-yl)-3-ethylazetidine-3-carboxylic acid;
1-(7-((2,6-dichlorobenzyl)oxy)chroman-3-yl)-3-propylazetidine-3-carboxylic acid;
(S)-1-(7-((2,6-dichlorobenzyl)oxy)chroman-3-yl)-3-propylazetidine-3-carboxylic acid;
2-((6-((2-chloro-6-ethylbenzyl)oxy)-1,2,3,4-tetrahydronaphthalen-2-yl)oxy)acetic acid;
2-((6-((2-chloro-6-cyclopropylbenzyl)oxy)-1,2,3,4-tetrahydronaphthalen-2-yl)oxy)acetic acid;
1-(7-((2,6-dichlorobenzyl)oxy)chroman-3-yl)azetidine-3-carboxylic acid, enantiomer 1;
1-(7-((2,6-dichlorobenzyl)oxy)chroman-3-yl)azetidine-3-carboxylic acid, enantiomer 2;
1-(7-((2-ethyl-6-fluorobenzyl)oxy)chroman-3-yl)azetidine-3-carboxylic acid, enantiomer 1;
1-(7-((2-ethyl-6-fluorobenzyl)oxy)chroman-3-yl)azetidine-3-carboxylic acid, enantiomer 2;
1-(7-((2-methoxy-4-propylbenzyl)oxy)chroman-3-yl)azetidine-3-carboxylic acid;
2-((6-((2,6-difluoro-3-methylbenzyl)oxy)-1,2,3,4-tetrahydronaphthalen-2-yl)oxy)acetic acid;
2-((6-((2-fluoro-3-methyl-6-chlorobenzyl)oxy)-1,2,3,4-tetrahydronaphthalen-2-yl)oxy)acetic acid;
2-((6-((2-chloro-5-(trifluoromethyl)benzyl)oxy)-1,2,3,4-tetrahydronaphthalen-2-yl)oxy)acetic acid;
2-((6-((2,6-difluoro-3-chlorobenzyl)oxy)-1,2,3,4-tetrahydronaphthalen-2-yl)oxy)acetic acid;
2-((6-((2-(trifluoromethyl)-5-chlorobenzyl)oxy)-1,2,3,4-tetrahydronaphthalen-2-yl)oxy)acetic acid;
2-((6-((3-methoxybenzyl)oxy)-1,2,3,4-tetrahydronaphthalen-2-yl)oxy)acetic acid;
2-((6-((2-methyl-5-fluorobenzyl)oxy)-1,2,3,4-tetrahydronaphthalen-2-yl)oxy)acetic acid;
2-((6-((3,5-dimethylbenzyl)oxy)-1,2,3,4-tetrahydronaphthalen-2-yl)oxy)acetic acid;
2-((6-((2-fluoro-6-methoxybenzyl)oxy)-1,2,3,4-tetrahydronaphthalen-2-yl)oxy)acetic acid;
2-((6-((2-fluoro-6-(trifluoromethyl)benzyl)oxy)-1,2,3,4-tetrahydronaphthalen-2-yl)oxy)acetic acid;
2-((6-((2,6-difluorobenzyl)oxy)-1,2,3,4-tetrahydronaphthalen-2-yl)oxy)acetic acid;
2-((6-((2-fluoro-5-methylbenzyl)oxy)-1,2,3,4-tetrahydronaphthalen-2-yl)oxy)acetic acid;
2-((6-((2-fluoro-5-(trifluoromethoxy)benzyl)oxy)-1,2,3,4-tetrahydronaphthalen-2-yl)oxy)acetic acid;
2-((6-((2,4-dichlorobenzyl)oxy)-1,2,3,4-tetrahydronaphthalen-2-yl)oxy)acetic acid;
2-((6-((2,5-difluorobenzyl)oxy)-1,2,3,4-tetrahydronaphthalen-2-yl)oxy)acetic acid;
2-((6-((2,5-dichlorobenzyl)oxy)-1,2,3,4-tetrahydronaphthalen-2-yl)oxy)acetic acid;
2-((6-((4-methoxybenzyl)oxy)-1,2,3,4-tetrahydronaphthalen-2-yl)oxy)acetic acid;
2-((6-((2-methoxy-5-fluorobenzyl)oxy)-1,2,3,4-tetrahydronaphthalen-2-yl)oxy)acetic acid;
2-((6-((2-chloro-6-(trifluoromethyl)benzyl)oxy)-1,2,3,4-tetrahydronaphthalen-2-yl)oxy)acetic acid;
2-((6((2-(trifluoromethyl)-5-fluorobenzyl)oxy)-1,2,3,4-tetrahydronaphthalen-2-yl)oxy)acetic acid;
2-((6-((2-chloro-6-fluorobenzyl)oxy)-1,2,3,4-tetrahydronaphthalen-2-yl)oxy)acetic acid;
2-((6-((2-methoxybenzyl)oxy)-1,2,3,4-tetrahydronaphthalen-2-yl)oxy)acetic acid;
2-((6-((2-chloro-5-fluorobenzyl)oxy)-1,2,3,4-tetrahydronaphthalen-2-yl)oxy)acetic acid;
2((6-((2-fluoro-5-(trifluoromethyl)benzyl)oxy)-1,2,3,4-tetrahydronaphthalen-2-yl)oxy)acetic acid;
2-((6-((2-fluoro-5-chlorobenzyl)oxy)-1,2,3,4-tetrahydronaphthalen-2-yl)oxy)acetic acid;
2-((6-((2,6-dimethylbenzyl)oxy)-1,2,3,4-tetrahydronaphthalen-2-yl)oxy)acetic acid;
2-((6-((2-methoxy-5-chlorobenzyl)oxy)-1,2,3,4-tetrahydronaphthalen-2-yl)oxy)acetic acid;
3-((6-((2-(trifluoromethyl)-5-methylbenzyl)oxy)-1,2,3,4-tetrahydronaphthalen-2-yl)oxy)propanoic acid;
3-((6-((2-(trifluoromethyl)benzyl)oxy)-1,2,3,4-tetrahydronaphthalen-2-yl)oxy)propanoic acid;
3-((6-((2-methylbenzyl)oxy)-1,2,3,4-tetrahydronaphthalen-2-yl)oxy)propanoic acid;
3-((6-((3-fluorobenzyl)oxy)-1,2,3,4-tetrahydronaphthalen-2-yl)oxy)propanoic acid;
3-((6-((3,4-dichlorobenzyl)oxy)-1,2,3,4-tetrahydronaphthalen-2-yl)oxy)propanoic acid;
3-((6-((4-methylthiobenzyl)oxy)-1,2,3,4-tetrahydronaphthalen-2-yl)oxy)propanoic acid;
3-((6-((4-(trifluoromethyl)benzyl)oxy)-1,2,3,4-tetrahydronaphthalen-2-yl)oxy)propanoic acid;
3-((6-((3-(trifluoromethoxy)benzyl)oxy)-1,2,3,4-tetrahydronaphthalen-2-yl)oxy)propanoic acid;
3-((6-((4-(trifluoromethoxy)benzyl)oxy)-1,2,3,4-tetrahydronaphthalen-2-yl)oxy)propanoic acid;
3-((6-((2,3-difluorobenzyl)oxy)-1,2,3,4-tetrahydronaphthalen-2-yl)oxy)propanoic acid;
3-((6-((3-chlorobenzyl)oxy)-1,2,3,4-tetrahydronaphthalen-2-yl)oxy)propanoic acid;
3-((6-((2-chlorobenzyl)oxy)-1,2,3,4-tetrahydronaphthalen-2-yl)oxy)propanoic acid;
3-((6-((2,3-dichlorobenzyl)oxy)-1,2,3,4-tetrahydronaphthalen-2-yl)oxy)propanoic acid;
3-((6-((2-(trifluoromethoxy)benzyl)oxy)-1,2,3,4-tetrahydronaphthalen-2-yl)oxy)propanoic acid;
3-((6-((4-chlorobenzyl)oxy)-1,2,3,4-tetrahydronaphthalen-2-yl)oxy)propanoic acid;
3-((6-((4-(tert-butyl)benzyl)oxy)-1,2,3,4-tetrahydronaphthalen-2-yl)oxy)propanoic acid;
3-((6-((3-(trifluoromethyl)benzyl)oxy)-1,2,3,4-tetrahydronaphthalen-2-yl)oxy)propanoic acid;
3-((6-((4-fluorobenzyl)oxy)-1,2,3,4-tetrahydronaphthalen-2-yl)oxy)propanoic acid;
2-((6-((2-(trifluoromethyl)-5-methylbenzyl)oxy)-1,2,3,4-tetrahydronaphthalen-2-yl)oxy)acetic acid;
2-((6-((2-(trifluoromethyl)benzyl)oxy)-1,2,3,4-tetrahydronaphthalen-2-yl)oxy)acetic acid;
2-((6-((2-methylbenzyl)oxy)-1,2,3,4-tetrahydronaphthalen-2-yl)oxy)acetic acid;
2-((6-((3-fluorobenzyl)oxy)-1,2,3,4-tetrahydronaphthalen-2-yl)oxy)acetic acid;
2-((6-((3,4-dichlorobenzyl)oxy)-1,2,3,4-tetrahydronaphthalen-2-yl)oxy)acetic acid;
2-((6-((2-methyl-3-(trifluoromethyl)benzyl)oxy)-1,2,3,4-tetrahydronaphthalen-2-yl)oxy)acetic acid;
2-((6-((4-methylthiobenzyl)oxy)-1,2,3,4-tetrahydronaphthalen-2-yl)oxy)acetic acid;
2-((6-((4-(trifluoromethyl)benzyl)oxy)-1,2,3,4-tetrahydronaphthalen-2-yl)oxy)acetic acid;
2-((6-((4-(trifluoromethoxy)benzyl)oxy)-1,2,3,4-tetrahydronaphthalen-2-yl)oxy)acetic acid;

2-((6-((2,3-difluorobenzyl)oxy)-1,2,3,4-tetrahydronaphthalen-2-yl)oxy)acetic acid;
2-((6-((3-chlorobenzyl)oxy)-1,2,3,4-tetrahydronaphthalen-2-yl)oxy)acetic acid;
2-((6-((2-chlorobenzyl)oxy)-1,2,3,4-tetrahydronaphthalen-2-yl)oxy)acetic acid;
2-((6-((2,3-dichlorobenzyl)oxy)-1,2,3,4-tetrahydronaphthalen-2-yl)oxy)acetic acid;
2-((6-((2-(trifluoromethoxy)benzyl)oxy)-1,2,3,4-tetrahydronaphthalen-2-yl)oxy)acetic acid;
2-((6-((4-chlorobenzyl)oxy)-1,2,3,4-tetrahydronaphthalen-2-yl)oxy)acetic acid;
2-((6-((2,6-dichlorobenzyl)oxy)-1,2,3,4-tetrahydronaphthalen-2-yl)oxy)acetic acid;
2-((6-((4-(tert-butyl)benzyl)oxy)-1,2,3,4-tetrahydronaphthalen-2-yl)oxy)acetic acid;
2-((6-((3,4-difluorobenzyl)oxy)-1,2,3,4-tetrahydronaphthalen-2-yl)oxy)acetic acid;
2-((6-((3-(trifluoromethyl)benzyl)oxy)-1,2,3,4-tetrahydronaphthalen-2-yl)oxy)acetic acid;
2-((6-((4-fluorobenzyl)oxy)-1,2,3,4-tetrahydronaphthalen-2-yl)oxy)acetic acid;
2-((6-((2-fluorobenzyl)oxy)-1,2,3,4-tetrahydronaphthalen-2-yl)oxy)acetic acid;
2-((6-((2-chloro-6-ethylbenzyl)oxy)-1,2,3,4-tetrahydronaphthalen-2-yl)amino)-1-(N-methylmethoxyamino)-1-ethanone;
(1-(6-((2-chloro-6-ethylbenzyl)oxy)-1,2,3,4-tetrahydronaphthalen-2-yl)-3-azetidinyl)(N-methylmethoxyamino)formaldehyde;
2-((6-((2-chloro-6-ethylbenzyl)oxy)-1,2,3,4-tetrahydronaphthalen-2-yl)amino)-1-(methoxyamino)-1-ethanone;
(1-(6-((2-chloro-6-ethylbenzyl)oxy)-1,2,3,4-tetrahydronaphthalen-2-yl)-3-azetidinyl)(methoxyamino)formaldehyde;
5-(((6-((2-chloro-6-ethylbenzyl)oxy)-1,2,3,4-tetrahydronaphthalen-2-yl)amino)methyl)-2H-isoxazol-3-one;
1-(6-bromo-7-((2,6-dichlorobenzyl)oxy)chroman-3-yl)azetidine-3-carboxylic acid;
1-(6-methyl-7-((2,6-dichlorobenzyl)oxy)chroman-3-yl)azetidine-3-carboxylic acid;
1-(6-fluoro-7-((2,6-dichlorobenzyl)oxy)chroman-4-yl)azetidine-3-carboxylic acid;
2-(1-(7-((2,6-dichlorobenzyl)oxy)isochroman-4-yl)azetidin-3-yl)acetic acid;
1-(8-((2,6-dichlorobenzyl)oxy)chroman-3-yl)azetidine-3-carboxylic acid;
1-(7-(phenethoxy)chroman-3-yl)azetidine-3-carboxylic acid;
1-(7-(2-chlorophenethoxy)chroman-3-yl)azetidine-3-carboxylic acid;
1-(7-(4-chlorophenethoxy)chroman-3-yl)azetidine-3-carboxylic acid;
1-(7-(2,6-dichlorophenoxy)chroman-3-yl)azetidine-3-carboxylic acid;
1-(7-(cyclobutylmethoxy)chroman-3-yl)azetidine-3-carboxylic acid;
1-(7-(cyclopropylmethoxy)chroman-3-yl)azetidine-3-carboxylic acid;
1-(8-(phenethoxy)chroman-3-yl)azetidine-3-carboxylic acid;
((7-((2-chloro-6-ethylbenzyl)oxy)chroman-3-yl)oxy)acetic acid;
((7-((2,6-difluoro-3-chlorobenzyl)oxy)chroman-3-yl)oxy)acetic acid;
((7-((2-fluoro-6-cyclopropylbenzyl)oxy)chroman-3-yl)oxy)acetic acid;
2-((6-((2-chloro-6-ethylbenzyl)oxy)-1,2,3,4-tetrahydronaphthalen-2-yl)amino)acetohydroxamic acid;
2-((7-(4-(benzyloxy)phenyl)chroman-3-yl)amino)acetic acid;
2-((7-(4-(benzyloxy)phenyl)chroman-3-yl)(methyl)amino)acetic acid;
((7-((2-chloro-6-ethylbenzyl)oxy)chroman-3-yl)oxy)acetic acid, enantiomer 1; and
((7-((2-chloro-6-ethylbenzyl)oxy)chroman-3-yl)oxy)acetic acid, enantiomer 2, or a pharmaceutically acceptable salt, solvate, tautomer, stereoisomer or N-oxide thereof.

11. A compound of formula:

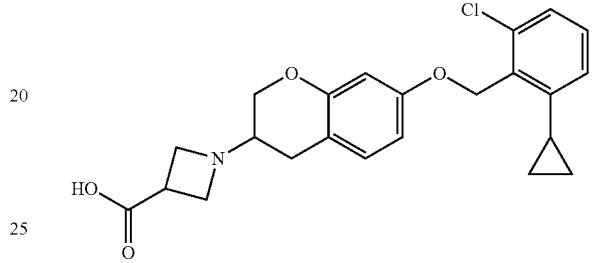

or a pharmaceutically acceptable salt, solvate, tautomer, stereoisomer or N-oxide thereof.

12. A compound of formula:

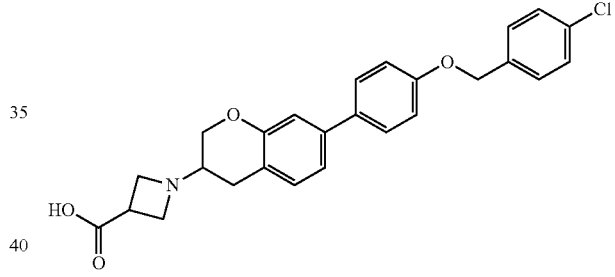

or a pharmaceutically acceptable salt, solvate, tautomer, stereoisomer or N-oxide thereof.

13. A compound of formula:

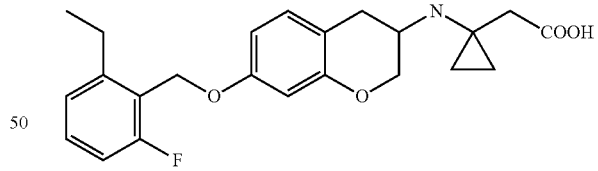

or a pharmaceutically acceptable salt, solvate, tautomer, stereoisomer or N-oxide thereof.

14. A compound of formula:

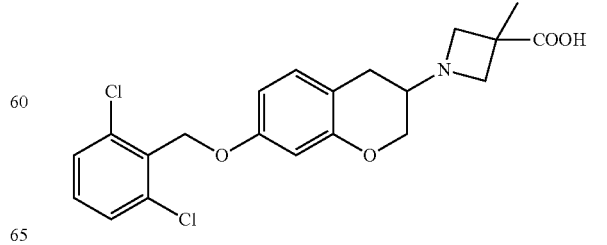

or a pharmaceutically acceptable salt, solvate, tautomer, stereoisomer or N-oxide thereof.

15. A compound of formula:

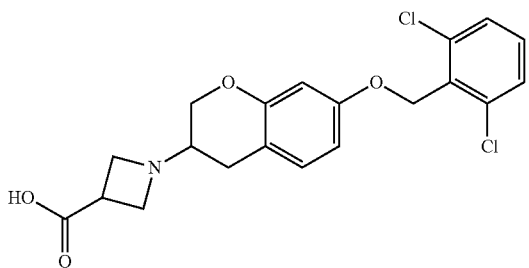 [SMILES: O=C(O)C1CN(C2COc3cc(OCc4c(Cl)cccc4Cl)ccc3C2)C1]

or a pharmaceutically acceptable salt, solvate, tautomer, stereoisomer or N-oxide thereof.

16. A compound of formula:

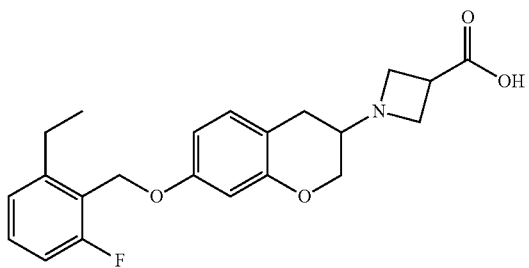 [SMILES: CCc1cccc(F)c1COc1ccc2c(c1)OCC(N1CC(C(=O)O)C1)C2]

or a pharmaceutically acceptable salt, solvate, tautomer, stereoisomer or N-oxide thereof.

17. A pharmaceutical composition comprising a compound according to claim 1 or a pharmaceutically acceptable salt, solvate, tautomer, stereoisomer or N-oxide thereof and at least one pharmaceutically acceptable auxiliary.

18. A method of treatment or alleviation of a disease or condition comprising administering to a patient in need thereof a compound according to claim 1 or a pharmaceutically acceptable salt, solvate, tautomer, stereoisomer, or N-oxide thereof, wherein the disease or condition is selected from the group consisting of Alzheimer's Disease (AD) and associated dementias, amyloid β-associated disorders, Parkinson's Disease (PD), multiple sclerosis, Huntington's Disease, stroke, pain, cancer-induced peripheral neuropathy (CIPN), Creutzfeldt-Jakob Disease and other Prion-related Disorders, age-related cognitive decline or memory impairment, dementia, diminished CNS function associated with traumatic brain injury, spinal cord injury, a demyelinating disorder, ulcerative colitis, atherosclerosis, sepsis syndrome and septic shock.

19. The method according to claim 18 wherein said pain is selected from the group consisting of neuropathic, back pain, pain-associated with multiple sclerosis, pain-associated with spinal cord injury, pain-associated with Parkinson's Disease, pain-associated with epilepsy, pain-associated with diabetes and pain-associated with cancer.

* * * * *